US011052368B2

(12) United States Patent
Weitz et al.

(10) Patent No.: US 11,052,368 B2
(45) Date of Patent: Jul. 6, 2021

(54) SYSTEMS AND METHODS FOR BARCODING NUCLEIC ACIDS

(71) Applicants: President and Fellows of Harvard College, Cambridge, MA (US); Vilnius University, Vilnius (LT)

(72) Inventors: David A. Weitz, Bolton, MA (US); Allon Moshe Klein, Boston, MA (US); Ilke Akartuna, Cambridge, MA (US); Linas Mazutis, Vilnius (LT); Marc W. Kirschner, Newton, MA (US)

(73) Assignees: Vilnius University, Vilnius (LT); President and Fellows of Harvard College, Cambridge, MA (US)

(*) Notice: Subject to any disclaimer, the term of this patent is extended or adjusted under 35 U.S.C. 154(b) by 190 days.

(21) Appl. No.: 15/991,600

(22) Filed: May 29, 2018

(65) Prior Publication Data

US 2018/0304222 A1 Oct. 25, 2018

Related U.S. Application Data

(63) Continuation of application No. 14/734,903, filed on Jun. 9, 2015, which is a continuation of application No. PCT/US2015/026443, filed on Apr. 17, 2015.

(60) Provisional application No. 62/072,944, filed on Oct. 30, 2014, provisional application No. 62/066,188, filed on Oct. 20, 2014, provisional application No. 62/065,348, filed on Oct. 17, 2014, provisional application No. 61/982,001, filed on Apr. 21, 2014.

(51) Int. Cl.
*B01J 19/00* (2006.01)
*B01L 3/00* (2006.01)
*B01F 13/00* (2006.01)
*C12Q 1/6806* (2018.01)
*B01L 7/00* (2006.01)

(52) U.S. Cl.
CPC ....... *B01J 19/0046* (2013.01); *B01F 13/0062* (2013.01); *B01L 3/502761* (2013.01); *B01L 3/502776* (2013.01); *B01L 3/502784* (2013.01); *C12Q 1/6806* (2013.01); *B01J 2219/00585* (2013.01); *B01J 2219/00722* (2013.01); *B01L 7/52* (2013.01); *B01L 2200/0652* (2013.01); *B01L 2300/021* (2013.01); *B01L 2300/0663* (2013.01); *B01L 2300/0858* (2013.01); *B01L 2300/0867* (2013.01); *B01L 2300/0883* (2013.01)

(58) Field of Classification Search
CPC .................................................. B01J 19/0046
USPC .......................................................... 506/16
See application file for complete search history.

(56) References Cited

U.S. PATENT DOCUMENTS

| 5,750,346 | A  | 5/1998  | Andre et al. |
| 6,013,445 | A  | 1/2000  | Albrecht et al. |
| 6,054,278 | A  | 4/2000  | Dodge et al. |
| 6,312,911 | B1 | 11/2001 | Bancroft et al. |
| 6,696,022 | B1 | 2/2004  | Chen et al. |
| 6,750,016 | B2 | 6/2004  | Mirkin et al. |
| 6,974,669 | B2 | 12/2005 | Mirkin et al. |
| 7,708,949 | B2 | 5/2010  | Stone et al. |
| 8,293,535 | B2 | 10/2012 | Farquar et al. |
| 8,337,778 | B2 | 12/2012 | Stone et al. |
| 8,592,150 | B2 | 11/2013 | Drmanac et al. |
| 8,765,485 | B2 | 7/2014  | Link et al. |
| 8,778,609 | B1 | 7/2014  | Umbarger |
| 8,829,171 | B2 | 9/2014  | Steemers et al. |
| 8,841,071 | B2 | 9/2014  | Link |
| 9,023,650 | B2 | 5/2015  | Farquar et al. |
| 9,388,465 | B2 | 7/2016  | Hindson et al. |
| 9,410,201 | B2 | 8/2016  | Hindson et al. |
| 9,567,631 | B2 | 2/2017  | Hindson et al. |
| 9,644,204 | B2 | 5/2017  | Hindson et al. |
| 9,689,024 | B2 | 6/2017  | Hindson et al. |
| 9,694,361 | B2 | 7/2017  | Bharadwaj et al. |
| 9,695,468 | B2 | 7/2017  | Hindson et al. |
| 9,701,998 | B2 | 7/2017  | Hindson et al. |
| 9,708,654 | B2 | 7/2017  | Hunicke-Smith et al. |
| 10,596,541 | B2 | 3/2020 | Weitz et al. |
| 2002/0026046 | A1 | 2/2002 | Pasloske et al. |

(Continued)

FOREIGN PATENT DOCUMENTS

| CN | 101946010 A1 | 1/2011 |
| CN | 102439177 A  | 5/2012 |

(Continued)

OTHER PUBLICATIONS

Extended European Search Report for Application No. EP 13758373.8 dated Nov. 24, 2015.

(Continued)

*Primary Examiner* — Karla A Dines
(74) *Attorney, Agent, or Firm* — Wolf, Greenfield & Sacks, P.C.

(57) ABSTRACT

The present invention generally relates to microfluidics and labeled nucleic acids. For example, certain aspects are generally directed to systems and methods for labeling nucleic acids within microfluidic droplets. In one set of embodiments, the nucleic acids may include "barcodes" or unique sequences that can be used to distinguish nucleic acids in a droplet from those in another droplet, for instance, even after the nucleic acids are pooled together. In some cases, the unique sequences may be incorporated into individual droplets using particles and attached to nucleic acids contained within the droplets (for example, released from lysed cells). In some cases, the barcodes may be used to distinguish tens, hundreds, or even thousands of nucleic acids, e.g., arising from different cells or other sources.

20 Claims, 69 Drawing Sheets

Specification includes a Sequence Listing.

(56) References Cited

U.S. PATENT DOCUMENTS

| | | |
|---|---|---|
| 2003/0082668 A1 | 5/2003 | Tamai et al. |
| 2003/0152994 A1 | 8/2003 | Woudenberg et al. |
| 2005/0266407 A1 | 12/2005 | Chee et al. |
| 2006/0137434 A1 | 6/2006 | Cohen et al. |
| 2006/0153924 A1 | 7/2006 | Griffiths et al. |
| 2007/0000342 A1 | 1/2007 | Link et al. |
| 2007/0031865 A1 | 2/2007 | Willoughby |
| 2007/0052781 A1 | 3/2007 | Fraden et al. |
| 2007/0077572 A1 | 4/2007 | Tawfik et al. |
| 2007/0195127 A1 | 8/2007 | Ahn et al. |
| 2008/0268450 A1 | 10/2008 | Nam et al. |
| 2009/0098555 A1 | 4/2009 | Roth et al. |
| 2009/0105959 A1 | 4/2009 | Braverman et al. |
| 2009/0181375 A1 | 7/2009 | Peter et al. |
| 2009/0181864 A1 | 7/2009 | Chai et al. |
| 2009/0203063 A1 | 8/2009 | Wheeler et al. |
| 2009/0208975 A1 | 8/2009 | D'Costa et al. |
| 2010/0022414 A1 | 1/2010 | Link et al. |
| 2010/0105052 A1 | 4/2010 | Drmanac et al. |
| 2010/0120097 A1 | 5/2010 | Aglyamova et al. |
| 2010/0136544 A1 | 6/2010 | Agresti et al. |
| 2010/0216151 A1 | 8/2010 | Lapidus et al. |
| 2010/0248237 A1 | 9/2010 | Froehlich et al. |
| 2010/0261230 A1 | 10/2010 | Liu et al. |
| 2010/0285975 A1 | 11/2010 | Mathies et al. |
| 2010/0323361 A1 | 12/2010 | Pugh et al. |
| 2011/0033854 A1 | 2/2011 | Andrei et al. |
| 2011/0267457 A1 | 11/2011 | Agresti et al. |
| 2011/0275063 A1 | 11/2011 | Weitz et al. |
| 2011/0281736 A1 | 11/2011 | Drmanac et al. |
| 2011/0318786 A1 | 12/2011 | Reichert et al. |
| 2012/0010091 A1 | 1/2012 | Linnarson |
| 2012/0015822 A1 | 1/2012 | Weitz et al. |
| 2012/0028818 A1 | 2/2012 | Ö et al. |
| 2012/0058468 A1 | 3/2012 | Mckeown |
| 2012/0122714 A1 | 5/2012 | Samuels et al. |
| 2012/0132288 A1 | 5/2012 | Weitz et al. |
| 2012/0157322 A1 | 6/2012 | Myllykangas et al. |
| 2012/0022094 A1 | 8/2012 | Samuels et al. |
| 2012/0196758 A1 | 8/2012 | Klausing et al. |
| 2012/0211084 A1 | 8/2012 | Weitz et al. |
| 2012/0220494 A1 | 8/2012 | Samuels et al. |
| 2012/0309002 A1 | 12/2012 | Link et al. |
| 2012/0322691 A1 | 12/2012 | Sachidanandam et al. |
| 2013/0005585 A1 | 1/2013 | Anderson et al. |
| 2013/0130919 A1 | 5/2013 | Chen et al. |
| 2013/0165346 A1 | 6/2013 | Wang et al. |
| 2013/0178369 A1 | 7/2013 | Burns et al. |
| 2013/0219534 A1 | 8/2013 | Wong et al. |
| 2013/0225418 A1 | 8/2013 | Watson |
| 2013/0261019 A1 | 10/2013 | Lin et al. |
| 2013/0261027 A1 | 10/2013 | Li et al. |
| 2013/0274117 A1 | 10/2013 | Church et al. |
| 2014/0057799 A1 | 2/2014 | Johnson et al. |
| 2014/0141436 A1 | 5/2014 | Erlich et al. |
| 2014/0194324 A1 | 7/2014 | Gormley et al. |
| 2014/0200162 A1 | 7/2014 | Saito et al. |
| 2014/0228255 A1 | 8/2014 | Hindson et al. |
| 2014/0274729 A1 | 9/2014 | Kurn et al. |
| 2014/0378345 A1 | 12/2014 | Hindson et al. |
| 2015/0011432 A1 | 1/2015 | Saxonov |
| 2015/0034163 A1 | 2/2015 | Abate et al. |
| 2015/0051117 A1 | 2/2015 | Church et al. |
| 2015/0057163 A1 | 2/2015 | Bernstein et al. |
| 2015/0298091 A1 | 10/2015 | Weitz et al. |
| 2015/0329852 A1 | 11/2015 | Nolan |
| 2015/0344938 A1 | 12/2015 | Andersen et al. |
| 2016/0145683 A1 | 5/2016 | Fan et al. |
| 2016/0194694 A1 | 7/2016 | Andersen et al. |
| 2016/0312213 A1 | 10/2016 | Rokhsar et al. |
| 2017/0028377 A1 | 2/2017 | Bernstein et al. |
| 2017/0029813 A1 | 2/2017 | Weitz et al. |
| 2018/0023133 A1 | 1/2018 | Rotem et al. |
| 2018/0071705 A1 | 3/2018 | Weitz et al. |
| 2018/0087078 A1 | 3/2018 | Weitz et al. |
| 2018/0155777 A1 | 6/2018 | Weitz et al. |
| 2018/0155778 A1 | 6/2018 | Weitz et al. |
| 2018/0265922 A1 | 9/2018 | Weitz et al. |
| 2018/0371540 A1 | 12/2018 | Hindson et al. |
| 2019/0361010 A1 | 11/2019 | Belhocine et al. |
| 2020/0123582 A1 | 4/2020 | Tan et al. |

FOREIGN PATENT DOCUMENTS

| | | |
|---|---|---|
| CN | 103717749 A | 4/2014 |
| CN | 20158002908.1 | 1/2021 |
| EP | 2 359 689 A1 | 8/2011 |
| EP | 18201501.6 | 10/2020 |
| EP | 18215320.5 | 11/2020 |
| JP | 2007-503984 A | 3/2007 |
| JP | 2010-520749 A | 6/2010 |
| JP | 2010-193884 A | 9/2010 |
| JP | 2011-509075 | 3/2011 |
| JP | 2014-512826 A | 5/2014 |
| JP | 2015-528283 A | 9/2015 |
| JP | 2017-515469 A | 6/2017 |
| WO | WO 2004/002627 A2 | 1/2004 |
| WO | WO 2004/091763 A2 | 10/2004 |
| WO | WO 2005/021151 A1 | 3/2005 |
| WO | WO 2005/062982 A2 | 7/2005 |
| WO | WO 2006/096571 A2 | 9/2006 |
| WO | WO 2007/089541 A2 | 8/2007 |
| WO | WO 2008/000090 A1 | 1/2008 |
| WO | WO 2008/109176 A2 | 9/2008 |
| WO | WO 2008/127789 A2 | 10/2008 |
| WO | WO 2009/011808 A1 | 1/2009 |
| WO | WO 2009/085215 A1 | 7/2009 |
| WO | WO 2010/025310 A2 | 3/2010 |
| WO | WO 2010/033200 A2 | 3/2010 |
| WO | WO 2010/080134 A1 | 7/2010 |
| WO | WO 2010/151776 A2 | 12/2010 |
| WO | WO 2011/056546 A1 | 5/2011 |
| WO | WO 2011/140510 A2 | 11/2011 |
| WO | WO 2012/003330 | 1/2012 |
| WO | WO 2012/016136 A2 | 2/2012 |
| WO | WO 2012/019765 | 2/2012 |
| WO | WO 2012/048340 | 4/2012 |
| WO | WO 2012/048341 A1 | 4/2012 |
| WO | WO 2012/083225 A2 | 6/2012 |
| WO | WO 2012/094642 A2 | 7/2012 |
| WO | WO 2012/112804 | 8/2012 |
| WO | WO 2012/128717 A1 | 9/2012 |
| WO | WO 2012/149042 | 11/2012 |
| WO | WO 2012/162267 A2 | 11/2012 |
| WO | WO 2013/011611 | 1/2013 |
| WO | WO 2013/116698 | 8/2013 |
| WO | WO 2013/123125 A1 | 8/2013 |
| WO | WO 2013/134261 A1 | 9/2013 |
| WO | WO 2013/188872 A1 | 12/2013 |
| WO | WO 2014/028537 | 2/2014 |
| WO | WO 2014/047561 A1 | 3/2014 |
| WO | WO 2014/145555 A1 | 9/2014 |
| WO | WO 2014/210353 | 12/2014 |
| WO | WO 2015/103339 A1 | 7/2015 |
| WO | WO 2015/160919 A1 | 10/2015 |
| WO | WO 2015/161177 A1 | 10/2015 |
| WO | WO 2015/164212 A1 | 10/2015 |
| WO | WO 2015/200541 A1 | 12/2015 |
| WO | WO 2016/040476 | 3/2016 |
| WO | WO 2016/168584 A1 | 10/2016 |

OTHER PUBLICATIONS

European Office Action for Application No. EP 13758373.8 dated Nov. 18, 2016.
European Office Action for Application No. EP 13758373.8 dated Oct. 12, 2017.
European Office Action for Application No. EP 3758373.8 dated Apr. 24, 2018.
European Search Report for Application No. EP 17201280.9 dated Feb. 12, 2018.
Extended European Search Report for Application No. EP 17201280.9 dated May 23, 2018.

(56) References Cited

OTHER PUBLICATIONS

International Search Report and Written Opinion for Application No. PCT/US2013/029123 dated May 23, 2013.
International Preliminary Report on Patentability for Application No. PCT/US2013/029123 dated Sep. 18, 2014.
Extended European Search Report for Application No. EP 15780044.2 dated Oct. 26, 2017.
International Search Report and Written Opinion for Application No. PCT/US2015/026338 dated Sep. 8, 2015.
International Preliminary Report on Patentability for Application No. PCT/US2015/026338 dated Oct. 27, 2016.
Extended European Search Report for Application No. EP 15780364.4 dated Oct. 23, 2017.
International Search Report and Written Opinion for Application No. PCT/US2015/026422 dated Sep. 2, 2015.
International Preliminary Report on Patentability for Application No. PCT/US2015/026422 dated Oct. 27, 2016.
Extended European Search Report for Application No. EP 15783629.7 dated Nov. 17, 2017.
Extended Eurpoean Search Report for Application No. EP 17198030.3 dated Jan. 19, 2018.
International Search Report and Written Opinion for Application No. PCT/US2015/026443, dated Jul. 27, 2015.
International Preliminary Report on Patentability for Application No. PCT/US2015/026443 dated Nov. 3, 2016.
International Search Report and Written Opinion for Application No. PCT/US2016/027734 dated Jul. 14, 2016.
International Preliminary Report on Patentability for Application No. PCT/US2016/027734 dated Oct. 26, 2017.
International Search Report and Written Opinion for Application No. PCT/US2017/043660 dated Nov. 6, 2017.
Office Action dated Oct. 6, 2017 for U.S. Appl. No. 15/303,874.
Office Action dated Oct. 6, 2017 for U.S. Appl. No. 15/303,893.
Office Action dated May 17, 2018 for U.S. Appl. No. 15/303,893.
Office Action dated Sep. 24, 2015 for U.S. Appl. No. 14/734,903.
Office Action dated Feb. 1, 2016 for U.S. Appl. No. 14/734,903.
Advisory Action dated May 19, 2016 for U.S. Appl. No. 14/734,903.
Office Action dated Oct. 7, 2016 for U.S. Appl. No. 14/734,903.
Office Action dated Apr. 14, 2017 for U.S. Appl. No. 14/734,903.
Advisory Action dated Aug. 2, 2017 for U.S. Appl. No. 14/734,903.
Office Action dated Sep. 12, 2017 for U.S. Appl. No. 14/734,903.
Office Action dated Apr. 30, 2018 for U.S. Appl. No. 15/723,490.
Office Action mailed Jun. 2, 2016 for U.S. Appl. No. 14/478,672.
Office Action dated Dec. 29, 2016 for U.S. Appl. No. 14/478,672.
Notice of Allowance dated Jun. 14, 2017 for U.S. Appl. No. 14/478,672.
Office Action dated Nov. 17, 2017 for U.S. Appl. No. 14/478,672.
Office Action dated Jun. 5, 2018 for U.S. Appl. No. 14/478,672.
[No author listed] Single-Cell Whole Transcriptome Profiling With the SOLiD System. AB Applied Biosystems. Apr. 2009 Publication 139AP16-01: 6 pages.
Barbazuk et al., SNP discovery via 454 transcriptome sequencing. Plant J. Sep. 2007;51(5):910-8. Epub Jul. 27, 2007.
Binladen et al., The use of coded PCR primers enables high-throughput sequencing of multiple homolog amplification products by 454 parallel sequencing. PLoS One. Feb. 14, 2007;2(2):e197.
Brouzes et al., Droplet microfluidic technology for single-cell high-throughput screening. Proc Natl Acad Sci U S A. Aug. 25, 2009;106(34):14195-200. doi: 10.1073/pnas.0903542106. Epub Jul. 15, 2009.
Cloonan et al. Stem cell transcriptome profiling via massive-scale mRNA sequencing. Nat Methods. Jul. 2008;5(7):613-9. doi: 10.1038/nmeth.1223. Epub May 30, 2008.
Dutchen, Beyond average. Harvard Medical School News. May 21, 2015. Accessed online May 28, 2015 at http://hms.harvard.edu/news/beyond-average. 6 pages.
Fan et al., Expression profiling. Combinatorial labeling of single cells for gene expression cytometry. Science. Feb. 6, 2015;347(6222): 1258367. doi: 10. 1 126/science.1258367.
Guo et al., Droplet microfluidics for high-throughput biological assays. Lab Chip. Jun. 21, 2012;12(12):2146-55. doi: 10.1039/c2lc21147e. Epub Feb. 9, 2012.
Hamady et al., Error-correcting barcoded primers for pyrosequencing hundreds of samples in multiplex. Nat Methods. Mar. 2008;5(3):235-7.
Heuze et al., Molecular analysis of a pro-T cell clone transformed by Abelson-murine leukemia virus, displaying progressive gamma delta T cell receptor gene rearrangement and surface expression. Eur J Immunol. Aug. 1992;22(8):2077-84.
Hug et al., A chromatin immunoprecipitation screen reveals protein kinase Cbeta as a direct RUNX1 target gene. J Biol Chem. Jan. 9, 2004;279(2):825-30. Epub Oct. 15, 2003.
Islam et al. Characterization of the single-cell transcriptional landscape by highly multiplex RNA-seq.Genome Research.2011.(21)1160-1167.
Islam et al., Quantitative single-cell RNA-seq with unique molecular identifiers.Nat Methods. Feb. 2014;11(2):163-6. doi:10.1038/nmeth.2772. Epub Dec. 22, 2013.
Jaitin et al., Massively parallel single-cell RNA-seq for marker-free decomposition of tissues into cell types. Science. Feb. 14, 2014;343(6172):776-9. doi: 10. 1 126/science.1247651.
Kalisky et al. Single-cell genomics. Nat Methods. Apr. 2011;8(4):311-4. doi: 10.1038/nmeth0411-311.
Karow, Harvard groups develop fast, inexpensive droplet methods for RNA-seq of thousands of single cells. GenomeWeb. May 21, 2015. Accessed online May 27, 2015 at https ://www. genome web. com/sequencing-technology /harvard-groups-develop-fast-inexpensivedroplet-methods-rna-seq-thousands. 4 pages.
Klein et al. Comparative genomic hybridization, loss of heterozygosity, and DNA sequence analysis of single cells. Proc Natl Acad Sci U S A. Apr. 13, 1999;96(8):4494-9.
Klein et al., Droplet barcoding for single-cell transcriptomics applied to embryonic stem cells. Cell. May 22, 2015;161(5):1187-201. doi:l0.1016/j.ce11.2015.04.044.
Koster et al., Drop-based microfluidic devices for encapsulation of single cells. Lab Chip. 2008; 8:1110-1115.
Kumaresan et al., High-Throughput Single Copy DNA Amplification and Cell Analysis in Engineered Nanoliter Droplets. Anal Chem. May 15, 2008;80(10):3522-9.
Li et al., Sequence-specific label-free DNA sensors based on silicon nanowires. Nano Lett Feb. 2004 4(2): 245-7.
Macosko et al., Highly parallel genome-wide expression profiling of individual cells using nanoliter droplets. Cell. May 2015;l61:1202-1214.
Margulies et al., Genome sequencing in microfabricated high-density picolitre reactors. Nature. Sep. 15, 2005;437(7057):376-80. Epub Jul. 31, 2005.
Meyer et al., Targeted high-throughput sequencing of tagged nucleic acid samples. Nucleic Acids Res. ePub Aug. 1, 2007; 35(15):e97,1-5.
Ng et al., Multiplex sequencing of paired-end ditags (MS-PET): a strategy for the ultra-high-throughput analysis of transcriptomes and genomes. Nucleic Acids Res. Jul. 13, 2006;34(12):e84.
Nielsen et al., DeepSAGE—digital transcriptomics with high sensitivity, simple experimental protocol and multiplexing of samples. Nucleic Acids Res. 2006;34(19):e133. Epub Oct. 5, 2006.
Novak et al., Single-cell multiplex gene detection and sequencing with microfluidically generated agarose emulsions. Angew Chem Int Ed Engl. Jan. 10, 2011;50(2):390-5. doi: 10.1002/anie. 201006089.
Okochi et al. Droplet-based gene expression analysis using a device with magnetic force-based-droplet-handling system.J of Bioscience and Bioengeneering.2010.(109)193-197.
O'Neill et al. Epigenetic characterization of the early embryo with a chromatin immunoprecipitation protocol applicable to small cell populations. Nat Genet. Jul. 2006;38(7):835-41. Epub Jun. 11, 2006.
Park et al., ChIP-seq: Advantages and challenges of a maturing technology. Nat Rev Genetics. Oct. 1, 2009; 10(10):669-680.
Rotem et al. Single-cell ChIP-seq reveals cell subpopulations defined by chromatin state. Nature Biotechnology. 2015. (33)1165-1175.

(56) References Cited

OTHER PUBLICATIONS

Rotem et al., High-Throughput Single-Cell Labeling (Hi-SCL) for RNA-Seq Using Drop-Based Microfluidics. PLoS One. May 22, 2015;10(5):e0116328. doi:l0.1371/journal.pone.0116328. eCollection 2015.
Schones et al., Dynamic regulation of nucleosome positioning in the human genome. Cell. Mar. 7, 2008; 132(5):887-898.
Sokoloff, Effects of Capillary Forces on a Hydrogel Sphere Pressed against a Surface. Langmuir. Jan. 12, 2016;32(1):135-9. doi: 10.1021/acs.langmuir.5b04012. Epub Dec. 24, 2015.
Tang et al.RNA-Seq analysis to capture the transcriptome landscape of a single cell. Nat Protoc. Mar. 2010;5(3):516-35. doi: 10.1038/nprot.2009.236. Epub Feb. 25, 2010.
Tewhey et al., Microdroplet-based PCR enrichment for large-scale targeted sequencing. Nat Biotechnol. Nov. 2009;27(11):1025-31. doi: 10.1038/nbt.1583.
Vigneault et al. Efficient microRNA capture and bar-coding via enzymatic ogigonucleotide adenylation.Nature Methods.2008.(5):777-779.
Wang et al., Novel thermosensitive hydrogel injection inhibits post-infarct ventricle remodelling. Eur J Heart Fail. Jan. 2009;11(1):14-19. doi: 10.1093/eurjhf/hfn009.
Weber et al., Chromosome-wide and promoter-specific analyses identify sites of differential DNA methylation in normal and transformed human cells. Nat Genet. Aug. 2005;37(8):853-62. Epub Jul. 10, 2005.
Wei et al., A global map of p53 transcription-factor binding sites in the human genome. Cell. Jan. 13, 2006;124(1):207-19.
Weinman et al., Isolating human transcription factor targets by coupling chromatin immunoprecipitation and CpG island microarray analysis. Genes Dev. Jan. 15, 2002; 16(2): 235-244. doi: 10.1101/gad.943102.
Zeng et al., High-Performance Single Cell Genetic Analysis Using Microfluidic Emulsion Generator Arrays. Anal Chem. Apr. 15, 2010;82(8):3183-90.
Zhang et al., A surface topography assisted droplet manipulation platform for biomarker detection and pathogen identification. Lab Chip. Feb. 7, 2011;11(3):398-406.
Zhang et al., Modeling ChIP sequencing in silicon with applications. PLoS Comput Biol. Aug. 22, 2008;4(8):e1000158. doi: 10.1371/journal.pcbi.1000158.
Zilionis et al., Single-cell barcoding and sequencing using droplet microfluidics. Nat Protoc. Jan. 2017;12(1):44-73. doi: 10.1038/nprot.2016.154. Epub Dec. 8, 2016.
Final Office Action dated Jun. 23, 2018 for U.S. Appl. No. 15/303,874.
European Office Action dated Oct. 22, 2018 for Application No. 17198030.3.
European Office Action dated Oct. 9, 2019 for Application No. EP 17201280.9.
Extended European Search Report for Application No. EP 18215320.5 dated Mar. 14, 2019.
Australian Examination Report dated Sep. 11, 2020 for Application No. AU 2015247416.
Chinese Office Action dated Jan. 28, 2019 for Application No. 201580029304.3.
European Communication dated Sep. 4, 2018 for Application No. EP15780044.2.
Japanese Office Action dated Apr. 2, 2019 for Application No. JP 2017-506636.
Chinese Office Action dated Nov. 29, 2018 for Application No. 201580029045.4.
Chinese Office Action dated Jun. 5, 2020 for Application No. 201580029045.4.
European Communication dated Sep. 4, 2018 for Application No. EP15780364.4.
European Office Action for Application No. EP 15780364.4 dated Aug. 29, 2019.
Australian Examination Report dated Sep. 25, 2018 for Application No. 2015250034.
Chinese Office Action dated Jun. 23, 2020 for Application No. 201580029081.0.
European Office Communication dated Jul. 6, 2018 for Application No. EP 15783629.7.
European Office Action dated Mar. 21, 2019 for Application No. 17198030.3.
Extended European Search Report dated Jan. 21, 2019 for Application No. 18201501.6.
European Office Action dated Oct. 1, 2019 for Application No. EP 18201501.6.
European Office Action dated Mar. 10, 2020 for Application No. EP18201501.6.
Japanese Office Action dated Mar. 19, 2019 for Application No. JP 2016-564093.
Japanese Office Action dated Nov. 26, 2019 for Application No. JP 2016-564093.
Japanese Office Action dated Aug. 4, 2020 for Application No. JP 2016-564093.
Chinese Office Action dated Apr. 26, 2020 for Application No. CN 201680031721.6.
European Office Action dated Dec. 16, 2019 for Application No. EP 16780825.2.
European Office Action dated Aug. 21, 2020 for Application No. EP 16780825.2.
Japanese Office Action dated Mar. 31, 2020 for Application No. 2017-554339.
International Preliminary Report on Patentability dated Feb. 7, 2019 for Application No. PCT/US2017/043660.
Final Office Action dated Jun. 22, 2018 for U.S. Appl. No. 15/303,874.
Office Action dated Apr. 29, 2019 for U.S. Appl. No. 15/303,874.
Office Action dated Nov. 22, 2019 for U.S. Appl. No. 15/303,874.
Final Office Action dated Jul. 22, 2020 for U.S. Appl. No. 15/303,874.
Office Action dated May 6, 2019 for U.S. Appl. No. 15/303,893.
Office Action dated Feb. 20, 2020 for U.S. Appl. No. 15/303,893.
Office Action dated Jul. 5, 2018 for U.S. Appl. No. 14/734,903.
Office Action dated Feb. 12, 2019 for U.S. Appl. No. 14/734,903.
Office Action dated Aug. 6, 2019 for U.S. Appl. No. 14/734,903.
Office Action dated Feb. 4, 2020 for U.S. Appl. No. 14/734,903.
Office Action dated Nov. 14, 2018 for U.S. Appl. No. 15/723,490.
Office Action dated May 1, 2019 for U.S. Appl. No. 15/723,490.
Office Action dated Dec. 6, 2018 for U.S. Appl. No. 14/478,672.
Office Action dated May 13, 2019 for U.S. Appl. No. 15/670,929.
Office Action dated Oct. 30, 2019 for U.S. Appl. No. 15/670,929.
Office Action dated Mar. 19, 2020 for U.S. Appl. No. 15/836,520.
Office Action dated Jul. 17, 2020 for U.S. Appl. No. 15/965,452.
Office Action dated Aug. 29, 2019 for U.S. Appl. No. 15/556,904.
Office Action dated Apr. 21, 2020 for U.S. Appl. No. 15/566,904.
Adli et al., Genome-wide chromatin maps derived from limited numbers of hematopoietic progenitors. Nat Methods. Aug. 2010;7(8):615-8.
Buermans et al., New methods for next generation sequencing based microRNA expression profiling. BMC Genomics. Dec. 20, 2010;11:716.
Cheng et al., Anisotropic colloidal crystal particles from microfluidics. J Colloid Interface Sci. 2014;421:64-70.
Clausell-Tormos et al., Droplet-based microfluidic platforms for the encapsulation and screening of Mammalian cells and multicellular organisms. Chem Biol. May 2008;15(5):427-37. doi: 1016/j.chembiol.2008.04.004. Erratum in: Chem Biol.Aug. 25, 2008;15(8):875.
Craig et al., Identification of genetic variants using bar-coded multiplexed sequencing. Nat Methods. Oct. 2008;5(10):887-93.
Eastburn Ultrahigh-throughput Mammalian single-cell reverse-transcriptase polymerase chain reaction in microfluidic drops. Anal Chem. Aug. 20, 2013;85(16):8016-21. doi: 10.1021/ac402057q. Epub Aug. 8, 2013. PubMed PMID: 23885761.
Kato, RNA fingerprinting by molecular indexing. Nucleic Acids Res. Jan. 15, 1996;24(2):394-5.
Lau et al., An abundant class of tiny RNAs with probable regulatory roles in Caenorhabditis elegans. Science. Oct. 26, 2001;294(5543):858-62.
Li et al., The Sequence Alignment/Map format and SAMtools. Bioinformatics. Aug. 15, 2009;25(16):2078-9.
Lu et al., Construction of small RNA cDNA libraries for deep sequencing. Methods. 2007;43(2):110-117.

(56) References Cited

OTHER PUBLICATIONS

Mazutis et al., Single-cell analysis and sorting using droplet-based microfluidics. Nat Protoc. May 2013;8(5):870-91. doi: 10.1038/nprot.2013.046. Epub Apr. 4, 2013.
Meyer et al., Illumina sequencing library preparation for highly multiplexed target capture and sequencing. Cold Spring Harb Protoc. Jun. 2010;2010(6):pdb.prot5448.
Meyer et al., Parallel tagged sequencing on the 454 platform. Nat Protoc. 2008;3(2):267-278.
Moreau et al., Chronological changes in microRNA expression in the developing human brain. PLoS One. Apr. 16, 2013;8(4):e60480.
O'Neill et al., Immunoprecipitation of native chromatin: NChIP. Methods. Sep. 2003;31(1):76-82.
Rizzo et al., Standardized collection of MNase-seq experiments enables unbiased dataset comparisons. BMC Mol Biol. May 6, 2012;13:15.
Ross et al., Reverse transcription with random pentadecamer primers improves the detection limit of a quantitative PCR assay for BCR-ABL transcripts in chronic myeloid leukemia: implications for defining sensitivity in minimal residual disease. Clin Chem. Sep. 2008;54(9):1568-71.
Rothberg et al., The development and impact of 454 sequencing. Nat Biotechnol. 2008;26(10):1117-1124.
Saha et al., Using the transcriptome to annotate the genome. Nat Biotechnol. May 2002;20(5):508-12.
Shi et al., Poly(T) adaptor RT-PCR. Methods Mol Biol. 2012;822:53-66.
Teh et al., Droplet microfluidics. Lab Chip. Feb. 2008;8(2):198-220. doi: 10.1039/b715524g. Epub Jan. 11, 2008.
Van Nieuwerburgh et al., Quantitative bias in Illumina TruSeq and a novel post amplification barcoding strategy for multiplexed DNA and small RNA deep sequencing. PLoS One. 2011;6(10):e26969.
Velculescu et al., Serial analysis of gene expression. Science. Oct. 20, 1995;270(5235):484-7.
Wal et al., Genome-wide mapping of nucleosome positions in yeast using high-resolution MNase ChIP-Seq. Methods Enzymol. 2012;513:233-50.
Zhang et al., High-resolution genome-wide mapping of the primary structure of chromatin. Cell. Jan. 21, 2011;144(2):175-86.
Zheng et al., Titration-free massively parallel pyrosequencing using trace amounts of starting material. Nucleic Acids Res. Jul. 2010;38(13):e137.
EP 17201280.9, Oct. 9, 2019, European Office Action.
EP 18215320.5, Mar. 14, 2019, Extended European Search Report.
AU 2015247416, Sep. 11, 2020, Australian Examination Report.
CN 201580029304.3, Jan. 28, 2019, Chinese Office Action.
EP15780044.2, Sep. 4, 2018, European Office Action.
JP 2017-506636, Apr. 2, 2019, Japanese Office Action.
CN 201580029045.4, Nov. 29, 2018, Chinese Office Action.
CN 201580029045.4, Jun. 5, 2020, Chinese Office Action.
EP15780364.4, Sep. 4, 2018, European Office Action.
EP 15780364.4, Aug. 29, 2019, European Office Action.
AU 2015250034, Sep. 25, 2018, Australian Examination Report.
CN 20158002908.1, Jun. 23, 2020, Chinese Office Action.
EP 15783629.7, Jul. 6, 2018, European Office Action.
EP 17198030.3, Mar. 21, 2019, European Office Action.
EP 18201501.6, Jan. 21, 2019, European Search Report.
EP 17201280.9, Oct. 1, 2019, European Office Action.
EP18201501.6, Mar. 10, 2020, European Office Action.
JP 2016-564093, Mar. 19, 2019, Japanese Office Action.
JP 2016-564093, Nov. 26, 2019, Japanese Office Action.
JP 2016-564093, Aug. 4, 2020, Japanese Office Action.
CN 201680031721.6, Apr. 26, 2020, Chinese Office Action.
EP 16780825.2, Dec. 16, 2019, European Office Action.
EP 16780825.2, Aug. 21, 2020, European Office Action.
JP 2017-554339, Mar. 31, 2020, Japanese Office Action.
PCT/US2017/043660, Feb. 7, 2019, International Preliminary Report on Patentability.
European Office Action for Application No. EP 18215320.5 dated Nov. 11, 2020.
Chinese Office Action dated Jan. 20, 2021 for Application No. 201580029081.0.
European Office Action dated Oct. 21, 2020 for Application No. 18201501.6.
Office Action dated Nov. 13, 2020 for U.S. Appl. No. 14/734,903.
Office Action dated Nov. 5, 2020 for U.S. Appl. No. 15/836,520.
Guo et al., Resolution of cell fate decisions revealed by single-cell gene expression analysis from zygote to blastocyst. Dev Cell. Apr. 20, 2010;18(4):675-85.
Tang et al., mRNA-Seq whole-transcriptome analysis of a single cell. Nat Methods. May 2009;6(5):377-82.
U.S. Appl. No. 15/303,874, filed Oct. 13, 2016, Bernstein et al.
U.S. Appl. No. 15/303,893, filed Oct. 13, 2016, Weitz et al.
U.S. Appl. No. 14/734,903, filed Jun. 9, 2015, Weitz et al.
U.S. Appl. No. 14/178,672, filed Sep. 5, 2014, Rotem et al.
U.S. Appl. No. 15/670,929, filed Aug. 7, 2017, Rotem et al.
U.S. Appl. No. 15/836,479, filed Dec. 8, 2017, Weitz et al.
U.S. Appl. No. 15/836,520, filed Dec. 8, 2017, Weitz et al.
U.S. Appl. No. 15/965,452, filed Apr. 27, 2018, Weitz et al.
U.S. Appl. No. 15/566,904, filed Oct. 16, 2017, Weitz et al.

1) Above-Poisson noise:

$$\underbrace{CV^2 - \frac{1}{\mu}}_{\text{observed}} = \underbrace{\left(CV^2_{\text{bio}} - \frac{1}{\mu_{\text{bio}}}\right)}_{\text{biological variability}} \underbrace{\left(1 + CV^2_{\text{method}}\right)}_{\text{noise inflation}} + \underbrace{CV^2_{\text{method}}}_{\text{background}}$$

2) Fano factor:

$$F = \underbrace{\beta F_{\text{bio}}}_{\text{sampling diminution}} + \underbrace{(1-\beta)}_{} + \underbrace{CV^2_{\text{method}}}_{\text{background}}$$

3) Gene correlations:

$$\underbrace{\text{corr}_{i,j}}_{\text{observed}} \approx \underbrace{\text{corr}^{(\text{bio})}_{i,j}}_{\text{biological}} \underbrace{\sqrt{\left(1 - F_i^{-1}\right)\left(1 - F_j^{-1}\right)}}_{\text{noise inflation}}$$

Fig. 14G

5'-/5Acryd//iSpPC/CGATGACG TAATACGACTCACTATAGGG ATACCACCATGG CTCTTTCCCTACACGACGCTCTTC CGATCT [barcode1] AAGGCGTCACAAGCAATCACTC [barcode2] NNNNNN TTTTTTTTTTTTTTTTTTTTV -3'
Fig. 20C
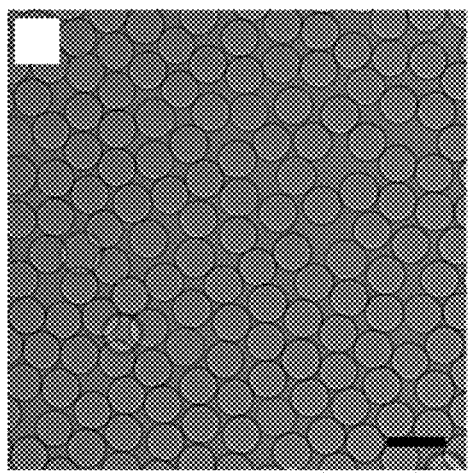
Fig. 21A
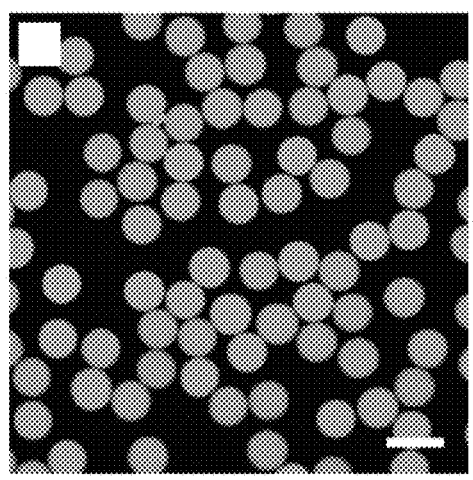
Fig. 21B
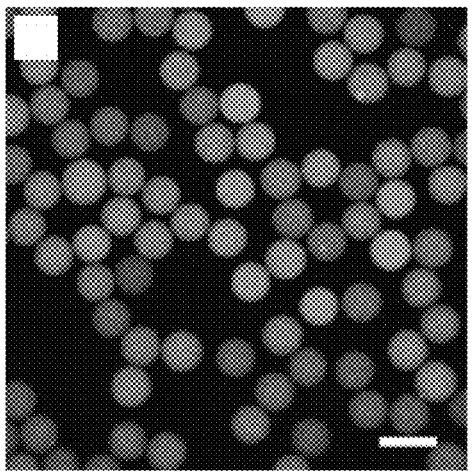
Fig. 21C
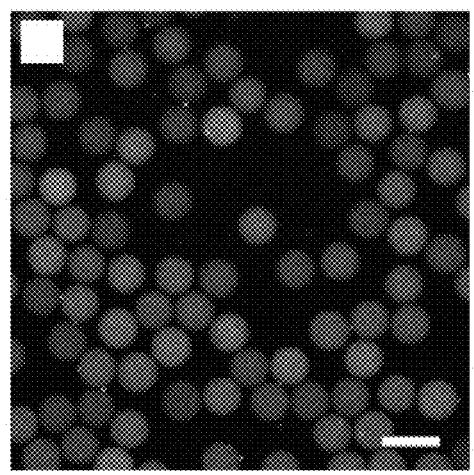
Fig. 21D

| Number cells/controls barcoded | Number shared barcodes: observed/expected | | | | | | |
|---|---|---|---|---|---|---|---|
| 140 | 1/0.6 | 1/0.9 | 0/0.9 | 1/0.9 | 3/2.1 | 3/2.3 | 2/2.8 |
| 0.88 | 608 | 2/3.8 | 4/3.9 | 7/3.9 | 9/8.9 | 17/10 | 14/12.1 |
| 0.83 | 0.95 | 921 | 7/5.9 | 5/5.9 | 22/13.5 | 26/15.1 | 20/18.3 |
| 0.81 | 0.91 | 0.92 | 945 | 8/6.1 | 12/13.9 | 15/15.5 | 24/18.8 |
| 0.81 | 0.89 | 0.91 | 0.82 | 951 | 11/14 | 17/15.6 | 23/18.9 |
| 0.68 | 0.92 | 0.98 | 0.95 | 0.86 | 2,159 | 36/35.6 | 47/43.1 |
| 0.81 | 0.92 | 0.89 | 0.97 | 0.99 | 0.99 | 2,420 | 70/48.1 |
| 0.94 | 0.87 | 0.93 | 0.98 | 0.95 | 0.93 | 0.93 | 2,930 |
(left side label: p-value random $384^2$ barcoding)
Fig.22A
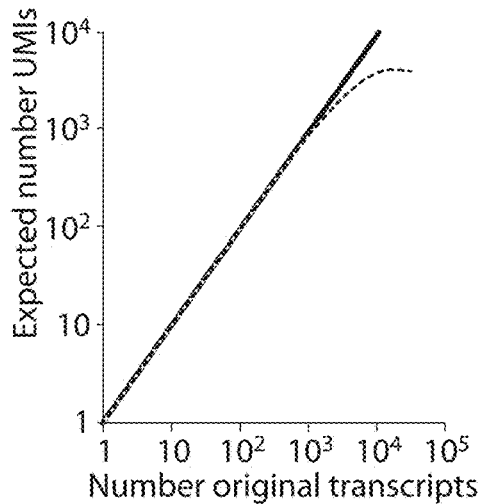
Fig.22B
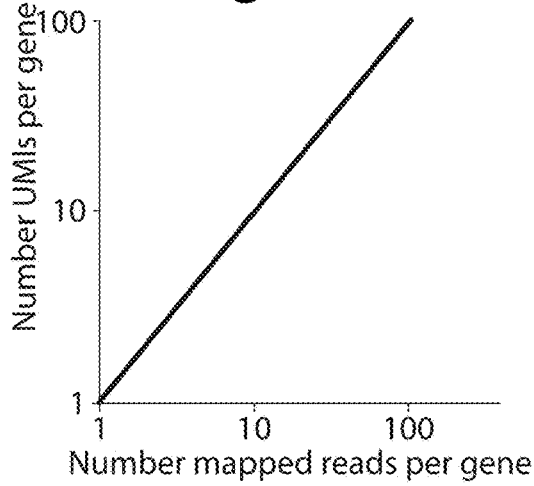
Fig.22C (Table 2)

| Gene symbol | v-score | q-value (BH-FDR-corrected p-value) | Maximum abundance (normalized counts, rounded) | | | | | |
|---|---|---|---|---|---|---|---|---|
| Sprr2b | 21.646 | 0 | | Laptm5 | 1.967 | 0.024794 | 22 | Eif4ebp1 | 1.577 | 0.075054 | 34 |
| Krt8 | 19.012 | 0 | | Dnmt3l | 1.954 | 0.024794 | 35 | Ptcd2 | 1.574 | 0.075054 | 14 |
| Sparc | 14.051 | 0 | | Krt19 | 1.939 | 0.024794 | 11 | Marcksl1 | 1.573 | 0.075054 | 19 |
| Bc1 | 12.630 | 0 | 94 | Wtap | 1.936 | 0.024794 | 65 | Actb | 1.570 | 0.075054 | 94 |
| Clu | 12.060 | 0 | 115 | Dusp9 | 1.924 | 0.024794 | 24 | Cep83 | 1.569 | 0.075054 | 16 |
| Krt18 | 9.637 | 0 | 259 | Gpx4 | 1.923 | 0.024794 | 53 | Tceb2 | 1.569 | 0.075054 | 29 |
| H19 | 7.345 | 0 | 269 | Tdh | 1.912 | 0.024794 | 41 | 2410006H16Rik | 1.567 | 0.075054 | 19 |
| Ccdc36 | 7.124 | 0 | 146 | P4hb | 1.909 | 0.024794 | 32 | Pkp2 | 1.566 | 0.075054 | 17 |
| Serpinh1 | 6.580 | 0 | 82 | Tspan17 | 1.898 | 0.024794 | 23 | Blvrb | 1.562 | 0.075054 | 17 |
| Hist1h2ao | 6.577 | 0 | 59 | S100a10 | 1.897 | 0.024794 | 34 | Ube2l6 | 1.561 | 0.075054 | 15 |
| Col4a1 | 6.194 | 0 | 248 | Slc2a3 | 1.895 | 0.032493 | 40 | Pcolce | 1.557 | 0.075054 | 14 |
| Fam25c | 5.457 | 0 | 67 | Ldha | 1.891 | 0.032493 | 35 | Tcl1 | 1.553 | 0.075054 | 11 |
| Lamb1 | 4.808 | 0 | 104 | Peg10 | 1.871 | 0.038635 | 36 | Klf2 | 1.553 | 0.075054 | 18 |
| Gm7102 | 4.557 | 0 | 53 | Rhox13 | 1.863 | 0.038635 | 15 | Hmces | 1.550 | 0.075054 | 17 |
| S100a6 | 4.253 | 0 | 92 | Igfbp2 | 1.860 | 0.038635 | 24 | D11Wsu47e | 1.548 | 0.075054 | 12 |
| Sfn | 4.209 | 0 | 55 | Tdgf1 | 1.858 | 0.038635 | 31 | Mfge8 | 1.545 | 0.075054 | 16 |
| Malat1 | 3.667 | 0 | 59 | Vim | 1.858 | 0.038635 | 15 | Rpl39l | 1.544 | 0.075054 | 12 |
| Lama1 | 3.666 | 0 | 60 | Tor4a | 1.849 | 0.038635 | 53 | Pdia6 | 1.544 | 0.075054 | 23 |
| Mt1 | 3.441 | 0 | 44 | Lamc1 | 1.840 | 0.053653 | 36 | Creld2 | 1.543 | 0.075054 | 17 |
| Hspa5 | 3.373 | 0 | 83 | Ldhb | 1.818 | 0.060827 | 14 | Utf1 | 1.541 | 0.075054 | 28 |
| Fabp3 | 3.283 | 0 | 44 | Lgmn | 1.809 | 0.067887 | 28 | Surf4 | 1.539 | 0.075054 | 21 |
| Tagln2 | 3.200 | 0 | 123 | Klf5 | 1.806 | 0.071607 | 19 | Gng5 | 1.539 | 0.075054 | 26 |
| Hist1h2ah | 3.005 | 0 | 56 | Upp1 | 1.805 | 0.071607 | 17 | Stmn2 | 1.538 | 0.075054 | 15 |
| Acaa1b | 2.982 | 0 | 52 | A630089N07Rik | 1.805 | 0.071607 | 45 | Trib3 | 1.533 | 0.075054 | 16 |
| Ly6a | 2.982 | 0 | 55 | Ngfrap1 | 1.800 | 0.071607 | 37 | Hist1h4i | 1.532 | 0.075054 | 9 |
| Sohlh2 | 2.966 | 0 | 38 | Dusp1 | 1.791 | 0.071607 | 14 | Hist1h3b | 1.528 | 0.075054 | 6 |
| | | | 34 | Slc2a1 | 1.790 | 0.071607 | 30 | Exoc3l | 1.528 | 0.075054 | 12 |
| | | | 30 | BC018473 | 1.786 | 0.071607 | 30 | Set | 1.527 | 0.075054 | 67 |
| | | | 30 | Pmvk | 1.783 | 0.071607 | 18 | Tpd52 | 1.527 | 0.075054 | 18 |
| | | | 47 | Calr | 1.780 | 0.071607 | 26 | Gabarapl2 | 1.527 | 0.075054 | 14 |

Fig. 26A

| Gene | Value | p-value | Count | Gene | Value | p-value | Count | Gene | Value | p-value | Count |
|---|---|---|---|---|---|---|---|---|---|---|---|
| Id1 | 2.965 | 0 | 24 | Pbld1 | 1.777 | 0.071607 | 54 | H2afx | 1.526 | 0.075054 | 15 |
| Fgd1 | 2.927 | 0 | 73 | Fabp5 | 1.777 | 0.071607 | 16 | Nxn | 1.526 | 0.075054 | 13 |
| Lrpap1 | 2.873 | 0 | 55 | Slc25a5 | 1.764 | 0.071607 | 21 | Cks2 | 1.522 | 0.075054 | 18 |
| Gm6878 | 2.862 | 0 | 28 | Eif2s2 | 1.741 | 0.071607 | 52 | Nme6 | 1.521 | 0.075054 | 23 |
| Cd63 | 2.840 | 0 | 51 | Asb13 | 1.738 | 0.07173 | 28 | Cd9 | 1.519 | 0.075054 | 30 |
| Bscl2 | 2.821 | 0 | 44 | Kif15 | 1.738 | 0.07173 | 22 | 2810403A07Rik | 1.519 | 0.075054 | 25 |
| Mt2 | 2.690 | 0 | 197 | Slc3a2 | 1.737 | 0.07173 | 39 | Arl6ip1 | 1.518 | 0.075054 | 17 |
| Gm20594 | 2.633 | 0 | 35 | Gm7325 | 1.726 | 0.07173 | 25 | Pim3 | 1.518 | 0.075054 | 23 |
| Papd5 | 2.629 | 0 | 51 | Atf5 | 1.724 | 0.07173 | 15 | Psap | 1.517 | 0.075054 | 18 |
| Slc29a1 | 2.622 | 0.016109 | 36 | Id3 | 1.703 | 0.075054 | 15 | Sscal | 1.516 | 0.075054 | 21 |
| Med10 | 2.605 | 0.016109 | 31 | Hspb1 | 1.684 | 0.075054 | 52 | Stmn1 | 1.514 | 0.075054 | 15 |
| Actg1 | 2.560 | 0.016109 | 162 | Ifitm1 | 1.681 | 0.075054 | 14 | Zfp296 | 1.512 | 0.075054 | 11 |
| Dcdc2c | 2.515 | 0.016109 | 38 | Erdr1 | 1.675 | 0.075054 | 40 | Pdlim7 | 1.506 | 0.075054 | 17 |
| Lgals1 | 2.451 | 0.01882 | 34 | Pgk1 | 1.669 | 0.075054 | 59 | Actn1 | 1.506 | 0.075054 | 24 |
| Anxa2 | 2.419 | 0.01882 | 26 | Htra1 | 1.660 | 0.075054 | 20 | Glrx5 | 1.505 | 0.075054 | 14 |
| Rhox5 | 2.381 | 0.01882 | 15 | Kpna2 | 1.657 | 0.075054 | 24 | Epha2 | 1.505 | 0.075054 | 23 |
| Mylpf | 2.380 | 0.01882 | 27 | Morf4l2 | 1.656 | 0.075054 | 26 | Exosc2 | 1.504 | 0.075054 | 29 |
| Hsp90b1 | 2.365 | 0.01882 | 43 | Ctsd | 1.652 | 0.075054 | 29 | Psmd7 | 1.503 | 0.075054 | 21 |
| Meg3 | 2.362 | 0.01882 | 31 | Cdc20 | 1.651 | 0.075054 | 20 | Gm6083 | 1.503 | 0.075054 | 30 |
| 2700046A07Rik | 2.317 | 0.01882 | 32 | Gpx1 | 1.649 | 0.075054 | 40 | Pkig | 1.502 | 0.075054 | 10 |
| Slc25a4 | 2.315 | 0.01882 | 32 | Id2 | 1.649 | 0.075054 | 14 | Bloc1s1 | 1.502 | 0.075054 | 20 |
| Ctgf | 2.309 | 0.01882 | 34 | Madd | 1.648 | 0.075054 | 38 | Supt4a | 1.501 | 0.075054 | 19 |
| Tmsb4x | 2.279 | 0.01882 | 61 | Rasgrp2 | 1.647 | 0.075054 | 12 | Dnmt3b | 1.500 | 0.075054 | 21 |
| Gsn | 2.264 | 0.01882 | 30 | Zfp286 | 1.644 | 0.075054 | 16 | Apoe | 1.496 | 0.075054 | 14 |
| Bhmt | 2.254 | 0.01882 | 20 | Pfdn2 | 1.637 | 0.075054 | 18 | Clic4 | 1.496 | 0.075054 | 24 |
| Ccnd3 | 2.245 | 0.01882 | 39 | Aes | 1.632 | 0.075054 | 25 | Bex1 | 1.495 | 0.075054 | 35 |
| Sept12 | 2.210 | 0.01882 | 17 | Ccne1 | 1.631 | 0.075054 | 19 | Cenpn | 1.492 | 0.075054 | 12 |
| Manf | 2.206 | 0.01882 | 32 | Sort1 | 1.629 | 0.075054 | 28 | Cox10 | 1.492 | 0.075054 | 15 |
| Trim71 | 2.184 | 0.01882 | 29 | Kctd15 | 1.629 | 0.075054 | 24 | Mdh2 | 1.490 | 0.075054 | 23 |
| Tagln | 2.138 | 0.01882 | 20 | Elp5 | 1.628 | 0.075054 | 23 | Nkain3 | 1.490 | 0.075054 | 66 |
| Col4a2 | 2.135 | 0.01882 | 35 | Bcas2 | 1.617 | 0.075054 | 41 | Srm | 1.491 | 0.075054 | 24 |
| Hsp90aa1 | 2.1215 | 0.01882 | 190 | Plec | 1.611 | 0.075054 | 21 | Tsc22d1 | 1.490 | 0.075054 | 27 |

Fig. 26B

| Gene | Value | P-value | Count | Gene | Value | P-value | Count | Gene | Value | P-value | Count |
|---|---|---|---|---|---|---|---|---|---|---|---|
| Ahcyl2 | 2.105 | 0.01882 | 30 | Map4k5 | 1.604 | 0.075054 | 35 | Qsox1 | 1.490 | 0.075054 | 26 |
| Best2 | 2.094 | 0.01882 | 19 | Fhnb | 1.600 | 0.075054 | 28 | Ulk1 | 1.489 | 0.075054 | 17 |
| Asns | 2.091 | 0.01882 | 28 | Fth1 | 1.600 | 0.075054 | 65 | Gpx3 | 1.488 | 0.075054 | 17 |
| Calcoco2 | 2.064 | 0.01882 | 25 | Glud1 | 1.599 | 0.075054 | 48 | Srgn | 1.488 | 0.075054 | 12 |
| Ctsl | 2.063 | 0.01882 | 28 | Akr1b3 | 1.598 | 0.075054 | 23 | Xrcc1 | 1.487 | 0.075054 | 12 |
| Dppa5a | 2.036 | 0.01882 | 133 | Mycn | 1.596 | 0.075054 | 19 | Rpl10l | 1.486 | 0.075054 | 13 |
| Fam229b | 2.024 | 0.01882 | 38 | Nanog | 1.596 | 0.075054 | 18 | Ung | 1.486 | 0.075054 | 17 |
| Chchd10 | 2.018 | 0.01882 | 29 | Acot13 | 1.595 | 0.075054 | 21 | Itpk1 | 1.485 | 0.075054 | 14 |
| Sbk1 | 1.987 | 0.024794 | 21 | Ikbip | 1.594 | 0.075054 | 23 | Mthfd2 | 1.485 | 0.075054 | 12 |
| E130012A19Rik | 1.975 | 0.024794 | 31 | Ckb | 1.594 | 0.075054 | 20 | Srrd | 1.483 | 0.075054 | 16 |
| | | | | Echdc2 | 1.589 | 0.075054 | 12 | Hspa12b | 1.396 | 0.075054 | 26 |
| Parvb | 1.481 | 0.075054 | 19 | Tex19.1 | 1.426 | 0.075054 | 18 | Qdpr | 1.396 | 0.075054 | 12 |
| Impa3 | 1.479 | 0.075054 | 14 | Ube3b | 1.425 | 0.075054 | 14 | Midn | 1.395 | 0.075054 | 20 |
| Thoc3 | 1.479 | 0.075054 | 21 | Col18a1 | 1.425 | 0.075054 | 15 | Mars | 1.395 | 0.075054 | 16 |
| Hn1 | 1.478 | 0.075054 | 16 | Lias | 1.425 | 0.075054 | 20 | Dap | 1.395 | 0.075054 | 10 |
| 1110008F13Rik | 1.478 | 0.075054 | 18 | Fscn1 | 1.423 | 0.075054 | 19 | 2200002D01Rik | 1.394 | 0.075054 | 11 |
| 2310036O22Rik | 1.477 | 0.075054 | 20 | Ltb | 1.423 | 0.075054 | 14 | Zdhhc7 | 1.392 | 0.075054 | 10 |
| Crip1 | 1.476 | 0.075054 | 16 | Psma2 | 1.422 | 0.075054 | 27 | Hap1 | 1.392 | 0.075054 | 12 |
| Esrrb | 1.475 | 0.075054 | 20 | Pmm1 | 1.422 | 0.075054 | 18 | Cdv3 | 1.392 | 0.075054 | 24 |
| Gtf3a | 1.475 | 0.075054 | 13 | Arpc1b | 1.422 | 0.075054 | 16 | Polr2e | 1.392 | 0.075054 | 22 |
| Aurka | 1.474 | 0.075054 | 10 | Mrpl34 | 1.422 | 0.075054 | 17 | Ctnnal1 | 1.390 | 0.075054 | 15 |
| Ass1 | 1.473 | 0.075054 | 15 | Grn | 1.422 | 0.075054 | 15 | Nlrp1a | 1.390 | 0.075054 | 41 |
| Rnaseh2c | 1.473 | 0.075054 | 14 | Cct5 | 1.421 | 0.075054 | 24 | Snx6 | 1.390 | 0.075054 | 10 |
| Tbc1d16 | 1.472 | 0.075054 | 23 | Cfdp1 | 1.421 | 0.075054 | 20 | Xpnpep1 | 1.390 | 0.075054 | 18 |
| Ube2s | 1.471 | 0.075054 | 31 | Ltbp4 | 1.421 | 0.075054 | 21 | Gm10845 | 1.390 | 0.075054 | 19 |
| Cdk2ap1 | 1.470 | 0.075054 | 15 | Tubb2b | 1.421 | 0.075054 | 14 | Trim25 | 1.390 | 0.075054 | 18 |
| Tmem230 | 1.469 | 0.075054 | 21 | Lima1 | 1.420 | 0.075054 | 15 | Gpx2 | 1.390 | 0.075054 | 8 |
| Pdgfa | 1.468 | 0.075054 | 10 | B3gnt7 | 1.419 | 0.075054 | 14 | Esd | 1.389 | 0.075054 | 14 |
| Rrp7a | 1.468 | 0.075054 | 13 | Tubb3 | 1.419 | 0.075054 | 12 | Sgk1 | 1.389 | 0.075054 | 13 |
| Tyw1 | 1.468 | 0.075054 | 36 | Fkbp3 | 1.419 | 0.075054 | 17 | Mrpl13 | 1.389 | 0.075054 | 12 |
| Erf | 1.464 | 0.075054 | 22 | Mybl2 | 1.419 | 0.075054 | 25 | Stmn3 | 1.389 | 0.075054 | 12 |
| Timm8b | 1.464 | 0.075054 | 12 | Txnrd1 | 1.417 | 0.075054 | 22 | Mrpl53 | 1.389 | 0.075054 | 9 |

Fig. 26C

| Gene | Value1 | Value2 | Num | Gene | Value1 | Value2 | Num | Gene | Value1 | Value2 | Num |
|---|---|---|---|---|---|---|---|---|---|---|---|
| D230025D16Rik | 1.464 | 0.075054 | 14 | Trmt1 | 1.417 | 0.075054 | 15 | Rwdd1 | 1.388 | 0.075054 | 16 |
| Scd2 | 1.463 | 0.075054 | 19 | Fkbp1a | 1.417 | 0.075054 | 32 | Fkbp4 | 1.388 | 0.075054 | 19 |
| Med13l | 1.463 | 0.075054 | 19 | Uchl1 | 1.417 | 0.075054 | 16 | Txnl1 | 1.388 | 0.075054 | 20 |
| Syce2 | 1.462 | 0.075054 | 13 | Psmd11 | 1.416 | 0.075054 | 12 | Asb6 | 1.387 | 0.075054 | 11 |
| Arf1 | 1.462 | 0.075054 | 34 | Mif4gd | 1.416 | 0.075054 | 13 | Chchd4 | 1.387 | 0.075054 | 13 |
| Fcf1 | 1.461 | 0.075054 | 10 | Pfdn6 | 1.416 | 0.075054 | 20 | Sqstm1 | 1.387 | 0.075054 | 19 |
| Etv4 | 1.459 | 0.075054 | 17 | 1700007K13Rik | 1.416 | 0.075054 | 8 | Guca1a | 1.386 | 0.075054 | 7 |
| Eid2 | 1.458 | 0.075054 | 8 | Rabac1 | 1.416 | 0.075054 | 11 | Glipr2 | 1.386 | 0.075054 | 13 |
| Polr2h | 1.456 | 0.075054 | 18 | Snrpa1 | 1.415 | 0.075054 | 16 | Prpsap1 | 1.386 | 0.075054 | 17 |
| Rad51 | 1.456 | 0.075054 | 13 | Dtd1 | 1.414 | 0.075054 | 11 | Rbmxl1 | 1.386 | 0.075054 | 16 |
| Dppa4 | 1.455 | 0.075054 | 17 | Ddx56 | 1.413 | 0.075054 | 20 | Eif3c | 1.385 | 0.075054 | 18 |
| Sertad1 | 1.454 | 0.075054 | 12 | Srpk1 | 1.413 | 0.075054 | 15 | Tspan4 | 1.385 | 0.075054 | 11 |
| Lincenc1 | 1.453 | 0.075054 | 11 | Krtcap2 | 1.413 | 0.075054 | 14 | Dmkn | 1.384 | 0.075054 | 10 |
| Cox7a2l | 1.451 | 0.075054 | 19 | Gorasp2 | 1.412 | 0.075054 | 14 | Rian | 1.384 | 0.075054 | 11 |
| Sf3b5 | 1.451 | 0.075054 | 13 | Matsu1 | 1.412 | 0.075054 | 12 | Copb2 | 1.384 | 0.075054 | 13 |
| Tra2b | 1.451 | 0.075054 | 19 | Wbp5 | 1.411 | 0.075054 | 18 | Ahsa1 | 1.384 | 0.075054 | 19 |
| Tinagl1 | 1.450 | 0.075054 | 14 | Mark3 | 1.409 | 0.075054 | 24 | Ndufb6 | 1.384 | 0.075054 | 12 |
| Tubb6 | 1.450 | 0.075054 | 14 | Tsta3 | 1.408 | 0.075054 | 12 | Atp6v0e | 1.383 | 0.075054 | 13 |
| Chchd3 | 1.450 | 0.075054 | 13 | Tpx2 | 1.408 | 0.075054 | 16 | Ccdc22 | 1.382 | 0.075054 | 11 |
| Fam195a | 1.449 | 0.075054 | 9 | Sec11c | 1.407 | 0.075054 | 15 | Rbm42 | 1.381 | 0.075054 | 12 |
| Abcd4 | 1.449 | 0.075054 | 27 | H2afz | 1.407 | 0.075054 | 34 | Cyc1 | 1.380 | 0.075054 | 21 |
| F830016B08Rik | 1.448 | 0.075054 | 26 | Nfyb | 1.407 | 0.075054 | 13 | Lmna | 1.380 | 0.075054 | 15 |
| U2af1 | 1.446 | 0.075054 | 21 | Atg101 | 1.407 | 0.075054 | 14 | Clic1 | 1.380 | 0.075054 | 10 |
| Rbfa | 1.444 | 0.075054 | 10 | Wars | 1.406 | 0.075054 | 17 | Klf4 | 1.379 | 0.075054 | 14 |
| Fn1 | 1.444 | 0.075054 | 23 | Atp6v0d1 | 1.406 | 0.075054 | 12 | Slc30a2 | 1.379 | 0.075054 | 11 |
| Cope | 1.444 | 0.075054 | 11 | Coq7 | 1.406 | 0.075054 | 10 | Psmd6 | 1.379 | 0.075054 | 16 |
| Dym | 1.443 | 0.075054 | 11 | Ctsh | 1.406 | 0.075054 | 16 | Scamp3 | 1.378 | 0.075054 | 16 |
| Calu | 1.443 | 0.075054 | 18 | 2810428I15Rik | 1.406 | 0.075054 | 15 | Calm1 | 1.378 | 0.075054 | 24 |
| Crlf2 | 1.442 | 0.075054 | 11 | Fam96b | 1.406 | 0.075054 | 14 | Qars | 1.376 | 0.075054 | 15 |
| Top2a | 1.441 | 0.075054 | 14 | Hbegf | 1.406 | 0.075054 | 15 | Mrpl43 | 1.376 | 0.075054 | 38 |
| Cstb | 1.441 | 0.075054 | 10 | Samm50 | 1.405 | 0.075054 | 15 | Adamts13 | 1.376 | 0.075054 | 18 |
| Ppa1 | 1.440 | 0.075054 | 17 | Zc3hc1 | 1.404 | 0.075054 | 19 | Ppie | 1.376 | 0.075054 | 11 |

Fig. 26D

| Gene | Value | p-value | Count | Gene | Value | p-value | Count | Gene | Value | p-value | Count |
|---|---|---|---|---|---|---|---|---|---|---|---|
| Arl6ip4 | 1.440 | 0.075054 | 10 | Rpap1 | 1.404 | 0.075054 | 17 | Mea1 | 1.375 | 0.075054 | 11 |
| Tuba4a | 1.439 | 0.075054 | 24 | Tpi1 | 1.403 | 0.075054 | 11 | Prpf3 | 1.375 | 0.075054 | 16 |
| Bzw2 | 1.438 | 0.075054 | 19 | Elof1 | 1.403 | 0.075054 | 12 | Atf4 | 1.375 | 0.075054 | 13 |
| Churc1 | 1.438 | 0.075054 | 34 | Tcea3 | 1.403 | 0.075054 | 13 | Spata33 | 1.375 | 0.075054 | 11 |
| Bud31 | 1.438 | 0.075054 | 20 | 1500012F01Rik | 1.402 | 0.075054 | 14 | Atp5j2 | 1.374 | 0.075054 | 19 |
| Aifm1 | 1.437 | 0.075054 | 16 | Cenpa | 1.401 | 0.075054 | 14 | Lrrc59 | 1.374 | 0.075054 | 23 |
| Ndufa13 | 1.436 | 0.075054 | 12 | Pecr | 1.400 | 0.075054 | 13 | Fam129b | 1.374 | 0.075054 | 14 |
| Dstn | 1.435 | 0.075054 | 18 | Myod1 | 1.400 | 0.075054 | 10 | Nhp2 | 1.373 | 0.075054 | 22 |
| Ocel1 | 1.435 | 0.075054 | 15 | Degs1 | 1.400 | 0.075054 | 14 | Aprt | 1.372 | 0.075054 | 22 |
| Galk1 | 1.435 | 0.075054 | 11 | Ndrg4 | 1.399 | 0.075054 | 16 | Cdc5l | 1.371 | 0.075054 | 19 |
| Hmox1 | 1.433 | 0.075054 | 12 | Lonp1 | 1.399 | 0.075054 | 16 | Gna11 | 1.371 | 0.075054 | 11 |
| Ubald2 | 1.433 | 0.075054 | 15 | Ppa2 | 1.399 | 0.075054 | 15 | Spns1 | 1.370 | 0.075054 | 19 |
| Romo1 | 1.432 | 0.075054 | 14 | Apitd1 | 1.399 | 0.075054 | 10 | Ntan1 | 1.370 | 0.075054 | 20 |
| Phc1 | 1.432 | 0.075054 | 23 | Dcun1d5 | 1.399 | 0.075054 | 11 | Actl6a | 1.369 | 0.075054 | 13 |
| Emc10 | 1.432 | 0.075054 | 13 | Ndufa4 | 1.398 | 0.075054 | 19 | Ywhaq | 1.369 | 0.075054 | 24 |
| Ptov1 | 1.431 | 0.075054 | 17 | Stx5a | 1.398 | 0.075054 | 9 | Chmp4b | 1.369 | 0.075054 | 17 |
| Snf8 | 1.430 | 0.075054 | 21 | Rheb | 1.398 | 0.075054 | 21 | Fto | 1.368 | 0.075054 | 24 |
| Calm2 | 1.429 | 0.075054 | 21 | Ddt | 1.397 | 0.075054 | 14 | Sdhc | 1.368 | 0.075054 | 17 |
| Mrpl14 | 1.429 | 0.075054 | 13 | Trappc3 | 1.397 | 0.075054 | 12 | Plin2 | 1.368 | 0.075054 | 11 |
| Pih1d1 | 1.427 | 0.075054 | 14 | Cbx3 | 1.397 | 0.075054 | 19 | Eif3g | 1.368 | 0.075054 | 19 |
| Dhx16 | 1.427 | 0.075054 | 19 | Slirp | 1.396 | 0.075054 | 21 | Mcm7 | 1.367 | 0.075054 | 16 |
| Siva1 | 1.427 | 0.075054 | 18 | Mrpl12 | 1.396 | 0.075054 | 14 | Crip2 | 1.334 | 0.075054 | 11 |
| Pop5 | 1.426 | 0.075054 | 11 | Tcf15 | 1.396 | 0.075054 | 12 | Slc6a8 | 1.333 | 0.075054 | 20 |
| Saal1 | 1.367 | 0.075054 | 14 | Gins4 | 1.349 | 0.075054 | 19 | Rpl39 | 1.333 | 0.075054 | 53 |
| Mrpl23 | 1.367 | 0.075054 | 17 | Slc15a4 | 1.349 | 0.075054 | 14 | Srp14 | 1.333 | 0.075054 | 15 |
| Cdkn1a | 1.367 | 0.075054 | 9 | Agpat2 | 1.349 | 0.075054 | 9 | Umps | 1.332 | 0.075054 | 14 |
| Emg1 | 1.366 | 0.075054 | 14 | Cdca5 | 1.349 | 0.075054 | 11 | Use1 | 1.332 | 0.075054 | 10 |
| Ccdc124 | 1.366 | 0.075054 | 19 | A430005L14Rik | 1.348 | 0.075054 | 12 | Nxt1 | 1.332 | 0.075054 | 11 |
| Bri3 | 1.366 | 0.075054 | 14 | Mrpl30 | 1.348 | 0.075054 | 15 | Ehd1 | 1.331 | 0.075054 | 27 |
| Csrp1 | 1.366 | 0.075054 | 17 | Rcl1 | 1.348 | 0.075054 | 15 | Timm10 | 1.331 | 0.075054 | 10 |
| Glul | 1.366 | 0.075054 | 20 | Tmem216 | 1.347 | 0.075054 | 8 | Srsf11 | 1.331 | 0.075054 | 15 |
| Socs2 | 1.366 | 0.075054 | 10 | Sall4 | 1.347 | 0.075054 | 20 | Cyb5a | 1.331 | 0.075054 | 13 |

Fig. 26E

| Gene | Val1 | Val2 | N | Gene | Val1 | Val2 | N | Gene | Val1 | Val2 | N |
|---|---|---|---|---|---|---|---|---|---|---|---|
| Ftl1 | 1.365 | 0.075054 | 185 | Bex4 | 1.347 | 0.075054 | 14 | Cox7a1 | 1.331 | 0.075054 | 7 |
| Sox2 | 1.365 | 0.075054 | 21 | Pttg1ip | 1.347 | 0.075054 | 14 | Taf11 | 1.331 | 0.075054 | 8 |
| Cdkn2aip | 1.364 | 0.075054 | 15 | Immt | 1.347 | 0.075054 | 21 | Pdhb | 1.331 | 0.075054 | 16 |
| Hs1bp3 | 1.364 | 0.075054 | 13 | Wdr74 | 1.347 | 0.075054 | 15 | Eif2b2 | 1.331 | 0.075054 | 11 |
| Fdft1 | 1.364 | 0.075054 | 13 | Pttg1 | 1.347 | 0.075054 | 10 | Lcmt1 | 1.330 | 0.075054 | 14 |
| Exosc8 | 1.364 | 0.075054 | 13 | Bub3 | 1.346 | 0.075054 | 10 | Fzr1 | 1.330 | 0.075054 | 9 |
| Guk1 | 1.364 | 0.075054 | 13 | Nodal | 1.346 | 0.075054 | 9 | Cggbp1 | 1.330 | 0.075054 | 22 |
| Deb1 | 1.363 | 0.075054 | 8 | Ppdpf | 1.346 | 0.075054 | 10 | Prdx6 | 1.330 | 0.075054 | 18 |
| Ndufb10 | 1.362 | 0.075054 | 12 | Atp5g1 | 1.346 | 0.075054 | 24 | Fbxo6 | 1.330 | 0.075054 | 8 |
| Rnf7 | 1.362 | 0.075054 | 19 | Eftud2 | 1.345 | 0.075054 | 16 | Tomm70a | 1.330 | 0.075054 | 22 |
| Ndufb11 | 1.362 | 0.075054 | 13 | Nop10 | 1.345 | 0.075054 | 15 | Serpinb6a | 1.330 | 0.075054 | 12 |
| Dynll1 | 1.362 | 0.075054 | 22 | Rbpms2 | 1.344 | 0.075054 | 13 | Rmrp | 1.330 | 0.075054 | 5 |
| Gstm1 | 1.361 | 0.075054 | 9 | Impact | 1.344 | 0.075054 | 19 | Psma1 | 1.330 | 0.075054 | 18 |
| Smn1 | 1.361 | 0.075054 | 14 | Vbp1 | 1.344 | 0.075054 | 14 | Ppm1a | 1.329 | 0.075054 | 11 |
| Vdac3 | 1.361 | 0.075054 | 14 | Plk1 | 1.344 | 0.075054 | 13 | Chtf18 | 1.329 | 0.075054 | 13 |
| Cdkn2aipnl | 1.360 | 0.075054 | 14 | Pebp1 | 1.344 | 0.075054 | 26 | Sec13 | 1.329 | 0.075054 | 11 |
| Safb2 | 1.360 | 0.075054 | 15 | Skap2 | 1.343 | 0.075054 | 11 | Ndufa10 | 1.329 | 0.075054 | 18 |
| Dctn6 | 1.360 | 0.075054 | 9 | Atp6v0b | 1.343 | 0.075054 | 16 | Slc7a3 | 1.328 | 0.075054 | 15 |
| Gnb2l1 | 1.360 | 0.075054 | 137 | Maged1 | 1.343 | 0.075054 | 12 | Dapk3 | 1.328 | 0.075054 | 10 |
| Psma5 | 1.360 | 0.075054 | 17 | Trmt112 | 1.343 | 0.075054 | 14 | Uqcc2 | 1.328 | 0.075054 | 17 |
| Dazap2 | 1.360 | 0.075054 | 9 | Tfg | 1.343 | 0.075054 | 11 | Rarg | 1.327 | 0.075054 | 12 |
| Isyna1 | 1.360 | 0.075054 | 11 | Tyw3 | 1.342 | 0.075054 | 15 | Polr2k | 1.327 | 0.075054 | 13 |
| Odc1 | 1.360 | 0.075054 | 35 | Ubqln1 | 1.342 | 0.075054 | 17 | Mfsd3 | 1.327 | 0.075054 | 12 |
| Psmb4 | 1.359 | 0.075054 | 25 | Ddost | 1.341 | 0.075054 | 28 | Gm9855 | 1.326 | 0.075054 | 12 |
| Timm23 | 1.359 | 0.075054 | 23 | Ccnb1 | 1.341 | 0.075054 | 13 | Scand1 | 1.326 | 0.075054 | 7 |
| 1110038F14Rik | 1.359 | 0.075054 | 9 | Slc25a20 | 1.341 | 0.075054 | 10 | Polr2i | 1.326 | 0.075054 | 14 |
| Tc2n | 1.359 | 0.075054 | 16 | Apoc1 | 1.340 | 0.075054 | 9 | Atp5e | 1.326 | 0.075054 | 18 |
| Srrt | 1.359 | 0.075054 | 22 | Dscr3 | 1.340 | 0.075054 | 17 | Ppp1r8 | 1.326 | 0.075054 | 15 |
| Defa6 | 1.359 | 0.075054 | 5 | Ssr2 | 1.340 | 0.075054 | 14 | Rilpl1 | 1.326 | 0.075054 | 8 |
| Hax1 | 1.359 | 0.075054 | 11 | Fgf4 | 1.340 | 0.075054 | 12 | Podxl | 1.326 | 0.075054 | 14 |
| Epas1 | 1.358 | 0.075054 | 13 | Myl12a | 1.340 | 0.075054 | 26 | Rpph1 | 1.325 | 0.075054 | 4 |
| Socs3 | 1.358 | 0.075054 | 12 | Mcm6 | 1.340 | 0.075054 | 22 | Lsr | 1.325 | 0.075054 | 10 |

Fig. 26F

| Gene | Val1 | Val2 | N | Gene | Val1 | Val2 | N | Gene | Val1 | Val2 | N |
|---|---|---|---|---|---|---|---|---|---|---|---|
| Rtcb | 1.358 | 0.075054 | 21 | Mrps12 | 1.339 | 0.075054 | 14 | Psmc1 | 1.325 | 0.075054 | 18 |
| Psmd2 | 1.358 | 0.075054 | 26 | Ubi5 | 1.339 | 0.075054 | 14 | Lin7b | 1.325 | 0.075054 | 6 |
| Ligl2 | 1.358 | 0.075054 | 12 | Trap1 | 1.339 | 0.075054 | 11 | Gabarapl1 | 1.325 | 0.075054 | 13 |
| Mcl1 | 1.358 | 0.075054 | 16 | Atp5o | 1.339 | 0.075054 | 21 | Zfp42 | 1.325 | 0.075054 | 17 |
| Cct4 | 1.357 | 0.075054 | 21 | Gtf2f1 | 1.339 | 0.075054 | 17 | Snrpf | 1.325 | 0.075054 | 24 |
| Suclg1 | 1.357 | 0.075054 | 13 | Pacsin2 | 1.339 | 0.075054 | 26 | Bcl3 | 1.324 | 0.075054 | 10 |
| 1110058L19Rik | 1.357 | 0.075054 | 9 | Dcaf7 | 1.339 | 0.075054 | 15 | Atic | 1.324 | 0.075054 | 17 |
| Ybx3 | 1.356 | 0.075054 | 24 | 2410004N09Rik | 1.338 | 0.075054 | 11 | Ddx39b | 1.324 | 0.075054 | 17 |
| P4ha2 | 1.356 | 0.075054 | 11 | Cisd3 | 1.338 | 0.075054 | 10 | Ppp2r5a | 1.323 | 0.075054 | 15 |
| Fkbp2 | 1.356 | 0.075054 | 12 | Asnsd1 | 1.338 | 0.075054 | 13 | Rangap1 | 1.323 | 0.075054 | 15 |
| Fblim1 | 1.355 | 0.075054 | 15 | Pomgnt1 | 1.337 | 0.075054 | 9 | Abhd17a | 1.323 | 0.075054 | 10 |
| Sf3b1 | 1.355 | 0.075054 | 31 | Rpa1 | 1.337 | 0.075054 | 17 | Smyd5 | 1.323 | 0.075054 | 11 |
| Psmb3 | 1.355 | 0.075054 | 34 | Mrpl4 | 1.337 | 0.075054 | 12 | Dpp7 | 1.323 | 0.075054 | 8 |
| Acer2 | 1.355 | 0.075054 | 26 | Adprh | 1.337 | 0.075054 | 10 | Dnpep | 1.323 | 0.075054 | 11 |
| Cacng7 | 1.354 | 0.075054 | 14 | Tomm40l | 1.336 | 0.075054 | 13 | Bms1 | 1.323 | 0.075054 | 16 |
| Mrps36 | 1.354 | 0.075054 | 10 | Ndufa6 | 1.336 | 0.075054 | 21 | Ptp4a2 | 1.323 | 0.075054 | 15 |
| Phf23 | 1.354 | 0.075054 | 12 | B4galt3 | 1.336 | 0.075054 | 12 | Lage3 | 1.323 | 0.075054 | 14 |
| Eif2b5 | 1.353 | 0.075054 | 14 | Mvd | 1.336 | 0.075054 | 12 | Cdca8 | 1.323 | 0.075054 | 16 |
| Ndufs7 | 1.352 | 0.075054 | 13 | Rbmxl2 | 1.336 | 0.075054 | 13 | Ankrd46 | 1.323 | 0.075054 | 8 |
| Tubg1 | 1.352 | 0.075054 | 9 | Hsph1 | 1.336 | 0.075054 | 22 | Ddx23 | 1.322 | 0.075054 | 13 |
| DnajC2 | 1.352 | 0.075054 | 17 | Lin28a | 1.336 | 0.075054 | 12 | Rfc2 | 1.322 | 0.075054 | 14 |
| Capns1 | 1.351 | 0.075054 | 22 | Got1 | 1.336 | 0.075054 | 15 | Uqcrb | 1.322 | 0.075054 | 13 |
| Utp3 | 1.351 | 0.075054 | 11 | Utp14a | 1.336 | 0.075054 | 9 | Txn1 | 1.322 | 0.075054 | 27 |
| Ctnnal | 1.351 | 0.075054 | 17 | Efcc1 | 1.336 | 0.075054 | 21 | Snhg5 | 1.322 | 0.075054 | 11 |
| Prr13 | 1.351 | 0.075054 | 11 | Ndufs3 | 1.336 | 0.075054 | 15 | Bcat1 | 1.322 | 0.075054 | 31 |
| Psph | 1.351 | 0.075054 | 10 | Fam64a | 1.335 | 0.075054 | 9 | Yrdc | 1.321 | 0.075054 | 16 |
| Prkcsh | 1.351 | 0.075054 | 21 | Txnip | 1.335 | 0.075054 | 13 | Tuba1b | 1.321 | 0.075054 | 43 |
| Mrpl54 | 1.351 | 0.075054 | 13 | AU022252 | 1.335 | 0.075054 | 12 | Vipas39 | 1.321 | 0.075054 | 8 |
| Slmo2 | 1.351 | 0.075054 | 9 | Tbrg1 | 1.335 | 0.075054 | 15 | Cops8 | 1.320 | 0.075054 | 15 |
| Mrpl46 | 1.350 | 0.075054 | 10 | Blmh | 1.335 | 0.075054 | 21 | Pcna | 1.320 | 0.075054 | 17 |
| Tprgl | 1.350 | 0.075054 | 13 | Uqcr10 | 1.334 | 0.075054 | 25 | Ydjc | 1.320 | 0.075054 | 12 |
| Trim28 | 1.350 | 0.075054 | 50 | Hexa | 1.334 | 0.075054 | 9 | Flna | 1.320 | 0.075054 | 19 |
| Ctcl | 1.350 | 0.075054 | 11 | Mrpl44 | 1.334 | 0.075054 | 10 | Ampd2 | 1.320 | 0.075054 | 12 |
| Ube2c | 1.349 | 0.075054 | 26 | Add1 | 1.334 | 0.075054 | 11 | Gpn1 | 1.320 | 0.075054 | 11 |
| Txn2 | 1.349 | 0.075054 | 15 | Mrps24 | 1.334 | 0.075054 | 16 | Sars | 1.320 | 0.075054 | 11 |

Fig. 26G

| Gene | Val1 | Val2 | N | Gene | Val1 | Val2 | N | Gene | Val1 | Val2 | N |
|---|---|---|---|---|---|---|---|---|---|---|---|
| Pfdn4 | 1.319 | 0.075054 | 13 | Tnk2 | 1.308 | 0.075054 | 12 | Coro1a | 1.297 | 0.075054 | 10 |
| Mfsd5 | 1.319 | 0.075054 | 11 | Nutf2 | 1.308 | 0.075054 | 12 | H1fx | 1.297 | 0.075054 | 8 |
| Igf2bp1 | 1.319 | 0.075054 | 45 | Ddx47 | 1.307 | 0.075054 | 10 | Psma6 | 1.297 | 0.075054 | 21 |
| Pgp | 1.318 | 0.075054 | 13 | Gpatch4 | 1.307 | 0.075054 | 16 | Stra13 | 1.297 | 0.075054 | 13 |
| Ear10 | 1.318 | 0.075054 | 6 | Rrp12 | 1.307 | 0.075054 | 11 | N6amt2 | 1.297 | 0.075054 | 10 |
| Cldn7 | 1.318 | 0.075054 | 14 | Tma7 | 1.307 | 0.075054 | 23 | Dus1l | 1.297 | 0.075054 | 11 |
| Cpsf4l | 1.318 | 0.075054 | 10 | Cuta | 1.307 | 0.075054 | 11 | Smarcb1 | 1.296 | 0.075054 | 13 |
| Mif | 1.317 | 0.075054 | 29 | Cox14 | 1.307 | 0.075054 | 10 | Tax1bp1 | 1.296 | 0.075054 | 12 |
| Nsmce4a | 1.317 | 0.075054 | 14 | Mdh1 | 1.307 | 0.075054 | 16 | Mtdh | 1.296 | 0.075054 | 21 |
| Poldl | 1.317 | 0.075054 | 16 | Tufm | 1.307 | 0.075054 | 16 | Rlim | 1.296 | 0.075054 | 23 |
| Pnp | 1.316 | 0.075054 | 15 | Tomm5 | 1.306 | 0.075054 | 11 | S100a11 | 1.295 | 0.075054 | 8 |
| Cib1 | 1.316 | 0.075054 | 9 | Cog8 | 1.306 | 0.075054 | 13 | Gde1 | 1.295 | 0.075054 | 8 |
| Tipin | 1.316 | 0.075054 | 12 | Mbd3 | 1.306 | 0.075054 | 24 | Plrg1 | 1.295 | 0.075054 | 10 |
| Vdac1 | 1.316 | 0.075054 | 26 | Uqcr11 | 1.306 | 0.075054 | 21 | Gabarap | 1.295 | 0.075054 | 12 |
| 4833439L19Rik | 1.316 | 0.075054 | 12 | Ap4m1 | 1.306 | 0.075054 | 11 | Ilk | 1.295 | 0.075054 | 8 |
| L1td1 | 1.315 | 0.075054 | 24 | Rbpj | 1.306 | 0.075054 | 18 | Fads1 | 1.294 | 0.075054 | 12 |
| Slc25a1 | 1.315 | 0.075054 | 9 | Nedd8 | 1.306 | 0.075054 | 18 | Dnajc21 | 1.294 | 0.075054 | 10 |
| Ints3 | 1.315 | 0.075054 | 13 | Gtsf1l | 1.305 | 0.075054 | 11 | Tpst2 | 1.294 | 0.075054 | 10 |
| Cdc16 | 1.315 | 0.075054 | 11 | 2500004C02Rik | 1.305 | 0.075054 | 21 | Lamtor4 | 1.294 | 0.075054 | 13 |
| Sdhb | 1.315 | 0.075054 | 10 | Uqcrh | 1.305 | 0.075054 | 20 | Skp1a | 1.294 | 0.075054 | 19 |
| Sfr1 | 1.315 | 0.075054 | 13 | Myl9 | 1.305 | 0.075054 | 14 | Msn | 1.294 | 0.075054 | 17 |
| Phlda3 | 1.315 | 0.075054 | 12 | Zfp771 | 1.305 | 0.075054 | 8 | Grhpr | 1.294 | 0.075054 | 9 |
| Ndufs2 | 1.314 | 0.075054 | 12 | Ifi30 | 1.305 | 0.075054 | 10 | Rsl1d1 | 1.293 | 0.075054 | 17 |
| Psrc1 | 1.314 | 0.075054 | 10 | Lsm4 | 1.304 | 0.075054 | 19 | Nrp | 1.293 | 0.075054 | 8 |
| Prdx2 | 1.314 | 0.075054 | 18 | Ywhab | 1.304 | 0.075054 | 20 | Psmc2 | 1.293 | 0.075054 | 15 |
| Fam168b | 1.314 | 0.075054 | 13 | Dnajb1 | 1.304 | 0.075054 | 10 | Me1 | 1.293 | 0.075054 | 12 |
| Ebp | 1.314 | 0.075054 | 10 | Polr2g | 1.304 | 0.075054 | 9 | Mrps35 | 1.292 | 0.075054 | 7 |
| Ss18 | 1.314 | 0.075054 | 10 | Oaz2 | 1.304 | 0.075054 | 14 | Gsta4 | 1.292 | 0.075054 | 18 |
| Sumo2 | 1.314 | 0.075054 | 22 | Pycr1 | 1.304 | 0.075054 | 8 | Ap1s1 | 1.292 | 0.075054 | 13 |
| Hdgf | 1.314 | 0.075054 | 41 | Dpy30 | 1.304 | 0.075054 | 19 | Zdhhc4 | 1.292 | 0.075054 | 8 |
| Ik | 1.314 | 0.075054 | 16 | Parp1 | 1.303 | 0.075054 | 16 | Phf10 | 1.292 | 0.075054 | 9 |
| Farsa | 1.314 | 0.075054 | 10 | Ugp2 | 1.303 | 0.075054 | 12 | Tfpi | 1.292 | 0.075054 | 21 |

Fig. 26H

| Gene | Value | p | N | Gene | Value | p | N | Gene | Value | p | N |
|---|---|---|---|---|---|---|---|---|---|---|---|
| Aimp2 | 1.314 | 0.075054 | 12 | Wdr5 | 1.303 | 0.075054 | 17 | Fdx1 | 1.292 | 0.075054 | 10 |
| Pgls | 1.314 | 0.075054 | 10 | Pold2 | 1.303 | 0.075054 | 11 | Ccng1 | 1.292 | 0.075054 | 12 |
| B9d1 | 1.314 | 0.075054 | 9 | Ergic3 | 1.303 | 0.075054 | 10 | Rab2a | 1.291 | 0.075054 | 11 |
| Chmp6 | 1.314 | 0.075054 | 8 | Rhoc | 1.303 | 0.075054 | 12 | Bax | 1.291 | 0.075054 | 27 |
| Aup1 | 1.314 | 0.075054 | 11 | Bub1b | 1.303 | 0.075054 | 14 | Ecsit | 1.291 | 0.075054 | 10 |
| Aldh2 | 1.314 | 0.075054 | 14 | Pbk | 1.303 | 0.075054 | 20 | Mrps30 | 1.290 | 0.075054 | 10 |
| Dnajc9 | 1.314 | 0.075054 | 15 | Phgdh | 1.302 | 0.075054 | 11 | Etv5 | 1.290 | 0.075054 | 15 |
| Tmed10 | 1.313 | 0.075054 | 13 | Cnn2 | 1.302 | 0.075054 | 12 | Ino80e | 1.290 | 0.075054 | 12 |
| Sap30 | 1.313 | 0.075054 | 10 | Slc50a1 | 1.302 | 0.075054 | 13 | 2810008D09Rik | 1.290 | 0.075054 | 5 |
| Mafl | 1.313 | 0.075054 | 11 | Ak4 | 1.302 | 0.075054 | 15 | Ubxn1 | 1.290 | 0.075054 | 21 |
| Drg1 | 1.313 | 0.075054 | 17 | Ndufb4 | 1.302 | 0.075054 | 10 | Hspa9 | 1.290 | 0.075054 | 24 |
| Snd1 | 1.312 | 0.075054 | 18 | Ptrf | 1.302 | 0.075054 | 10 | Nudt1 | 1.289 | 0.075054 | 12 |
| Acaa1a | 1.312 | 0.075054 | 12 | Scyl1 | 1.302 | 0.075054 | 12 | 2700094K13Rik | 1.289 | 0.075054 | 18 |
| Polr2j | 1.312 | 0.075054 | 16 | Cyth2 | 1.302 | 0.075054 | 10 | Clstn1 | 1.289 | 0.075054 | 10 |
| Pes1 | 1.312 | 0.075054 | 17 | Xrcc5 | 1.301 | 0.075054 | 14 | Psmd12 | 1.289 | 0.075054 | 14 |
| N4bp3 | 1.312 | 0.075054 | 9 | Cox6a1 | 1.301 | 0.075054 | 26 | Cmtm7 | 1.289 | 0.075054 | 10 |
| Gars | 1.312 | 0.075054 | 17 | Zdhhc18 | 1.301 | 0.075054 | 14 | Kat2a | 1.289 | 0.075054 | 15 |
| Ccz1 | 1.312 | 0.075054 | 9 | Bloc1s2 | 1.301 | 0.075054 | 8 | Phkg1 | 1.288 | 0.075054 | 20 |
| Tuba1c | 1.312 | 0.075054 | 37 | Mast2 | 1.301 | 0.075054 | 10 | Arhgap8 | 1.288 | 0.075054 | 12 |
| Nfkbia | 1.312 | 0.075054 | 9 | 1110038B12Rik | 1.301 | 0.075054 | 18 | Atp5k | 1.288 | 0.075054 | 31 |
| Nono | 1.312 | 0.075054 | 29 | Aspscr1 | 1.300 | 0.075054 | 15 | Tdrp | 1.288 | 0.075054 | 12 |
| Mtch1 | 1.312 | 0.075054 | 21 | Cops3 | 1.300 | 0.075054 | 13 | Nutf2-ps1 | 1.288 | 0.075054 | 16 |
| Ndufb8 | 1.312 | 0.075054 | 16 | Nenf | 1.300 | 0.075054 | 11 | Mrpl47 | 1.288 | 0.075054 | 10 |
| Sec61b | 1.311 | 0.075054 | 17 | Ndufs6 | 1.300 | 0.075054 | 18 | Pdia3 | 1.287 | 0.075054 | 13 |
| Ppm1g | 1.311 | 0.075054 | 18 | 1190005I06Rik | 1.299 | 0.075054 | 6 | Iscu | 1.287 | 0.075054 | 20 |
| Mrps2 | 1.311 | 0.075054 | 11 | Hsbp1 | 1.299 | 0.075054 | 12 | Jmjd6 | 1.287 | 0.075054 | 12 |
| Gnai2 | 1.311 | 0.075054 | 14 | Tmed9 | 1.299 | 0.075054 | 10 | Ndufs1 | 1.287 | 0.075054 | 10 |
| Zw10 | 1.311 | 0.075054 | 9 | Gm3258 | 1.299 | 0.075054 | 10 | Kif22 | 1.287 | 0.075054 | 17 |
| Sfxn1 | 1.311 | 0.075054 | 12 | Rpl36al | 1.299 | 0.075054 | 43 | Scamp4 | 1.287 | 0.075054 | 12 |
| Atp9a | 1.310 | 0.075054 | 15 | Jam2 | 1.299 | 0.075054 | 21 | Drosha | 1.287 | 0.075054 | 11 |
| Ccdc93 | 1.309 | 0.075054 | 22 | Eci2 | 1.299 | 0.075054 | 10 | Snrnp25 | 1.287 | 0.075054 | 9 |
| 2010107E04Rik | 1.309 | 0.075054 | 18 | Gm16062 | 1.299 | 0.075054 | 14 | Rrp15 | 1.287 | 0.075054 | 12 |

Fig. 26I

| Gene | Val1 | Val2 | N | Gene | Val1 | Val2 | N | Gene | Val1 | Val2 | N |
|---|---|---|---|---|---|---|---|---|---|---|---|
| Rpp25 | 1.309 | 0.075054 | 11 | Bola1 | 1.299 | 0.075054 | 8 | Ruvbi1 | 1.287 | 0.075054 | 16 |
| Cd99 | 1.309 | 0.075054 | 10 | Mrpl20 | 1.298 | 0.075054 | 15 | Cita | 1.287 | 0.075054 | 19 |
| Pfn1 | 1.309 | 0.075054 | 10 | Ube2q1 | 1.298 | 0.075054 | 9 | Pdlim1 | 1.287 | 0.075054 | 11 |
| Dcaf15 | 1.309 | 0.075054 | 11 | Csrp2 | 1.298 | 0.075054 | 15 | Eras | 1.287 | 0.075054 | 9 |
| Dus2 | 1.309 | 0.075054 | 18 | Map1lc3b | 1.298 | 0.075054 | 16 | Prdx4 | 1.287 | 0.075054 | 11 |
| Ezh2 | 1.308 | 0.075054 | 13 | Hnrnph1 | 1.298 | 0.075054 | 17 | Rab1b | 1.287 | 0.075054 | 13 |
| Cnn3 | 1.308 | 0.075054 | 22 | Ccdc12 | 1.298 | 0.075054 | 8 | Idh3g | 1.287 | 0.075054 | 10 |
| Sumo1 | 1.308 | 0.075054 | 15 | Ddx1 | 1.298 | 0.075054 | 13 | Rcor2 | 1.287 | 0.075054 | 14 |
| Lsm10 | 1.308 | 0.075054 | 9 | Sar1b | 1.298 | 0.075054 | 8 | 1110008P14Rik | 1.287 | 0.075054 | 10 |
| Pa2g4 | 1.308 | 0.075054 | 30 | Elp3 | 1.298 | 0.075054 | 17 | Csnk1e | 1.287 | 0.075054 | 24 |
| Tomm20 | 1.308 | 0.075054 | 41 | Mafg | 1.297 | 0.075054 | 12 | Grcc10 | 1.287 | 0.075054 | 10 |
| Tmem147 | 1.308 | 0.075054 | 9 | Irf3 | 1.297 | 0.075054 | 22 | Hras | 1.287 | 0.075054 | 15 |
| Nudt21 | 1.287 | 0.075054 | 11 | Ier3ip1 | 1.278 | 0.075054 | 17 | Cap1 | 1.268 | 0.075698 | 14 |
| Gjb3 | 1.286 | 0.075054 | 8 | Stau1 | 1.278 | 0.075054 | 21 | Dcakd | 1.268 | 0.075698 | 10 |
| Acaa2 | 1.286 | 0.075054 | 11 | Tmem208 | 1.278 | 0.075054 | 9 | Pabpc4 | 1.268 | 0.075698 | 16 |
| Ppp2r2d | 1.286 | 0.075054 | 13 | Arrb2 | 1.278 | 0.07553 | 16 | Gak | 1.268 | 0.075698 | 13 |
| Nthl1 | 1.286 | 0.075054 | 9 | Aldh7a1 | 1.277 | 0.07553 | 10 | Mpdu1 | 1.267 | 0.075698 | 15 |
| Chmp2a | 1.286 | 0.075054 | 11 | Eif6 | 1.277 | 0.07553 | 15 | Pomp | 1.267 | 0.075698 | 20 |
| Gatsl3 | 1.286 | 0.075054 | 8 | Vmp1 | 1.277 | 0.07553 | 10 | Idh1 | 1.267 | 0.075698 | 13 |
| Erp29 | 1.285 | 0.075054 | 14 | Trpt1 | 1.277 | 0.075698 | 11 | Poldip2 | 1.267 | 0.075698 | 12 |
| Hsd17b10 | 1.285 | 0.075054 | 10 | Ddx21 | 1.277 | 0.075698 | 17 | Rpusd1 | 1.267 | 0.075698 | 10 |
| Plaur | 1.285 | 0.075054 | 10 | Rps19bp1 | 1.277 | 0.075698 | 12 | Agl | 1.267 | 0.075698 | 43 |
| Capza1 | 1.285 | 0.075054 | 15 | Gdi2 | 1.277 | 0.075698 | 18 | Sept1 | 1.267 | 0.075698 | 8 |
| Mtch2 | 1.285 | 0.075054 | 10 | Sephs2 | 1.276 | 0.075698 | 15 | Lsm7 | 1.267 | 0.075698 | 13 |
| Bcap31 | 1.284 | 0.075054 | 12 | Gbx2 | 1.276 | 0.075698 | 7 | Nubp2 | 1.267 | 0.075698 | 8 |
| Eed | 1.284 | 0.075054 | 15 | Sdha | 1.276 | 0.075698 | 15 | Atp5l | 1.267 | 0.075698 | 20 |
| Ccnb2 | 1.284 | 0.075054 | 11 | Nop2 | 1.276 | 0.075698 | 12 | Fxr1 | 1.267 | 0.075698 | 11 |
| Ddit4 | 1.284 | 0.075054 | 10 | H2afy | 1.275 | 0.075698 | 15 | Pam16 | 1.267 | 0.075698 | 15 |
| Vps4b | 1.284 | 0.075054 | 16 | Pld3 | 1.275 | 0.075698 | 13 | Epcam | 1.267 | 0.075698 | 13 |
| Apex1 | 1.284 | 0.075054 | 11 | Gss | 1.275 | 0.075698 | 11 | Edf1 | 1.267 | 0.075698 | 19 |
| Thap4 | 1.284 | 0.075054 | 11 | Map7d2 | 1.275 | 0.075698 | 16 | Parl | 1.267 | 0.075698 | 10 |
| Imp4 | 1.284 | 0.075054 | 12 | Cox7a2 | 1.275 | 0.075698 | 21 | Rpn1 | 1.266 | 0.075698 | 14 |

Fig. 26J

| | | | | | |
|---|---|---|---|---|---|
| Atp5g3 | 1.284 | 0.075054 | 29 | Med24 | 1.275 | 0.075698 | 11 | Gcat | 1.266 | 0.075698 | 13 |
| 3110001I22Rik | 1.284 | 0.075054 | 17 | Ccnd4 | 1.275 | 0.075698 | 10 | Slc9a3r1 | 1.266 | 0.075698 | 11 |
| Herpud1 | 1.283 | 0.075054 | 8 | Stmn1-rs1 | 1.275 | 0.075698 | 12 | Sf3b3 | 1.266 | 0.075698 | 18 |
| Cirbp | 1.283 | 0.075054 | 9 | Mgea5 | 1.274 | 0.075698 | 15 | Gon4l | 1.266 | 0.075698 | 14 |
| Rrm2 | 1.283 | 0.075054 | 14 | Bnip3l | 1.274 | 0.075698 | 16 | Uba2 | 1.266 | 0.075698 | 14 |
| Pef1 | 1.283 | 0.075054 | 11 | Hyou1 | 1.274 | 0.075698 | 13 | Stoml1 | 1.266 | 0.075698 | 12 |
| Ctps | 1.283 | 0.075054 | 13 | Chrac1 | 1.274 | 0.075698 | 8 | Sod2 | 1.266 | 0.075698 | 11 |
| Ly6e | 1.283 | 0.075054 | 13 | Apol7a | 1.274 | 0.075698 | 13 | Rangrf | 1.265 | 0.075698 | 13 |
| Gldc | 1.283 | 0.075054 | 11 | Trp53 | 1.274 | 0.075698 | 18 | Slc20a2 | 1.265 | 0.075698 | 13 |
| Gsr | 1.283 | 0.075054 | 12 | Adck5 | 1.274 | 0.075698 | 8 | Usmg5 | 1.265 | 0.075698 | 20 |
| Spcs2 | 1.283 | 0.075054 | 15 | Nid2 | 1.274 | 0.075698 | 14 | Gm561 | 1.265 | 0.075698 | 9 |
| Eif3b | 1.283 | 0.075054 | 34 | Zfp451 | 1.273 | 0.075698 | 14 | Pol1d | 1.265 | 0.075698 | 19 |
| Usp10 | 1.283 | 0.075054 | 13 | Tnip1 | 1.273 | 0.075698 | 10 | Uhrf1 | 1.265 | 0.075698 | 15 |
| Rpa2 | 1.283 | 0.075054 | 19 | Mgat4b | 1.273 | 0.075698 | 10 | Atp6v1g1 | 1.265 | 0.075698 | 13 |
| Mrpl55 | 1.283 | 0.075054 | 13 | Snrpd2 | 1.273 | 0.075698 | 30 | Rps27l | 1.265 | 0.075698 | 29 |
| Mrpl15 | 1.282 | 0.075054 | 13 | Timm13 | 1.273 | 0.075698 | 18 | Igf2 | 1.265 | 0.075698 | 12 |
| Rab35 | 1.282 | 0.075054 | 9 | Fbxo15 | 1.273 | 0.075698 | 12 | Phb2 | 1.265 | 0.075698 | 19 |
| Ubc | 1.282 | 0.075054 | 16 | Syngr2 | 1.273 | 0.075698 | 10 | Arpc2 | 1.265 | 0.075698 | 14 |
| 0610007P14Rik | 1.282 | 0.075054 | 8 | Cox7b | 1.273 | 0.075698 | 24 | Plvap | 1.265 | 0.075698 | 11 |
| Cpsf3 | 1.282 | 0.075054 | 11 | Atp6v1e1 | 1.273 | 0.075698 | 10 | Cd81 | 1.265 | 0.075698 | 15 |
| Tceb1 | 1.282 | 0.075054 | 13 | Card10 | 1.273 | 0.075698 | 8 | Mapkapk2 | 1.264 | 0.075698 | 11 |
| Wnt7b | 1.282 | 0.075054 | 10 | Mpzl1 | 1.273 | 0.075698 | 11 | Nme4 | 1.264 | 0.075698 | 8 |
| G3bp2 | 1.282 | 0.075054 | 24 | Slc29a4 | 1.272 | 0.075698 | 7 | Lgals3 | 1.264 | 0.075698 | 11 |
| Ubqln4 | 1.281 | 0.075054 | 13 | Mfsd11 | 1.272 | 0.075698 | 22 | Lrrc14 | 1.264 | 0.075698 | 11 |
| Unc45a | 1.281 | 0.075054 | 9 | Mrps9 | 1.272 | 0.075698 | 12 | Ccdc3 | 1.264 | 0.075698 | 9 |
| Wdr61 | 1.281 | 0.075054 | 9 | Ipo4 | 1.272 | 0.075698 | 11 | Bet1l | 1.264 | 0.075698 | 9 |
| Zfpl1 | 1.281 | 0.075054 | 10 | 6430706D22Rik | 1.272 | 0.075698 | 11 | Hist1h1b | 1.264 | 0.075698 | 8 |
| Nup62 | 1.281 | 0.075054 | 17 | Ppp1r14b | 1.271 | 0.075698 | 14 | Hnrnph3 | 1.264 | 0.075698 | 11 |
| Cox6c | 1.281 | 0.075054 | 16 | Msh2 | 1.271 | 0.075698 | 20 | Tbc1d13 | 1.264 | 0.075698 | 15 |
| Nars | 1.281 | 0.075054 | 12 | Acta1 | 1.271 | 0.075698 | 14 | Lamtor2 | 1.263 | 0.075698 | 15 |
| Cipc | 1.281 | 0.075054 | 13 | Sec23b | 1.271 | 0.075698 | 10 | Aph1a | 1.263 | 0.075698 | 14 |
| Psmd13 | 1.281 | 0.075054 | 22 | Ninj1 | 1.271 | 0.075698 | 8 | Nme1 | 1.263 | 0.075698 | 16 |

Fig. 26K

| Gene | Val1 | Val2 | N | Gene | Val1 | Val2 | N | Gene | Val1 | Val2 | N |
|---|---|---|---|---|---|---|---|---|---|---|---|
| Slc25a3 | 1.281 | 0.075054 | 28 | Gps1 | 1.270 | 0.075698 | 13 | Hnrnpdl | 1.263 | 0.075698 | 16 |
| Sin3b | 1.281 | 0.075054 | 12 | Cryz | 1.270 | 0.075698 | 10 | Dynlrb1 | 1.263 | 0.075698 | 10 |
| Pde6d | 1.281 | 0.075054 | 12 | Eif3m | 1.270 | 0.075698 | 14 | Prmt7 | 1.263 | 0.075698 | 13 |
| Ndufaf2 | 1.281 | 0.075054 | 11 | F3 | 1.270 | 0.075698 | 16 | Pwp2 | 1.263 | 0.075698 | 12 |
| Klf9 | 1.280 | 0.075054 | 17 | Mrpl2 | 1.270 | 0.075698 | 9 | Lamp1 | 1.262 | 0.075698 | 24 |
| Znrd1 | 1.280 | 0.075054 | 12 | Lta4h | 1.270 | 0.075698 | 16 | Ndufa9 | 1.262 | 0.075698 | 10 |
| Cox6b1 | 1.280 | 0.075054 | 13 | Cnpy2 | 1.270 | 0.075698 | 12 | Zfp511 | 1.262 | 0.075698 | 10 |
| Ece2 | 1.280 | 0.075054 | 11 | Nsmce1 | 1.270 | 0.075698 | 11 | Rexo2 | 1.262 | 0.075698 | 16 |
| Sh3bgrl3 | 1.280 | 0.075054 | 12 | Rfc5 | 1.270 | 0.075698 | 14 | Nol7 | 1.262 | 0.075698 | 13 |
| Icam1 | 1.280 | 0.075054 | 9 | Tomm22 | 1.270 | 0.075698 | 22 | Dlst | 1.262 | 0.075698 | 18 |
| Mageb16 | 1.280 | 0.075054 | 11 | Ssrp1 | 1.269 | 0.075698 | 20 | Atox1 | 1.261 | 0.076367 | 20 |
| Myo9b | 1.279 | 0.075054 | 12 | Psmd4 | 1.269 | 0.075698 | 21 | Ccm2 | 1.261 | 0.076367 | 11 |
| Sra1 | 1.279 | 0.075054 | 10 | Timm50 | 1.269 | 0.075698 | 7 | Poli | 1.261 | 0.076367 | 13 |
| Ddx49 | 1.279 | 0.075054 | 12 | Elovl6 | 1.269 | 0.075698 | 15 | Gtf2h4 | 1.261 | 0.076367 | 12 |
| Ptms | 1.279 | 0.075054 | 15 | Snhg1 | 1.269 | 0.075698 | 13 | Copz1 | 1.260 | 0.076367 | 16 |
| Psmc4 | 1.279 | 0.075054 | 18 | Pol1rc | 1.269 | 0.075698 | 12 | Ift43 | 1.260 | 0.076367 | 10 |
| Bsg | 1.279 | 0.075054 | 20 | Zmynd19 | 1.269 | 0.075698 | 11 | Fsd1 | 1.260 | 0.076367 | 8 |
| Akt | 1.279 | 0.075054 | 16 | Lphn1 | 1.269 | 0.075698 | 21 | Hdac1 | 1.260 | 0.076367 | 14 |
| Dohh | 1.279 | 0.075054 | 12 | Atp1b1 | 1.268 | 0.075698 | 12 | Prss50 | 1.260 | 0.076367 | 14 |
| Wdr75 | 1.279 | 0.075054 | 11 | Ssbp1 | 1.268 | 0.075698 | 18 | Arl6ip5 | 1.260 | 0.076367 | 10 |
| Snai3 | 1.279 | 0.075054 | 8 | Dusp12 | 1.268 | 0.075698 | 11 | Cyb5r3 | 1.260 | 0.076367 | 14 |
| Aen | 1.279 | 0.075054 | 13 | Spr | 1.268 | 0.075698 | 13 | Myl6 | 1.260 | 0.076367 | 32 |
| Tbc1d10b | 1.279 | 0.075054 | 12 | Cir1 | 1.268 | 0.075698 | 15 | Hs2st1 | 1.259 | 0.077442 | 19 |
| Riok2 | 1.278 | 0.075054 | 12 | Ywhah | 1.268 | 0.075698 | 13 | Nup85 | 1.259 | 0.077442 | 15 |
| Tfdp1 | 1.259 | 0.077442 | 10 | Noc4l | 1.252 | 0.077442 | 13 | Rapgef1 | 1.259 | 0.079253 | 20 |
| Rhebl1 | 1.259 | 0.077442 | 13 | Zswim7 | 1.252 | 0.077442 | 8 | 3110040N11Rik | 1.245 | 0.079253 | 8 |
| Ndufb7 | 1.259 | 0.077442 | 14 | Coro1b | 1.252 | 0.077442 | 11 | Akt1 | 1.245 | 0.079253 | 11 |
| Ltv1 | 1.259 | 0.077442 | 13 | Ier2 | 1.251 | 0.077442 | 9 | Hirip3 | 1.245 | 0.079508 | 11 |
| Mtfr1 | 1.259 | 0.077442 | 10 | Timm10b | 1.251 | 0.077442 | 11 | Samd1 | 1.245 | 0.079508 | 11 |
| Tram1 | 1.258 | 0.077442 | 9 | Arhgap21 | 1.251 | 0.077442 | 12 | AK010878 | 1.245 | 0.079508 | 21 |
| Ssr4 | 1.258 | 0.077442 | 9 | Pxn | 1.251 | 0.077442 | 10 | Mrpl16 | 1.245 | 0.079508 | 9 |
| Arl3 | 1.258 | 0.077442 | 8 | Mrpl52 | 1.251 | 0.077442 | 9 | Rgl2 | 1.245 | 0.079508 | 8 |

Fig. 26L

| Gene | Ratio | p-value | Count |
|---|---|---|---|
| Snrpc | 1.258 | 0.077442 | 16 |
| Park7 | 1.258 | 0.077442 | 27 |
| Eif4ebp3 | 1.258 | 0.077442 | 8 |
| Drap1 | 1.258 | 0.077442 | 19 |
| Rab33b | 1.258 | 0.077442 | 24 |
| Flot1 | 1.258 | 0.077442 | 9 |
| Fntb | 1.258 | 0.077442 | 11 |
| Wdr45b | 1.257 | 0.077442 | 11 |
| Odf2 | 1.257 | 0.077442 | 11 |
| Slc10a1 | 1.257 | 0.077442 | 17 |
| Cenpt | 1.257 | 0.077442 | 11 |
| Nrde2 | 1.257 | 0.077442 | 14 |
| Ndufab1 | 1.257 | 0.077442 | 12 |
| Gcsh | 1.257 | 0.077442 | 10 |
| Msantd2 | 1.257 | 0.077442 | 7 |
| Haus4 | 1.257 | 0.077442 | 9 |
| Itm2b | 1.257 | 0.077442 | 14 |
| Ict1 | 1.256 | 0.077442 | 9 |
| Ndufa3 | 1.256 | 0.077442 | 11 |
| Dnajc8 | 1.256 | 0.077442 | 13 |
| Akap8l | 1.256 | 0.077442 | 12 |
| Dnajc19 | 1.256 | 0.077442 | 18 |
| 1810022K09Rik | 1.256 | 0.077442 | 10 |
| Smim11 | 1.256 | 0.077442 | 8 |
| Dhx30 | 1.256 | 0.077442 | 10 |
| Ccnd1 | 1.256 | 0.077442 | 9 |
| Mgl2 | 1.256 | 0.077442 | 23 |
| Atp6v1f | 1.256 | 0.077442 | 12 |
| Rpl30 | 1.255 | 0.077442 | 49 |
| Ubap2 | 1.255 | 0.077442 | 12 |
| Rhoa | 1.255 | 0.077442 | 26 |
| Map2k2 | 1.255 | 0.077442 | 12 |
| Dynll2 | 1.251 | 0.077442 | 14 |
| Fmr1nb | 1.251 | 0.077442 | 11 |
| Bag1 | 1.251 | 0.077442 | 13 |
| Tmem11 | 1.251 | 0.077442 | 9 |
| Cdt1 | 1.251 | 0.077442 | 15 |
| Me2 | 1.251 | 0.077442 | 11 |
| Coa3 | 1.251 | 0.077442 | 8 |
| Nipsnap3b | 1.251 | 0.077442 | 9 |
| Bag6 | 1.250 | 0.077442 | 12 |
| Mcm5 | 1.250 | 0.077442 | 16 |
| Zfp13 | 1.250 | 0.077442 | 15 |
| Rad21 | 1.250 | 0.077442 | 15 |
| Laptm4a | 1.250 | 0.077442 | 14 |
| Hat1 | 1.250 | 0.077442 | 24 |
| Fbl | 1.250 | 0.077442 | 21 |
| Ppil3 | 1.250 | 0.077442 | 12 |
| Mest | 1.250 | 0.077442 | 13 |
| Dtymk | 1.250 | 0.077442 | 16 |
| Slbp | 1.249 | 0.07782 | 11 |
| Llph | 1.249 | 0.07782 | 20 |
| Perp | 1.249 | 0.07782 | 9 |
| Pagr1a | 1.249 | 0.07782 | 11 |
| Ercc3 | 1.249 | 0.07782 | 12 |
| 1110004F10Rik | 1.249 | 0.078195 | 15 |
| Rp9 | 1.249 | 0.078195 | 10 |
| Pop4 | 1.249 | 0.078195 | 9 |
| Arg2 | 1.249 | 0.078195 | 11 |
| Eif4b | 1.249 | 0.078195 | 24 |
| Pitrm1 | 1.249 | 0.078255 | 13 |
| Jagn1 | 1.249 | 0.078255 | 9 |
| Utp11l | 1.249 | 0.078255 | 8 |
| Snupn | 1.249 | 0.078255 | 10 |
| Psma4 | 1.245 | 0.079508 | 26 |
| Ogfod3 | 1.244 | 0.079508 | 9 |
| Mtx1 | 1.244 | 0.080016 | 12 |
| Ahcy | 1.244 | 0.080453 | 17 |
| Nelfe | 1.244 | 0.080453 | 11 |
| Tmem60 | 1.244 | 0.080453 | 10 |
| Phax | 1.244 | 0.080453 | 15 |
| Rab14 | 1.244 | 0.080453 | 12 |
| Fam89b | 1.244 | 0.080453 | 9 |
| 2410015M20Rik | 1.244 | 0.080453 | 13 |
| Acadvl | 1.244 | 0.080453 | 10 |
| Pmf1 | 1.243 | 0.080453 | 10 |
| Psmb2 | 1.243 | 0.080453 | 15 |
| Farsb | 1.243 | 0.080453 | 16 |
| Ube2a | 1.243 | 0.080453 | 11 |
| Pced1b | 1.243 | 0.080453 | 12 |
| Hspb8 | 1.243 | 0.080453 | 7 |
| Ywhae | 1.243 | 0.080453 | 26 |
| BC031181 | 1.243 | 0.080453 | 10 |
| Zcchc17 | 1.243 | 0.080453 | 8 |
| Fam162a | 1.242 | 0.080453 | 9 |
| Otud6b | 1.242 | 0.080453 | 14 |
| Sap30l | 1.242 | 0.080453 | 9 |
| Nop56 | 1.242 | 0.080453 | 29 |
| Anxa7 | 1.242 | 0.080515 | 18 |
| Rbm12b2 | 1.242 | 0.080515 | 9 |
| Hiat1 | 1.242 | 0.080515 | 9 |
| Dclk2 | 1.241 | 0.080515 | 12 |
| Akr1e1 | 1.241 | 0.080515 | 10 |
| Bivra | 1.241 | 0.080515 | 6 |
| Pgam1 | 1.241 | 0.080515 | 25 |
| Irf2bpl | 1.241 | 0.080515 | 16 |

| Gene | Val1 | Val2 | N | Gene | Val1 | Val2 | N | Gene | Val1 | Val2 | N |
|---|---|---|---|---|---|---|---|---|---|---|---|
| Mrps34 | 1.255 | 0.077442 | 6 | Drg2 | 1.249 | 0.078255 | 10 | Wbp1 | 1.241 | 0.080515 | 10 |
| Zdhhc12 | 1.255 | 0.077442 | 10 | Pecam1 | 1.248 | 0.078255 | 8 | Serf2 | 1.241 | 0.080515 | 24 |
| Wbp11 | 1.255 | 0.077442 | 16 | Psat1 | 1.248 | 0.078255 | 16 | 2810004N23Rik | 1.241 | 0.080515 | 10 |
| Birc5 | 1.255 | 0.077442 | 18 | Nucks1 | 1.248 | 0.078255 | 27 | Msh6 | 1.241 | 0.080515 | 13 |
| Shmt1 | 1.255 | 0.077442 | 15 | Evl | 1.248 | 0.078255 | 8 | Bap1 | 1.241 | 0.080515 | 11 |
| Cst3 | 1.255 | 0.077442 | 14 | Uhrf2 | 1.248 | 0.078686 | 9 | Morc1 | 1.240 | 0.080515 | 12 |
| Maea | 1.254 | 0.077442 | 15 | Ap2m1 | 1.248 | 0.078686 | 17 | Ccdc163 | 1.240 | 0.080515 | 9 |
| Gadd45gip1 | 1.254 | 0.077442 | 13 | Tra2a | 1.248 | 0.078686 | 11 | Tmem97 | 1.240 | 0.080515 | 9 |
| Ppib | 1.254 | 0.077442 | 16 | Tfcp2l1 | 1.248 | 0.078686 | 22 | Trappc1 | 1.240 | 0.080515 | 9 |
| Gpr108 | 1.254 | 0.077442 | 8 | Tex264 | 1.248 | 0.078686 | 9 | Bcat2 | 1.240 | 0.080515 | 8 |
| Chchd6 | 1.254 | 0.077442 | 7 | Csnk1g2 | 1.248 | 0.078686 | 10 | Cenpm | 1.240 | 0.080515 | 9 |
| Eif2d | 1.254 | 0.077442 | 13 | Myeov2 | 1.247 | 0.078686 | 16 | Cotl1 | 1.240 | 0.080515 | 9 |
| Zmiz2 | 1.254 | 0.077442 | 16 | Ints9 | 1.247 | 0.078686 | 14 | Mpv17l2 | 1.240 | 0.080515 | 7 |
| Clpp | 1.254 | 0.077442 | 22 | Myadm | 1.247 | 0.078686 | 16 | Nob1 | 1.240 | 0.080515 | 13 |
| Skiv2l2 | 1.253 | 0.077442 | 10 | Tns3 | 1.247 | 0.078686 | 12 | 1810037I17Rik | 1.240 | 0.080515 | 9 |
| Anp32e | 1.253 | 0.077442 | 15 | Tecr | 1.247 | 0.078686 | 11 | Pno1 | 1.240 | 0.080515 | 9 |
| Wdr46 | 1.253 | 0.077442 | 17 | Pycr2 | 1.247 | 0.078686 | 9 | Kif4 | 1.240 | 0.080515 | 15 |
| Rpn2 | 1.253 | 0.077442 | 12 | Arpc5l | 1.247 | 0.078686 | 10 | Rrp9 | 1.240 | 0.080515 | 14 |
| Bcam | 1.253 | 0.077442 | 8 | Cox5b | 1.247 | 0.078686 | 26 | Ostc | 1.239 | 0.080515 | 10 |
| Abce1 | 1.253 | 0.077442 | 13 | Adap1 | 1.247 | 0.078686 | 11 | Nit2 | 1.239 | 0.080515 | 12 |
| Slc25a12 | 1.253 | 0.077442 | 14 | Lypla2 | 1.246 | 0.078686 | 10 | Ftsj2 | 1.239 | 0.080515 | 12 |
| Anxa5 | 1.253 | 0.077442 | 14 | Hk2 | 1.246 | 0.078686 | 17 | Uchl3 | 1.239 | 0.080515 | 9 |
| Zc3h10 | 1.253 | 0.077442 | 11 | Mrpl40 | 1.246 | 0.078686 | 11 | Yeats4 | 1.239 | 0.080515 | 12 |
| Dnttip2 | 1.253 | 0.077442 | 16 | Msmo1 | 1.246 | 0.078686 | 6 | Dppa3 | 1.239 | 0.080515 | 15 |
| Plscr1 | 1.252 | 0.077442 | 10 | Ndufa8 | 1.246 | 0.078686 | 10 | 1110001J03Rik | 1.239 | 0.080515 | 7 |
| Cdk2ap2 | 1.252 | 0.077442 | 9 | Nifk | 1.246 | 0.078686 | 15 | 2310009B15Rik | 1.239 | 0.080515 | 7 |
| Gm12669 | 1.252 | 0.077442 | 12 | St6galnac2 | 1.246 | 0.078686 | 11 | Atp5c1 | 1.239 | 0.080515 | 22 |
| Smpd1 | 1.252 | 0.077442 | 8 | Nradd | 1.246 | 0.078686 | 13 | Ndufb9 | 1.239 | 0.080515 | 16 |
| Mff | 1.252 | 0.077442 | 11 | Mcts2 | 1.246 | 0.078792 | 8 | Pet112 | 1.239 | 0.080515 | 11 |
| Mogs | 1.252 | 0.077442 | 7 | Crampl1 | 1.246 | 0.078792 | 19 | Egfl7 | 1.238 | 0.080515 | 14 |
| Atp1a1 | 1.252 | 0.077442 | 15 | Nacc1 | 1.246 | 0.078792 | 20 | Taf9 | 1.238 | 0.080515 | 8 |
| Rsrp1 | 1.252 | 0.077442 | 9 | Magoh | 1.246 | 0.078792 | 13 | 2610507B11Rik | 1.238 | 0.080515 | 16 |
| Atpif1 | 1.252 | 0.077442 | 13 | Tspo | 1.246 | 0.078792 | 11 | Arl2 | 1.238 | 0.080515 | 11 |
| Srp9 | 1.252 | 0.077442 | 14 | Prss43 | 1.245 | 0.078792 | 26 | Rabggtb | 1.238 | 0.080515 | 14 |
| Wbp11 | 1.252 | 0.077442 | 16 | Ing1 | 1.245 | 0.078792 | 11 | Mat2a | 1.238 | 0.080515 | 19 |
| Rnf220 | 1.252 | 0.077442 | 11 | Sept11 | 1.245 | 0.078792 | 13 | Avpi1 | 1.238 | 0.080515 | 10 |

| Gene | Val1 | Val2 | Count | Gene | Val1 | Val2 | Count | Gene | Val1 | Val2 | Count |
|---|---|---|---|---|---|---|---|---|---|---|---|
| Dctpp1 | 1.238 | 0.080515 | 20 | Cdk4 | 1.231 | 0.08545 | 13 | Mt3 | 1.224 | 0.089235 | 10 |
| Dctn3 | 1.238 | 0.080999 | 12 | Mtg2 | 1.231 | 0.08545 | 7 | Chmp1a | 1.224 | 0.089235 | 11 |
| Mrps18a | 1.238 | 0.081183 | 9 | Inpp5d | 1.231 | 0.08545 | 11 | Msc | 1.224 | 0.089235 | 10 |
| Slc35a4 | 1.238 | 0.081183 | 11 | Cct2 | 1.231 | 0.08545 | 27 | Mcm4 | 1.224 | 0.089235 | 17 |
| Metap1 | 1.238 | 0.081183 | 11 | Actr3 | 1.231 | 0.08545 | 17 | Ube2d3 | 1.224 | 0.089235 | 17 |
| Mrps10 | 1.237 | 0.081183 | 20 | Top3b | 1.230 | 0.08545 | 10 | Nhp2l1 | 1.224 | 0.089235 | 19 |
| Lmnb1 | 1.237 | 0.081183 | 10 | Ube2g2 | 1.230 | 0.08545 | 9 | Ranbp1 | 1.224 | 0.089235 | 24 |
| Rnf167 | 1.237 | 0.081515 | 23 | Ergic1 | 1.230 | 0.08545 | 12 | Ifrd1 | 1.224 | 0.089235 | 7 |
| Ywhag | 1.237 | 0.081515 | 24 | Ndufa11 | 1.230 | 0.08545 | 18 | Ndufa2 | 1.224 | 0.089235 | 21 |
| Zfp706 | 1.237 | 0.081515 | 7 | Rer1 | 1.230 | 0.08545 | 10 | Pou5f1 | 1.224 | 0.089235 | 55 |
| Plod1 | 1.237 | 0.081515 | 12 | Aco2 | 1.230 | 0.085902 | 14 | Timm17a | 1.224 | 0.089235 | 10 |
| Gtf2f2 | 1.237 | 0.081646 | 10 | Pspc1 | 1.230 | 0.087351 | 9 | Cks1b | 1.224 | 0.089235 | 16 |
| Farp1 | 1.237 | 0.081646 | 11 | Gltscr2 | 1.230 | 0.087351 | 15 | Gmppa | 1.224 | 0.089235 | 9 |
| D8Ertd738e | 1.237 | 0.081646 | 13 | 1700037H04Rik | 1.230 | 0.087351 | 14 | Fbxo45 | 1.224 | 0.089235 | 9 |
| Ndufa12 | 1.237 | 0.081646 | 20 | Mphosph8 | 1.229 | 0.087439 | 11 | Dppa2 | 1.224 | 0.089235 | 12 |
| Jarid2 | 1.237 | 0.081646 | 9 | Urah | 1.229 | 0.087439 | 10 | Orai1 | 1.223 | 0.089235 | 7 |
| Ntmt1 | 1.237 | 0.081646 | 38 | Stk11 | 1.229 | 0.087439 | 10 | Prr5 | 1.223 | 0.089235 | 7 |
| Naca | 1.237 | 0.081646 | 19 | Rpl7l1 | 1.229 | 0.087439 | 48 | Nrbp1 | 1.223 | 0.089235 | 10 |
| Aldoa | 1.236 | 0.081646 | 9 | Aqp3 | 1.229 | 0.087439 | 6 | Uqcrfs1 | 1.223 | 0.089235 | 10 |
| Zswim1 | 1.236 | 0.081646 | 10 | Ascc1 | 1.229 | 0.087439 | 10 | Gm10094 | 1.222 | 0.089235 | 10 |
| Pgs1 | 1.236 | 0.081973 | 11 | Polr2f | 1.229 | 0.087439 | 16 | Josd2 | 1.222 | 0.089235 | 8 |
| Phldb1 | 1.236 | 0.081973 | 8 | Kif11 | 1.229 | 0.087439 | 16 | Ndufb3 | 1.222 | 0.089235 | 8 |
| Cers5 | 1.236 | 0.081973 | 11 | Mapre1 | 1.228 | 0.087439 | 24 | Coq2 | 1.222 | 0.089235 | 9 |
| Cul7 | 1.236 | 0.081973 | 9 | Nr4a1 | 1.228 | 0.087439 | 9 | Upf3a | 1.222 | 0.089235 | 8 |
| Tspan3 | 1.236 | 0.081973 | 12 | Ints5 | 1.228 | 0.087439 | 11 | Pxk | 1.222 | 0.089235 | 13 |
| F2rl1 | 1.236 | 0.082051 | 15 | Uspl1 | 1.228 | 0.087439 | 11 | Pgd | 1.222 | 0.089235 | 17 |
| Lsm3 | 1.236 | 0.082051 | 10 | Usp22 | 1.228 | 0.087439 | 10 | Yars | 1.222 | 0.089235 | 12 |
| Eif2 | 1.236 | 0.082051 | 12 | Rad23b | 1.228 | 0.087439 | 17 | Cdc45 | 1.222 | 0.089235 | 9 |
| Ift20 | 1.236 | 0.082051 | 13 | Eif3l | 1.228 | 0.087439 | 10 | Dnajc11 | 1.222 | 0.089235 | 11 |
| Rev1 | 1.236 | 0.082051 | 10 | Dut | 1.228 | 0.087439 | 15 | Gtf2e2 | 1.222 | 0.089235 | 11 |
| Tbcb | 1.236 | 0.082051 | 11 | Cep89 | 1.228 | 0.087439 | 8 | Tax1bp3 | 1.222 | 0.089235 | 8 |
| Ankrd54 | 1.236 | 0.0820515 | 11 | Tmbim6 | 1.228 | 0.087439 | 17 | Tarbp2 | 1.222 | 0.089235 | 14 |

Fig. 26O

| Gene | Val1 | Val2 | N | Gene | Val1 | Val2 | N | Gene | Val1 | Val2 | N |
|---|---|---|---|---|---|---|---|---|---|---|---|
| Nckap1l | 1.236 | 0.082051 | 11 | Sugt1 | 1.228 | 0.088122 | 11 | Cops5 | 1.222 | 0.089235 | 16 |
| Kcmf1 | 1.236 | 0.082051 | 17 | Fxr2 | 1.228 | 0.088122 | 15 | Lsm6 | 1.222 | 0.089235 | 12 |
| Mkrn1 | 1.236 | 0.082374 | 25 | Zgjp1 | 1.228 | 0.088122 | 8 | Rce1 | 1.222 | 0.089235 | 8 |
| Arhgdia | 1.236 | 0.082374 | 19 | Slc35b1 | 1.228 | 0.088122 | 10 | Gadd45b | 1.222 | 0.089235 | 8 |
| Gldnos | 1.236 | 0.082374 | 19 | H2afv | 1.228 | 0.088122 | 17 | Unc50 | 1.222 | 0.089235 | 9 |
| Tbrg4 | 1.235 | 0.082374 | 18 | Rhot2 | 1.228 | 0.088122 | 8 | Akap8 | 1.222 | 0.089235 | 10 |
| Tjap1 | 1.235 | 0.082374 | 7 | Eif1 | 1.227 | 0.088122 | 35 | Bckdha | 1.221 | 0.089235 | 8 |
| Chmp3 | 1.235 | 0.082426 | 10 | Kdelr1 | 1.227 | 0.088486 | 12 | Isca1 | 1.221 | 0.089235 | 9 |
| Dtnbp1 | 1.235 | 0.082426 | 5 | Unc119 | 1.227 | 0.088486 | 8 | Derl1 | 1.221 | 0.089235 | 10 |
| Nsf | 1.235 | 0.082426 | 15 | Lmnb2 | 1.227 | 0.088486 | 10 | Nusap1 | 1.221 | 0.089235 | 10 |
| Grtp1 | 1.235 | 0.082426 | 8 | Mphosph6 | 1.227 | 0.088486 | 11 | Abtb1 | 1.221 | 0.089235 | 8 |
| Supt5 | 1.235 | 0.082426 | 17 | Hmgn2 | 1.227 | 0.088486 | 15 | Evi5 | 1.221 | 0.089235 | 24 |
| Morf4l1 | 1.235 | 0.082426 | 27 | Hsdl1 | 1.227 | 0.088486 | 12 | Lpar6 | 1.221 | 0.089235 | 9 |
| Tcf3 | 1.235 | 0.082426 | 11 | Dnmt1 | 1.227 | 0.088486 | 8 | Rgs19 | 1.221 | 0.089235 | 12 |
| Enoph1 | 1.235 | 0.082426 | 9 | Rdh14 | 1.227 | 0.088486 | 10 | Eprs | 1.221 | 0.089235 | 16 |
| Pole4 | 1.235 | 0.082426 | 14 | Isca2 | 1.227 | 0.088486 | 11 | Oser1 | 1.221 | 0.089235 | 8 |
| Prelid1 | 1.234 | 0.082426 | 23 | Tmem126a | 1.226 | 0.088486 | 15 | 3110062M04Rik | 1.221 | 0.089235 | 8 |
| Atxn10 | 1.234 | 0.082426 | 14 | Dhrs4 | 1.226 | 0.088486 | 12 | 2700060E02Rik | 1.221 | 0.089235 | 20 |
| Ppp2r2a | 1.234 | 0.082426 | 18 | Mak16 | 1.226 | 0.088486 | 14 | Tagap1 | 1.221 | 0.089235 | 7 |
| Slc39a7 | 1.234 | 0.082426 | 11 | Ddx24 | 1.226 | 0.088486 | 13 | Tmem192 | 1.221 | 0.089235 | 7 |
| U2af2 | 1.234 | 0.082426 | 15 | Pvrl2 | 1.226 | 0.088486 | 7 | Trappc2l | 1.220 | 0.089235 | 8 |
| BC030867 | 1.234 | 0.082426 | 10 | Man2c1 | 1.226 | 0.088486 | 6 | Tbx3 | 1.220 | 0.089235 | 18 |
| Ccndbp1 | 1.234 | 0.082426 | 7 | Creld1 | 1.226 | 0.088486 | 11 | Adipor2 | 1.220 | 0.089235 | 16 |
| Bod1 | 1.233 | 0.082426 | 9 | Lgsn | 1.226 | 0.088486 | 10 | Dpm3 | 1.220 | 0.089235 | 10 |
| Dctd | 1.233 | 0.082426 | 9 | Uck2 | 1.226 | 0.088486 | 11 | Ddx41 | 1.220 | 0.089235 | 8 |
| Tpm1 | 1.233 | 0.082426 | 15 | Ldlrap1 | 1.226 | 0.088486 | 11 | Tmem69 | 1.220 | 0.089235 | 12 |
| Chchd1 | 1.233 | 0.082426 | 10 | Ndufv3 | 1.226 | 0.088486 | 8 | Hadh | 1.220 | 0.089235 | 9 |
| Preb | 1.233 | 0.082938 | 10 | Banf1 | 1.226 | 0.088486 | 9 | Gstf2t | 1.220 | 0.089235 | 21 |
| Taldo1 | 1.233 | 0.083351 | 14 | Phb | 1.225 | 0.088486 | 15 | Vps36 | 1.220 | 0.089235 | 7 |
| Cox5a | 1.233 | 0.083351 | 27 | Prkar1a | 1.225 | 0.088919 | 8 | Acads | 1.220 | 0.089235 | 10 |
| Myo1c | 1.233 | 0.083351 | 17 | Timm8a1 | 1.225 | 0.088919 | 7 | Cacybp | 1.220 | 0.089235 | 17 |
| Hs6st1 | 1.233 | 0.084271 | 14 | Rps6ka1 | 1.225 | 0.089235 | 10 | Tjp2 | 1.220 | 0.089235 | 13 |

Fig. 26P

| Gene | Val1 | Val2 | Count | Gene | Val1 | Val2 | Count | Gene | Val1 | Val2 | Count |
|---|---|---|---|---|---|---|---|---|---|---|---|
| Polr2d | 1.233 | 0.084271 | 9 | Trmt6 | 1.225 | 0.089235 | 12 | Mad2l2 | 1.220 | 0.089235 | 10 |
| Mrpl33 | 1.232 | 0.084271 | 10 | Dmwd | 1.225 | 0.089235 | 9 | Pdk1 | 1.220 | 0.089235 | 16 |
| Gadd45a | 1.232 | 0.084271 | 9 | Ndufaf3 | 1.225 | 0.089235 | 7 | Nop14 | 1.220 | 0.089235 | 13 |
| Fdps | 1.232 | 0.084581 | 12 | Rassf7 | 1.225 | 0.089235 | 9 | Asna1 | 1.220 | 0.089235 | 13 |
| Orc2 | 1.232 | 0.084581 | 17 | Gtf2i | 1.225 | 0.089235 | 11 | Taf13 | 1.220 | 0.089235 | 8 |
| Fam207a | 1.232 | 0.084581 | 14 | Baz2b | 1.225 | 0.089235 | 17 | Ube2e3 | 1.219 | 0.089235 | 11 |
| Smg7 | 1.232 | 0.084581 | 10 | Scgb3a1 | 1.225 | 0.089235 | 8 | Rnf25 | 1.219 | 0.089235 | 9 |
| Haus1 | 1.231 | 0.08545 | 9 | Egln2 | 1.225 | 0.089235 | 10 | Angptl4 | 1.219 | 0.089235 | 7 |
| Snrpg | 1.231 | 0.08545 | 38 | Naa38 | 1.225 | 0.089235 | 17 | Csnk1a1 | 1.219 | 0.089235 | 10 |
| Ddx39 | 1.231 | 0.08545 | 15 | Grb7 | 1.224 | 0.089235 | 10 | Gns | 1.219 | 0.089235 | 8 |
| Glrx3 | 1.231 | 0.08545 | 15 | Ndufs8 | 1.224 | 0.089235 | 9 | Snord64 | 1.219 | 0.089235 | 4 |
| Tsen15 | 1.231 | 0.08545 | 8 | Wdr83 | 1.224 | 0.089235 | 9 | Pdcd5 | 1.219 | 0.089235 | 14 |
| Stt3a | 1.219 | 0.089235 | 12 | Etf1 | 1.213 | 0.089235 | 16 | Sqle | 1.208 | 0.092108 | 8 |
| Rab3gap1 | 1.219 | 0.089235 | 20 | Dctn1 | 1.213 | 0.089235 | 12 | Rab3ip | 1.208 | 0.092108 | 10 |
| Dync1i2 | 1.219 | 0.089235 | 11 | Arih2 | 1.213 | 0.089235 | 14 | Slc25a28 | 1.207 | 0.092108 | 9 |
| Champ1 | 1.219 | 0.089235 | 10 | Nck1 | 1.213 | 0.089235 | 7 | Srf | 1.207 | 0.092108 | 9 |
| Exosc5 | 1.219 | 0.089235 | 11 | Bst2 | 1.213 | 0.089235 | 8 | Pisd-ps3 | 1.207 | 0.092108 | 6 |
| Ascc2 | 1.219 | 0.089235 | 8 | Ppp1r10 | 1.212 | 0.089235 | 9 | E430025E21Rik | 1.207 | 0.092108 | 12 |
| Cnot10 | 1.219 | 0.089235 | 17 | Smyd2 | 1.212 | 0.089235 | 10 | Mrpl15 | 1.207 | 0.092108 | 21 |
| Mrps17 | 1.218 | 0.089235 | 8 | Cpsf3l | 1.212 | 0.089235 | 13 | Echs1 | 1.207 | 0.092108 | 8 |
| Tma16 | 1.218 | 0.089235 | 10 | Smad4 | 1.212 | 0.089235 | 11 | Fmnl3 | 1.206 | 0.092108 | 8 |
| Gprc5a | 1.218 | 0.089235 | 11 | Klc3 | 1.212 | 0.089235 | 9 | Mbtd1 | 1.206 | 0.092108 | 11 |
| Dok2 | 1.218 | 0.089235 | 9 | 4930444M15Rik | 1.212 | 0.089235 | 9 | Atp5d | 1.206 | 0.092108 | 21 |
| Snrpa | 1.218 | 0.089235 | 18 | Ccnt1 | 1.212 | 0.089235 | 7 | Crls1 | 1.206 | 0.092108 | 11 |
| Rnf115 | 1.218 | 0.089235 | 10 | Atrx | 1.212 | 0.089235 | 17 | Exosc6 | 1.206 | 0.092108 | 10 |
| Eml2 | 1.218 | 0.089235 | 9 | Rbbp7 | 1.212 | 0.089235 | 12 | Pcbp4 | 1.206 | 0.092108 | 8 |
| Cox6b2 | 1.218 | 0.089235 | 8 | Mbnl2 | 1.212 | 0.089235 | 12 | Psme4 | 1.206 | 0.092108 | 20 |
| Prdm15 | 1.217 | 0.089235 | 14 | Phlda1 | 1.212 | 0.089235 | 11 | Syf2 | 1.206 | 0.092108 | 11 |
| Itga3 | 1.217 | 0.089235 | 11 | Rbm17 | 1.212 | 0.089235 | 12 | Nkain1 | 1.206 | 0.092108 | 21 |
| Rnf126 | 1.217 | 0.089235 | 13 | Tox4 | 1.212 | 0.089235 | 16 | Psmd3 | 1.206 | 0.092108 | 19 |
| Idh3b | 1.217 | 0.089235 | 10 | Srp72 | 1.212 | 0.089235 | 11 | Srp68 | 1.206 | 0.092108 | 12 |
| Cisd1 | 1.217 | 0.089235 | 10 | Uqcrq | 1.212 | 0.089235 |  | Mrps21 | 1.206 | 0.092108 | 10 |

Fig. 26Q

| Gene | Ratio | p-value | N | Gene | Ratio | p-value | N | Gene | Ratio | p-value | N |
|---|---|---|---|---|---|---|---|---|---|---|---|
| Fam107b | 1.217 | 0.089235 | 10 | Mreg | 1.212 | 0.089235 | 11 | Lasp1 | 1.206 | 0.092108 | 15 |
| Eif4e | 1.217 | 0.089235 | 12 | Epm2aip1 | 1.211 | 0.089235 | 22 | Otx2 | 1.206 | 0.092108 | 8 |
| Aars | 1.217 | 0.089235 | 12 | Zscan10 | 1.211 | 0.089235 | 10 | Amn | 1.206 | 0.092108 | 9 |
| Nsf1c | 1.217 | 0.089235 | 11 | Lmo4 | 1.211 | 0.089235 | 15 | 2510039O18Rik | 1.206 | 0.092108 | 9 |
| Nup43 | 1.217 | 0.089235 | 10 | Cenph | 1.211 | 0.089235 | 9 | Dbf4 | 1.206 | 0.092108 | 13 |
| Mrps16 | 1.217 | 0.089235 | 15 | Fgfr1 | 1.211 | 0.089235 | 11 | Triml2 | 1.206 | 0.092108 | 8 |
| Psmg4 | 1.216 | 0.089235 | 8 | Apmap | 1.211 | 0.089235 | 10 | Hagh | 1.206 | 0.092108 | 10 |
| Zmat2 | 1.216 | 0.089235 | 13 | E2f6 | 1.211 | 0.089235 | 10 | Pigp | 1.206 | 0.092108 | 27 |
| Fxyd6 | 1.216 | 0.089235 | 11 | Thap7 | 1.211 | 0.089235 | 13 | LOC101056043 | 1.205 | 0.092108 | 10 |
| Mcm3 | 1.216 | 0.089235 | 21 | Itga6 | 1.211 | 0.089235 | 8 | Glo1 | 1.205 | 0.092108 | 16 |
| Rtn4 | 1.216 | 0.089235 | 14 | Tppp3 | 1.211 | 0.089235 | 18 | Tnfrsf12a | 1.205 | 0.092384 | 8 |
| Frat2 | 1.216 | 0.089235 | 10 | Ube2m | 1.211 | 0.089235 | 13 | Taf12 | 1.205 | 0.092384 | 8 |
| Adss | 1.216 | 0.089235 | 14 | Gm13051 | 1.211 | 0.089352 | 15 | Tssc4 | 1.205 | 0.092384 | 10 |
| Gemin2 | 1.216 | 0.089235 | 9 | Nsun2 | 1.211 | 0.089352 | 3 | Ptdss2 | 1.205 | 0.092583 | 9 |
| Cct3 | 1.216 | 0.089235 | 29 | Snora73b | 1.211 | 0.089352 | 13 | Ciapin1 | 1.205 | 0.092583 | 21 |
| Copa | 1.216 | 0.089235 | 15 | Gm5801 | 1.210 | 0.089352 | 42 | Hint2 | 1.204 | 0.092583 | 8 |
| Shfm1 | 1.216 | 0.089235 | 20 | Tubb4b | 1.210 | 0.089352 | 9 | Znhit3 | 1.204 | 0.092583 | 11 |
| Lamtor5 | 1.215 | 0.089235 | 10 | Slc25a33 | 1.210 | 0.089352 | 10 | Ola1 | 1.204 | 0.092583 | 14 |
| Rcn1 | 1.215 | 0.089235 | 12 | Strip1 | 1.210 | 0.090159 | 26 | Lamtor3 | 1.204 | 0.092583 | 8 |
| Rras2 | 1.215 | 0.089235 | 9 | Chd4 | 1.210 | 0.090584 | 43 | Cct7 | 1.204 | 0.092583 | 31 |
| Khdrbs3 | 1.215 | 0.089235 | 9 | Tuba1a | 1.210 | 0.09065 | 8 | Faf1 | 1.204 | 0.092583 | 11 |
| Rab1 | 1.215 | 0.089235 | 12 | Taf1c | 1.210 | 0.09065 | 11 | Emc4 | 1.204 | 0.092583 | 8 |
| Psme1 | 1.215 | 0.089235 | 7 | Ncapg | 1.210 | 0.09065 | 9 | Tyro3 | 1.204 | 0.092583 | 16 |
| Ap1m1 | 1.215 | 0.089235 | 9 | Dpp3 | 1.210 | 0.09065 | 9 | Dpp9 | 1.204 | 0.092583 | 9 |
| Vps28 | 1.215 | 0.089235 | 7 | Myd88 | 1.210 | 0.09065 | 17 | Phlda2 | 1.204 | 0.092583 | 6 |
| Rtca | 1.215 | 0.089235 | 8 | Snrnp200 | 1.210 | 0.09065 | 11 | Ap4s1 | 1.204 | 0.092583 | 7 |
| Fars2 | 1.215 | 0.089235 | 10 | Folr1 | 1.209 | 0.09065 | 9 | Ttc1 | 1.204 | 0.092583 | 8 |
| Phtf2 | 1.215 | 0.089235 | 12 | Mrps28 | 1.209 | 0.09065 | 11 | Ccnf | 1.204 | 0.092583 | 10 |
| Cd2bp2 | 1.215 | 0.089235 | 12 | Lrch4 | 1.209 | 0.090849 | 8 | Noc2l | 1.203 | 0.092811 | 12 |
| Nudt4 | 1.215 | 0.089235 | 12 | Cd151 | 1.209 | 0.090849 | 8 | Gadd45g | 1.203 | 0.092811 | 9 |
| Fam13b | 1.215 | 0.089235 | 8 | Mcts1 | 1.209 | 0.090849 | 22 | Numa1 | 1.203 | 0.092811 | 15 |
| Ap2b1 | 1.215 | 0.089235 | 13 | Nudc | 1.209 | 0.090849 | | Ssbp3 | 1.203 | 0.092811 | 13 |

Fig. 26R

| Gene | | | | Gene | | | | Gene | | | |
|---|---|---|---|---|---|---|---|---|---|---|---|
| Rraga | 1.215 | 0.089235 | 9 | Phyhd1 | 1.209 | 0.090849 | 12 | Mrpl37 | 1.203 | 0.093266 | 10 |
| Tmem41a | 1.215 | 0.089235 | 8 | Mtfmt | 1.209 | 0.091736 | 20 | Xrcc6 | 1.203 | 0.093266 | 10 |
| Msantd3 | 1.215 | 0.089235 | 8 | Hdgfrp2 | 1.209 | 0.091842 | 12 | Ap2a2 | 1.203 | 0.093266 | 12 |
| Zdhhc9 | 1.215 | 0.089235 | 8 | Mapk13 | 1.209 | 0.091842 | 13 | Mbtps1 | 1.203 | 0.093266 | 12 |
| Aven | 1.214 | 0.089235 | 9 | Lman2 | 1.209 | 0.091842 | 13 | Atp5j | 1.203 | 0.093266 | 17 |
| Ralbp1 | 1.214 | 0.089235 | 14 | 1500011K16Rik | 1.209 | 0.091842 | 10 | Akirin1 | 1.203 | 0.093266 | 11 |
| Pdcd6 | 1.214 | 0.089235 | 8 | Tmem134 | 1.209 | 0.091842 | 10 | Rnps1 | 1.203 | 0.093266 | 15 |
| Sptan1 | 1.214 | 0.089235 | 19 | Wdr3 | 1.209 | 0.091842 | 11 | Fam192a | 1.203 | 0.093266 | 8 |
| Gnb2 | 1.214 | 0.089235 | 18 | Bloc1s4 | 1.209 | 0.091842 | 7 | Jak3 | 1.203 | 0.093623 | 9 |
| Ptpn6 | 1.214 | 0.089235 | 8 | Ppp5c | 1.209 | 0.091842 | 12 | Tars | 1.203 | 0.093623 | 15 |
| Plekhj1 | 1.214 | 0.089235 | 9 | Mdk | 1.208 | 0.092006 | 12 | Sept2 | 1.203 | 0.09376 | 18 |
| Vmn2r15 | 1.214 | 0.089235 | 7 | Cog4 | 1.208 | 0.092006 | 9 | Cnih1 | 1.202 | 0.09376 | 10 |
| Jam3 | 1.214 | 0.089235 | 9 | 2410003L11Rik | 1.208 | 0.092006 | 6 | Zic3 | 1.202 | 0.09376 | 17 |
| Rbm19 | 1.214 | 0.089235 | 12 | Ddx50 | 1.208 | 0.092006 | 13 | Zfp428 | 1.202 | 0.09376 | 10 |
| H1f0 | 1.214 | 0.089235 | 8 | Selk | 1.208 | 0.092006 | 10 | FoxK2 | 1.202 | 0.09376 | 11 |
| Ddx54 | 1.214 | 0.089235 | 11 | Ddah1 | 1.208 | 0.092006 | 13 | Txndc15 | 1.202 | 0.094119 | 7 |
| Tmem115 | 1.214 | 0.089235 | 8 | Fem1b | 1.208 | 0.092006 | 15 | Mcm10 | 1.202 | 0.094119 | 11 |
| Klk8 | 1.214 | 0.089235 | 9 | Ilf2 | 1.208 | 0.092006 | 10 | Rmnd5a | 1.202 | 0.094119 | 16 |
| Ankfy1 | 1.214 | 0.089235 | 30 | St14 | 1.208 | 0.092006 | 13 | Arfgap1 | 1.202 | 0.094119 | 9 |
| Rnh1 | 1.214 | 0.089235 | 8 | Klhl13 | 1.208 | 0.092006 | 9 | D2Wsu81e | 1.202 | 0.094119 | 7 |
| Sfswap | 1.214 | 0.089235 | 9 | Eif3f | 1.208 | 0.092006 | 15 | Rae1 | 1.202 | 0.094119 | 14 |
| Scrib | 1.213 | 0.089235 | 15 | Sucla2 | 1.208 | 0.092006 | 9 | Mrpl11 | 1.202 | 0.094119 | 13 |
| Asrgl1 | 1.213 | 0.089235 | 7 | Smdt1 | 1.208 | 0.092006 | 14 | Timp1 | 1.202 | 0.094119 | 7 |
| Ctbp2 | 1.213 | 0.089235 | 19 | Nfatc2ip | 1.208 | 0.092006 | 15 | Ckap2l | 1.202 | 0.094119 | 7 |
| Ttc13 | 1.202 | 0.094119 | 8 | Mrps33 | 1.197 | 0.095294 | 12 | Nicn1 | 1.192 | 0.099753 | 8 |
| Ccna2 | 1.202 | 0.094119 | 12 | Timm22 | 1.197 | 0.095294 | 10 | Nfu1 | 1.192 | 0.099753 | 7 |
| Fam63a | 1.202 | 0.094119 | 10 | Lrwd1 | 1.197 | 0.095294 | 8 | Rhox6 | 1.192 | 0.099753 | 6 |
| Pafah1b3 | 1.202 | 0.094119 | 7 | Mien1 | 1.197 | 0.095294 | 10 | Vps4a | 1.192 | 0.099753 | 9 |
| Dpm2 | 1.201 | 0.094253 | 10 | Golph3 | 1.197 | 0.095294 | 8 | Zdhhc16 | 1.192 | 0.099753 | 9 |
| Dhcr24 | 1.201 | 0.094253 | 13 | Srsf7 | 1.197 | 0.095294 | 17 | Plp2 | 1.191 | 0.099753 | 12 |
| Uqcrc2 | 1.201 | 0.094253 | 15 | Dqx1 | 1.197 | 0.095294 | 12 | Crl1 | 1.191 | 0.099753 | 9 |
| Myo10 | 1.201 | 0.094253 | 11 | Ncbp1 | 1.197 | 0.095294 | 9 | Zfp330 | 1.191 | 0.099753 | 9 |

Fig. 26S

| Gene | Ratio | p-value | N | Gene | Ratio | p-value | N | Gene | Ratio | p-value | N |
|---|---|---|---|---|---|---|---|---|---|---|---|
| Clasrp | 1.201 | 0.094253 | 10 | Grpel1 | 1.196 | 0.095294 | 12 | Elf3 | 1.191 | 0.099753 | 10 |
| Pstk | 1.201 | 0.094253 | 9 | Mpc2 | 1.196 | 0.095294 | 9 | Tomm34 | 1.191 | 0.099753 | 9 |
| Rbm14 | 1.201 | 0.094399 | 8 | Smc4 | 1.196 | 0.095294 | 11 | Fam110a | 1.191 | 0.099753 | 11 |
| Brd2 | 1.201 | 0.094399 | 20 | Rcc2 | 1.196 | 0.095294 | 29 | Dguok | 1.191 | 0.099753 | 8 |
| Fastk | 1.201 | 0.094399 | 9 | BC005624 | 1.196 | 0.095294 | 11 | Cdkal1 | 1.191 | 0.099753 | 9 |
| Sec63 | 1.201 | 0.094399 | 13 | Mrpl22 | 1.196 | 0.095294 | 7 | 1110007C09Rik | 1.191 | 0.099753 | 7 |
| Flot2 | 1.201 | 0.094399 | 9 | Naa10 | 1.196 | 0.095294 | 11 | Ncoa5 | 1.191 | 0.099753 | 10 |
| Tmem259 | 1.201 | 0.094399 | 14 | Mrps18b | 1.196 | 0.095294 | 12 | Anxa11 | 1.191 | 0.099753 | 7 |
| Mob4 | 1.201 | 0.094399 | 12 | Enah | 1.196 | 0.095294 | 20 | Sirt4 | 1.191 | 0.099753 | 8 |
| Dnajc15 | 1.201 | 0.094399 | 7 | Rbbp5 | 1.196 | 0.095459 | 9 | Hmbs | 1.191 | 0.099753 | 9 |
| Trim35 | 1.201 | 0.094399 | 10 | Fam96a | 1.196 | 0.095459 | 8 | Anxa3 | 1.191 | 0.099753 | 10 |
| Pla2g1b | 1.201 | 0.094399 | 7 | Gm5860 | 1.196 | 0.095459 | 21 | Ppp1cc | 1.191 | 0.099753 | 18 |
| Asun | 1.200 | 0.094399 | 17 | Arglu1 | 1.196 | 0.095459 | 11 | Fbxo42 | 1.190 | 0.099753 | 13 |
| Mtap | 1.200 | 0.094399 | 10 | Rpusd4 | 1.196 | 0.095459 | 7 | Ufc1 | 1.190 | 0.099753 | 11 |
| Znhit1 | 1.200 | 0.094399 | 9 | Anp32b | 1.196 | 0.095459 | 26 | Nt5dc2 | 1.190 | 0.099753 | 8 |
| Pepd | 1.200 | 0.094399 | 10 | Tmx2 | 1.196 | 0.095459 | 12 | Fh1 | 1.190 | 0.099753 | 8 |
| Ngdn | 1.200 | 0.094399 | 8 | Mettl9 | 1.196 | 0.095459 | 8 | Polr2c | 1.190 | 0.099753 | 12 |
| Coq6 | 1.200 | 0.094399 | 7 | Med28 | 1.196 | 0.095459 | 15 | Vdac2 | 1.190 | 0.099753 | 23 |
| Grwd1 | 1.200 | 0.094399 | 10 | Mcm2 | 1.196 | 0.095459 | 20 | Atxn7l3b | 1.190 | 0.099753 | 15 |
| Fig4 | 1.200 | 0.094399 | 11 | Get4 | 1.196 | 0.095459 | 15 | Afg3l2 | 1.190 | 0.099753 | 9 |
| Cox20 | 1.200 | 0.094399 | 9 | Tcf15 | 1.195 | 0.095459 | 9 | Tex13 | 1.190 | 0.099753 | 12 |
| Abcg2 | 1.200 | 0.094399 | 9 | Ubr7 | 1.195 | 0.095459 | 11 | Mrto4 | 1.190 | 0.099753 | 10 |
| Ntpcr | 1.200 | 0.094399 | 7 | Srsf3 | 1.195 | 0.095459 | 21 | Tspyl2 | 1.190 | 0.099753 | 8 |
| Canx | 1.200 | 0.094399 | 20 | Xbp1 | 1.195 | 0.096124 | 11 | Otulin | 1.190 | 0.099753 | 8 |
| Ptbp1 | 1.200 | 0.094399 | 29 | Phyh | 1.195 | 0.096124 | 8 | Mrps11 | 1.190 | 0.099753 | 8 |
| Etaa1 | 1.200 | 0.094399 | 12 | Ddah2 | 1.195 | 0.096372 | 8 | Vkorc1 | 1.190 | 0.099753 | 9 |
| Atad3a | 1.200 | 0.094399 | 13 | Rbm39 | 1.195 | 0.096372 | 16 | Ppp1r15b | 1.190 | 0.099753 | 13 |
| Taf10 | 1.199 | 0.094399 | 9 | Rap1b | 1.195 | 0.096372 | 10 | Ngrn | 1.190 | 0.099753 | 9 |
| Klhl21 | 1.199 | 0.094399 | 14 | Basp1 | 1.195 | 0.096372 | 12 | H3f3a | 1.190 | 0.099753 | 25 |
| Zcrb1 | 1.199 | 0.094399 | 11 | Alg3 | 1.195 | 0.09666 | 9 | Cwc15 | 1.189 | 0.099753 | 10 |
| Mrpl18 | 1.199 | 0.094399 | 13 | Nr0b1 | 1.195 | 0.09666 | 7 | Grb2 | 1.189 | 0.099753 | 16 |
| Sdf2l1 | 1.199 | 0.094399 | 12 | Polg | 1.194 | 0.096948 | 9 | Loxl2 | 1.189 | 0.099753 | 28 |

Fig. 26T

| Gene | Value1 | Value2 | Count | Gene | Value1 | Value2 | Count | Gene | Value1 | Value2 | Count |
|---|---|---|---|---|---|---|---|---|---|---|---|
| Athl1 | 1.199 | 0.094399 | 12 | Rpp25l | 1.194 | 0.096948 | 9 | Snx32 | 1.189 | 0.099753 | 8 |
| Cmtm6 | 1.199 | 0.094399 | 12 | Lin37 | 1.194 | 0.096948 | 5 | Npdc1 | 1.189 | 0.099753 | 8 |
| Emc3 | 1.199 | 0.094399 | 9 | R3hdm4 | 1.194 | 0.097607 | 8 | 2310011J03Rik | 1.189 | 0.099753 | 9 |
| Metrn | 1.199 | 0.094399 | 7 | Gemin4 | 1.194 | 0.097607 | 10 | Zfp936 | 1.189 | 0.099753 | 8 |
| Thoc7 | 1.199 | 0.094399 | 13 | BC052040 | 1.194 | 0.097607 | 9 | Pdap1 | 1.189 | 0.099753 | 26 |
| Prc1 | 1.199 | 0.094399 | 9 | Zfp598 | 1.194 | 0.097607 | 8 | Rgs2 | 1.189 | 0.099753 | 13 |
| Srm1 | 1.199 | 0.094399 | 17 | Prmt1 | 1.194 | 0.097935 | 20 | Cdc34 | 1.189 | 0.099753 | 22 |
| Glt25d1 | 1.199 | 0.094399 | 11 | Rfc3 | 1.194 | 0.097935 | 11 | Dgkd | 1.189 | 0.099753 | 9 |
| Hars | 1.199 | 0.094399 | 13 | Cops4 | 1.194 | 0.09805 | 12 | Snord47 | 1.189 | 0.099753 | 5 |
| Rexo4 | 1.199 | 0.094399 | 10 | Aplp2 | 1.194 | 0.09805 | 12 | Tagln3 | 1.189 | 0.099753 | 6 |
| Lpar5 | 1.199 | 0.094399 | 9 | Mrps18c | 1.194 | 0.09805 | 8 | Gm12504 | 1.189 | 0.099753 | 41 |
| Rab40c | 1.198 | 0.094616 | 12 | Pnpo | 1.194 | 0.09805 | 11 | Lamtor1 | 1.189 | 0.099753 | 13 |
| Cnot2 | 1.198 | 0.094616 | 15 | Vat1 | 1.193 | 0.09805 | 9 | Suds3 | 1.189 | 0.099753 | 11 |
| Thop1 | 1.198 | 0.094616 | 9 | Nkiras2 | 1.193 | 0.09805 | 9 | Prdx5 | 1.189 | 0.099753 | 7 |
| Rad17 | 1.198 | 0.094616 | 9 | Etfb | 1.193 | 0.09805 | 11 | Gar1 | 1.189 | 0.099753 | 15 |
| Rela | 1.198 | 0.094616 | 9 | Esyt1 | 1.193 | 0.098419 | 9 | 1110065P20Rik | 1.188 | 0.099753 | 7 |
| Syce1 | 1.198 | 0.094616 | 8 | Tatdn2 | 1.193 | 0.098985 | 9 | Adck4 | 1.188 | 0.099753 | 8 |
| Jkamp | 1.198 | 0.094616 | 9 | Zfp787 | 1.193 | 0.098985 | 10 | Mrpl10 | 1.188 | 0.099753 | 10 |
| Rbm38 | 1.198 | 0.094616 | 9 | Sdhd | 1.193 | 0.098985 | 11 | Cpsf4 | 1.188 | 0.099921 | 9 |
| Bckdhb | 1.198 | 0.094616 | 7 | Vars | 1.193 | 0.098985 | 12 | Pbdc1 | 1.188 | 0.099921 | 22 |
| Mfsd10 | 1.198 | 0.094616 | 8 | Abcf1 | 1.193 | 0.098985 | 14 | Gcfm | 1.188 | 0.099921 | 12 |
| Mthfd1 | 1.198 | 0.094616 | 13 | Prkab1 | 1.193 | 0.099182 | 9 | Fam136a | 1.188 | 0.099921 | 10 |
| Exosc4 | 1.198 | 0.094616 | 12 | Khsrp | 1.193 | 0.099182 | 17 | Mlh1 | 1.188 | 0.099921 | 7 |
| Uqcrc1 | 1.198 | 0.094618 | 15 | Acvr2b | 1.192 | 0.099182 | 7 | Usp48 | 1.188 | 0.099921 | 11 |
| Zc3h15 | 1.198 | 0.094618 | 13 | Nr1h4 | 1.192 | 0.099182 | 9 | Dctn2 | 1.188 | 0.099921 | 14 |
| Ccdc181 | 1.198 | 0.094618 | 8 | Ccdc166 | 1.192 | 0.09942 | 7 | Timeless | 1.188 | 0.099921 | 14 |
| Fbxw11 | 1.198 | 0.094618 | 14 | Ehd4 | 1.192 | 0.09942 | 10 | U2af1l4 | 1.188 | 0.099921 | 8 |
| Rrbp1 | 1.198 | 0.094618 | 16 | Sec11a | 1.192 | 0.09942 | 14 | Snhg8 | 1.187 | 0.099921 | 12 |
| Mzt2 | 1.198 | 0.094618 | 9 | Cpsf1 | 1.192 | 0.09942 | 10 | Cdc42 | 1.187 | 0.099921 | 22 |
| Surf2 | 1.198 | 0.094618 | 7 | Ecd | 1.192 | 0.099753 | 13 | Hint1 | 1.187 | 0.099921 | 26 |
| Las1l | 1.198 | 0.094618 | 15 | Mrps6 | 1.192 | 0.099753 | 7 | Arpc3 | 1.187 | 0.099921 | 10 |
| Pla2g6 | 1.198 | 0.094618 | 12 | Hsf1 | 1.192 | 0.099753 | 9 | Mfap3 | 1.187 | 0.099921 | 18 |

Fig. 26U

| | | | | | | |
|---|---|---|---|---|---|---|
| Mknk2 | 1.198 | 0.094618 | 8 | Wdr45 | 1.192 | 0.099753 | 11 | Nif3l1 | 1.187 | 0.099921 | 12 |
| Ttc27 | 1.198 | 0.094958 | 11 | Smarca4 | 1.192 | 0.099753 | 14 | Pdia4 | 1.187 | 0.099921 | 9 |
| Ppp2r5d | 1.197 | 0.094958 | 13 | Sar1a | 1.192 | 0.099753 | 16 | Tmem160 | 1.187 | 0.099921 | 8 |
| Prpf38a | 1.197 | 0.095294 | 8 | Csnk2a1 | 1.192 | 0.099921 | 24 | Hhex | 1.187 | 0.099921 | 9 |
| Abcf2 | 1.187 | 0.099921 | 15 | Mbip | 1.186 | 0.099921 | 7 | Nt5c | 1.186 | 0.099921 | 7 |
| Manba1 | 1.187 | 0.099921 | 10 | Trmt61a | 1.186 | 0.099921 | 7 | | | | |
| Fis1 | 1.186 | 0.099921 | 10 | Ppp1r18 | 1.186 | 0.099921 | 8 | | | | |
| Pgrmc1 | 1.186 | 0.099921 | 8 | Gm6792 | 1.186 | 0.099921 | 6 | | | | |

Fig. 26V

SEQUENCE LISTING

```
<160> NUMBER OF SEQ ID NOS: 17

<210> SEQ ID NO 1
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 1
cgatgacgtt atacgactca ctatagggat accaccatgg ctctttccct acacgacgct    60
cttc                                                                 64

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 2
taatacgact cactataggg                                                20

<210> SEQ ID NO 3
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 3
ctctttccct acacgacgct cttc                                           24

<210> SEQ ID NO 4
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 4
aaggcgtcac aagcaatcac tc                                             22

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 5
tttttttttt tttttttttv                                                20

<210> SEQ ID NO 6
<211> LENGTH: 134
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (71)..(78)
<223> OTHER INFORMATION: n is any nucleotide
<220> FEATURE:
<221> NAME/KEY: misc_feature
<222> LOCATION: (101)..(114)
<223> OTHER INFORMATION: n is any nucleotide
```

<400> SEQUENCE: 6
cgatgacgta atacgactca ctagggat accaccatgg ctctttccct acacgacgct    60
cttccgatct nnnnnnnnaa ggcgtcacaa gcaatcactc nnnnnnnnnn nnnntttttt   120
tttttttttt tttv                                                    134

<210> SEQ ID NO 7
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 7
cgatgacgta atacgactca ctagggat accaccatgg ctctttccct acacgacgct    60
cttc                                                               64

<210> SEQ ID NO 8
<211> LENGTH: 63
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (23)..(33)
<223> OTHER INFORMATION: n is any nucleotide

<400> SEQUENCE: 8
aaggcgtcac aagcaatcac tcnnnnnnnn nnnagatcgg aagagcgtcg tgtagggaaa    60
gag                                                                 63

<210> SEQ ID NO 9
<211> LENGTH: 56
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(34)
<223> OTHER INFORMATION: n is any nucleotide

<400> SEQUENCE: 9
baaaaaaaaa aaaaaaaaaa nnnnnnnnnn nnnnaaggcg tcacaagcaa tcactc        56

<210> SEQ ID NO 10
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 10
agatcggaag agcgtcgtgt agggaaagag                                    30

<210> SEQ ID NO 11
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 11

```
aaggcgtcac aagcaatcac tc                                               22

<210> SEQ ID NO 12
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 12
aaaaaaaaaa aaaaaaaaaa                                                  20

<210> SEQ ID NO 13
<211> LENGTH: 136
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (71)..(80)
<223> OTHER INFORMATION: n is any nucleotide
<220> FEATURE:
<221> NAME/KEY: misc_feature
<222> LOCATION: (103)..(116)
<223> OTHER INFORMATION: n is any nucleotide

<400> SEQUENCE: 13
cgatgacgta atacgactca ctatagggat accaccatgg ctctttccct acacgacgct      60
cttccgatct nnnnnnnnnn gagtgattgc ttgtgacgcc ttnnnnnnnn nnnnnntttt     120
tttttttttt tttttv                                                    136

<210> SEQ ID NO 14
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 14
agatcggaag agcggttcag caggaatgcc                                       30

<210> SEQ ID NO 15
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 15
gtctcggcat tcctgctgaa c                                                21

<210> SEQ ID NO 16
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 16
aatgatacgg cgaccaccga gatctacact ctttccctac acga                       44

<210> SEQ ID NO 17
<211> LENGTH: 47
<212> TYPE: DNA
<213> ORGANISM: Artificial Sequence
```

```
<220> FEATURE:
<223> OTHER INFORMATION: Synthetic Polynucleotide

<400> SEQUENCE: 17
caagcagaag acggcatacg agatcggtct cggcattcct gctgaac                    47
```

SYSTEMS AND METHODS FOR BARCODING NUCLEIC ACIDS

RELATED APPLICATIONS

This application is a continuation of Ser. No. 14/734,903, filed Jun. 9, 2015, entitled "Systems And Methods For Barcoding Nucleic Acids," by Weitz, et al., which is a continuation of International Patent Application Serial No. PCT/US2015/026443, filed Apr. 17, 2015, entitled "Systems And Methods For Barcoding Nucleic Acids," by Weitz, et al., which claims the benefit of U.S. Provisional Patent Application Ser. No. 61/982,001, filed Apr. 21, 2014; U.S. Provisional Patent Application Ser. No. 62/065,348, filed Oct. 17, 2014; U.S. Provisional Patent Application Ser. No. 62/066,188, filed Oct. 20, 2014; and U.S. Provisional Patent Application Ser. No. 62/072,944, filed Oct. 30, 2014. Each of these is incorporated herein by reference.

GOVERNMENT FUNDING

This invention was made with government support under Grant No. R21DK098818 awarded by the National Institutes of Health. The government has certain rights in the invention.

FIELD

The present invention generally relates to microfluidics and labeled nucleic acids.

BACKGROUND

Much of the physiology of metazoans is reflected in the temporal and spatial variation of gene expression among constituent cells. Some of this variation is stable and has helped us to define adult cell types, as well as numerous intermediate cell types in development. Other variation results from dynamic physiological events such as the cell cycle, changes in cell microenvironment, development, aging, and infection. Still other expression changes appear to be stochastic in nature, and may have important consequences. To understand gene expression in development and physiology, it has been a dream of biologists to map gene expression changes not only in RNA levels, but also in protein levels, and even to monitor post-translational modifications in every cell.

The methods available today for RNA sequence analysis (RNA-Seq) have the capacity to quantify the abundance of RNA molecules in a population of cells with great sensitivity. With some considerable effort these methods have been harnessed to analyze RNA content in single cells. What is limiting are effective ways isolate and process large numbers of individual cells for in-depth RNA sequencing, and to do so quantitatively. This requires the isolation of cells under uniform conditions, preferably with minimal loss of cells, especially in the case of clinical samples. The requirements for the number of cells, the depth of coverage, and the accuracy of the measurements of RNA abundance will depend on experimental considerations, which will include factors such as the difficulty of obtaining material, the uniqueness of the material, the complexity of the cell population, and the extent to which cells are diversified in gene expression space. Lacking today high capacity single cell transcriptome data, it is hard to know the depth of coverage needed, but the presence of rare cell types in populations of interest, such as occult tumor cells or tissue stem cell sub-populations, combined with other independent drivers of heterogeneity such as cell cycle and stochastic effects, suggests a demand for analyzing large numbers of cells.

Although analysis of RNA abundance by RNA-seq is well-established, the accuracy of single cell RNA-Seq is much more sensitive than bulk assays to the efficiency of its enzymatic steps; furthermore the need for PCR or linear amplification from single cells risks introducing considerable errors. There are also major obstacles to parallel processing of thousands or even tens of thousands of cells, and to handling small samples of cells efficiently so that nearly every cell is measured. Over the past decade, microfluidics has emerged as a promising technology for single-cell studies with the potential to address these challenges. Yet the number of single cells that can be currently processed with microfluidic chips remains low at 70-90 cells per run, which sets a limit for analysis of large numbers of cells in terms of running costs and the limited time during which cells remain viable for analysis. Moreover, capture efficiencies of cells into microfluidic chambers are often low, a potential issue for rare or clinical samples where the number of cells available is limited.

SUMMARY

The present invention generally relates to microfluidics and labeled nucleic acids. The subject matter of the present invention involves, in some cases, interrelated products, alternative solutions to a particular problem, and/or a plurality of different uses of one or more systems and/or articles.

In one aspect, the present invention is generally directed to an article. In one set of embodiments, the article comprises a plurality of at least 10 microfluidic droplets, each of the droplets containing cell lysate including nucleic acid fragments. In some cases, a plurality of the nucleic acid fragments within a droplet are each bound to an oligonucleotide tag. In certain embodiments, the oligonucleotide tag within the droplet is distinguishable from oligonucleotide tags within the other droplets of the plurality of droplets.

The article, in another set of embodiments, includes a plurality of at least 10 microfluidic droplets, each of the droplets containing cell lysate. In some embodiments, at least about 90% of the droplets contains only one particle. In some cases, the particle comprises an oligonucleotide covalently bonded thereto.

According to yet another set of embodiments, the article comprises a plurality of particles, at least about 90% of the particles comprising an oligonucleotide covalently bonded thereto, the oligonucleotide comprising at least 2 primer sites and at least 2 barcode regions. In some embodiments, at least about 90% of the particles are distinguishable from the other particles of the plurality of particles on the basis of the barcode regions of the oligonucleotides.

In one set of embodiments, the article comprises a plurality of at least 10,000 microfluidic droplets. In some embodiments, at least some of the droplets containing cell lysate include nucleic acid fragments. In certain cases, a plurality of the nucleic acid fragments within a droplet are bound to an oligonucleotide tag. The oligonucleotide tag within the droplet, in one embodiment, is distinguishable from oligonucleotide tags within the other droplets of the plurality of 10,000 microfluidic droplets.

The article, in another set of embodiments, includes a plurality of at least 10,000 microfluidic droplets. In some embodiments, at least some of the droplets contain cell lysate. At least about 90% of the plurality of 10,000 microfluidic droplets may contain only one particle in certain cases. In some embodiments, the particle may comprise an oligonucleotide covalently bonded thereto. The oligonucleotide within a droplet may be distinguishable from oligonucleotides within the other droplets of the plurality of 10,000 microfluidic droplets in various instances.

In another aspect, the present invention is generally directed to a method. In one set of embodiments, the method includes acts of encapsulating a cell and a particle within a microfluidic droplet, the particle comprising an oligonucleotide tag covalently bonded thereto, lysing the cell within the droplet to release nucleic acid from the cell, and bonding the released nucleic acid and the oligonucleotide tag within the droplet.

The method, in another set of embodiments, includes acts of providing a plurality of microfluidic droplets containing cells, at least about 90% of the droplets containing one cell or no cell, lysing the cells within the plurality of microfluidic droplets to release nucleic acid from the cells, and bonding the nucleic acid to oligonucleotide tags, wherein for at least about 90% of the droplets. In some cases, the oligonucleotide tag within the droplet may be distinguishable from oligonucleotide tags within the other droplets of the plurality of droplets.

According to still another set of embodiments, the method includes acts of providing a plurality of particles, attaching first oligonucleotides to the plurality of particles such that at least about 90% of the particles has covalently bonded thereto only one first oligonucleotide, where the first oligonucleotides are taken from a pool of at least 10 unique first oligonucleotides; and attaching second oligonucleotides to the first oligonucleotides such that at least about 90% of the first oligonucleotides has covalently bonded thereto only one second oligonucleotide, where the second oligonucleotides are taken from a pool of at least 10 unique second oligonucleotides.

In accordance with one set of embodiments, the method includes acts of encapsulating a cell and a hydrogel microsphere or particle within a droplet, where the hydrogel microsphere or particle has attached thereto a barcoded nucleic acid, lysing the cell within the droplet to release RNA and/or DNA from the cell, and enzymatically reacting the RNA and/or DNA with the barcoded nucleic acid.

The method, in another set of embodiments, comprises providing droplets containing cells such that no more than 10% of the droplets contains two or more cells, lysing the cells within the plurality of droplets to release RNA and/or DNA from the cells, and uniquely labeling the RNA and/or DNA with a droplet-specific barcode.

According to still another set of embodiments, the method includes acts of providing droplets containing cells such that no more than 10% of the droplets contains two or more cells, lysing the cells within the plurality of droplets to release RNA and/or DNA from the cells, and uniquely labeling the RNA and/or DNA with a barcode selected from a pool of at least 10,000 barcodes.

In yet another set of embodiments, the method includes acts of providing a plurality of microspheres or particles carrying nucleic acid, covalently attaching an oligonucleotide to the microspheres or particles, enzymatically extending the oligonucleotides with a first barcode selected at random from a pre-defined pool of first barcodes, and enzymatically extending the oligonucleotides with a second barcode selected at random from a pre-defined pool of second barcodes.

In one set of embodiments, the method includes encapsulating a plurality of cells and a plurality of particles within a plurality of at least 10,000 microfluidic droplets, at least some of the particles comprising an oligonucleotide tag covalently bonded thereto, such that the droplets of the plurality of the at least 10,000 droplets contain one or more oligonucleotide tags distinguishable from oligonucleotide tags contained in other droplets of the plurality of droplets, lysing at least some of the cells within the droplets to release nucleic acid from the cell, and bonding the released nucleic acids and the oligonucleotide tags within at least some of the droplets.

In another set of embodiments, the method includes providing a plurality of at least 10,000 microfluidic droplets containing cells, at least about 90% of the plurality of droplets containing one cell or no cell, lysing the cells within the plurality of microfluidic droplets to release nucleic acid from the cells, and bonding the released nucleic acid to oligonucleotide tags, wherein for at least about 90% of the droplets, the oligonucleotide tag within the droplet is distinguishable from oligonucleotide tags within other droplets of the plurality of droplets.

The method, according to yet another set of embodiments, includes encapsulating a cell and a hydrogel microsphere or particle within a droplet, where the hydrogel microsphere or particle may have attached thereto a barcoded nucleic acid, lysing the cell within the droplet to release nucleic acid from the cell, and enzymatically reacting the released nucleic acid with the barcoded nucleic acid.

The method, in accordance with still another set of embodiments, is directed to providing a plurality of at least about 10,000 microfluidic droplets containing cells such that no more than 10% of the droplets contains two or more cells, lysing the cells within the plurality of droplets to release nucleic acid from the cells, and uniquely labeling the released nucleic acid with a droplet-specific barcode.

In yet another set of embodiments, the method comprises providing droplets containing cells such that no more than 10% of the droplets contains two or more cells, lysing the cells within the plurality of droplets to release nucleic acid from the cells, and uniquely labeling the released nucleic acid with a barcode selected from a pool of at least 10,000 distinguishable barcodes.

The method, in another set of embodiments, includes providing a plurality of at least about 10,000 microfluidic droplets containing cells such that no more than 10% of the droplets contains two or more cells, lysing the cells within the plurality of droplets to release nucleic acid from the cells, and uniquely labeling the released nucleic acid with a droplet-specific barcode. In yet another set of embodiments, the method includes providing droplets containing cells such that no more than 10% of the droplets contains two or more cells, lysing the cells within the plurality of droplets to release nucleic acid from the cells, and uniquely labeling the released nucleic acid with a barcode selected from a pool of at least 10,000 distinguishable barcodes.

In another aspect, the present invention encompasses methods of making one or more of the embodiments described herein. In still another aspect, the present invention encompasses methods of using one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 14A-14G illustrate droplet integrity and random barcoding, in accordance with another embodiment of the invention;

FIGS. 20A-20C illustrate synthesis of oligonucleotide tags for particles, in still another embodiment of the invention;

FIGS. 21A-21H illustrate quantification of DNA, in one embodiment of the invention;

FIGS. 22A-22E illustrate random barcoding and unique molecular identifier (UMIs) filtering, in another embodiment of the invention;

FIGS. 26A-26V show Table 2; and

DETAILED DESCRIPTION

The present invention generally relates to microfluidics and labeled nucleic acids. For example, certain aspects are generally directed to systems and methods for labeling nucleic acids within microfluidic droplets. In one set of embodiments, the nucleic acids may include "barcodes" or unique sequences that can be used to distinguish nucleic acids in a droplet from those in another droplet, for instance, even after the nucleic acids are pooled together. In some cases, the unique sequences may be incorporated into individual droplets using particles and attached to nucleic acids contained within the droplets (for example, released from lysed cells). In some cases, the barcodes may be used to distinguish tens, hundreds, or even thousands of nucleic acids, e.g., arising from different cells or other sources.

Certain aspects of the present invention are generally directed to systems and methods for containing or encapsulating nucleic acids with oligonucleotide tags within microfluidic droplets or other suitable compartments, and covalently bonding them together. In some cases, the nucleic acids may arise from lysed cells or other material within the droplets. The oligonucleotide tags within a droplet may be distinguishable from oligonucleotide tags in other droplets, e.g., within a plurality or population of droplets. For instance, the oligonucleotide tags may contain one or more unique sequences or "barcodes" that are different between the various droplets; thus, the nucleic acid within each droplet can be uniquely identified by determining the barcodes associated with the nucleic acid. This may be important, for example, if the droplets are "broken" and the nucleic acids from different droplets are subsequently combined or merged together, e.g., for sequencing or other analysis.

In some embodiments, the oligonucleotide tags are introduced into the droplets by initially attaching the oligonucleotide tags to a particle (e.g., a hydrogel or a polymeric particle), then subsequently releasing them from the particle after the particle has been incorporated into a droplet. The particles may be prepared in some cases such that most or all of the particles have only one uniquely distinguishable oligonucleotide tag, relative to other particles having other distinguishable oligonucleotide tags). If the particles are present within the droplets at a density of 1 particle/droplet (or less), then once the oligonucleotide tags are released from the particle, then most or all of the droplets will contain one unique oligonucleotide tag (or no unique oligonucleotide), thus allowing each droplet (and the nucleic acids contained therein) to be uniquely identified.

Figure 1:
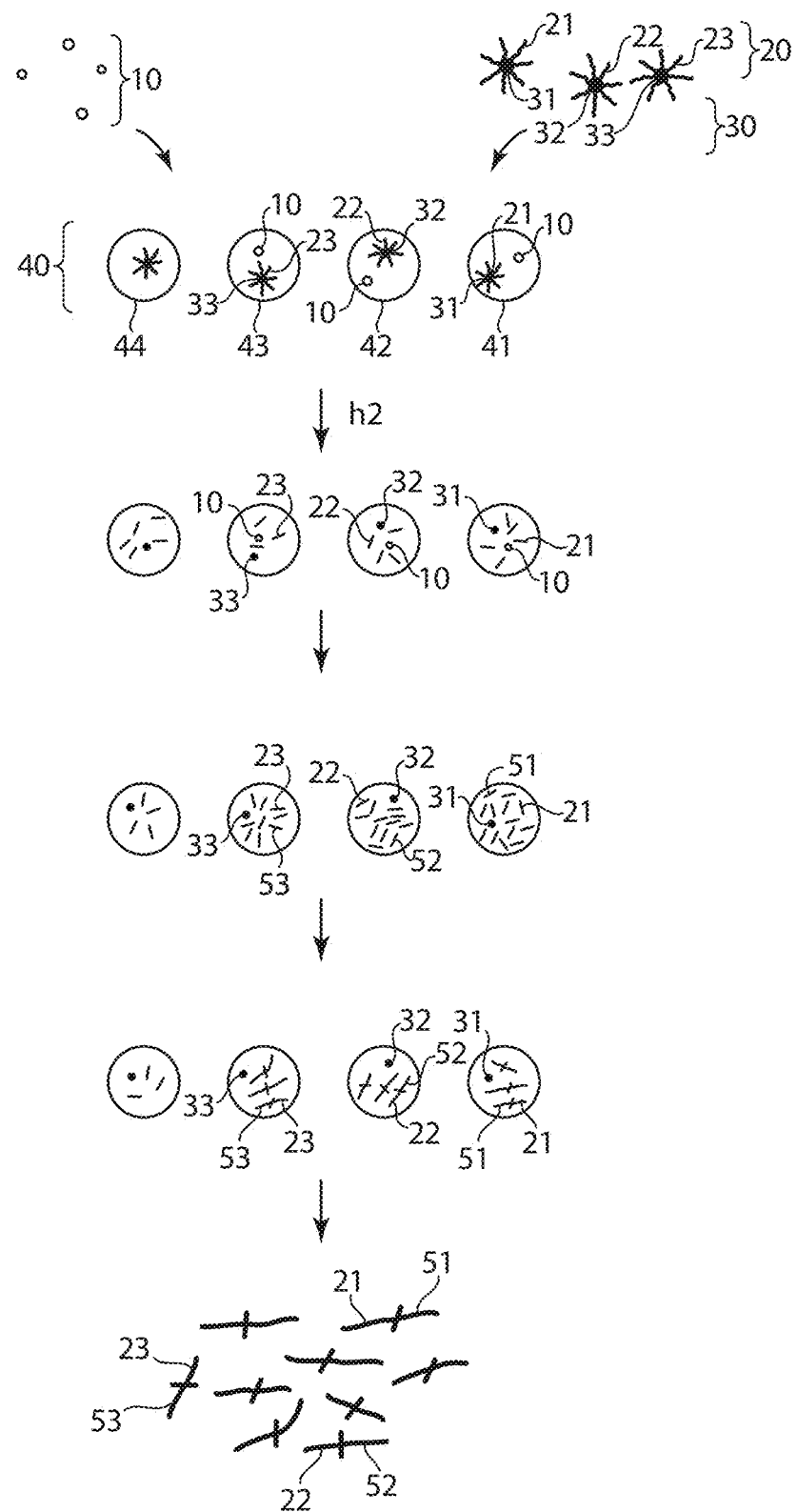
FIG. 1 illustrates a flowchart in accordance with one embodiment of the invention.

Turning now to FIG. 1, an example of one aspect of the invention is now provided. However, it should be understood that this is by way of example only; other examples and embodiments of the invention are discussed in further detail below. In the non-limiting example of FIG. 1, a population of cells 10 is desired to be analyzed, e.g., by sequencing their DNA, by identifying certain proteins or genes that may be suspected of being present in at least some of the cells, by determining their mRNA or transcriptome, or the like. Although cells are used in this example as a source of nucleic acid material, this is by way of example, and in other embodiments, the nucleic acid may be introduced into the droplets from other sources, or using other techniques.

The cells may first be encapsulated in a series of microfluidic droplets 40. Those of ordinary skill in the art will be aware of techniques for encapsulating cells within microfluidic droplets; see, for example, U.S. Pat. Nos. 7,708,949, 8,337,778, 8,765,485, or Int. Pat. Apl. Pub. Nos. WO 2004/091763 and WO 2006/096571, each incorporated herein by reference. In some cases, the cells may be encapsulated at a density of less than 1 cell/droplet (and in some cases, much less than 1 cell/droplet) to ensure that most or all of the droplets have only zero or one cell present in them. Thus, as is shown in FIG. 1, each of droplets 41, 42, 43 . . . have either zero or one cell present in them.

Also encapsulated in the droplets are oligonucleotide tags 20, present on particles 30. Particles 30 may be, for example, microparticles, and may be a hydrogel or a polymeric particle, or other types of particles such as those described herein. The particles and the cells may be encapsulated within the droplets simultaneously or sequentially, in any suitable order. In one set of embodiments, each particle contains a unique oligonucleotide tag, although there may be multiple copies of the tag present on a particle. For instance, each of the oligonucleotide tags may have one or more unique sequences or "barcodes" that are present. Thus, for example, particle 31 contains only copies of oligonucleotide tag 21, particle 32 contains only copies of oligonucleotide tag 22, particle 33 contains only copies of oligonucleotide tag 33, etc. In some cases, the particles may be present in the droplets at a density of less than 1 particle/droplet (and in some cases, much less than 1 particle/droplet) to ensure that most or all of the droplets have only zero or one particle present in them. In addition, in certain embodiments, the oligonucleotide tags may be cleavable or otherwise releasable from the particles.

It should be noted that according to certain embodiments of the invention, the oligonucleotide tags are initially attached to particles to facilitate the introduction of only one unique oligonucleotide tag to each droplet, as is shown in FIG. 1. (In other embodiments, however, a plurality of oligonucleotide tags may be present, e.g., containing the same unique barcode.) For example, if the particles are present in the droplets at a density of less than 1 particle/droplet, then most or all of the droplets will each have only a single particle, and thus only a single type of oligonucleotide tag, that is present. Accordingly, as is shown in FIG. 1, the oligonucleotide tags may be cleaved or otherwise released from the particles, e.g., such that each droplet 41, 42, 43, . . . contains a unique oligonucleotide tag 21, 22, 23, . . . that is different than the other oligonucleotide tags that may be present in the other droplets. Thus, each oligonucleotide tag present within a droplet will be distinguishable from the oligonucleotide tags that are present in the other droplets. Although light (hv) is used in FIG. 1 to cleave the oligonucleotides from the particles, it should be understood that this is by way of example only, and that other methods of cleavage or release can also be used, e.g., as discussed herein. For example, in one set of embodiments, agarose particles containing oligonucleotides (e.g., physically) may be used, and the oligonucleotides may be released by heating the agarose, e.g., until the agarose at least partially liquefies or softens.

In some cases, the cells are lysed to release nucleic acid or other materials 51, 52, 53, . . . from the cells. For example, the cells may be lysed using chemicals or ultrasound. The cells may release, for instance, DNA, RNA, mRNA, proteins, enzymes or the like. In some cases, the nucleic acids that are released may optionally undergo amplification, for example, by including suitable reagents specific to the amplification method. Examples of amplification methods known to those of ordinary skill in the art include, but are not limited to, polymerase chain reaction (PCR), reverse transcriptase (RT) PCR amplification, in vitro transcription amplification (IVT), multiple displacement amplification (MDA), or quantitative real-time PCR (qPCR).

Some or all of the nucleic acid or other material 51, 52, 53, . . . may be associated with the oligonucleotide tags present in the droplets, e.g., by covalently bonding. For example, the nucleic acid or other material 51, 52, 53 may be ligated or enzymatically attached to the oligonucleotide tags present in the droplets. Thus, as is shown in FIG. 1, droplet 41 exhibits nucleic acids 51 attached to oligonucleotide tags 21, droplet 42 exhibits nucleic acids 52 attached to oligonucleotide tags 22, droplet 43 exhibits nucleic acids 53 attached to oligonucleotide tags 23, etc. Thus, the nucleic acids within each droplet are distinguishable from the nucleic acids within the other droplets of the plurality of droplets 50 by way of the oligonucleotide tags, which are unique to each droplet in this example.

It should also be understood that although FIG. 1 depicts cleavage of the oligonucleotide tags from the particles followed by lysis of the cells, in other embodiments, these need not necessarily occur in this order. For example, cell lysis may occur after cleavage, or both may occur simultaneously.

Droplet 41, 42, 43, . . . may then be "burst" or "broken" to release their contents, and in some cases, the nucleic acids present in each droplet may be combined or pooled together, as is shown in FIG. 1. However, since the nucleic acids are labeled by the different oligonucleotide tags, the nucleic acids from one droplet (i.e., from one cell) can still be distinguished from those from other droplets (or other cells) using the oligonucleotide tags. Accordingly, subsequent analysis (e.g., sequencing) of the combined pool of nucleic acids may be performed, and the source of each nucleic acid (e.g., individual cells) may be determined be determining the different oligonucleotide tags.

Thus, for example, a population of normal cells and cancer cells (e.g., arising from a tissue sample or biopsy) may be analyzed in such a fashion, and the cancer cells may be identified as having abnormal DNA, even if present in a large pool of normal cells. For example, due to the ability to track DNA on a cellular level using the oligonucleotide tags, the abnormal DNA can still be identified even if outnumbered by a large volume of normal DNA. As other non-limiting examples, stem cells may be isolated from normal cells, or the isolation of rare cell types in a population of interest may be performed.

In another aspect, the present invention provides systems and methods for the parallel capture and barcoding of DNA or RNA from large numbers of cells, e.g., for the purpose of profiling cell populations, or other purposes such as those described herein. In some embodiments, this relies on the encapsulation of barcoded nucleic acids or other suitable oligonucleotide tags, e.g., attached to particles or microspheres (for example, hydrogel or polymer microspheres)

together with cells and/or other reagents that may be used for RNA and/or DNA capture and/or amplification.

In one set of embodiments, the contents arising from substantially each individual cell may be labeled, e.g., with a unique barcode (which may be randomly determined, or determined as discussed herein), which may allow in some cases for hundreds, thousands, tens of thousands, or even hundreds of thousands or more of different cells to be barcoded or otherwise labeled in a single experiment, e.g., to determine or define the heterogeneity between cells in a population or for screening cell populations, etc. Other purposes have been described herein.

In one set of embodiments, a microfluidic system is used to capture single cells into individual droplets (e.g., 50 pL to 10 nL volume), e.g., in a single reaction vessel. Each cell may be lysed and its RNA and/or DNA uniquely barcoded or labeled with a droplet-specific barcode, e.g., through an enzymatic reaction, through ligation, etc. Examples of microfluidic systems, including those with dimensions other than these, are also provided herein. Some embodiments might also be used, in some embodiments, to quantify protein abundance in single cells in parallel to RNA or DNA, e.g., by first treating cells with DNA-tagged antibodies, in which case the DNA tags can be similarly barcoded with a droplet-specific barcode. Once the cell components in droplets have been barcoded, the droplets may be broken or burst and the sample can be processed, e.g., in bulk, for high-throughput sequencing or other applications. After sequencing, the data can be split or otherwise analyzed according to the DNA barcodes.

To perform parallel barcoding of DNA, RNA and/or DNA-antibody tags in single cells, a single hydrogel or polymer particle or microsphere may be encapsulated into each droplet together with biological or chemical reagents and a cell, in accordance with one set of embodiments. Particles or microspheres carrying a high concentration (e.g. 1 to 100 micromolar) of DNA fragments (hereafter "primers") may encode (a) a barcode sequence selected at random from a pool of, e.g., at least 10,000 barcodes (or at least 30,000 barcodes, at least 100,000 barcodes, at least 300,000 barcodes, or at least 1,000,000 barcodes, etc.), with the same barcode found on all nucleic acid fragments on the particles or microspheres; and/or encode (b) one or more a primer sequences used for hybridization and capture of DNA or RNA. The number of distinct barcodes may be at least 10-fold, and in some cases at least 100-fold, larger than the number of cells to be captured, in order to reduce the possibility of two or more cells occupying different droplets with particles or microspheres that carry the same barcode. For example, with 150,000 barcodes and 1,000 cells, on average just 3 cells will acquire a duplicate barcode (resulting in 997 detected barcodes).

In some embodiments, the encapsulation conditions are chosen such droplets contain one particle (or microsphere) and one cell. The presence of empty droplets and/or droplets with single particles but without cells, and/or droplets with cells but without particles, may not substantially affect performance. However, the presence of two or more particles or two or more cells in one droplet may lead to errors that can be difficult to control for, so the incidence of such events is kept to minimum in some instances, for example, less than about 10% or less than about 5%. Excepting the cells and particles, other biological and chemical reagents may be distributed equally among the droplets. The co-encapsulated cells and particles may be collected and processed according to the aim of the particular application. For example, in one particular embodiment, the DNA or RNA of single cells is captured by the primers introduced with particle, and may then be converted into barcoded complimentary DNA upon reverse transcription or other DNA polymerization reaction.

After purification and optional DNA amplification, the base composition and barcode identity of cellular nucleic acids may be determined, for instance, by sequencing or other techniques. Alternatively, in some embodiments, primers introduced with particles or microspheres can be used for amplification of specific nucleic acid sequences from a genome.

In some embodiments, the barcoded primers introduced using particles or microspheres can be cleaved therefrom by, e.g., light, chemical, enyzmatic or other techniques, e.g., to improve the efficiency of priming enzymatic reactions in droplets. However, the cleavage of the primers can be performed at any step or point, and can be defined by the user in some cases. Such cleavage may be particularly important in certain circumstances and/or conditions; for example, some fraction of RNA and DNA molecules in single cells might be very large, or might be associated in complexes and therefore will not diffuse efficiently to the surface or interior of the particle or microsphere. However, in other embodiments, cleavage is not essential.

Techniques such as these can be used to analyze, for example, genomes, single nucleotide polymorphisms, specific gene expression levels, non-coding RNA, the whole transcriptome (or a portion thereof), entire genes or their sections, etc. However, the invention should not be limited to only these applications.

In one non-limiting embodiment, the 3' end of a barcoded primer is terminated with a poly-T sequences that may be used to capture cellular mRNA for whole-transcriptome profiling. The resulting library combining all cells can optionally be enriched using PCR-based methods or using hybridization capture-based methods (such as Agilent Sure-Select), e.g., to allow sequencing of only a sub-set of genes of interest. In another embodiment, the 3' end of the barcoded primers may terminate with a random DNA sequence that can be used to capture the RNA in the cell. In another embodiment, the 3' end of the barcoded primers may terminate with a specific DNA sequence, e.g., that can be used to capture DNA or RNA species ("genes") of interest, or to hybridize to a DNA probe that is delivered into the droplets in addition to the particles or microspheres, for example, together with the enzyme reagents. In another embodiment, a particle or microsphere may carry a number of different primers to target several genes of interest. Yet another embodiment is directed to optimization of the size of droplets and the concentration of reaction components required for droplet barcoding.

Still another aspect of the present invention is generally directed to creating barcoded nucleic acids attached to the particles or microspheres. The nucleic acids may be attached to the surface of the particles or microspheres, or in some cases, attached or incorporated within the particle. For instance, the nucleic acids may be incorporated into the particle during formation of the particle, e.g., physically and/or chemically.

For example, one set of embodiments is generally directed to creating particles or microspheres carrying nucleic acid fragments (each encoding a barcode, a primer, and/or other sequences possibly used for capture, amplification and/or sequencing of nucleic acids). Microspheres may refer to a hydrogel particle (polyacrylamide, agarose, etc.), or a colloidal particle (polystyrene, magnetic or polymer particle, etc.) of 1 to 500 micrometer in size, or other dimensions such as those described herein. The microspheres may be porous in some embodiments. Other suitable particles or microspheres that can be used are discussed in more detail herein.

The preparation of DNA-carrying particles or microspheres, in some cases, may rely on the covalent attachment or other techniques of incorporation of an initial DNA oligonucleotide to the particles or microspheres, followed by enzymatic extension of each oligonucleotide by one or more barcodes selected, e.g., at random, from a pre-defined pool. The final number of possible unique barcodes may depend in some cases on the size of the pre-defined barcode pool and/or on the number of extension steps. For example, using a pool of 384 pre-defined barcodes and 2 extension steps, each particle or microsphere carries one of $384^2=147,456$ possible barcodes; using 3 extension steps, each particle or microsphere carries one of $384^3=56,623,104$ possible barcodes; and so on. Other numbers of steps may also be used in some cases; in addition, each pool may have various numbers of pre-defined barcodes (not just 384), and the pools may have the same or different numbers of pre-defined barcodes. The pools may include the same and/or different sequences.

Accordingly, in some embodiments, the possible barcodes that are used are formed from one or more separate "pools" of barcode elements that are then joined together to produce the final barcode, e.g., using a split-and-pool approach. A pool may contain, for example, at least about 300, at least about 500, at least about 1,000, at least about 3,000, at least about 5,000, or at least about 10,000 distinguishable barcodes. For example, a first pool may contain $x_1$ elements and a second pool may contain $x_2$ elements; forming a barcode containing an element from the first pool and an element from the second pool may yield, e.g., $x_1 x_2$ possible barcodes that could be used. It should be noted that $x_1$ and $x_2$ may or may not be equal. This process can be repeated any number of times; for example, the barcode may include elements from a first pool, a second pool, and a third pool (e.g., producing $x_1 x_2 x_3$ possible barcodes), or from a first pool, a second pool, a third pool, and a fourth pool (e.g., producing $x_1 x_2 x_3 x_4$ possible barcodes), etc. There may also be 5, 6, 7, 8, or any other suitable number of pools. Accordingly, due to the potential number of combinations, even a relatively small number of barcode elements can be used to produce a much larger number of distinguishable barcodes.

In some cases, such use of multiple pools, in combination, may be used to create substantially large numbers of useable barcodes, without having to separately prepare and synthesize large numbers of barcodes individually. For example, in many prior art systems, requiring 100 or 1,000 barcodes would require the individual synthesis of 100 or 1,000 barcodes. However, if larger numbers of barcodes are needed, e.g., for larger numbers of cells to be studied, then correspondingly larger numbers of barcodes would need to be synthesized. Such systems become impractical and unworkable at larger numbers, such as 10,000, 100,000, or 1,000,000 barcodes. However, by using separate "pools" of barcodes, larger numbers of barcodes can be achieved without necessarily requiring each barcode to be individually synthesized. As a non-limiting example, a first pool of 1,000 distinguishable barcodes (or any other suitable number) and a second pool of 1,000 distinguishable barcodes can be synthesized, requiring the synthesis of 2,000 barcodes (or only 1,000 if the barcodes are re-used in each pool), yet they may be combined to produce $1,000 \times 1,000=1,000,000$ distinguishable barcodes, e.g., where each distinguishable barcode comprises a first barcode taken from the first pool and a second barcode taken from the second pool. Using 3, 4, or more pools to assemble the barcode may result in even larger numbers of barcodes that may be prepared, without substantially increasing the total number of distinguishable barcodes that would need to be synthesized.

In some aspects, the DNA fragments or oligonucleotides can be released from the particles or microspheres using a variety of techniques including light, temperature, chemical, and/or enzymatic treatment. For example, with light, nucleic acid fragments may be released at a selected time and/or under desirable conditions, thus providing flexibility for their use.

In some embodiments, the particles or microspheres can be stored for long periods of time and used as a reagent for subsequent applications.

In yet another aspect, the present invention provides systems and methods for the parallel capture, barcoding and quantification of a panel of tens to hundreds, or more, of specific DNA and/or RNA sequences from large numbers of single cells, e.g., for the purpose of profiling cell populations or other purposes. Certain embodiments rely on encapsulation of barcoded nucleic acids, e.g., attached to particles such as hydrogel or polymer microspheres, together with cells and/or other reagents for, for example, RNA and/or DNA capture and amplification.

In some cases, systems and methods for labeling specific sets of genes (e.g., tens, or hundreds of genes, or more in some cases) arising from individual cells with a unique, random barcode, allowing hundreds, thousands, or even hundreds of thousands or more of different cells to be labeled or barcoded, e.g., in a single experiment, for the purpose of defining the heterogeneity between cells in a population or for screening cell populations, or for other purposes.

For example, in situations where a large number of cells are to be analyzed through multiplexed high-throughput sequencing, it may be desirable in some embodiments to focus on a sub-set of genes of interest, for example between tens to hundreds of genes, rather than whole-transcriptome or whole-genome capture and sequencing.

Some embodiments are directed to the parallel barcoding of the contents of cells focusing on specific sequences of cellular DNA or RNA. These may include, for example, the synthesis of DNA-barcoded microspheres (or other particles), and/or the use of such microspheres for the capture and barcoding of single cells in individual droplets (for example, 50 pL to 10 nL in volume, or other volumes described herein), e.g., in a single reaction vessel. In some cases, substantially each cell may be lysed and its RNA and/or DNA uniquely barcoded (tagged) with a droplet-specific nucleic acid barcode, e.g., through an enzymatic reaction. In some embodiments, modifying the DNA-barcoded microspheres may be performed in such a way that they target only a specific panel of DNA sequences, rather than either using one sequence of interest or using random sequences. This may allow a high concentration of sequence-specific barcoded primers to be delivered into each droplet, which may, in some instances, allow that the enzymatic barcoding and synthesis of complementary DNA occurs primarily for the sequences of interest. This may be used, for example, with any enzymatic approach in which a panel of sequence-specific primers can be used to capture genes of interest.

Some embodiments of the invention may be used to quantify protein abundance in single cells in parallel to RNA or DNA, for example, by first treating cells with DNA-tagged antibodies, in which case one or more of the sequences or oligonucleotides on the particle or microsphere can be made complementary to the DNA tags delivered by the antibodies. In some cases, once the cell components in droplets have been barcoded, the droplets can be broken or burst and the sample can be processed, e.g., in bulk, for applications such as high-throughput sequencing. After sequencing, the data may be split, in certain embodiments, according to the DNA barcodes thus providing information about the type, sequence, molecule count, origin of nucleic acids and/or proteins of interest, or the like.

In accordance with still another aspect, the present invention provides for optimizing reaction conditions for the enzymatic processing of cells within small volumes, for example, for cases where direct testing of the reactions would be extremely slow as it would require creating multiple microfluidic devices, or running microfluidic devices with large numbers of test samples. In some cases, this may also report specifically on the ideal volume required for enzymatic reverse transcription of mRNA into complementary DNA from single cells lysed in small volumes.

Certain embodiments of the invention provide for optimizing microfluidic reactions on single cells using reactions with a volume greater than 5 microliters, that can be performed using normal molecular biology reagents, e.g., without a microfluidic apparatus. This may be useful in certain applications, e.g., for testing parameters such as reaction volume over multiple orders of magnitude, which would otherwise require the design and synthesis of multiple test microfluidic devices, and the side-by-side comparison of the performance of such devices. It may also be useful for rapidly optimizing the conditions of microfluidic reactions, such as the optimal concentration of different reaction components.

In one set of embodiments, a bulk reaction is used to simulate the precise conditions present in a microfluidic volume. This is general and can be applied to optimize other aspects of microfluidic reactions, or other reactions. For example, this may be applied to test the ability of different additives to relieve inhibition of a reverse transcription (RT) reaction, and DNA primer concentrations necessary for performing RT reactions from lysed single cells in small volumes may be defined in certain embodiments.

The above discussions are non-limiting examples of various embodiments of the present invention. However, other embodiments are also possible. Accordingly, more generally, various aspects of the invention are directed to various systems and methods for systems and methods for labeling nucleic acids within microfluidic droplets, as discussed below.

In one aspect, the present invention is generally directed to systems and methods for labeling nucleic acids within a population of droplets, e.g., microfluidic droplets. In some cases, the microfluidic droplets may have an average diameter of the droplets of less than about 1 mm and/or the microfluidic droplets may be substantially monodisperse, e.g., as discussed herein.

In some cases, an oligonucleotide tag comprising DNA and/or other nucleic acids may be attached to particles and delivered to the droplets. In some cases, the oligonucleotide tags are attached to particles to control their delivery into droplets, e.g., such that a droplet will typically have at most one particle in it. In some cases, upon delivery into a droplet, the oligonucleotide tags may be removed from the particle, e.g., by cleavage, by degrading the particle, etc. However, it should be understood that in other embodiments, a droplet may contain 2, 3, or any other number of particles, which may have oligonucleotide tags that are the same or different.

The oligonucleotide tags may be of any suitable length or comprise any suitable number of nucelotides. The oligonucleotide tags may comprise DNA, RNA, and/or other nucleic acids such as PNA, and/or combinations of these and/or other nucleic acids. In some cases, the oligonucleotide tag is single stranded, although it may be double stranded in other cases. For example, the oligonucleotide tag may have a length of at least about 10 nt, at least about 30 nt, at least about 50 nt, at least about 100 nt, at least about 300 nt, at least about 500 nt, at least about 1000 nt, at least about 3000 nt, at least about 5000 nt, at least about 10,000 nt, etc. In some cases, the oligonucleotide tag may have a length of no more than about 10,000 nt, no more than about 5000 nt, no more than about 3000 nt, no more than about 1000 nt, no more than about 500 nt, no more than about 300 nt, no more than about 100 nt, no more than about 50 nt, etc. Combinations of any of these are also possible, e.g., the oligonucleotide tag may be between about 10 nt and about 100 nt. The length of the oligonucleotide tag is not critical, and a variety of lengths may be used in various embodiments.

The oligonucleotide tag may contain a variety of sequences. For example, the oligonucleotide tag may contain one or more primer sequences, one or more unique or "barcode" sequences, one or more promoter sequences, one or more spacer sequences, or the like. The oligonucleotide tag may also contain, in some embodiments one or more cleavable spacers, e.g., photocleavable linker. The oligonucleotide tag may be attached to a particle chemically (e.g., via a linker) or physically (e.g., without necessarily requiring a linker), e.g., such that the oligonucleotide tags can be removed from the particle via cleavage. Other examples include portions that may be used to increase the bulk of the oligonucleotide tag (e.g., using specific sequences or nonsense sequences), to facilitate handling (for example, a tag may include a poly-A tail), to increase selectivity of binding (e.g., as discussed below), to facilitate recognition by an enzyme (e.g., a suitable ligase), to facilitate identification, or the like. Examples of these and/or other sequences are described in further detail herein.

As an example, in some embodiments, the oligonucleotide tags may comprise a "barcode" or a unique sequence. The sequence may be selected such that some or most of the oligonucleotide tags (e.g., present on a particle and/or in a droplet) have the unique sequence (or combination of sequences that is unique), but other oligonucleotide tags (e.g., on other particles or droplets) do not have the unique sequence or combination of sequences. Thus, for example, the sequences may be used to uniquely identify or distinguish a droplet, or nucleic acid contained arising from the droplet (e.g., from a lysed cell) from other droplets, or other nucleic acids (e.g., released from other cells) arising from other droplets.

The sequences may be of any suitable length. The length of the barcode sequence is not critical, and may be of any length sufficient to distinguish the barcode sequence from other barcode sequences. One, two, or more "barcode" sequence may be present in an oligonucleotide tag. A barcode sequence may have a length of 5, 6, 7, 8, 9, 10, 11, 12, 13, 14, 15, 16, 17, 18, 19, 20, 21, 22, 23, 24, or 25 nt. More than 25 nucleotides may also be present in some cases.

In some cases, the unique or barcode sequences may be taken from a "pool" of potential barcode sequences. If more than one barcode sequence is present in an oligonucleotide tag, the barcode sequences may be taken from the same, or different pools of potential barcode sequences. The pool of sequences may be selected using any suitable technique, e.g., randomly, or such that the sequences allow for error detection and/or correction, for example, by being separated by a certain distance (e.g., Hamming distance) such that errors in reading of the barcode sequence can be detected, and in some cases, corrected. The pool may have any number of potential barcode sequences, e.g., at least 100, at least 300, at least 500, at least 1,000, at least 3,000, at least 5,000, at least 10,000, at least 30,000, at least 50,000, at least 100,000, at least 300,000, at least 500,000, or at least 1,000,000 barcode sequences.

In some cases, the oligonucleotide tag may contain one or more promoter sequences, e.g., to allow for production of the tags, to allow for enzymatic amplification, or the like. Those of ordinary skill in the art will be aware of primer sequences, e.g., P5 or P7. Many such primer sequences are available commercially. Examples of promoters include, but are not limited to, T7 promoters, T3 promoters, or SP6 promoters.

In some cases, the oligonucleotide tag may contain one or more primer sequences. Typically, a primer is a single-stranded or partially double-stranded nucleic acid (e.g., DNA) that serves as a starting point for nucleic acid synthesis, allowing polymerase enzymes such as nucleic acid polymerase to extend the primer and replicate the complementary strand. A primer may be complementary to and to hybridize to a target nucleic acid. In some embodiments, a primer is a synthetic primer. In some embodiments, a primer is a non-naturally-occurring primer. A primer typically has a length of 10 to 50 nucleotides. For example, a primer may have a length of 10 to 40, 10 to 30, 10 to 20, 25 to 50, 15 to 40, 15 to 30, 20 to 50, 20 to 40, or 20 to 30 nucleotides. In some embodiments, a primer has a length of 18 to 24 nucleotides. Examples of primers include, but are not limited to, P5 primer, P7 primer, PE1 primer, PE2 primer, A19 primer, or other primers discussed herein.

In some cases, the oligonucleotide tag may contain nonsense or random sequences, e.g., to increase the mass or size of the oligonucleotide tag. The random sequence can be of any suitable length, and there may be one or more than one present. As non-limiting examples, the random sequence may have a length of 10 to 40, 10 to 30, 10 to 20, 25 to 50, 15 to 40, 15 to 30, 20 to 50, 20 to 40, or 20 to 30 nucleotides.

In some cases, the oligonucleotide tag may comprise one or more sequences able to specifically bind a gene or other entity. For example, in one set of embodiments, the oligonucleotide tag may comprise a sequence able to recognize mRNA, e.g., one containing a poly-T sequence (e.g., having several T's in a row, e.g., 4, 5, 6, 7, 8, or more T's).

In one set of embodiments, the oligonucleotide tag may contain one or more cleavable linkers, e.g., that can be cleaved upon application of a suitable stimulus. For example, the cleavable sequence may be a photocleavable linker that can be cleaved by applying light or a suitable chemical or enzyme. A non-limiting example of a photocleavable linker can be seen in FIG. 20A. In some cases, for example, a plurality of particles (for instance, containing oligonucleotide tags on their surfaces) may be prepared and added to droplets, e.g., such that, on average, each droplet contains one particle, or less (or more) in some cases. After being added to the droplet, the oligonucleotide tags may be cleaved from the particles, e.g., using light or other suitable cleavage techniques, to allow the oligonucleotide tags to become present in solution, i.e., within the interior of the droplet. In such fashion, oligonucleotide tags can be easily loaded into droplets by loading of the particles into the droplets in some embodiments, then cleaved off to allow the oligonucleotide tags to be in solution, e.g., to interact with nucleotides or other species, such as is discussed herein.

In addition, in one set of embodiments, the oligonucleotide tag may comprise an antibody, e.g., that can specifically bind to a protein suspected of being present in the cell (or droplet). For example, the droplet may contain one or more antibodies tagged with an oligonucleotide tag as described herein.

The oligonucleotide tag may be attached to a particle, e.g., as discussed herein. In some embodiments, a particle may comprise only one oligonucleotide tag, although multiple copies of the oligonucleotide tag may be present on the particle; other particles may comprise different oligonucleotide tags that are distinguishable, e.g., using the barcode sequences described herein.

Any suitable method may be used to attach the oligonucleotide tag to the particle. The exact method of attachment is not critical, and may be, for instance, chemical or physical. For example, the oligonucleotide tag may be covalently bonded to the particle via a biotin-steptavidin linkage, an amino linkage, or an acrylic phosphoramidite linkage. See, e.g., FIG. 20A for an example of an acrylic phosphoramidite linkage. In another set of embodiments, the oligonucleotide may be incorporated into the particle, e.g., physically, where the oligonucleotide may be released by altering the particle. Thus, in some cases, the oligonucleotide need not have a cleavable linkage. For instance, in one set of embodiments, an oligonucleotide may be incorporated into particle, such as an agarose particle, upon formation of the particle. Upon degradation of the particle (for example, by heating the particle until it begins to soften, degrade, or liquefy), the oligonucleotide may be released from the particle.

The particle is a microparticle in certain aspects of the invention. The particle may be of any of a wide variety of types; as discussed, the particle may be used to introduce a particular oligonucleotide tag into a droplet, and any suitable particle to which oligonucleotide tags can associate with (e.g., physically or chemically) may be used. The exact form of the particle is not critical. The particle may be spherical or non-spherical, and may be formed of any suitable material. In some cases, a plurality of particles is used, which have substantially the same composition and/or substantially the same average diameter. The "average diameter" of a plurality or series of particles is the arithmetic average of the average diameters of each of the particles. Those of ordinary skill in the art will be able to determine the average diameter (or other characteristic dimension) of a plurality or series of particles, for example, using laser light scattering, microscopic examination, or other known techniques. The average diameter of a single particle, in a non-spherical particle, is the diameter of a perfect sphere having the same volume as the non-spherical particle. The average diameter of a particle (and/or of a plurality or series of particles) may be, for example, less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers in some cases. The average diameter may also be at least about 1 micrometer, at least about 2 micrometers, at least about 3 micrometers, at least about 5 micrometers, at least about 10 micrometers, at least about 15 micrometers, or at least about 20 micrometers in certain cases.

The particle may be, in one set of embodiments, a hydrogel particle. See, e.g., Int. Pat. Apl. Pub. No. WO 2008/109176, entitled "Assay and other reactions involving droplets" (incorporated herein by reference) for examples of hydrogel particles, including hydrogel particles containing DNA. Examples of hydrogels include, but are not limited to agarose or acrylamide-based gels, such as polyacrylamide, poly-N-isopropylacrylamide, or poly N-isopropylpolyacrylamide. For example, an aqueous solution of a monomer may be dispersed in a droplet, and then polymerized, e.g., to form a gel. Another example is a hydrogel, such as alginic acid that can be gelled by the addition of calcium ions. In some cases, gelation initiators (ammonium persulfate and TEMED for acrylamide, or $Ca^{2+}$ for alginate) can be added to a droplet, for example, by co-flow with the aqueous phase, by co-flow through the oil phase, or by coalescence of two different drops, e.g., as discussed in U.S. patent application Ser. No. 11/360,845, filed Feb. 23, 2006, entitled "Electronic Control of Fluidic Species," by Link, et al., published as U.S. Patent Application Publication No. 2007/000342 on Jan. 4, 2007; or in U.S. patent application Ser. No. 11/698,298, filed Jan. 24, 2007, entitled "Fluidic Droplet Coalescence," by Ahn, et al.; each incorporated herein by reference in their entireties.

In another set of embodiments, the particles may comprise one or more polymers. Exemplary polymers include, but are not limited to, polystyrene (PS), polycaprolactone (PCL), polyisoprene (PIP), poly(lactic acid), polyethylene, polypropylene, polyacrylonitrile, polyimide, polyamide, and/or mixtures and/or co-polymers of these and/or other polymers. In addition, in some cases, the particles may be magnetic, which could allow for the magnetic manipulation of the particles. For example, the particles may comprise iron or other magnetic materials. The particles could also be functionalized so that they could have other molecules attached, such as proteins, nucleic acids or small molecules. Thus, some embodiments of the present invention are directed to a set of particles defining a library of, for example, nucleic acids, proteins, small molecules, or other species such as those described herein. In some embodiments, the particle may be fluorescent.

In one set of embodiments, droplets are formed containing a cell or other source of nucleic acid, and a particle, e.g., comprising an oligonucleotide tag as described above. Any suitable method may be chosen to create droplets, and a wide variety of different techniques for forming droplets will be known to those of ordinary skill in the art. For example, a junction of channels may be used to create the droplets. The junction may be, for instance, a T-junction, a Y-junction, a channel-within-a-channel junction (e.g., in a coaxial arrangement, or comprising an inner channel and an outer channel surrounding at least a portion of the inner channel), a cross (or "X") junction, a flow-focusing junction, or any other suitable junction for creating droplets. See, for example, International Patent Application No. PCT/US2004/010903, filed Apr. 9, 2004, entitled "Formation and Control of Fluidic Species," by Link, et al., published as WO 2004/091763 on Oct. 28, 2004, or International Patent Application No. PCT/US2003/020542, filed Jun. 30, 2003, entitled "Method and Apparatus for Fluid Dispersion," by Stone, et al., published as WO 2004/002627 on Jan. 8, 2004, each of which is incorporated herein by reference in its entirety. In some embodiments, the junction may be configured and arranged to produce substantially monodisperse droplets. The droplets may also be created on the fluidic device, and/or the droplets may be created separately then brought to the device.

If cells are used, the cells may arise from any suitable source. For instance, the cells may be any cells for which nucleic acid from the cells is desired to be studied or sequenced, etc., and may include one, or more than one, cell type. The cells may be for example, from a specific population of cells, such as from a certain organ or tissue (e.g., cardiac cells, immune cells, muscle cells, cancer cells, etc.), cells from a specific individual or species (e.g., human cells, mouse cells, bacteria, etc.), cells from different organisms, cells from a naturally-occurring sample (e.g., pond water, soil, etc.), or the like. In some cases, the cells may be dissociated from tissue.

In addition, certain embodiments of the invention involve the use of other discrete compartments, for example, microwells of a microwell plate, individual spots on a slide or other surface, or the like. In some cases, each of the compartments may be in a specific location that will not be accidentally mixed with other compartments. The compartments may be relatively small in some cases, for example, each compartment may have a volume of less than about 1 ml, less than about 300 microliters, less than about 100 microliters, less than about 30 microliters, less than about 10 microliters, less than about 3 microliters, less than about 1 microliter, less than about 500 nl, less than about 300 nl, less than about 100 nl, less than about 50 nl, less than about 30 nl, or less than about 10 nl.

In one set of embodiments, the droplets (or other compartments) are loaded such that, on the average, each droplet has less than 1 particle in it. For example, the average loading rate may be less than about 1 particle/droplet, less than about 0.9 particles/droplet, less than about 0.8 particles/droplet, less than about 0.7 particles/droplet, less than about 0.6 particles/droplet, less than about 0.5 particles/droplet, less than about 0.4 particles/droplet, less than about 0.3 particles/droplet, less than about 0.2 particles/droplet, less than about 0.1 particles/droplet, less than about 0.05 particles/droplet, less than about 0.03 particles/droplet, less than about 0.02 particles/droplet, or less than about 0.01 particles/droplet. In some cases, lower particle loading rates may be chosen to minimize the probability that a droplet will be produced having two or more particles in it. Thus, for example, at least about 50%, at least about 60%, at least about 70%, at least about 80%, at least about 90%, at least about 95%, at least about 97%, at least about 98%, or at least about 99% of the droplets may contain either no particle or only one particle.

Similarly, in some embodiments, the droplets (or other compartments) are loaded such that, on the average, each droplet has less than 1 cell in it. For example, the average loading rate may be less than about 1 cell/droplet, less than about 0.9 cells/droplet, less than about 0.8 cells/droplet, less than about 0.7 cells/droplet, less than about 0.6 cells/droplet, less than about 0.5 cells/droplet, less than about 0.4 cells/droplet, less than about 0.3 cells/droplet, less than about 0.2 cells/droplet, less than about 0.1 cells/droplet, less than about 0.05 cells/droplet, less than about 0.03 cells/droplet, less than about 0.02 cells/droplet, or less than about 0.01 cells/droplet. In some cases, lower cell loading rates may be chosen to minimize the probability that a droplet will be produced having two or more cells in it. Thus, for example, at least about 50%, at least about 60%, at least about 70%, at least about 80%, at least about 90%, at least about 95%, at least about 97%, at least about 98%, or at least about 99% of the droplets may contain either no cell or only one cell. In addition, it should be noted that the average rate of particle loading and the average rate of cell loading within the droplets may be the same or different.

In some cases, a relatively large number of droplets may be created, e.g., at least about 10, at least about 30, at least about 50, at least about 100, at least about 300, at least about 500, at least about 1,000, at least about 3,000, at least about 5,000, at least about 10,000, at least about 30,000, at least about 50,000, at least about 100,000 droplets, etc. In some cases, as previously discussed, some or all of the droplets may be distinguishable, e.g., on the basis of the oligonucleotide tags present in at least some of the droplets (e.g., which may comprise one or more unique sequences or barcodes). In some cases, at least about 50%, at least about 60%, at least about 70%, at least about 80%, at least about 90%, at least about 95%, at least about 97%, at least about 98%, or at least about 99% of the droplets may be distinguishable.

After loading of the particles and cells into droplets, the oligonucleotide tags may be released or cleaved from the particles, in accordance with certain aspects of the invention. As noted above, any suitable technique may be used to release the oligonucleotide tags from the droplets, such as light (e.g., if the oligonucleotide tag includes a photocleavable linker), a chemical, or an enzyme, etc. If a chemical or an enzyme is used, the chemical or enzyme may be introduced into the droplet after formation of the droplet, e.g., through picoinjection or other methods such as those discussed in Int. Pat. Apl. Pub. No. WO 2010/151776, entitled "Fluid Injection" (incorporated herein by reference), through fusion of the droplets with droplets containing the chemical or enzyme, or through other techniques known to those of ordinary skill in the art.

As discussed, in certain aspects, the droplets may contain nucleic acid. The nucleic acid may arise from a cell, or from other suitable sources. In one set of embodiments, if cells are present, the cells may be lysed within the droplets, e.g., to release DNA and/or RNA from the cell, and/or to produce a cell lysate within the droplet. For instance, the cells may be lysed via exposure to a lysing chemical or a cell lysis reagent (e.g., a surfactant such as Triton-X or SDS, an enzyme such as lysozyme, lysostaphin, zymolase, cellulase, mutanolysin, glycanases, proteases, mannase, proteinase K, etc.), or a physical condition (e.g., ultrasound, ultraviolet light, mechanical agitation, etc.). If a lysing chemical is used, the lysing chemical may be introduced into the droplet after formation of the droplet, e.g., through picoinjection or other methods such as those discussed in U.S. patent application Ser. No. 13/379,782, filed Dec. 21, 2011, entitled "Fluid Injection," published as U.S. Pat. Apl. Pub. No. 2012/0132288 on May 31, 2012, incorporated herein by reference in its entirety, through fusion of the droplets with droplets containing the chemical or enzyme, or through other techniques known to those of ordinary skill in the art. Lysing of the cells may occur before, during, or after release of the oligonucleotide tags from the particles. In some cases, lysing a cell will cause the cell to release its contents, e.g., cellular nucleic acids, proteins, enzymes, sugars, etc. In some embodiments, some of the cellular nucleic acids may also be joined to one or more oligonucleotide tags contained within the droplet, e.g., as discussed herein. For example, in one set of embodiments, RNA transcripts typically produced within the cells may be released and then joined to the nucleic acid tags.

In some embodiments, once released, the released nucleic acids from the cell (e.g., DNA and/or RNA) may be bonded to the oligonucleotide tags, e.g., covalently, through primer extension, through ligation, or the like. Any of a wide variety of different techniques may be used, and those of ordinary skill in the art will be aware of many such techniques. The exact joining technique used is not necessarily critical, and can vary between embodiments.

For instance, in certain embodiments, the nucleic acids may be joined with the oligonucleotide tags using ligases. Non-limiting examples of ligases include DNA ligases such as DNA Ligase I, DNA Ligase II, DNA Ligase III, DNA Ligase IV, T4 DNA ligase, T7 DNA ligase, T3 DNA Ligase, E. coli DNA Ligase, Taq DNA Ligase, or the like. Many such ligases may be purchased commercially. As additional examples, in some embodiments, two or more nucleic acids may be ligated together using annealing or a primer extension method.

In yet another set of embodiments, the nucleic acids may be joined with the oligonucleotide tags and/or amplified using PCR (polymerase chain reaction) or other suitable amplification techniques, including any of those recited herein. Typically, in PCR reactions, the nucleic acids are heated to cause dissociation of the nucleic acids into single strands, and a heat-stable DNA polymerase (such as Taq polymerase) is used to amplify the nucleic acid. This process is often repeated multiple times to amplify the nucleic acids.

In one set of embodiments, PCR or nucleic acid amplification may be performed within the droplets. For example, the droplets may contain a polymerase (such as Taq polymerase), and DNA nucleotides, and the droplets may be processed (e.g., via repeated heated and cooling) to amplify the nucleic acid within the droplets. The polymerase and nucleotides may be added at any suitable point, e.g., before, during, or after various nucleic acids encoding various conditions are added to the droplets. For instance, a droplet may contain polymerase and DNA nucleotides, which is fused to the droplet to allow amplification to occur. Those of ordinary skill in the art will be aware of suitable PCR techniques and variations, such as assembly PCR or polymerase cycling assembly, which may be used in some embodiments to produce an amplified nucleic acid. Non-limiting examples of such procedures are also discussed below. In addition, in some cases, suitable primers may be used to initiate polymerization, e.g., P5 and P7, or other primers known to those of ordinary skill in the art. In some embodiments, primers may be added to the droplets, or the primers may be present on one or more of the nucleic acids within the droplets. Those of ordinary skill in the art will be aware of suitable primers, many of which can be readily obtained commercially.

In some cases, the droplets may be burst, broken, or otherwise disrupted. A wide variety of methods for "breaking" or "bursting" droplets are available to those of ordinary skill in the art, and the exact method chosen is not critical. For example, droplets contained in a carrying fluid may be disrupted using techniques such as mechanical disruption or ultrasound. Droplets may also be disrupted using chemical agents or surfactants, for example, 1H,1H,2H,2H-perfluorooctanol.

Nucleic acids (labeled with oligonucleotide tags) from different droplets may then be pooled or combined together or analyzed, e.g., sequenced, amplified, etc. The nucleic acids from different droplets, may however, remain distinguishable due to the presence of different oligonucleotide tags (e.g., containing different barcodes) that were present in each droplet prior to disruption.

For example, the nucleic acids may be amplified using PCR (polymerase chain reaction) or other amplification techniques. Typically, in PCR reactions, the nucleic acids are heated to cause dissociation of the nucleic acids into single strands, and a heat-stable DNA polymerase (such as Taq polymerase) is used to amplify the nucleic acid. This process is often repeated multiple times to amplify the nucleic acids.

In one set of embodiments, the PCR may be used to amplify the nucleic acids. Those of ordinary skill in the art will be aware of suitable PCR techniques and variations, such as assembly PCR or polymerase cycling assembly, which may be used in some embodiments to produce an amplified nucleic acid. Non-limiting examples of such procedures are also discussed below. In addition, in some cases, suitable primers may be used to initiate polymerization, e.g., P5 and P7, or other primers known to those of ordinary skill in the art. Those of ordinary skill in the art will be aware of suitable primers, many of which can be readily obtained commercially. Other non-limiting examples of amplification methods known to those of ordinary skill in the art that may be used include, but are not limited to, reverse transcriptase (RT) PCR amplification, in vitro transcription amplification (IVT), multiple displacement amplification (MDA), or quantitative real-time PCR (qPCR).

In some embodiments, the nucleic acids may be sequenced using a variety of techniques and instruments, many of which are readily available commercially. Examples of such techniques include, but are not limited to, chain-termination sequencing, sequencing-by-hybridization, Maxam-Gilbert sequencing, dye-terminator sequencing, chain-termination methods, Massively Parallel Signature Sequencing (Lynx Therapeutics), polony sequencing, pyro-sequencing, sequencing by ligation, ion semiconductor sequencing, DNA nanoball sequencing, single-molecule real-time sequencing, nanopore sequencing, microfluidic Sanger sequencing, digital RNA sequencing ("digital RNA-seq"), etc. The exact sequencing method chosen is not critical.

In addition, in some cases, the droplets may also contain one or more DNA-tagged antibodies, e.g., to determine proteins in the cell, e.g., by suitable tagging with DNA. Thus, for example, a protein may be detected in a plurality of cells as discussed herein, using DNA-tagged antibodies specific for the protein.

Additional details regarding systems and methods for manipulating droplets in a microfluidic system follow, e.g., for determining droplets (or species within droplets), sorting droplets, etc. For example, various systems and methods for screening and/or sorting droplets are described in U.S. patent application Ser. No. 11/360,845, filed Feb. 23, 2006, entitled "Electronic Control of Fluidic Species," by Link, et al., published as U.S. Patent Application Publication No. 2007/000342 on Jan. 4, 2007, incorporated herein by reference. As a non-limiting example, by applying (or removing) a first electric field (or a portion thereof), a droplet may be directed to a first region or channel; by applying (or removing) a second electric field to the device (or a portion thereof), the droplet may be directed to a second region or channel; by applying a third electric field to the device (or a portion thereof), the droplet may be directed to a third region or channel; etc., where the electric fields may differ in some way, for example, in intensity, direction, frequency, duration, etc.

In certain embodiments of the invention, sensors are provided that can sense and/or determine one or more characteristics of the fluidic droplets, and/or a characteristic of a portion of the fluidic system containing the fluidic droplet (e.g., the liquid surrounding the fluidic droplet) in such a manner as to allow the determination of one or more characteristics of the fluidic droplets. Characteristics determinable with respect to the droplet and usable in the invention can be identified by those of ordinary skill in the art. Non-limiting examples of such characteristics include fluorescence, spectroscopy (e.g., optical, infrared, ultraviolet, etc.), radioactivity, mass, volume, density, temperature, viscosity, pH, concentration of a substance, such as a biological substance (e.g., a protein, a nucleic acid, etc.), or the like.

In some cases, the sensor may be connected to a processor, which in turn, cause an operation to be performed on the fluidic droplet, for example, by sorting the droplet, adding or removing electric charge from the droplet, fusing the droplet with another droplet, splitting the droplet, causing mixing to occur within the droplet, etc., for example, as previously described. For instance, in response to a sensor measurement of a fluidic droplet, a processor may cause the fluidic droplet to be split, merged with a second fluidic droplet, etc.

One or more sensors and/or processors may be positioned to be in sensing communication with the fluidic droplet. "Sensing communication," as used herein, means that the sensor may be positioned anywhere such that the fluidic droplet within the fluidic system (e.g., within a channel), and/or a portion of the fluidic system containing the fluidic droplet may be sensed and/or determined in some fashion. For example, the sensor may be in sensing communication with the fluidic droplet and/or the portion of the fluidic system containing the fluidic droplet fluidly, optically or visually, thermally, pneumatically, electronically, or the like. The sensor can be positioned proximate the fluidic system, for example, embedded within or integrally connected to a wall of a channel, or positioned separately from the fluidic system but with physical, electrical, and/or optical communication with the fluidic system so as to be able to sense and/or determine the fluidic droplet and/or a portion of the fluidic system containing the fluidic droplet (e.g., a channel or a microchannel, a liquid containing the fluidic droplet, etc.). For example, a sensor may be free of any physical connection with a channel containing a droplet, but may be positioned so as to detect electromagnetic radiation arising from the droplet or the fluidic system, such as infrared, ultraviolet, or visible light. The electromagnetic radiation may be produced by the droplet, and/or may arise from other portions of the fluidic system (or externally of the fluidic system) and interact with the fluidic droplet and/or the portion of the fluidic system containing the fluidic droplet in such as a manner as to indicate one or more characteristics of the fluidic droplet, for example, through absorption, reflection, diffraction, refraction, fluorescence, phosphorescence, changes in polarity, phase changes, changes with respect to time, etc. As an example, a laser may be directed towards the fluidic droplet and/or the liquid surrounding the fluidic droplet, and the fluorescence of the fluidic droplet and/or the surrounding liquid may be determined. "Sensing communication," as used herein may also be direct or indirect. As an example, light from the fluidic droplet may be directed to a sensor, or directed first through a fiber optic system, a waveguide, etc., before being directed to a sensor.

Non-limiting examples of sensors useful in the invention include optical or electromagnetically-based systems. For example, the sensor may be a fluorescence sensor (e.g., stimulated by a laser), a microscopy system (which may include a camera or other recording device), or the like. As another example, the sensor may be an electronic sensor, e.g., a sensor able to determine an electric field or other electrical characteristic. For example, the sensor may detect capacitance, inductance, etc., of a fluidic droplet and/or the portion of the fluidic system containing the fluidic droplet.

As used herein, a "processor" or a "microprocessor" is any component or device able to receive a signal from one or more sensors, store the signal, and/or direct one or more responses (e.g., as described above), for example, by using a mathematical formula or an electronic or computational circuit. The signal may be any suitable signal indicative of the environmental factor determined by the sensor, for example a pneumatic signal, an electronic signal, an optical signal, a mechanical signal, etc.

In one set of embodiments, a fluidic droplet may be directed by creating an electric charge and/or an electric dipole on the droplet, and steering the droplet using an applied electric field, which may be an AC field, a DC field, etc. As an example, an electric field may be selectively applied and removed (or a different electric field may be applied, e.g., a reversed electric field) as needed to direct the fluidic droplet to a particular region. The electric field may be selectively applied and removed as needed, in some embodiments, without substantially altering the flow of the liquid containing the fluidic droplet. For example, a liquid may flow on a substantially steady-state basis (i.e., the average flowrate of the liquid containing the fluidic droplet deviates by less than 20% or less than 15% of the steady-state flow or the expected value of the flow of liquid with respect to time, and in some cases, the average flowrate may deviate less than 10% or less than 5%) or other predetermined basis through a fluidic system of the invention (e.g., through a channel or a microchannel), and fluidic droplets contained within the liquid may be directed to various regions, e.g., using an electric field, without substantially altering the flow of the liquid through the fluidic system.

In some embodiments, the fluidic droplets may be screened or sorted within a fluidic system of the invention by altering the flow of the liquid containing the droplets. For instance, in one set of embodiments, a fluidic droplet may be steered or sorted by directing the liquid surrounding the fluidic droplet into a first channel, a second channel, etc.

In another set of embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels can be controlled to direct the droplet selectively into one of the channels, and changes in pressure can be effected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. The liquid reservoirs may be positioned such that, when activated, the movement of liquid caused by the activated reservoirs causes the liquid to flow in a preferred direction, carrying the fluidic droplet in that preferred direction. For instance, the expansion of a liquid reservoir may cause a flow of liquid towards the reservoir, while the contraction of a liquid reservoir may cause a flow of liquid away from the reservoir. In some cases, the expansion and/or contraction of the liquid reservoir may be combined with other flow-controlling devices and methods, e.g., as described herein. Non-limiting examples of devices able to cause the expansion and/or contraction of a liquid reservoir include pistons and piezoelectric components. In some cases, piezoelectric components may be particularly useful due to their relatively rapid response times, e.g., in response to an electrical signal. In some embodiments, the fluidic droplets may be sorted into more than two channels.

As mentioned, certain embodiments are generally directed to systems and methods for sorting fluidic droplets in a liquid, and in some cases, at relatively high rates. For example, a property of a droplet may be sensed and/or determined in some fashion (e.g., as further described herein), then the droplet may be directed towards a particular region of the device, such as a microfluidic channel, for example, for sorting purposes. In some cases, high sorting speeds may be achievable using certain systems and methods of the invention. For instance, at least about 10 droplets per second may be determined and/or sorted in some cases, and in other cases, at least about 20 droplets per second, at least about 30 droplets per second, at least about 100 droplets per second, at least about 200 droplets per second, at least about 300 droplets per second, at least about 500 droplets per second, at least about 750 droplets per second, at least about 1,000 droplets per second, at least about 1,500 droplets per second, at least about 2,000 droplets per second, at least about 3,000 droplets per second, at least about 5,000 droplets per second, at least about 7,500 droplets per second, at least about 10,000 droplets per second, at least about 15,000 droplets per second, at least about 20,000 droplets per second, at least about 30,000 droplets per second, at least about 50,000 droplets per second, at least about 75,000 droplets per second, at least about 100,000 droplets per second, at least about 150,000 droplets per second, at least about 200,000 droplets per second, at least about 300,000 droplets per second, at least about 500,000 droplets per second, at least about 750,000 droplets per second, at least about 1,000,000 droplets per second, at least about 1,500,000 droplets per second, at least about 2,000,000 or more droplets per second, or at least about 3,000,000 or more droplets per second may be determined and/or sorted.

In some aspects, a population of relatively small droplets may be used. In certain embodiments, as non-limiting examples, the average diameter of the droplets may be less than about 1 mm, less than about 500 micrometers, less than about 300 micrometers, less than about 200 micrometers, less than about 100 micrometers, less than about 75 micrometers, less than about 50 micrometers, less than about 30 micrometers, less than about 25 micrometers, less than about 20 micrometers, less than about 15 micrometers, less than about 10 micrometers, less than about 5 micrometers, less than about 3 micrometers, less than about 2 micrometers, less than about 1 micrometer, less than about 500 nm, less than about 300 nm, less than about 100 nm, or less than about 50 nm. The average diameter of the droplets may also be at least about 30 nm, at least about 50 nm, at least about 100 nm, at least about 300 nm, at least about 500 nm, at least about 1 micrometer, at least about 2 micrometers, at least about 3 micrometers, at least about 5 micrometers, at least about 10 micrometers, at least about 15 micrometers, or at least about 20 micrometers in certain cases. The "average diameter" of a population of droplets is the arithmetic average of the diameters of the droplets.

In some embodiments, the droplets may be of substantially the same shape and/or size (i.e., "monodisperse"), or of different shapes and/or sizes, depending on the particular application. In some cases, the droplets may have a homogenous distribution of cross-sectional diameters, i.e., the droplets may have a distribution of diameters such that no more than about 5%, no more than about 2%, or no more than about 1% of the droplets have a diameter less than about 90% (or less than about 95%, or less than about 99%) and/or greater than about 110% (or greater than about 105%, or greater than about 101%) of the overall average diameter of the plurality of droplets. Some techniques for producing homogenous distributions of cross-sectional diameters of droplets are disclosed in International Patent Application No. PCT/US2004/010903, filed Apr. 9, 2004, entitled "Formation and Control of Fluidic Species," by Link et al., published as WO 2004/091763 on Oct. 28, 2004, incorporated herein by reference.

Those of ordinary skill in the art will be able to determine the average diameter of a population of droplets, for example, using laser light scattering or other known techniques. The droplets so formed can be spherical, or non-spherical in certain cases. The diameter of a droplet, in a non-spherical droplet, may be taken as the diameter of a perfect mathematical sphere having the same volume as the non-spherical droplet.

In some embodiments, one or more droplets may be created within a channel by creating an electric charge on a fluid surrounded by a liquid, which may cause the fluid to separate into individual droplets within the liquid. In some embodiments, an electric field may be applied to the fluid to cause droplet formation to occur. The fluid can be present as a series of individual charged and/or electrically inducible droplets within the liquid. Electric charge may be created in the fluid within the liquid using any suitable technique, for example, by placing the fluid within an electric field (which may be AC, DC, etc.), and/or causing a reaction to occur that causes the fluid to have an electric charge.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. Techniques for producing a suitable electric field (which may be AC, DC, etc.) are known to those of ordinary skill in the art. For example, in one embodiment, an electric field is produced by applying voltage across a pair of electrodes, which may be positioned proximate a channel such that at least a portion of the electric field interacts with the channel. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof.

In another set of embodiments, droplets of fluid can be created from a fluid surrounded by a liquid within a channel by altering the channel dimensions in a manner that is able to induce the fluid to form individual droplets. The channel may, for example, be a channel that expands relative to the direction of flow, e.g., such that the fluid does not adhere to the channel walls and forms individual droplets instead, or a channel that narrows relative to the direction of flow, e.g., such that the fluid is forced to coalesce into individual droplets. In some cases, the channel dimensions may be altered with respect to time (for example, mechanically or electromechanically, pneumatically, etc.) in such a manner as to cause the formation of individual droplets to occur. For example, the channel may be mechanically contracted ("squeezed") to cause droplet formation, or a fluid stream may be mechanically disrupted to cause droplet formation, for example, through the use of moving baffles, rotating blades, or the like. Other techniques of creating droplets include, for example mixing or vortexing of a fluid.

Certain embodiments are generally directed to systems and methods for splitting a droplet into two or more droplets. For example, a droplet can be split using an applied electric field. The droplet may have a greater electrical conductivity than the surrounding liquid, and, in some cases, the droplet may be neutrally charged. In certain embodiments, in an applied electric field, electric charge may be urged to migrate from the interior of the droplet to the surface to be distributed thereon, which may thereby cancel the electric field experienced in the interior of the droplet. In some embodiments, the electric charge on the surface of the droplet may also experience a force due to the applied electric field, which causes charges having opposite polarities to migrate in opposite directions. The charge migration may, in some cases, cause the drop to be pulled apart into two separate droplets.

Some embodiments of the invention generally relate to systems and methods for fusing or coalescing two or more droplets into one droplet, e.g., where the two or more droplets ordinarily are unable to fuse or coalesce, for example, due to composition, surface tension, droplet size, the presence or absence of surfactants, etc. In certain cases, the surface tension of the droplets, relative to the size of the droplets, may also prevent fusion or coalescence of the droplets from occurring.

As a non-limiting example, two droplets can be given opposite electric charges (i.e., positive and negative charges, not necessarily of the same magnitude), which can increase the electrical interaction of the two droplets such that fusion or coalescence of the droplets can occur due to their opposite electric charges. For instance, an electric field may be applied to the droplets, the droplets may be passed through a capacitor, a chemical reaction may cause the droplets to become charged, etc. The droplets, in some cases, may not be able to fuse even if a surfactant is applied to lower the surface tension of the droplets. However, if the droplets are electrically charged with opposite charges (which can be, but are not necessarily of, the same magnitude), the droplets may be able to fuse or coalesce. As another example, the droplets may not necessarily be given opposite electric charges (and, in some cases, may not be given any electric charge), and are fused through the use of dipoles induced in the droplets that causes the droplets to coalesce. Also, the two or more droplets allowed to coalesce are not necessarily required to meet "head-on." Any angle of contact, so long as at least some fusion of the droplets initially occurs, is sufficient. See also, e.g., U.S. patent application Ser. No. 11/698,298, filed Jan. 24, 2007, entitled "Fluidic Droplet Coalescence," by Ahn, et al., published as U.S. Patent Application Publication No. 2007/0195127 on Aug. 23, 2007, incorporated herein by reference in its entirety.

In one set of embodiments, a fluid may be injected into a droplet. The fluid may be microinjected into the droplet in some cases, e.g., using a microneedle or other such device. In other cases, the fluid may be injected directly into a droplet using a fluidic channel as the droplet comes into contact with the fluidic channel. Other techniques of fluid injection are disclosed in, e.g., International Patent Application No. PCT/US2010/040006, filed Jun. 25, 2010, entitled "Fluid Injection," by Weitz, et al., published as WO 2010/151776 on Dec. 29, 2010; or International Patent Application No. PCT/US2009/006649, filed Dec. 18, 2009, entitled "Particle-Assisted Nucleic Acid Sequencing," by Weitz, et al., published as WO 2010/080134 on Jul. 15, 2010, each incorporated herein by reference in its entirety.

A variety of materials and methods, according to certain aspects of the invention, can be used to form articles or components such as those described herein, e.g., channels such as microfluidic channels, chambers, etc. For example, various articles or components can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, *Scientific American,* 248:44-55, 1983 (Angell, et al).

In one set of embodiments, various structures or components of the articles described herein can be formed of a polymer, for example, an elastomeric polymer such as polydimethylsiloxane ("PDMS"), polytetrafluoroethylene ("PTFE" or Teflon®), or the like. For instance, according to one embodiment, a microfluidic channel may be implemented by fabricating the fluidic system separately using PDMS or other soft lithography techniques (details of soft lithography techniques suitable for this embodiment are discussed in the references entitled "Soft Lithography," by Younan Xia and George M. Whitesides, published in the *Annual Review of Material Science,* 1998, Vol. 28, pages 153-184, and "Soft Lithography in Biology and Biochemistry," by George M. Whitesides, Emanuele Ostuni, Shuichi Takayama, Xingyu Jiang and Donald E. Ingber, published in the *Annual Review of Biomedical Engineering,* 2001, Vol. 3, pages 335-373; each of these references is incorporated herein by reference).

Other examples of potentially suitable polymers include, but are not limited to, polyethylene terephthalate (PET), polyacrylate, polymethacrylate, polycarbonate, polystyrene, polyethylene, polypropylene, polyvinylchloride, cyclic olefin copolymer (COC), polytetrafluoroethylene, a fluorinated polymer, a silicone such as polydimethylsiloxane, polyvinylidene chloride, bis-benzocyclobutene ("BCB"), a polyimide, a fluorinated derivative of a polyimide, or the like. Combinations, copolymers, or blends involving polymers including those described above are also envisioned. The device may also be formed from composite materials, for example, a composite of a polymer and a semiconductor material.

In some embodiments, various structures or components of the article are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, waxes, metals, or mixtures or composites thereof heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, dodecyltrichlorosilanes, etc.

Silicone polymers are used in certain embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of various structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures or channels from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, structures can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," *Anal. Chem.,* 70:474-480, 1998 (Duffy et al.), incorporated herein by reference.

Thus, in certain embodiments, the design and/or fabrication of the article may be relatively simple, e.g., by using relatively well-known soft lithography and other techniques such as those described herein. In addition, in some embodiments, rapid and/or customized design of the article is possible, for example, in terms of geometry. In one set of embodiments, the article may be produced to be disposable, for example, in embodiments where the article is used with substances that are radioactive, toxic, poisonous, reactive, biohazardous, etc., and/or where the profile of the substance (e.g., the toxicology profile, the radioactivity profile, etc.) is unknown. Another advantage to forming channels or other structures (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

The following documents are incorporated herein by reference in their entirety for all purposes: U.S. Pat. Apl. Ser. No. 61/980,541, entitled "Methods and Systems for Droplet Tagging and Amplification," by Weitz, et al.; U.S. Pat. Apl. Ser. No. 61/981,123, entitled "Systems and Methods for Droplet Tagging," by Bernstein, et al.; Int. Pat. Apl. Pub. No. WO 2004/091763, entitled "Formation and Control of Fluidic Species," by Link et al.; Int. Pat. Apl. Pub. No. WO 2004/002627, entitled "Method and Apparatus for Fluid Dispersion," by Stone et al.; Int. Pat. Apl. Pub. No. WO 2006/096571, entitled "Method and Apparatus for Forming Multiple Emulsions," by Weitz et al.; Int. Pat. Apl. Pub. No. WO 2005/021151, entitled "Electronic Control of Fluidic Species," by Link et al.; Int. Pat. Apl. Pub. No. WO 2011/056546, entitled "Droplet Creation Techniques," by Weitz, et al.; Int. Pat. Apl. Pub. No. WO 2010/033200, entitled "Creation of Libraries of Droplets and Related Species," by Weitz, et al.; U.S. Pat. Apl. Pub. No. 2012-0132288, entitled "Fluid Injection," by Weitz, et al.; Int. Pat. Apl. Pub. No. WO 2008/109176, entitled "Assay And Other Reactions Involving Droplets," by Agresti, et al.; and Int. Pat. Apl. Pub. No. WO 2010/151776, entitled "Fluid Injection," by Weitz, et al.

Also incorporated herein by reference are U.S. Prov. Pat. Apl. Ser. No. 61/982,001, filed Apr. 21, 2014; U.S. Prov. Pat. Apl. Ser. No. 62/065,348, filed Oct. 17, 2014; U.S. Prov. Pat. Apl. Ser. No. 62/066,188, filed Oct. 20, 2014; and U.S. Prov. Pat. Apl. Ser. No. 62/072,944, filed Oct. 30, 2014.

In addition, the following are incorporated herein by reference in their entireties: U.S. Pat. Apl. Ser. No. 61/981,123 filed Apr. 17, 2014; a PCT application filed Apr. 17, 2015, entitled "Systems and Methods for Droplet Tagging"; U.S. Pat. Apl. Ser. No. 61/981,108 filed Apr. 17, 2014; a PCT application filed on Apr. 17, 2015, entitled "Methods and Systems for Droplet Tagging and Amplification"; a U.S. patent application filed on Apr. 17, 2015, entitled "Immobilization-Based Systems and Methods for Genetic Analysis and Other Applications"; a U.S. patent application filed on Apr. 17, 2015, entitled "Barcoding Systems and Methods for Gene Sequencing and Other Applications"; and U.S. Pat. Apl. Ser. No. 62/072,944, filed Oct. 30, 2014.

The following examples are intended to illustrate certain embodiments of the present invention, but do not exemplify the full scope of the invention.

Example 1

This example makes use of hydrogel or polymer microspheres, each carrying DNA fragments (primers) at a concentration of 1-100 micromolar. These primers can be cleaved from the microspheres by chemicals or by light, with each DNA fragment encoding (a) a barcode sequence selected at random from a pool of at least 10,000 barcodes (but more from typically over 100,000 barcodes), with the same barcode found on all nucleic acid fragments on each microsphere; and (b) one or more a primer sequences used for hybridization and capture of DNA or RNA; (c) optionally, additional DNA sequences, for example a random nucleotide sequence for barcoding each molecule, or sequences used for amplification or capture of the barcoded products. Synthesis of these microspheres is described in more detail below.

In this example for droplet production, a microfluidic device prepared by soft-lithography is used. Its schematics are indicated in FIG. 2 but emulsification can be also performed using other tools such as capillaries or tubing, for example. Other microfluidic configurations can also be used. Using this microfluidic device, droplets of ~4 nL volume were produced (FIGS. 3 and 4), but the size of the droplets could be readily adjusted based on the requirements of the enzymatic barcoding reaction.

The microfluidic device used in this example has one inlet for droplet carrier oil, and additional inlets for components of the droplet aqueous phase (FIG. 14). For the carrier oil, fluorinated oil (e.g. HFE-7500) containing ~0.75% (v/v) surfactant (PFPE-PEG-PFPE tri-block copolymer containing two perfluoropolyether blocks (PFPE) and one poly (ethylene)glycol (PEG) block) was used. The surfactant was used to prevent droplets from coalescing, and the amount may be adjusted, for instance, based on its physicochemical properties. The carrier oil used for emulsification is not limited to fluorinated liquids and alternative fluids such as based on hydrocarbons (e.g. mineral oil, hexane, etc.), silicon oil and other type of oils can be employed successfully. The three inlets used in this example delivered the following components: (1) a suspension of dissociated cells; (2) a cell lysis reagent; (3) a suspension of barcoded primer-carrying hydrogel or polymer microspheres; and (4) a reaction mixture used to enzymatically generate barcoded DNA complementary to the captured DNA or RNA. It is possible to pre-combine some of these components in some cases, e.g. (2) and (4).

The cell suspension was prepared in this example with the following considerations. If cells were adherent or from tissue, the cells could be first dissociated and optionally filtered or centrifuged to remove clumps of two or more cells. The mass density of the cell suspension buffer (typically PBS) was adjusted to minimize precipitation of cells during injection, for example by adding Optiprep at ~16% (v/v). The cell number density (cells per unit volume) may be adjusted to minimize incidences of two or more cells becoming captured in the same droplet. The precise calculation of the correct number density depends, for example, on factors such as the amount of multi-cell events that can be tolerated, and on the droplet volume, and on the relative droplet volume contributed by the cell suspension. For example, for 4 nL droplets with 50% of the droplet volume contributed by the cell suspension, a number density of 50 cells/microliter could be used to lead to an average occupancy of 0.1 cells/droplet, leading to approximately 5% of cell-containing droplets having more than one cell. If necessary, a small magnetic stirrer bar could be introduced into the cell syringe to allow continuous or occasional mixing of the cell suspension. During injection into the microfluidic device, the cells can be kept cold using an ice pack or other suitable techniques of cooling.

The enzyme reaction mix and/or lysis reagent(s) were prepared in this example such that their final concentrations after mixing with the cell suspension and with the microspheres were suitable for cell lysis and performance of the enzymatic reaction (e.g. reverse transcription reaction).

If using hydrogel microspheres, these spheres can be packed (concentrated) such that their delivery into droplets becomes ordered and synchronized, ensuring that the majority of droplets host exactly one microsphere. When using rigid polymer microspheres, these may be ordered, for example, using flow. In some cases, the aim is to ensure that the number of droplets having a single microsphere is relatively high, and the number of droplets of having 0 or 2 microspheres is rare or even negligible.

To further increase the co-encapsulation events of cells and microspheres, for example, one cell and one DNA-barcoded microsphere per droplet, the cells could be ordered prior encapsulation.

As one non-limiting example, the aqueous phase is delivered into the device with flow rates of 100 microliters/hour, 100 microliters/hour and 10-15 microliters/hour respectively for the cell suspension, the lysis/reaction mix, and the concentrated hydrogel microsphere suspension. For example, the number density of the cell suspension may be adjusted to 50,000/mL such that 5,000 cells are captured for barcoding within one hour of emulsification. However, the flow rates of all phases can be adjusted independently between 1 and 10,000 microliters/hr, depending on the particular application.

After (or during) the encapsulation step, cells may be lysed and DNA fragments attached to the microsphere surface may be released inside the droplets using, e.g., light, chemical, enzymatic or other techniques.

The released DNA fragments may be used as primers for cell-encoded nucleic acid amplification. For example, mRNA from the cells can be converted to cDNA using reverse transcription, or in another example, genes encoding cellular proteins can be synthesized using DNA polymerase.

Figure 5:
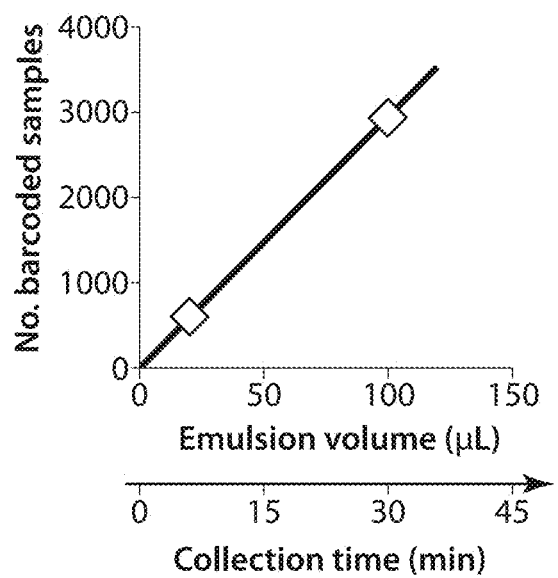
FIG. 5 illustrates sample count as a function of collection time, in one embodiment of the invention.

To release the synthesized nucleic acid (DNA or RNA) into a mixture, the droplets may be broken in some cases, e.g., by chemical or physical techniques. The released DNA may be collected and if necessary, can be amplified or further processed. The number of cells to be analyzed can be adjusted, for example, by first transferring a fraction of the droplet emulsion into a new reaction tube before droplet breaking (FIG. 5). For example, after collection of 200 microliters of droplet emulsion containing 5,000 cells, the emulsion can be first split into five tubes of 40 microliters, each containing approximately 1,000 cells. If desirable these samples can be processed separately. In addition, other adjustments can be performed in other embodiments.

Figure 6:
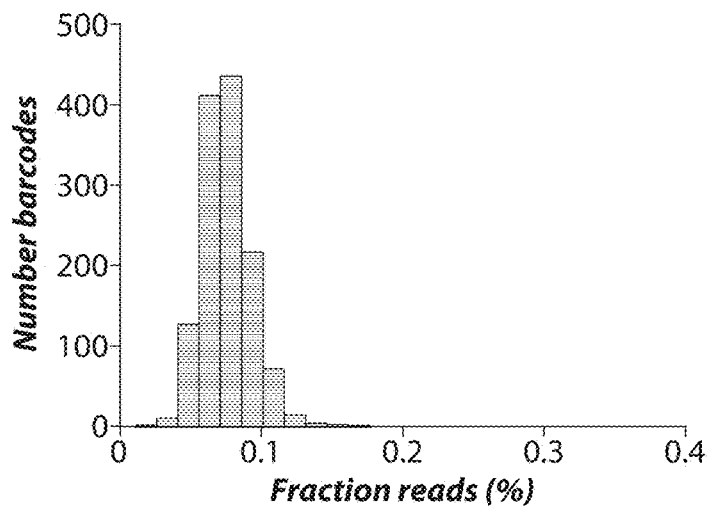
FIG. 6 illustrates a distribution of read sequences, in another embodiment of the invention.

The base composition of nucleic acids, including the barcode and the captured sequence, can be determined by DNA sequencing or other techniques (FIG. 6).

Diagnostic tests can be carried out, for example, using quantitative real-time PCR (qPCR) to compare the abundance of captured DNA or RNA barcoded in droplets, to the abundance achieved when the enzymatic reactions are performed under controlled conditions, such as outside of droplets in a pooled bulk reaction, or using purified DNA or RNA from an equivalent number of cells. qPCR makes use of two primers, one hybridizing to the end of the barcoded DNA fragments delivered by the microspheres; the other hybridizing to a target DNA or RNA sequence to be captured.

The above can be used to analyze, as non-limiting examples, genomes, single nucleotide polymorphisms, specific gene expression levels, non-coding RNA, the whole transcriptome, entire genes or their sections, etc.

Figure 2A:
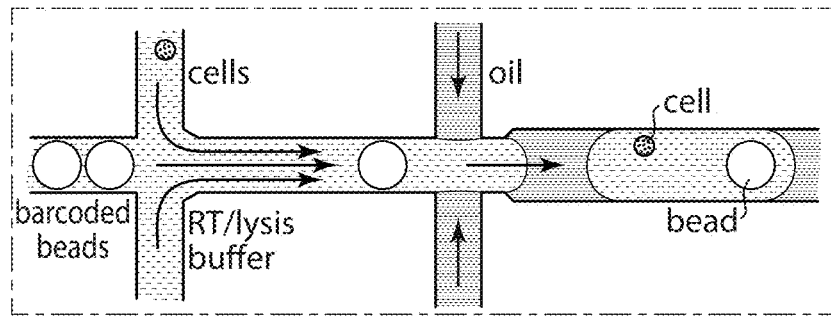
FIGS. 2A-2B illustrate a microfluidic device in another embodiment of the invention.
Figure 2B:
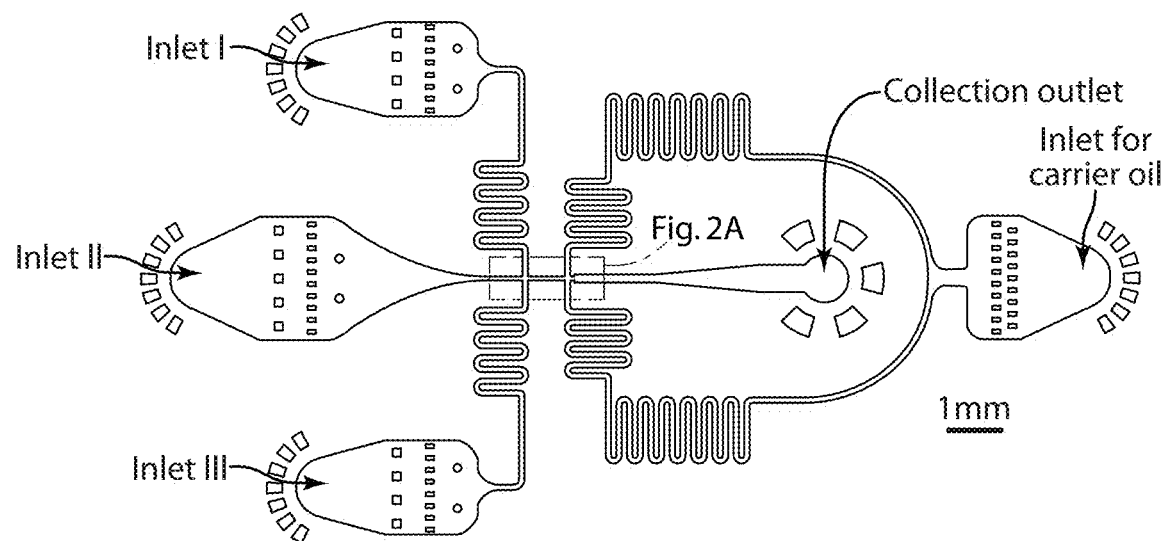
Figure 3:
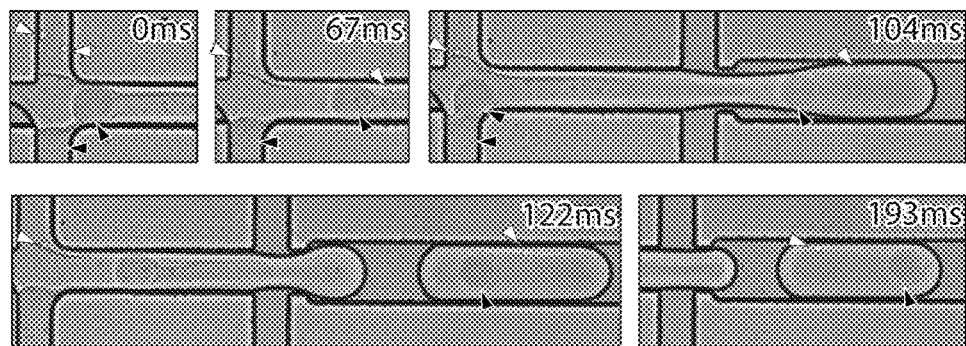
FIG. 3 illustrates cells and particles within droplets in yet another embodiment of the invention.
Figure 4:
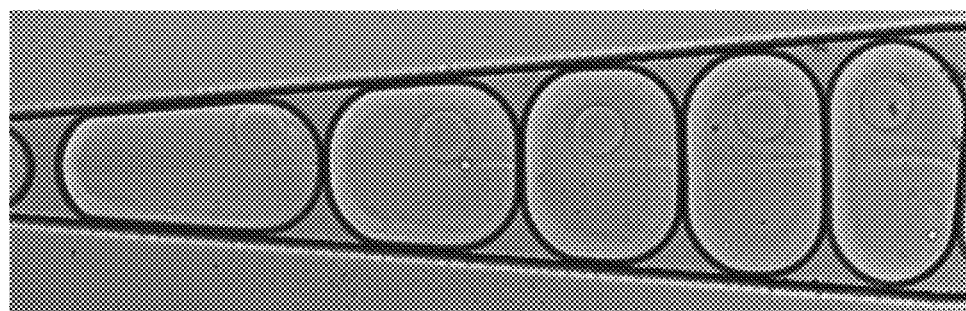
FIG. 4 illustrates a microfluidic channel containing cells and particles within droplets in still another embodiment of the invention.

FIG. 2 shows schematics and operation of a microfluidic device, in accordance with one example of an embodiment of the invention. Other microfluidic device designs are also possible, e.g., as discussed herein. FIG. 2A shows schematics indicating the operation of a system. Cells, barcoded microspheres (barcoded beads) and reagents are encapsulated into droplets using a microfluidic device. FIG. 2B shows a device having three inlets and one outlet. The inlets are used to introduce i) cells, ii) DNA-barcoded microspheres, iii) biological and/or chemical reagents and iv) carrier oil. Gels, cells and reagents can be introduced into device through any of the three inlets I, II, III. Encapsulation occurs at the flow-focusing junction and encapsulated samples are then collected at the outlet. The flow rate of each inlet can be adjusted in order to obtain optimal conditions for cell and DNA-barcoded microsphere co-encapsulation. FIG. 3 shows digital images of cells and DNA-barcoded microspheres co-encapsulated together. Upper arrows show cells, lower arrows show microspheres. Time from the first frame is indicated. FIG. 4 shows an example of a device outlet showing microsphere and cell co-encapsulation. FIG. 5 shows the number of barcoded samples vs emulsion volume and encapsulation (collection) time, produced in accordance with one embodiment of the invention. FIG. 6 shows a distribution of sequencing reads per abundant barcode showing largely uniform barcoding, in one embodiment of the invention.

Example 2

Figure 7:
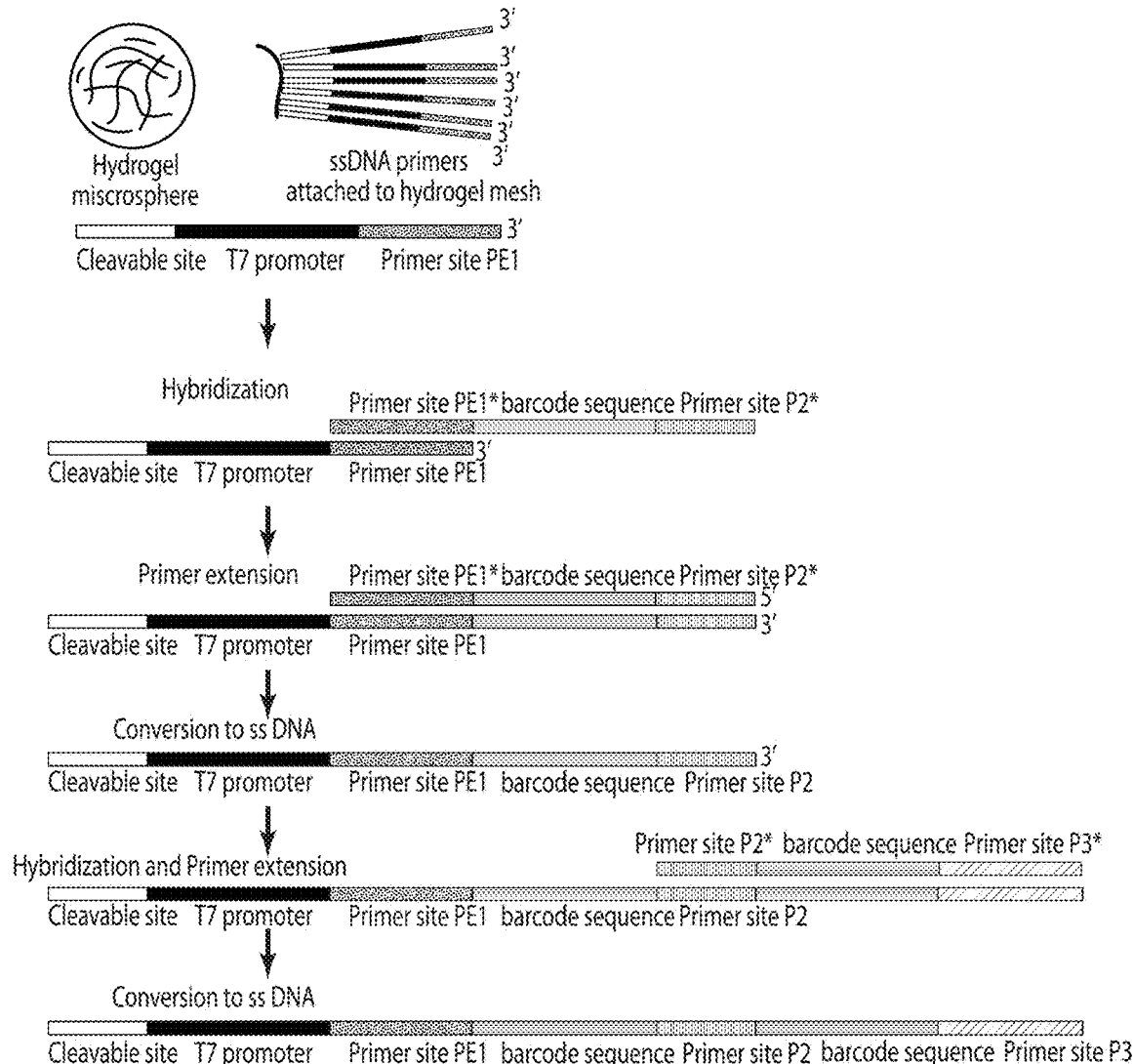
FIG. 7 illustrates production of oligonucleotide tags, in yet another embodiment of the invention.

This example illustrates certain techniques for creating barcoded nucleic acids attached to the microspheres. First, the microspheres are synthesized incorporating a DNA primer (P1) into the hydrogel (FIG. 7). Several techniques of producing microspheres or various types hydrogel particles may be used. The microspheres described in this example makes use of polyacrylamide (pAc) hydrogel but alternative hydrogel materials can also be used (e.g. agarose, poly-N-isopropylacrylamide (pNIPAM) and others).

In one embodiment, an aqueous solution containing acrylamide (Ac), N,N'-methylenebisacrylamide (bis-Ac) and acrylic phosphoramidite modified DNA (Ac-DNA) and/or ammonium persulfate (APS) is prepared mixing individual components together.

Based on the pore size of the hydrogel mesh and the concentration of primer needed for the subsequent applications the amount of Ac and bis-Ac components as well as Ac-DNA concentration can be adjusted accordingly. For example, in one case, a mixture of ~0.0258% acrylamide, ~0.036% (v/v) N,N'-methylenebisacrylamide, 1-50 micromolar Ac-DNA, and ~0.2% APS is emulsified by a carrier oil containing 0.1-0.6% (v/v) polymerization inducer (N, N, N', N'-tetramethylethylenediamine refered as TEMED) for the production of hydrogel microspheres. As a carrier oil, fluorinated oil (e.g. HFE-7500) may be used, containing ~1.5% (v/v) surfactant (PFPE-PEG-PFPE tri-block copolymer containing two perfluoropolyether blocks (PFPE) and one poly (ethylene)glycol (PEG) block). The surfactant may be used, for example, to prevent droplets against coalescence. In some embodiments, its amount should be adjusted based on its physicochemical properties. The carrier oil used for emulsification is not limited to fluorinated liquids, and alternative fluids based on hydrocarbons (e.g. mineral oil, silicone oil, hexane, etc.) can be employed in other embodiments.

Figure 8:
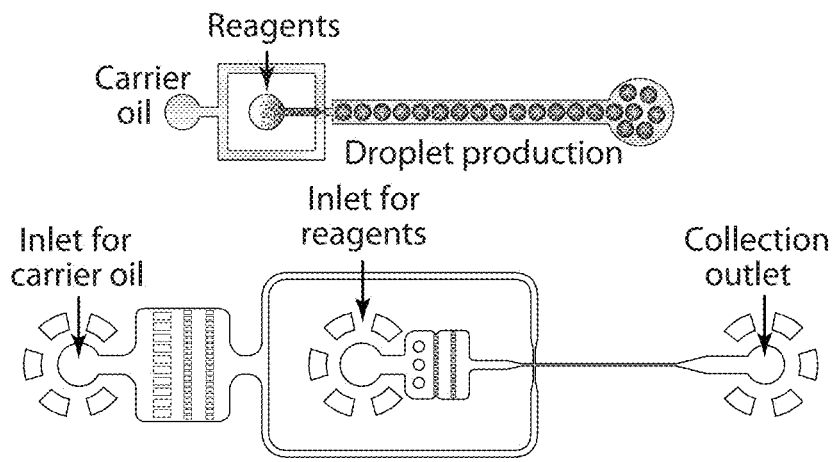
FIG. 8 illustrates a microfluidic device in another embodiment of the invention.

In this example for droplet production, a microfluidic device prepared by soft-lithography was used. Its schematics are indicated in FIG. 8, but emulsification can be also performed using other tools such as capillaries or tubing, for example. In addition, microfluidic devices having different schematics may also be used.

Using this microfluidic device, droplets of approximately 62 micrometers in diameter were produced (FIG. 9), but the size of droplets can be adjusted based on the requirements of other applications.

In this example, the droplets were collected into a tube and then incubated at ~65° C. for >2 hour to induce the polymerization of polyacrylamide. The incubation period and temperature needed for polymerization could be varied accordingly. Polymerization of droplets can also be induced by light or various chemical means.

After polymerization, the emulsion may be broken by techniques such as chemical (e.g. perfluoroctanol) or physical techniques (e.g. electric field), which may cause the contents of the emulsion (e.g., the microspheres) to be released into the bulk solution. The released microspheres were then washed in hexane and aqueous buffers. In a typical example procedure, the microspheres were treated with hexane containing 1% (v/v) Span 80 and then three times with aqueous buffer (e.g. 10 mM Tris-HCl (pH 7.0), 10 mM EDTA and 0.1% (v/v) Tween-20), and were then suspended in a buffer of desirable composition (e.g. 10 mM Tris-HCl (pH 7.0), 0.1 mM EDTA and 0.1% (v/v) Tween-20). The final volume of the microspheres could differ from that seen during synthesis, and varies with conditions of the hydrogel suspension buffer.

The microspheres could be stored for extended periods of time, for example at 4° C. in a solution containing 10 mM EDTA, or in a solution containing 5 mM EDTA and 50% glycerol at −20° C.

The incorporation of nucleic acid or primer into the microspheres or on its surface depends, for example, on functional groups present on the primers and/or the material from which the microspheres are composed of. As a non-limiting example, a nucleic acid containing acrylic phosphoramidite at its 5' end can be incorporated into a polyacrylamide mesh of certain microspheres during polymerization process. As another example, acrydite-modified oligonucleotides can react covalently with thiol groups and thus, microspheres having thiol groups would bind acrydite-modified oligonucleotides. In another example, oligonucleotides having amino groups can be covalently bound to the carboxy group of certain microspheres. In yet another example, oligonucleotides with a biotin group can be attached to streptavidin-coated microspheres. In yet another example, the particle may include antibodies or antibody fragments able to recognize certain oligonucleotide sequences present on the tags. [MOVE TO MAIN BODY OF TEXT] Therefore, different types of incorporation of nucleic acids into/onto the microspheres are possible.

In one embodiment, primers P1 containing sequence for capture of a target nucleic acid (e.g. RNA or DNA), amplification (such as carrying a T7 promoter sequences or hybridization site for PCR primer), and/or sequencing may be used. In another embodiment, the P1 primer has a photocleavable site.

In one embodiment, the structure of P1 primer (direction from 5' to 3') is the following: acrylic phosphoramidite-photo-cleavable spacer-nucleotide sequence of T7 promoter-nucleotide sequence for sequencing (PE1).

In another embodiment, the structure of the DNA primer $Ar_1$ from the first pool of DNA primers (direction from 5' to 3') is the following: adapter sequence (P2)-barcode sequence-nucleotide sequence complimentary to PE1.

In another embodiment, the structure of the DNA primer $N_2$ from the second pool of DNA primers (direction from 5' to 3') is the following: Sequence of interest (P3)-barcode sequence-nucleotide sequence complimentary to P2.

In some cases, the microspheres carrying P1 primers may be split equally into $N_1$ pools, and each pool may be hybridized to one of $N_1$ distinct DNA templates, which have (sequentially from the 3' end to the 5' end): a DNA sequence complimentary to part or all of the P1 primer allowing to form duplex with DNA P1 primer; one of $N_1$ unique nucleic acid barcodes composed of more than 6 defined nucleotides that are identical for all molecules within the same pool; optionally, a random nucleic acid sequence composed of more than 5 random nucleotides that differ between molecules with the same pool; and a DNA sequence (P2) that can be used as a hybridization site for subsequent barcoding. The P2 sequence may contain sequence used for priming a sequencing reaction in later steps.

An enzymatic reaction may be performed on each of the $N_1$ pools leading to the extension of the P1 nucleic acid fragment by a copy of the template DNA fragments in each pool. In some cases, a ligation reaction can be used, e.g., instead of a polymerization reaction. The enzymatic reaction may be halted by addition of inhibitors such as EDTA, vanadium, or by other means.

The microspheres may be pooled together and optionally washed to remove the enzymes, or any excess template molecules.

The DNA fragments on the microspheres may be converted into single stranded DNA, for example, by removing the template molecules through denaturation, for example by washing the microspheres repeatedly in 0.1 M sodium hydroxide, or by other techniques.

The microspheres now ending with the P2 sequence may be split equally into $N_2$ pools (typically $N_2=N_1$, although this is not required), and each pool may be hybridized to one of $N_2$ distinct DNA templates (as in step (2)), which have (sequentially from the 3' end to the 5' end): a DNA sequence complimentary to part or all of the P2 primer allowing to form duplex with DNA P2 primer; one of $N_2$ unique nucleic acid barcodes composed of more than 6 defined nucleotides that are identical for all molecules within the same pool; a random nucleic acid sequence composed of more than 5 random nucleotides that differ between molecules within the same pool; and a DNA sequence site (P3) that may be used, for example, as a hybridization site for subsequent elongation, or as a primer sequence used for single cell analysis operations (such as capture of DNA or RNA molecules).

In some embodiments, some of these steps may be repeated.

In some cases, microspheres may be produced, carrying single-stranded DNA fragments encoding primer P1, followed by a first barcode, followed by a sequence P2, followed by a second barcode, followed by sequence P3. The number of unique microsphere pools is $N_1 \times N_2$ (see also FIGS. 10 and 11).

In some cases, the prepared microspheres can be stored for extended periods of time and used as a reagent in subsequent application.

If required, additional repeats can be carried out with additional pools of $N_{3,4}, \ldots$ barcode templates, each adding a barcode and sequence P4, P5, etc. The number of unique microsphere pools may grow with each step to $N_1 \times N_2 \times N_3 \times \ldots$.

Optionally, all of the microspheres can be hybridized together to a mixture of M DNA templates which have (sequentially from the 3' end to the 5' end): a DNA sequence complimentary to part or all of the final P3 (or P4, P5 etc) primer allowing to form duplex with DNA P3 (or P4, P5 etc.) primer, and one of M sequences $S_1, \ldots, S_M$ that will be used as specific primer sequences for single cell analysis operations (such as capture of specific DNA or RNA molecules). These steps may be repeated. This may yield the same number of $N_1 \times N_2 \times N_3 \times \ldots$ pools of microspheres each carrying the above sequences but now the DNA fragments belong to M species of molecules that are identical excepting a final M possible sequences $S_1, \ldots, S_M$.

In some cases, this may produce result in microspheres coated with ssDNA fragments, each of which encodes in the following order (from 5' to 3'): the P1 primer, for example containing a T7 promoter site and primer site PE1 that could be used as a site for but not limited to for nucleic acid amplification and sequencing; two or more DNA barcodes (each composed of 6 or more nucleotides), which are identical for all primers coating a single bead, but differs between beads; optionally, a molecule-specific DNA barcode (composed of 5 or more random nucleotides); the P2 "primer site 2" that could be used as a primer for sequencing or/and for hybridization to DNA or RNA in single cells for reverse transcription or PCR amplification; the P3 "primer site 3" that could be used as a primer for sequencing or/and for hybridization to DNA or RNA in single cells for reverse transcription or PCR amplification. One P3 fragment can also encode one out of multiple gene specific primers (GSP), thus each bead coated with multiple ssDNA fragments will contain all of the GSPs.

The microspheres carrying barcoded-DNA primers can be used, for example, as reagents for sequencing or/and for hybridization to DNA or RNA in single cells, for reverse transcription or PCR amplification and other applications that involve DNA capture, amplification and sequencing.

FIG. 7 illustrates microspheres carrying PE1 primers hybridized to a pool of single stranded DNA (ssDNA) primers carrying barcode sequence and primer sites PE1* and P2*. In this example, the primer is then extended using DNA polymerase. The extended primer is then converted to ssDNA (e.g. using increased temperature or alkaline solution). The obtained ssDNA primer may then be hybridized to a second pool of primers carrying a second barcode sequence and primer sites P2* and P3*. After primer extension and conversion to ssDNA the microspheres can be used for different applications, for example, applications aimed at capturing and sequencing nucleic acids in a sample.

FIG. 8 illustrates schematics and design of microfluidic device used to produce DNA-carrying microspheres, in accordance with one embodiment of the invention. The device in this example includes one inlet for carrier oil and one inlet for reagents. The droplets are generated at the flow focusing junction where two phases meet. The droplets are collected at the collection outlet.

Figure 9A:
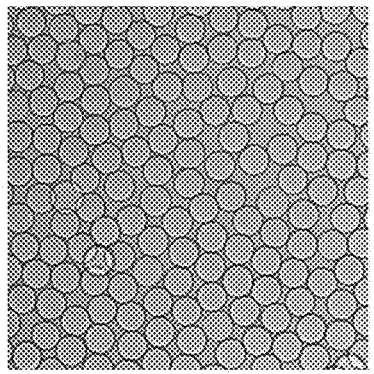
FIGS. 9A-9B illustrates particles containing oligonucleotide tags, in yet another embodiment of the invention.
Figure 9B:
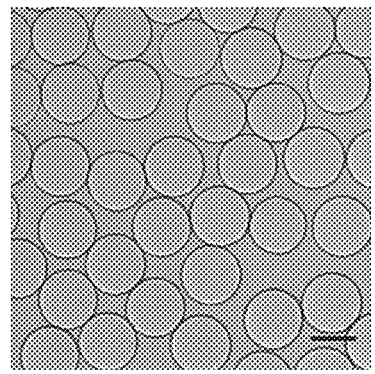

FIGS. 9A and 9B are bright field images of DNA-carrying microspheres, produced in accordance with one embodiment of the invention. In this example, the microspheres composed of polyacrylamide hydrogel and DNA primer attached to the polymer mesh. Scale bar is 50 micrometers.

Figure 10A:
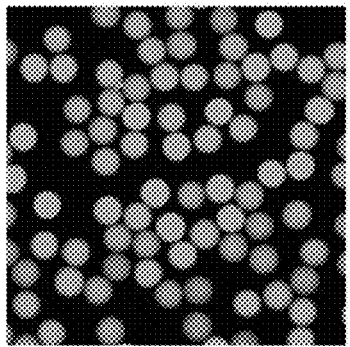
FIGS. 10A-10C illustrates extended oligonucleotide tags contained within droplets, in still another embodiment of the invention.
Figure 10B:
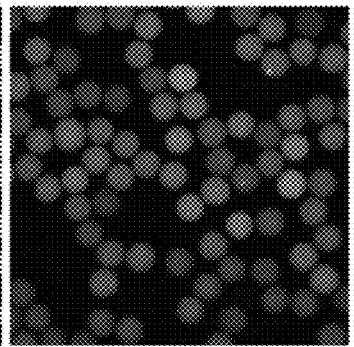
Figure 10C:
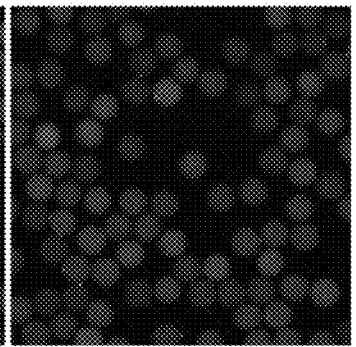

FIG. 10 illustrates the evaluation of DNA extension efficiency of microspheres carrying barcoded-DNA primers, in another embodiment. FIG. 10A shows microspheres with DNA hybridized to a PE1 site with a FAM fluorescent probe, FIG. 10B shows microspheres with DNA hybridized to a P2 site with a FAM fluorescent probe. FIG. 10C shows microspheres with DNA hybridized to a P3 site with a fluorescent probe. These results show that DNA extension can be performed in hydrogel microspheres.

Figure 11:
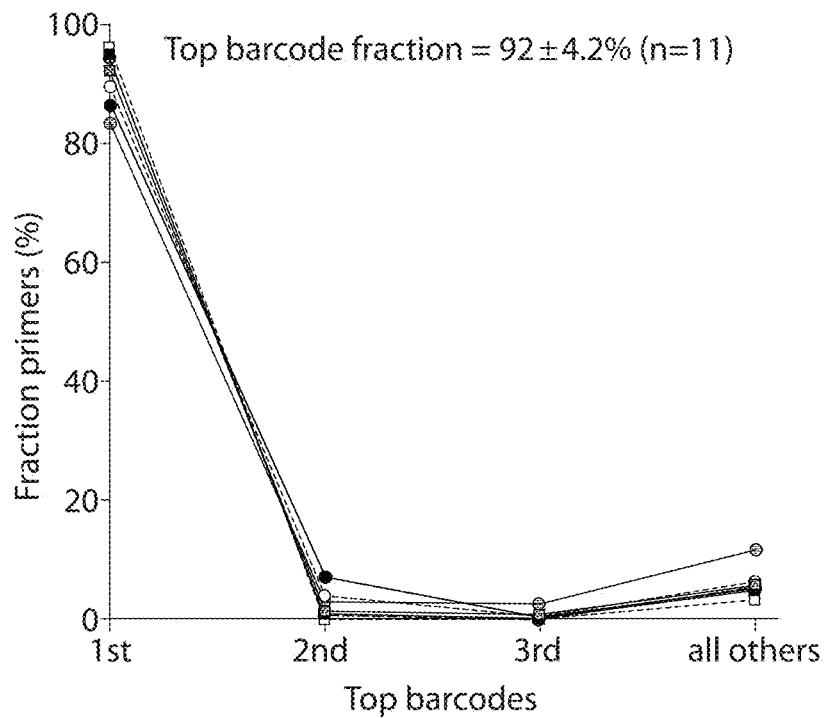
FIG. 11 illustrates sequencing of DNA fragments, in another embodiment of the invention.

FIG. 11 illustrates high-throughput sequencing of DNA fragments from 11 individual microspheres, in yet another embodiment. An average of 140,000 molecules were sequenced from each microsphere. The plot shows the fraction of these ("primers") carrying the same barcodes on each microsphere, out of $384^2$ possible barcodes. The identity of the barcodes is different for each of the microspheres. Each line corresponds to one microsphere. Under ideal conditions, 100% of DNA fragments on each microsphere would carry the same barcode, and 0% would carry the $2^{nd}$, $3^{rd}$, or other barcodes. The average achieved in this sample is 92% of the DNA fragments carrying the same barcode.

Example 3

This example uses DNA barcoded microspheres are synthesized as described above, resulting in microspheres carrying the following single stranded DNA fragments with the following sequence elements (5' to 3'): the P1 primer, for example containing a T7 promoter site and primer site PE1 that could be used as a site for but not limited to for nucleic acid amplification and sequencing; two or more DNA barcodes (each composed of 6 or more nucleotides), which are identical for all primers coating a single bead, but differs between beads; optionally, a molecule-specific DNA barcode (composed of 5 or more random nucleotides); the P2 "primer site 2" that could be used as a primer for sequencing or/and for hybridization to DNA or RNA in single cells for reverse transcription or PCR amplification; and the P3 "primer site 3" that could be used as a primer for sequencing or/and for hybridization to DNA or RNA in single cells for reverse transcription or PCR amplification.

In this example, after synthesis of the DNA barcoded microspheres, the microspheres are pooled and then hybridized to a single mixture of M DNA templates which have (sequentially from the 3' end to the 5' end): a DNA sequence complimentary to part or all of the final P3 primer allowing to form duplex with the DNA P3 primer, and one of M sequences $S_1, \ldots, S_M$ that will be used as specific primer sequences for single cell analysis operations such as capture of specific DNA or RNA molecules. These steps may be repeated, yielding the same number of $N_1 \times N_2$ pools of microspheres each carrying the sequences specified in 1, but now the DNA fragments belong to M species of molecules that are identical excepting a final M possible sequences $S_1, \ldots, S_M$.

In some cases, the DNA microspheres may be synthesized according to other methods to produce resulting microspheres have the same sequences described above.

Example 4

This example shows that the reverse transcription (RT) of mRNA into complementary DNA from lysed cells becomes strongly inhibited for reaction volumes smaller than 3 nL per cell, specifically with the reaction yield Y follows a first-order inhibition with the droplet volume V, i.e. $Y=1/(1+K_{50}/V)$, where $K_{50}=1-3.3$ nL is the volume at which 50% inhibition occurs for at least three different cell culture lines tested (MCF7, K562 and THP-1 cells). By contrast, much of the current work with droplet microfluidics has focused on encapsulating cells in droplets with a volume of 10-100 pL volume. At such volumes reverse transcription reactions would be heavily inhabited.

FIG. 6 illustrates bulk tests for optimal droplet volume, in accordance with one embodiment of the invention.

In this example, tests of reaction efficacy on single cells in microfluidic volumes can be carried out by simulating droplet conditions in reaction wells containing 5 microliters or more of reaction mix, which may be adjusted to simulate the conditions within a single droplet.

To mimic a microfluidic volume of size V, intact cells were added to the bulk reaction at a final concentration of 1 cell per volume V. Thus, a single cell within a 4 nL droplet corresponds to running a reaction with a cell lysate of a concentration of 250 cells/microliters.

In addition, to mimic a microfluidic volume of size V, any reagents that are administered discreetly into droplets, such as by the use of microspheres that each carry m moles of reagent, the reagents are added to the bulk reaction at a final concentration of m moles per volume V. For example, if 1 femtomole of DNA fragments are delivered on microspheres into 4 nL droplets, the same DNA fragments would be added at a concentration of 0.42 micromolar to the bulk reactions.

Bulk reactions can be carried out in parallel in a 12-well, 96-well, or 384-well format to identify optimal reaction conditions.

Figure 12:
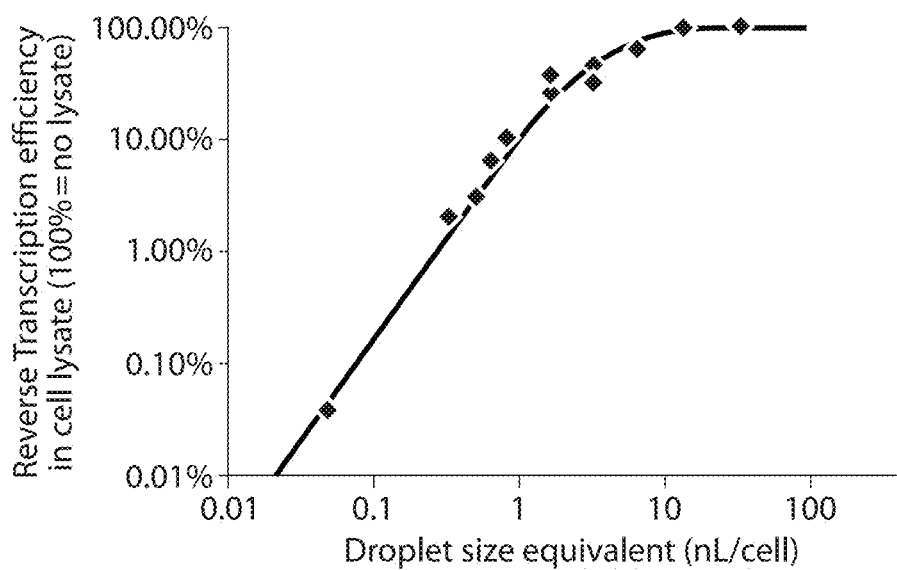
FIG. 12 illustrate reverse transcription efficiency as a function of droplet size, in accordance with another embodiment of the invention.

Such diagnostic tests may provide a rapid method for optimizing the droplet size and composition for barcoding. For example, with three cell lines tested, a strong inhibition of the barcoding reaction when the droplets were made smaller than 3 nL volume was observed. See FIG. 12.

Example 5

To interpret the gene expression of healthy and diseased tissues, it has been a dream of biologists to map gene expression changes in every cell. With such data one might hope to identify and track heterogeneous cell sub-populations, and infer regulatory relationships between genes and pathways. "Omics" methods such as RNA sequencing have been harnessed to analyze single cells, but what is limiting are effective ways to routinely isolate and process large numbers of individual cells for in-depth sequencing, and to do so quantitatively. This example illustrates a droplet-microfluidic approach for parallel barcoding thousands of individual cells for subsequent profiling by next-generation sequencing. This shows a low noise profile and is readily adaptable to other sequencing-based assays. These examples apply the technique to mouse embryonic stem (ES) cells to define the ES cell population structure and the heterogeneous onset of ES cell differentiation by LIF withdrawal. These results demonstrate the applications of droplet barcoding for deconstructing cell populations and inferring gene expression relationships with high-throughput single cell data.

These examples took advantage of droplet microfluidics to develop a novel technique for parallel barcoding of thousands of individual cells for subsequent profiling by next-generation sequencing (drop-Seq). The implementation used in these examples has a theoretical capacity to barcode tens of thousands of cells in a single run, although in practice some of the experiments focused on hundreds to thousands of cells per run, since sequencing depth becomes limiting at very high cell counts. These examples evaluated drop-SEQ by profiling mouse embryonic stem (ES) cells before and after LIF withdrawal. A total of over 10,000 barcoded cells and control droplets were profiled, with ~3,000 ES and differentiating cells sequenced at greater depth for subsequent analysis. The following analysis identified the presence of rare sub-populations expressing markers of distinct lineages that would be difficult to classify from profiling a few hundred cells. It was also found that key pluripotency factors fluctuated in a correlated manner across the entire ES cell population, and the possibility that such fluctuations might be used to associate novel factors with the pluripotent state was explored. Upon differentiation, dramatic changes were observed in the correlation structure of gene expression fluctuations, resulting from asynchronous inactivation of pluripotency factors, and the emergence of novel cell states. Altogether, these results show the potential of drop-SEQ to deconstruct cell populations and to infer gene expression relationships within a single experiment.

Figure 13A:
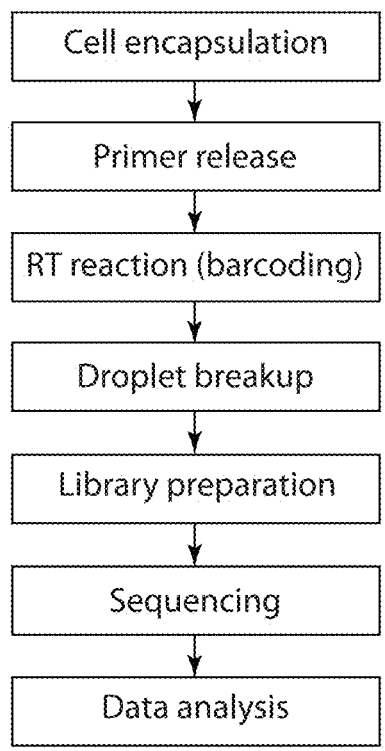
FIGS. 13A-13H illustrate microfluidic droplets for DNA barcoding thousands of cells, in one embodiment of the invention.

Design and implementation of a microfluidic platform for droplet barcoding and analysis of single cells. A protocol for RNA sequencing (RNA-Seq) was used, where mRNA is barcoded during a reverse transcription reaction, and cells are subsequently pooled and processed further for sequencing (FIG. 13A). For this, the drop-SEQ platform (FIGS. 13A-13E and FIG. 18) encapsulated cells into droplets with lysis buffer, reverse transcription (RT) reagents, and barcoded oligonucleotide primers. mRNA released from each lysed cell remained trapped in the same droplet and was barcoded during synthesis of complementary DNA (cDNA). After barcoding, the material from all cells was combined by breaking the droplets, and the cDNA library was processed for sequencing (FIG. 13A).

Figure 13B:
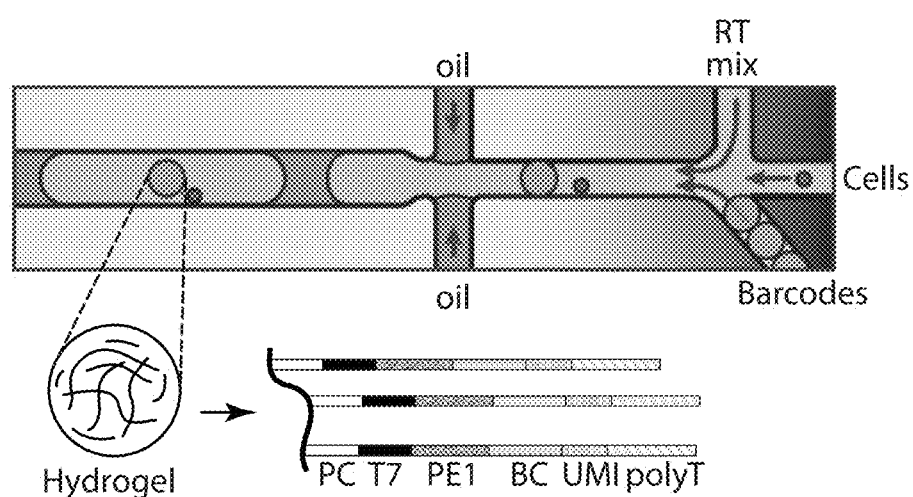

One challenge in implementing this strategy was to ensure that each droplet carried primers encoding the same unique barcode, which should be different from barcodes in other droplets. This challenge was overcome by synthesizing a library of barcoded hydrogel microspheres (BHMs) that were co-encapsulated with cells (FIG. 13B). Each hydrogel carried covalently coupled, photo-releasable primers encoding one of $384^2$ (i.e. 147,456) pre-defined barcodes. This pool size allowed randomly labeling 3,000 cells with 99% unique labeling, and 10,000 cells with 97% unique labeling (see below). FIGS. 19-21 describe a method used to synthesize BHMs using a split-pool approach; see below. This can be extended in a straightforward manner to yield larger numbers of barcodes for larger-scale cell capture, for example for targeted sequencing applications.

Figure 13C:
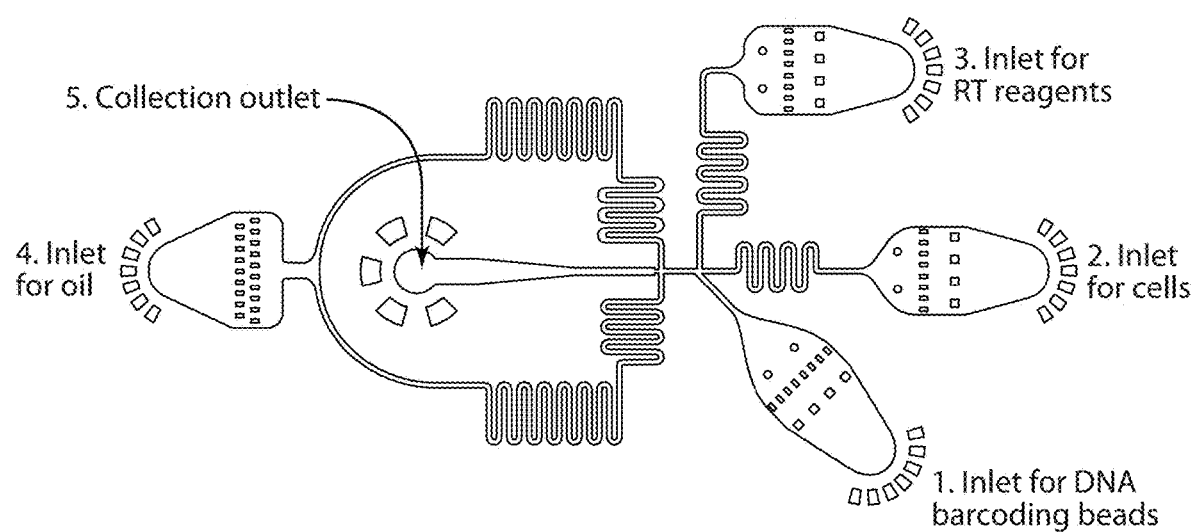
Figure 13D:
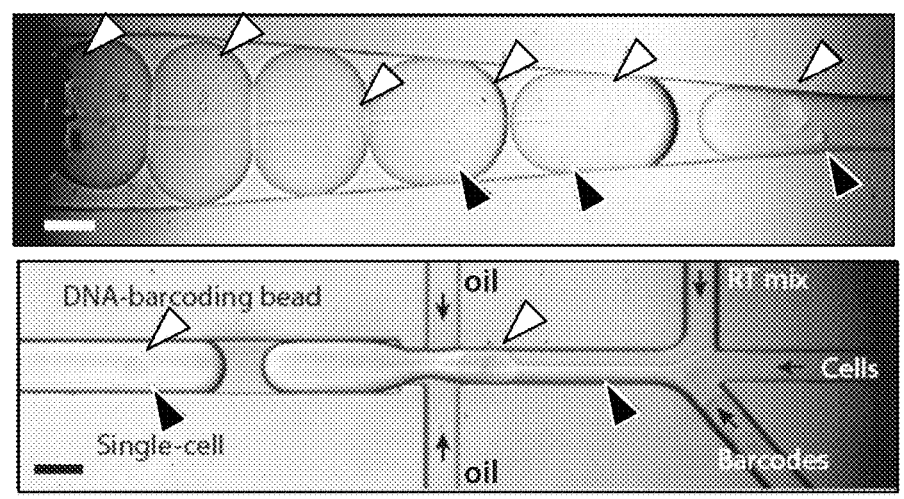
Figure 13E:
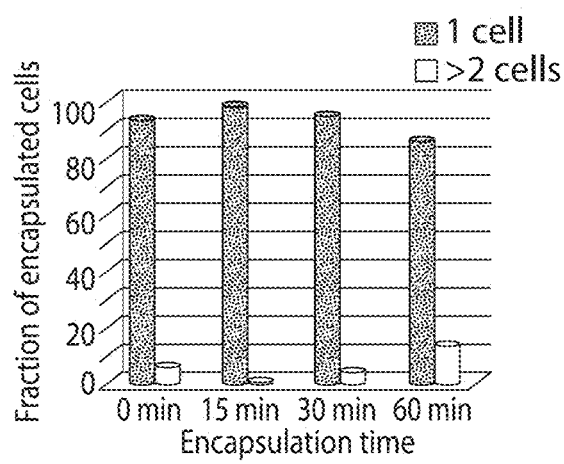
Figure 13F:
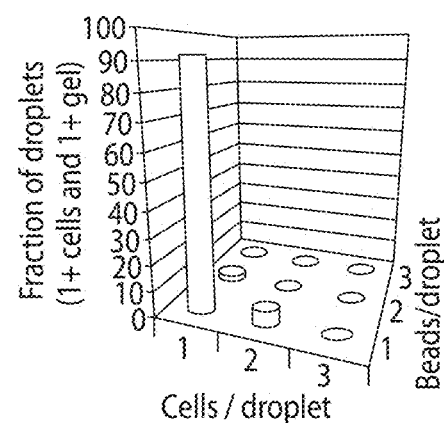
Figure 13G:
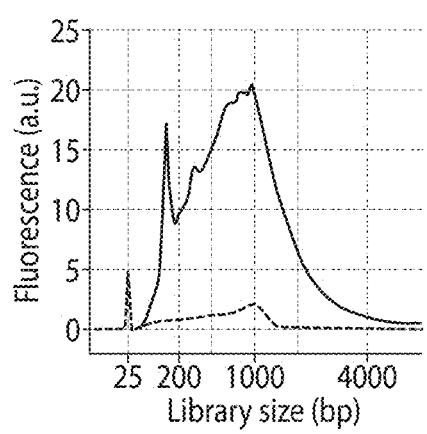

To co-encapsulate the BHMs and cells, a microfluidic device with four inlets for i) the BHMs, ii) cells, iii) RT/lysis reagents and iv) carrier oil; and one outlet port for droplet collection was used (FIGS. 13C-13D). The device generated monodisperse droplets which varied in the range of 1-5 nL at a rate of ~10-50 drops per second, simultaneously mixing aliquots from the inlets (FIG. 13E). The flow of close-packed deformable hydrogels inside the chip could be efficiently synchronized, allowing nearly 100% hydrogel droplet occupancy. This feature ensured that randomly distributed cells arriving into droplets would be nearly always exposed to a BHM. In typical conditions, the cell concentration was set to occupy only 10% of droplets to ensure a low probability of two-cell events (FIG. 13E). In these experiments, droplets contained at least one cell and one gel to produce a barcoded library for sequencing. Typically, over 90% of productive droplets contained exactly one cell and one gel (FIG. 13F). The efficiency of the RT reaction was also tested with primers in solution or still bound to BHMs, and it was found that primer release was important for an efficient RT reaction from lysed cells in droplets (FIG. 13G). Therefore, prior to the RT reaction, the BHM-bound primers were photo-released into the droplets by exposure to UV light (FIG. 13A).

Figure 13H:
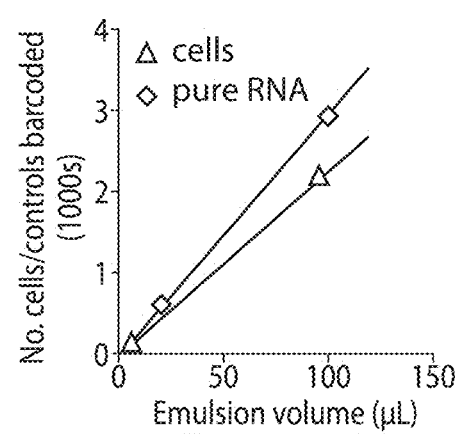

In these examples, the samples of a few hundred to a few thousand cells were sequenced to avoid extremely shallow sequencing depth, but this could also be used to readily capture and barcode higher cell numbers, e.g., with a throughput of 4,000-6,000 cells per hour. Indeed, after sequencing, it was found that the number of barcoded samples scaled generally linearly with emulsion volume collected (FIG. 13H), with approximately 2,000-3,000 cells or control droplets barcoded for every 100 microliters of emulsion (~30 minutes collection time).

FIG. 13 shows an example of a droplet microfluidic platform for DNA barcoding thousands of cells. FIG. 13A shows an overview of drop-SEQ workflow; on-chip operations occur in the first three boxes, off-chip operations occur in the next three boxes, and sequencing/data analysis occur in the last two boxes. FIG. 13B is a schematic of the microfluidic device for combining DNA-barcoded hydrogel microspheres (BHMs) (big circles) with cells (small circles) and RT/lysis mix. BHMs primer legend: PC=photocleavable linker; T7=T7 RNA polymerase promoter; PE1=sequencing primer; BC=BHM-specific barcode; UMI=unique molecular identifier. FIG. 13C shows a microfluidic device design. FIG. 13D shows snapshots of microfluidic modules for encapsulation (right) and collection (left). Cells and BHMs are annotated with lower and upper arrows, respectively. Other arrows indicate direction of the flow. Scale bars, 100 micrometers. FIG. 13E shows statistics of droplet occupancy over time. FIG. 13F shows statistics of cell and DNA-barcoding bead co-encapsulation events. Over 90% of cells are encapsulated with a single DNA-barcoding bead. FIG. 13G shows BioAnalyzer traces of the prepared library with primers photo-released from the beads before (upper curve) or after (lower curve) reverse transcription. FIG. 13H shows the number of barcodes detected for pure RNA and mES cells, with 2,159 cells collected per 100 microliter emulsion (30 minutes collection time).

Figure 18:
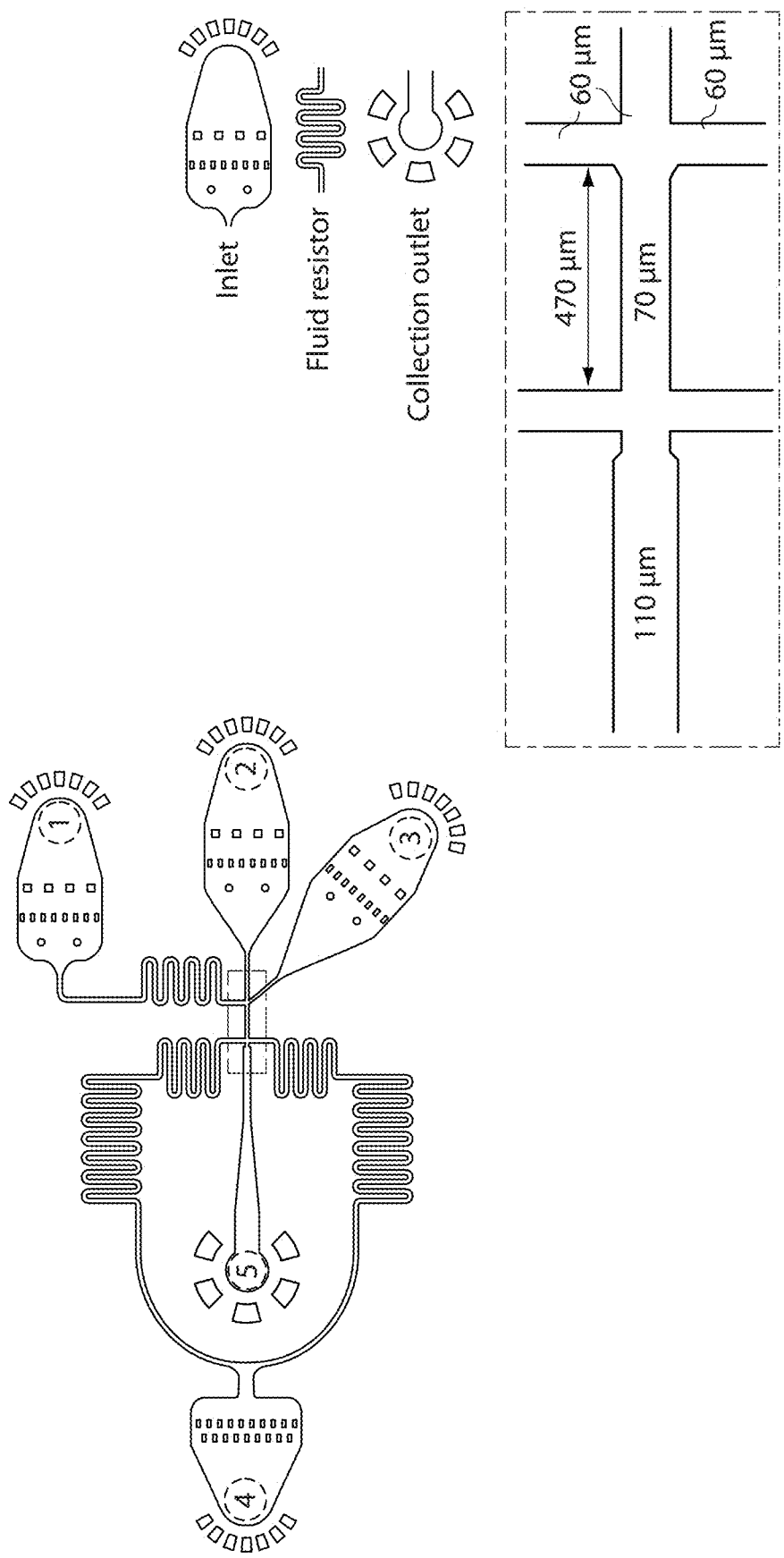
FIG. 18 illustrates a microfluidic device in another embodiment of the invention.

FIG. 18 shows the design of droplet microfluidics device used in this example. The device included three inlets for RT and lysis reagent mix (1), cell suspension (2), DNA barcoding beads (3) and one inlet for the continuous phase (4). The fluid resistors incorporated into device damping fluctuations arising due to mechanical instabilities of syringe pumps. The aliquot samples were brought together via 60 micrometer wide channels into the main 70 micrometer wide channel where they flowed laminarly before being encapsulated into droplets at the flow-focusing junction (dashed box). Droplets are collected at the outlet (5) in form of an emulsion.

Figure 19A:
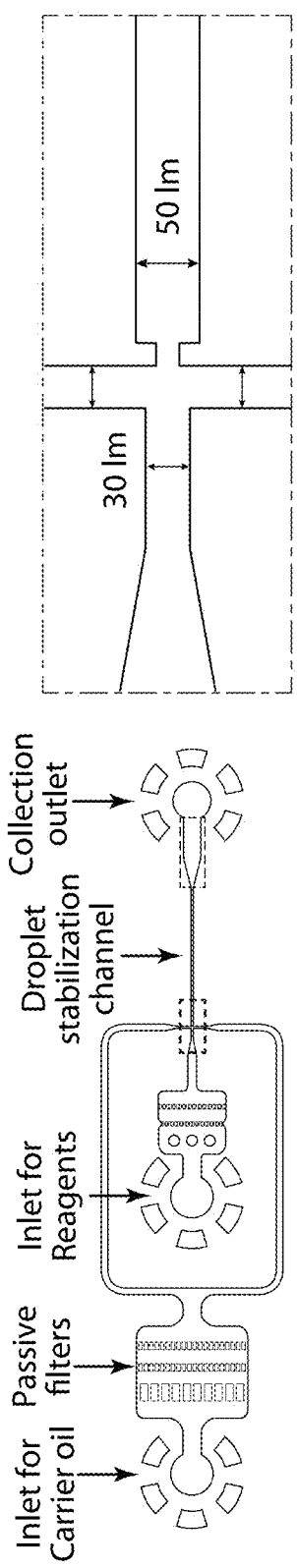
FIG. 19A-19B illustrate certain microfluidic devices, in yet another embodiment of the invention.
Figure 19B:
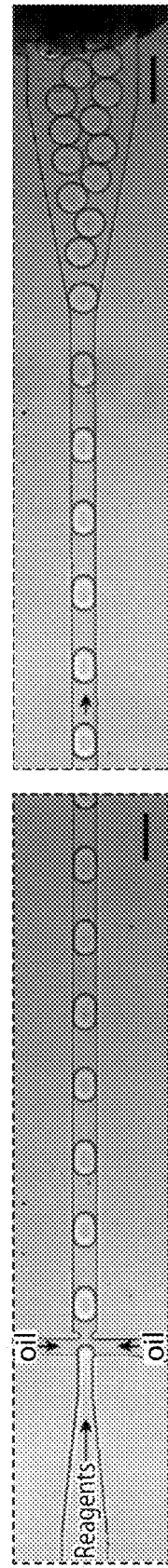

FIG. 19 shows the design of droplet microfluidics device for production of DNA-barcoding hydrogel beads. FIG. 19A shows an example design of the device. The device comprises one inlet for aqueous phase (reagents) and one inlet for continuous phase (carrier oil). Monodisperse hydrogel droplets were generated at the flow-focusing nozzle those dimensions are indicated in the dashed box on the right. Droplets were stabilized by surfactant in the 2000 micrometer long channel and collected in form of an emulsion at the outlet port. FIG. 19B shows digital images of hydrogel droplet production, stabilization and collection. Microfluidic channels are 50 micrometers deep. Scale bars denote 100 micrometers.

Figure 20A:
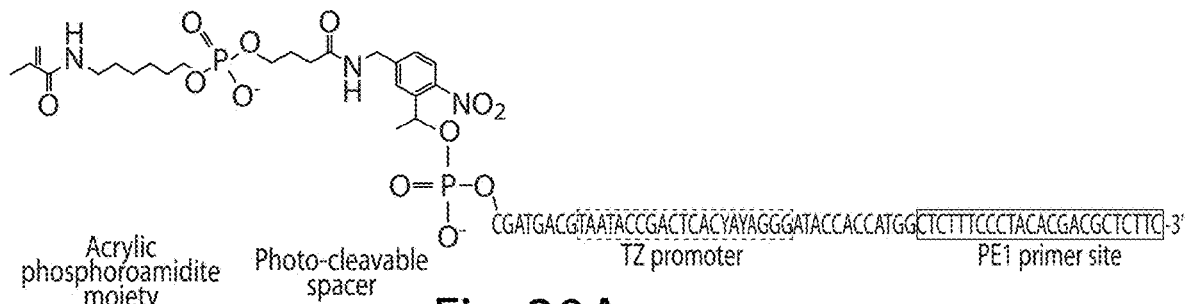
Figure 20B:
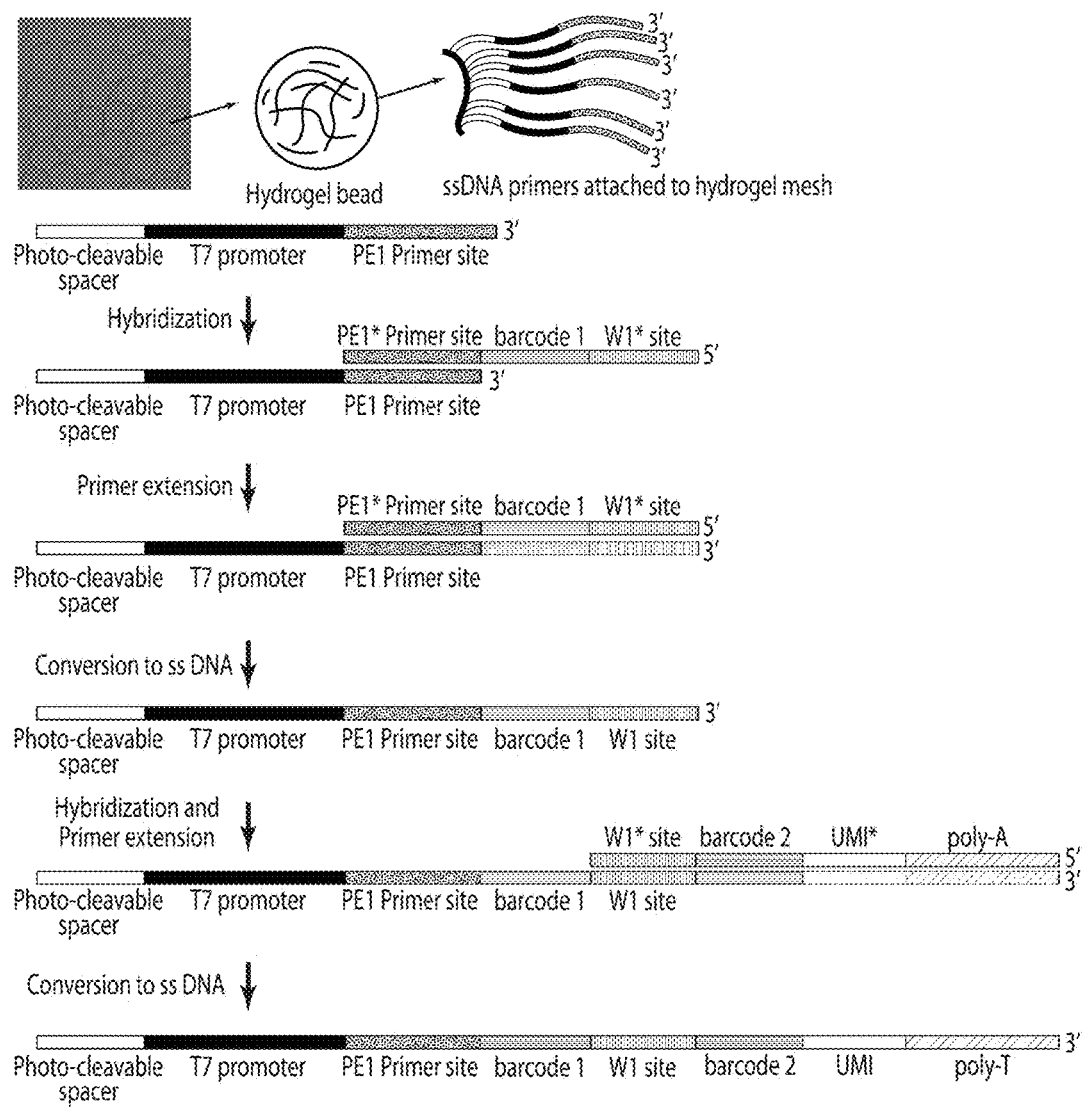
Figure 21E:
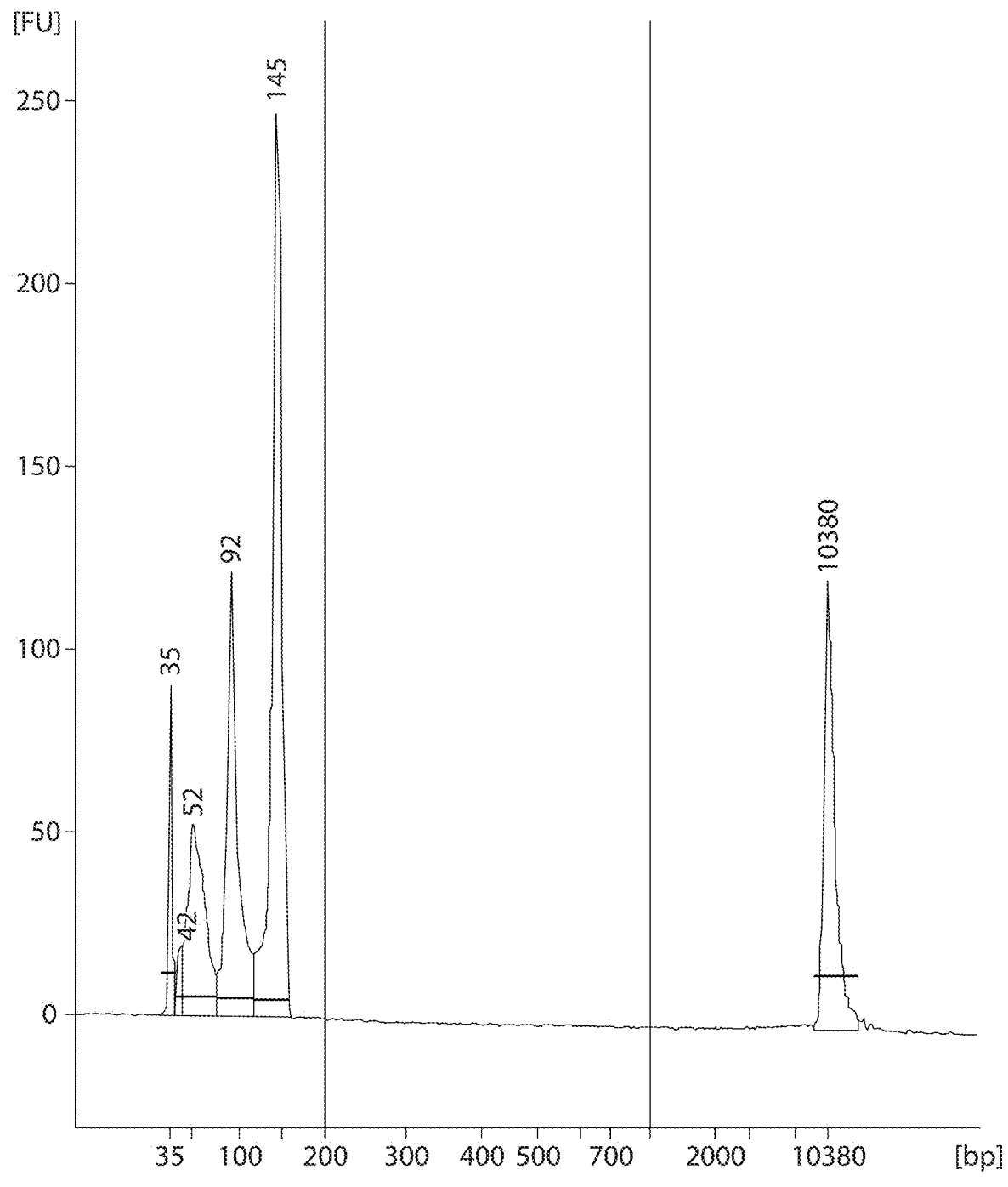
Figure 21F:
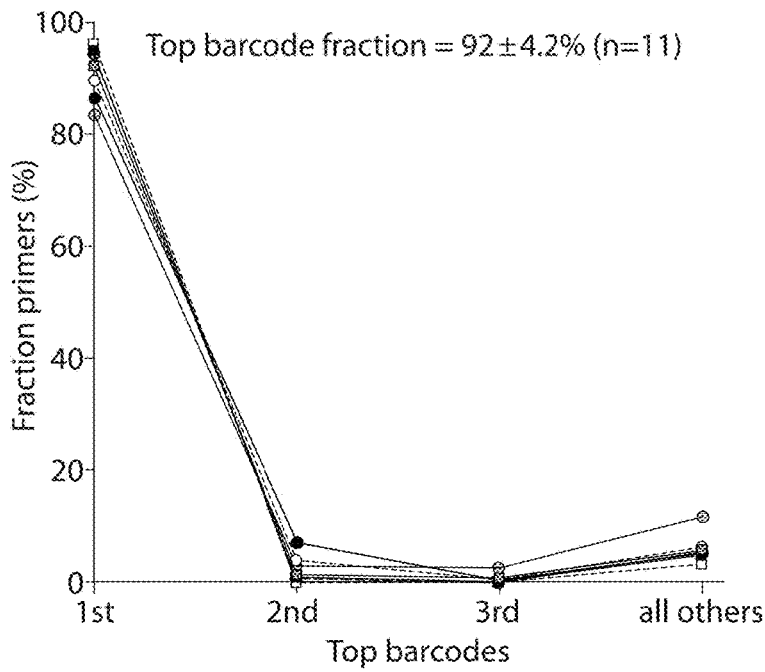
Figure 21G:
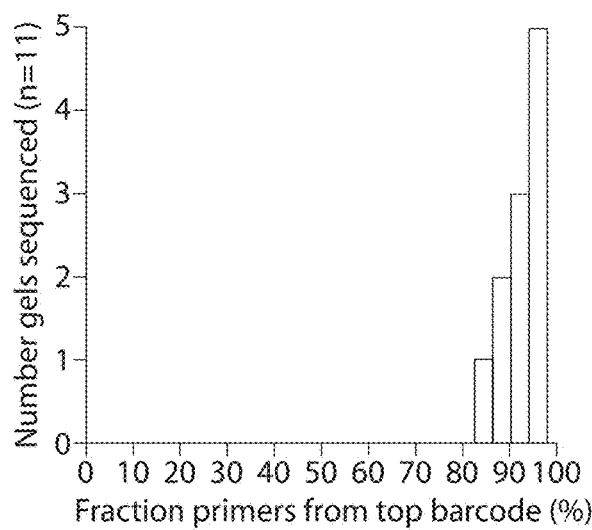
Figure 21H:
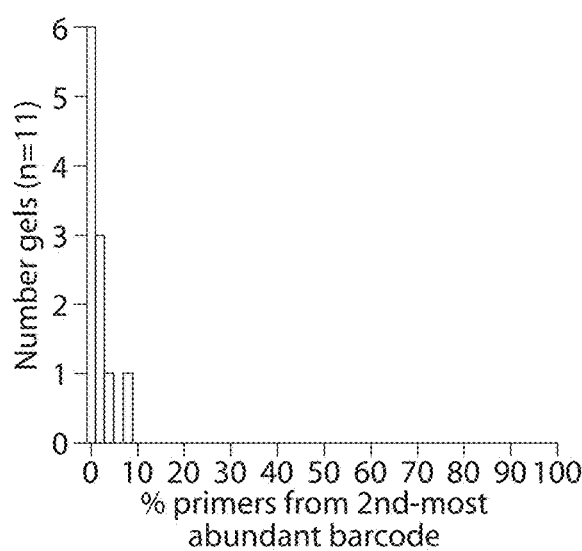

FIG. 20 shows synthesis of DNA-barcoding beads. FIG. 20A shows the structure DNA oligonucleotide containing acrylic phosphoroamidite moiety (left) and photo-cleavable spacer (right) attached to the 5' end of DNA primer carrying T7 RNA polymerase promoter (left on sequence) and PE1 primer site (right on sequence). FIG. 20B shows schematics of synthesis of barcoded hydrogel microspheres. In the first step the ssDNA primers, attached to polyacrylamide hydrogel, were hybridized to complimentary DNA oligonucleotides carrying PE1* and W1* primer sites and the first half of DNA barcode. The resulting DNA heteroduplex was converted to dsDNA by Bst 2.0 DNA polymerase (where the dashed lines indicate newly synthesized DNA strand) and denaturated back to ssDNA form by alkaline treatment. In the second step, the process was repeated with a second DNA oligonucleotide carrying W1* sequence, the second-half of DNA barcode, unique molecular identifier (UMI) and polyA sequence. After primer extension and denaturation the DNA-barcoding beads contain T7 promoter, PE1 primer site, DNA barcode, W1 site, UMI and polyT sequence. FIG. 20C shows the DNA sequence of a fully assembled primer. The highlighted text indicates different parts of oligonucleotide with T7 promoter (TAATACGACTCATATAGGG), PE1 primer site (CTCTTTCCCTACACGACGCTCTTC) two DNA barcodes ([barcode1] and [barcode2]), W1 adaptor site (AAGGCGTCACAAGCAATCACTC) UMI (NNNNNN) and poly-T tail (TTTTTTTTTTTTT-TTTTTTTV). The chemical moieties for acrylic phosporamidite and photo-cleavable spacer are denoted as/5Acryd/ and/iSpPC/respectively. The DNA sequences of [barcode1] and [barcode2] is 8 nucleotides long each.

FIG. 21 shows quantification of DNA primers incorporated into barcoded hydrogel microspheres (BHMs). FIGS. 21A-21D show iImaging of BHMs post-synthesis, showing a bright field image of BHMs 63 micrometers in size (FIG. 21A), and fluorescent confocal imaging after hybridization with complimentary DNA probes targeting PE1 sequence (FIG. 21B), W1 sequence (FIG. 21C) and polyT sequence (FIG. 21D). Scale bars, 100 micrometers. FIG. 21E shows a BioAnalyzer electropherogram of DNA primers after photo-cleavage from BHMs, showing the presence of full-length barcodes (largest peaks), as well as synthesis intermediates (two smaller peaks). Peaks at 35 and 10380 base pairs are gel migration markers. Numbers above the peaks indicate theoretical fragment size in base pairs, but these are not accurate for the single stranded DNA products. FIGS. 21F-21H show results from deep sequencing the barcoded product of 11 individual BHMs. FIG. 21F shows a rank plot of barcode abundances on each gel; FIGS. 21G and 21H show histograms of the fraction occupied on each BHM by the most-abundant and second-most abundant barcodes detailed in FIG. 21G and FIG. 21H. Perfect synthesis would result in 100% occupied by the top barcode, and 0% by all other barcodes. It was observed that an average of ~92% of all primers attached to each BHM carried the same dominant barcode.

Example 6

Figure 14A:
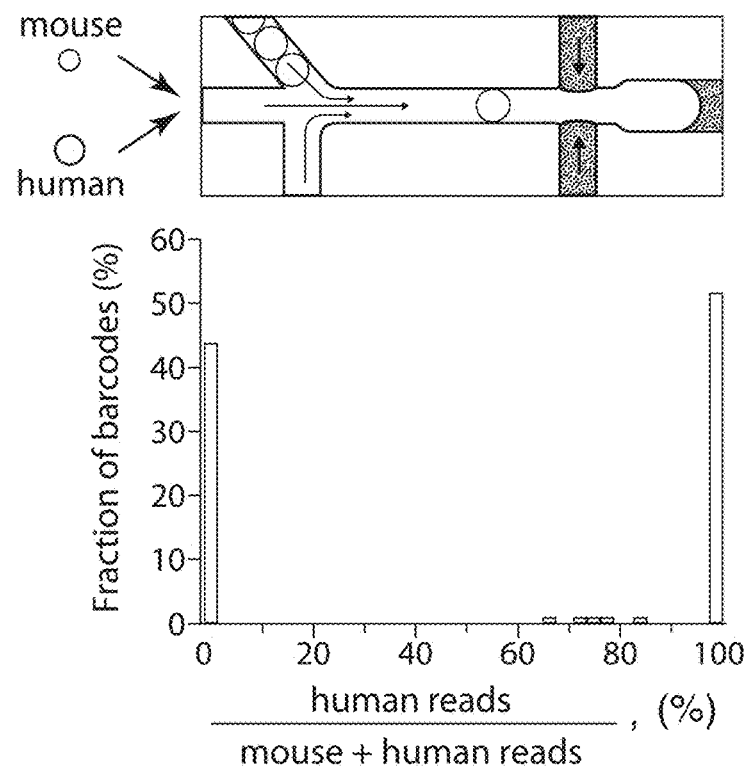

Validation of random barcoding and droplet integrity. The ability of the drop-Seq platform to effectively compartmentalize and barcode cells was tested in this example by applying this to a mixture of cells from mouse and human origin (mouse ES cells and K562 erythroleukemia cells) at approximately equal proportions (FIG. 14A). In this test each barcode should associate entirely with either mouse or human mapped transcripts, with only a small fraction of 2-cell events leading to the appearance of barcodes associating with both mouse and human. After sequencing, FIG. 14A shows that drop-SEQ provided unambiguous identification of cells in the composite cell mixture: 96% of barcodes tagged reads mapped to either the mouse or human transcriptome with more than 99% purity, and only 4% of barcodes showed a mixture of both organisms. This already low error rate could be reduced even further by diluting cell suspensions to reduce co-encapsulation events, or by sorting droplets on-chip prior to collection to eliminate multi-cell events.

Also explicitly tested was that cell barcodes were randomly sampled from the intended pool of $384^2$ possible barcodes to ensure a very low probability of repeated barcodes. A comparison of barcode identities across eight independent runs covering a total of 11,085 control droplets and cells consistently showed excellent agreement with random sampling from the pool of 384² barcodes (FIG. 22A).

FIG. 14 shows tests of droplet integrity and random barcoding. FIG. 14A shows schematic and results of droplet integrity control experiment: mouse and human cells are co-encapsulated to allow unambiguous identification of barcodes shared across multiple cells; 4% of barcodes share mixed mouse/human reads.

Figure 22D:
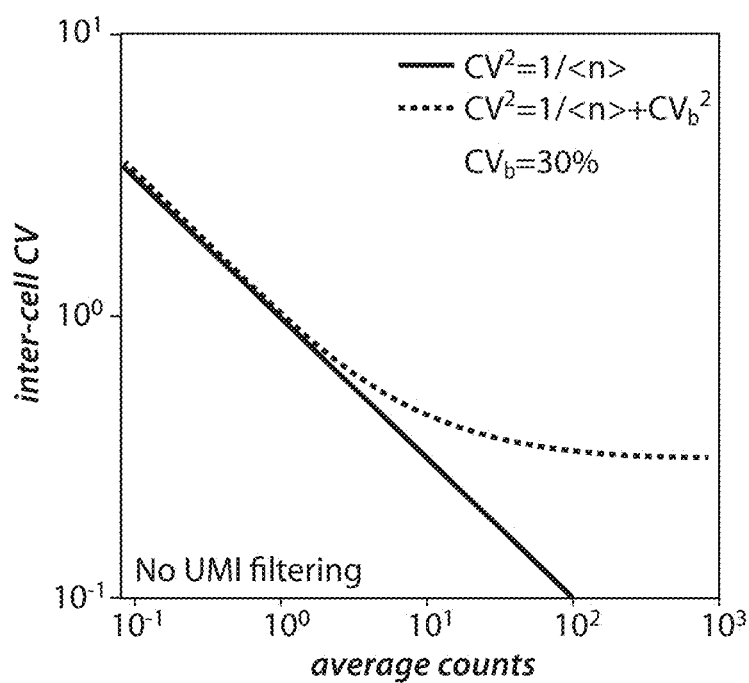
Figure 22E:
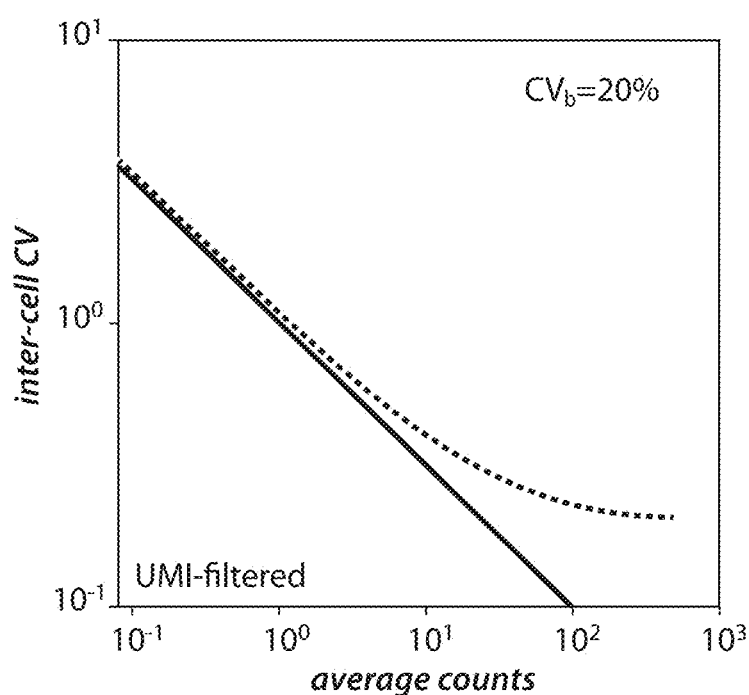
Figure 23A:
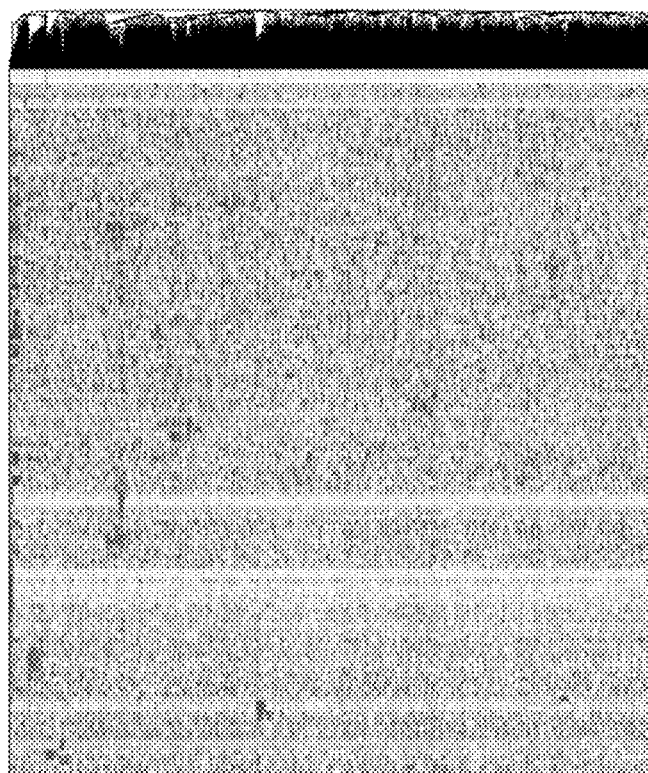
FIGS. 23A-23D illustrate single cell gene expression of mES cells, in one embodiment of the invention.
Figure 23B:
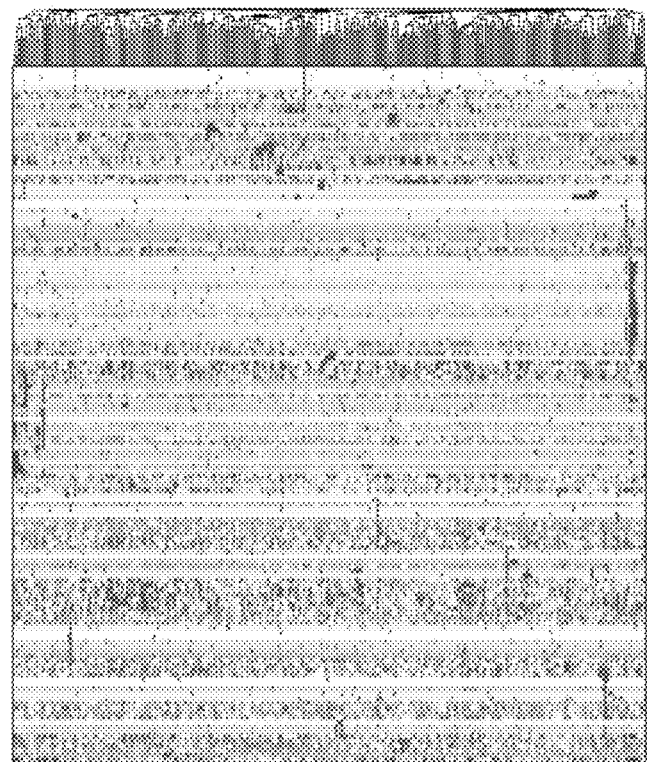
Figure 23C:
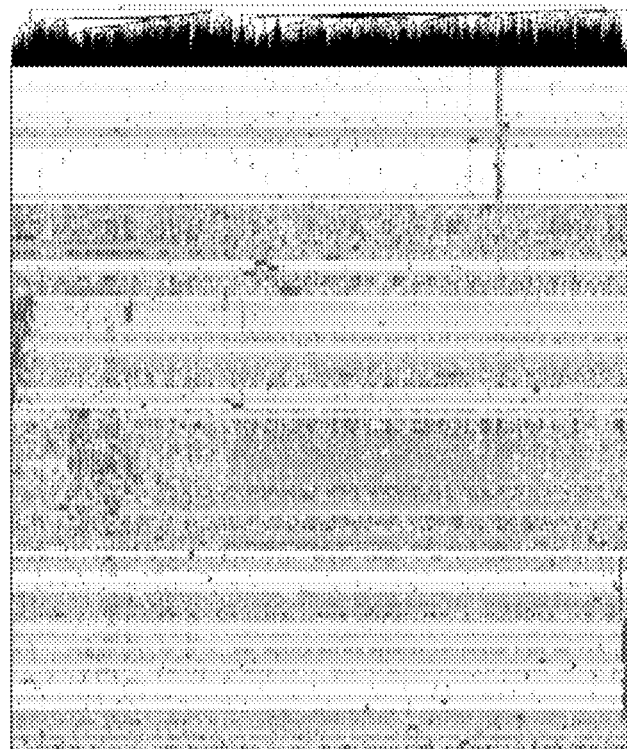
Figure 23D:
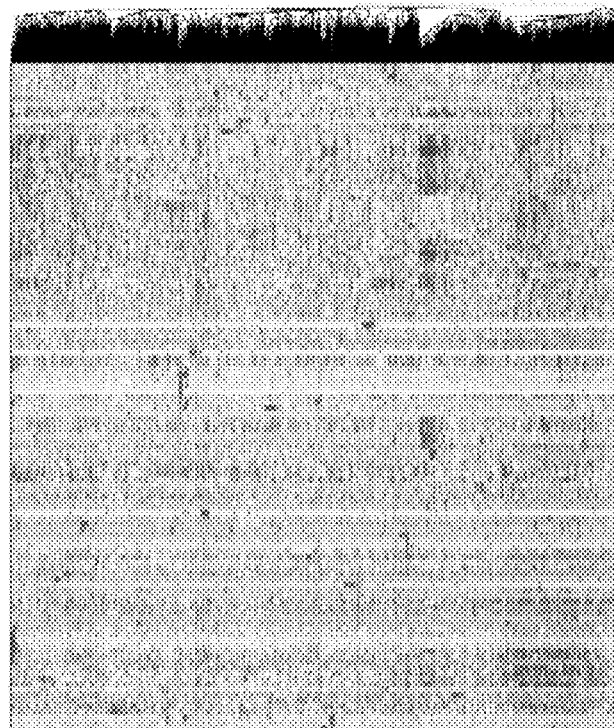
Figure 24A:
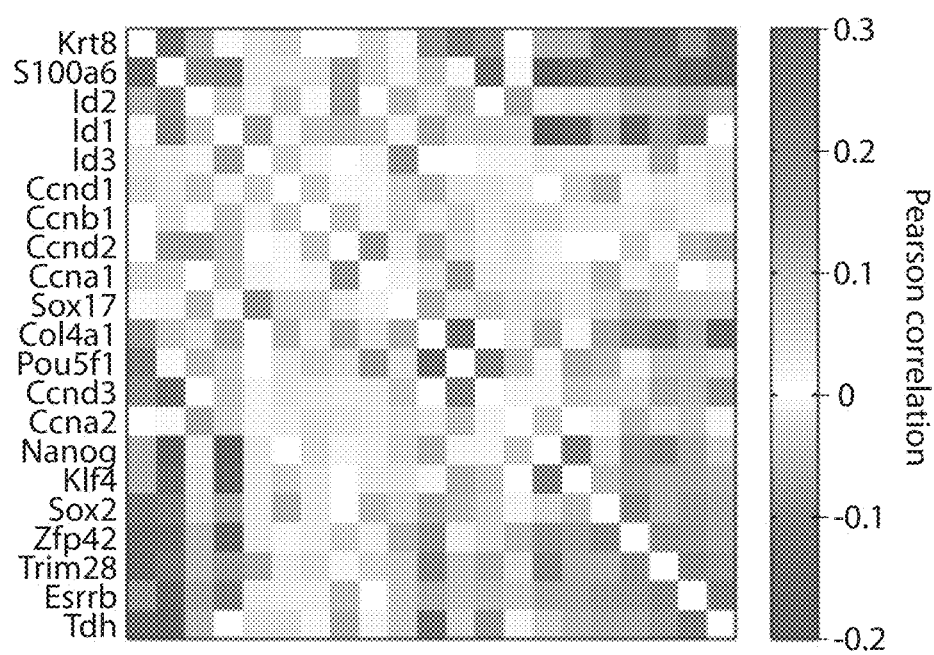
FIGS. 24A-24G illustrate the structure of the mES cell population, in another embodiment of the invention.
Figure 24B:
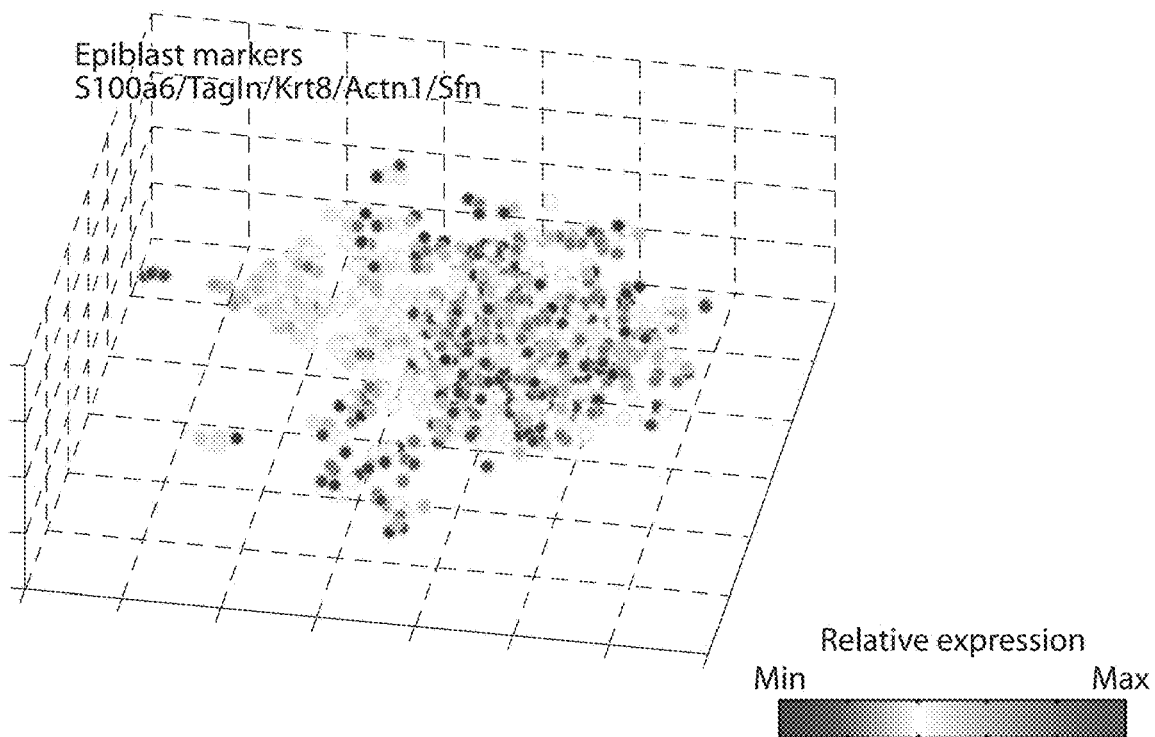
Figure 24C:
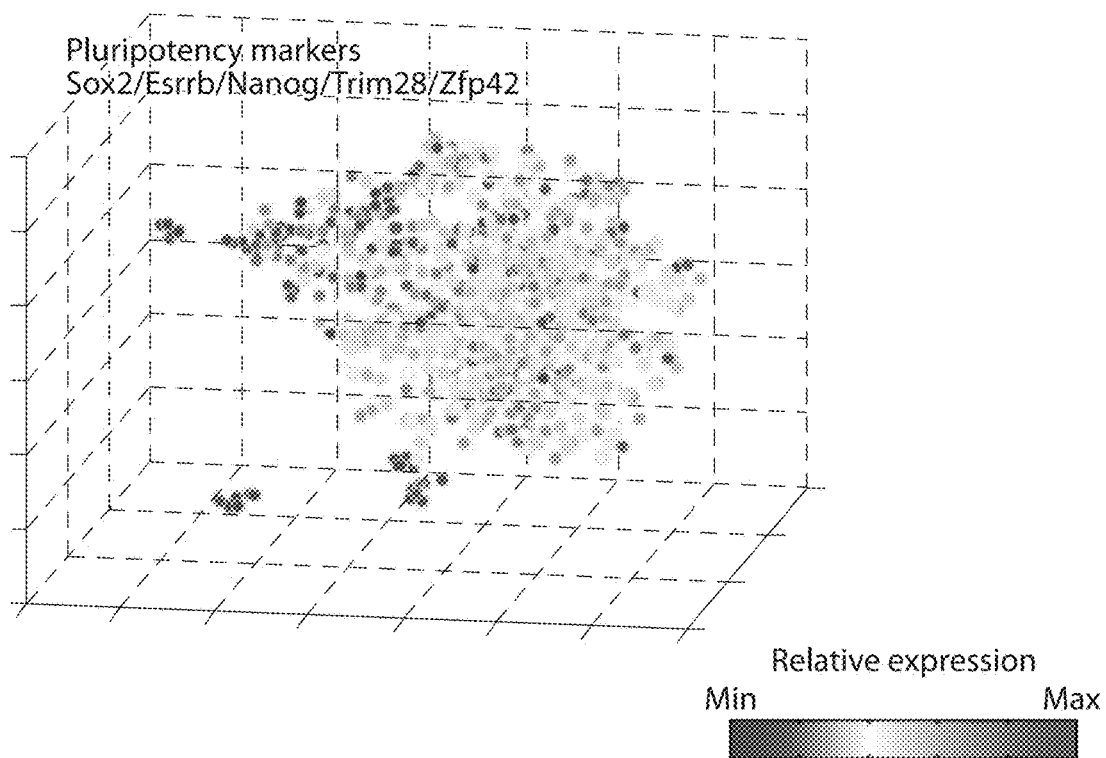
Figure 24D:
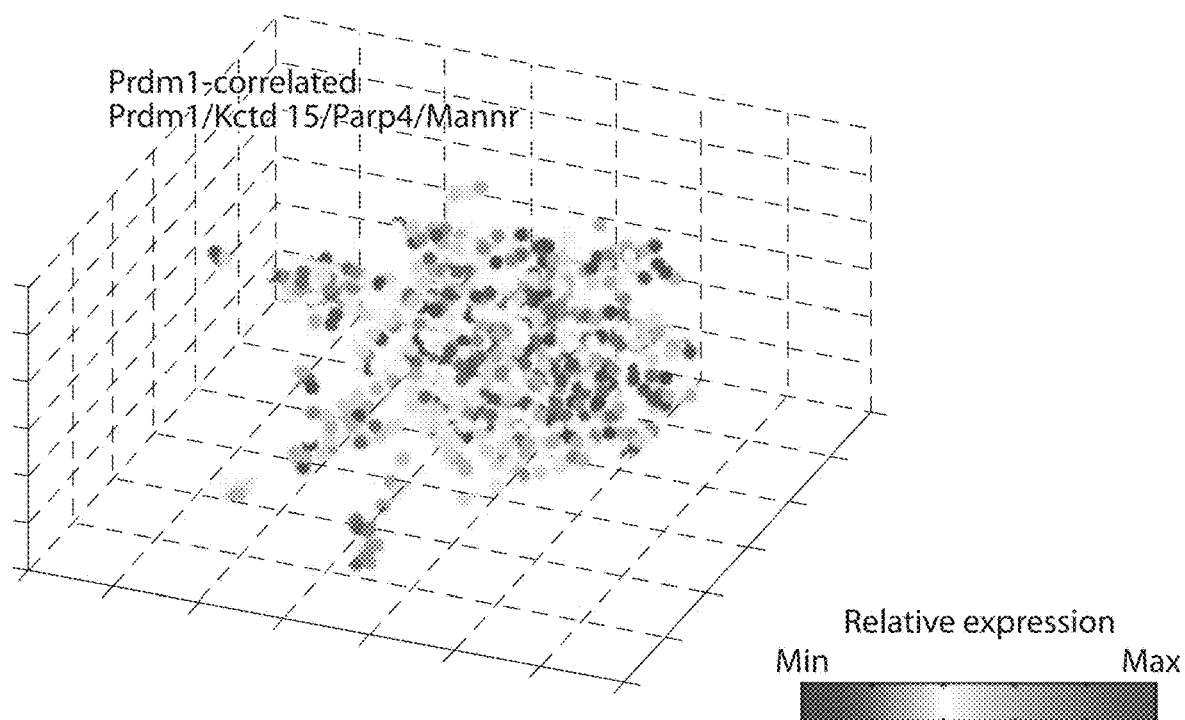
Figure 24E:
Figure 24F:
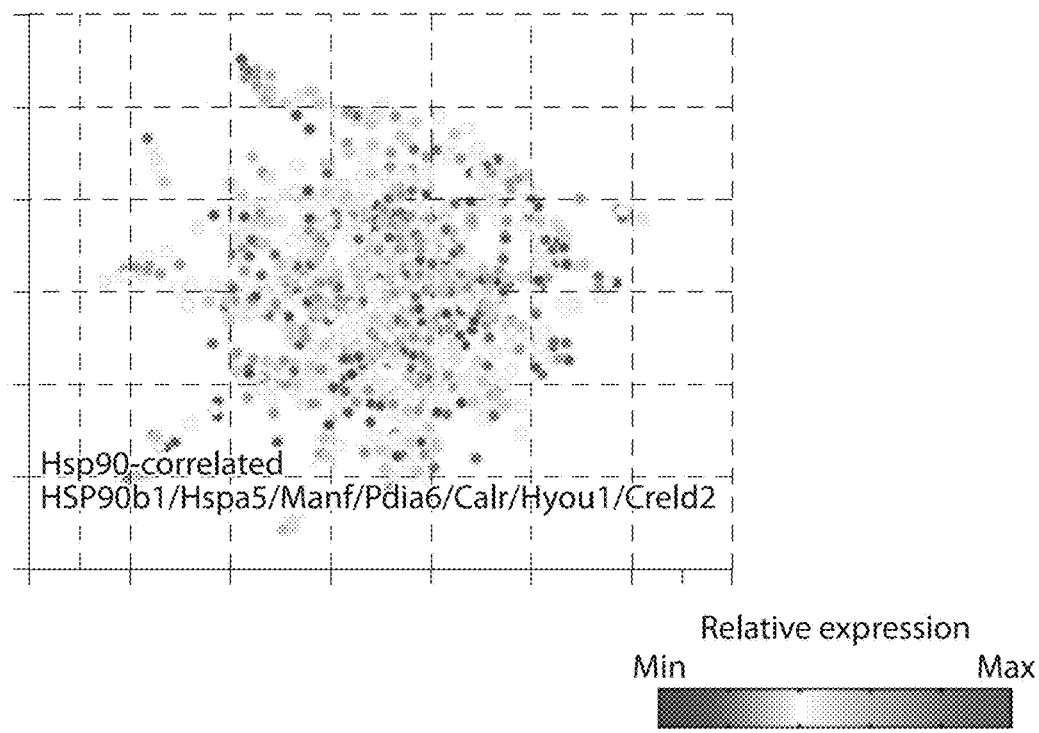
Figure 24G:
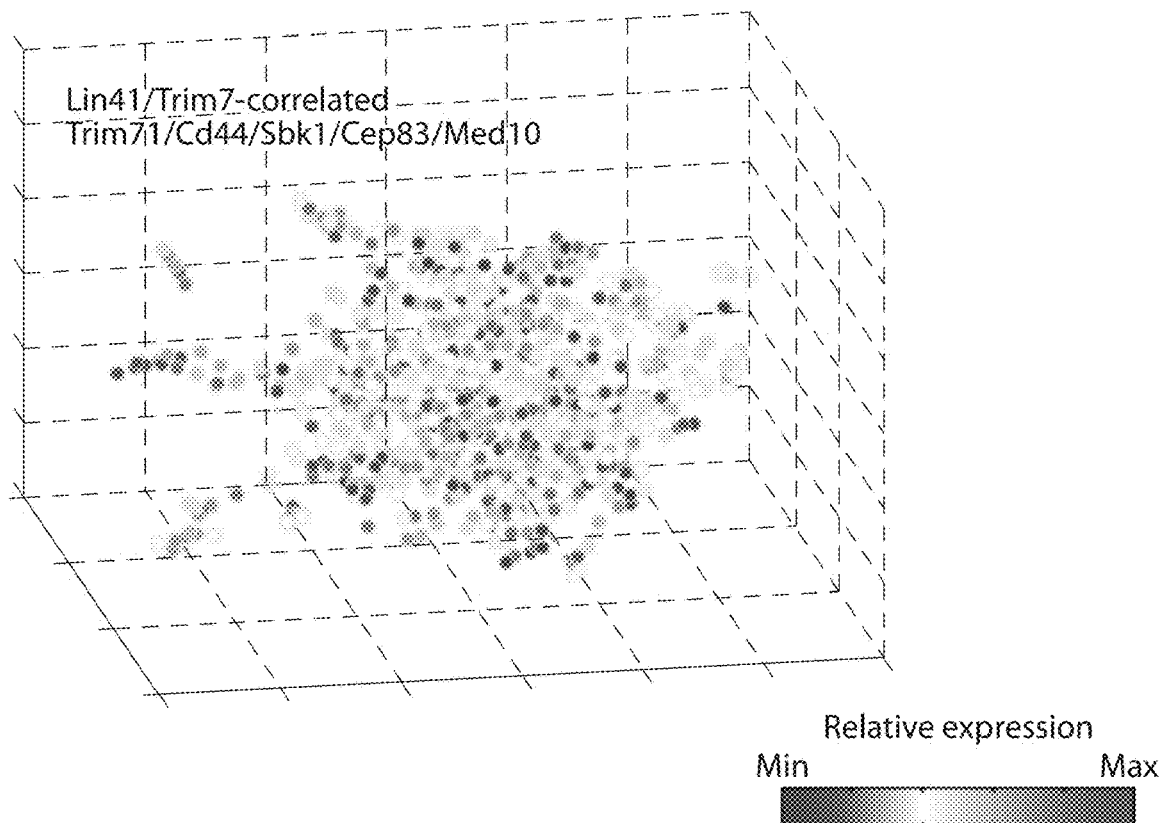

FIG. 22 shows random barcoding and unique molecular identifier (UMIs) filtering. FIG. 21A shows pair-wise tests of random barcoding for eight drop-Seq runs covering between 140-2,930 cells or pure RNA control droplets. Upper triangle shows the observed (left) and expected (right) number of shared barcodes for each pair of runs with 3842 random barcoding. Lower triangle shows p-values assuming uniform random barcoding from a pool of 3842 barcodes, which predicts that the observed number of shared barcodes should be hypergeometrically distributed about the expected value. The p values have not been corrected for multiple hypothesis testing. FIGS. 22B-22D show UMI filtering. FIG. 21B shows the expected number of observed UMIs as a function of the number of detected mRNA molecules (black curve) can be shown to have the for $n_{obs}(m) = N_{UMI}(1 - e^{m/N_{UMI}})$, where m is the number of detected mRNA molecules, and $N_{UMI} = 4,096$ is the total size of the available UMI pool. This function is contrasted with the ideal linear relationship (approximately straight line), showing the point of saturation. FIG. 22C is an example of the number of mapped reads vs. number of distinct UMIs per gene in the data from a single mES cell; data points correspond to unique gene symbols. The curve indicates no amplification bias, i.e. where each mapped read corresponds to a distinct UMI. Most genes show some amplification bias. FIGS. 22D and 22E show log-log plots of the inter-cell CV (standard deviation/mean) as a function of the mean transcript abundance for genes detected in the mES cell population, without UMI filtering (FIG. 22D), and following UMI filtering (FIG. 22E). Each data point corresponds to a single gene symbol.

Example 7

Baseline technical noise for the drop-SEQ platform. Two sources of technical noise in single cell RNA-Seq are (a) variability between cells in mRNA capture efficiency, (b) the intrinsic sampling noise resulting from capturing finite numbers of mRNA transcripts in each cell. The CEL-Seq protocol has been reported to suffer from a low capture efficiency of ~4% or less, and from a variability in capture efficiency of ~25% for pure RNA controls and ~50% for cells (coefficients of variation between samples) when performed in microtitre plates. Less is known about the impact of bioinformatic analysis on single cell sequencing data, but a potential problem may arise from attributing ambiguous reads to multiple genes leading to spurious gene pair correlations. Technical noise can also arise during library amplification, but this noise source is mostly eliminated through the use of random unique molecular identifier (UMI) sequences, which allow bioinformatic removal of duplicated reads. This example illustrates implementation of a UMI-based filtering using random hexamers in all experiments leading to a significant reduction in method noise (FIG. 22).

Figure 14B:
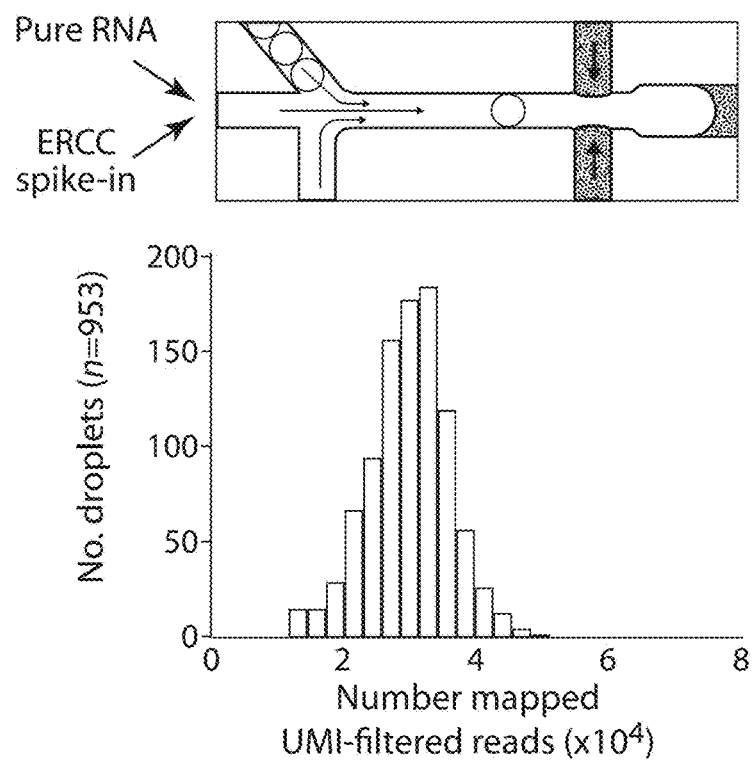
Figure 14C:
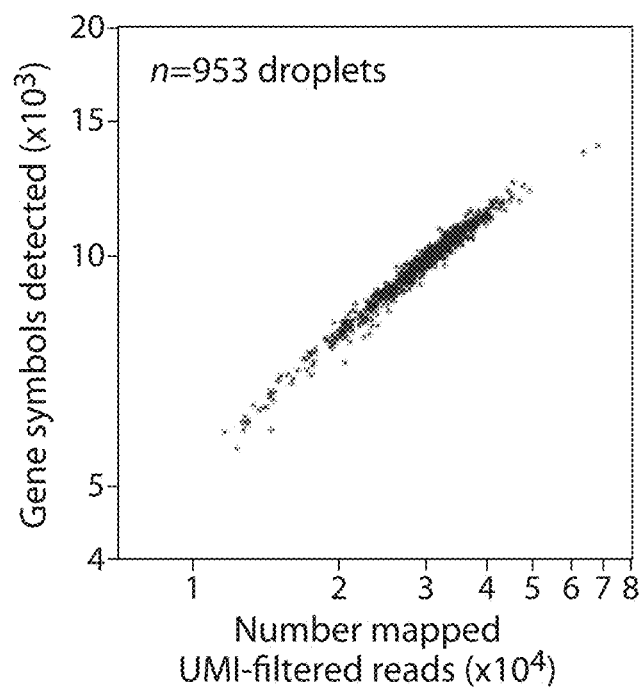

To test how technical noise in this system compares to previous applications of CEL-Seq, a technical control sample was analyzed that included total RNA diluted to single cell concentration (10 pg per droplet), mixed with ERCC RNA spike-in controls of known concentration (FIG. 14B). 953 barcoded control droplets were sequenced in a single run with an average of 30×10³ (+/−21%) UMI-filtered mapped (UMIFM) reads per droplet (FIG. 14B). Between five to fifteen thousand unique gene symbols were identified in each droplet (25,209 detected in total), with the number correlating strongly with UMIFM counts (FIG. 14C). This showed an excellent linear readout of UMIFM counts compared to ERCC spike-in input concentration (FIG. 14D) down to concentrations of 0.5 molecules/droplet on average; below that limit, there was a slight tendency to over-count the number of observed transcripts.

Figure 14D:
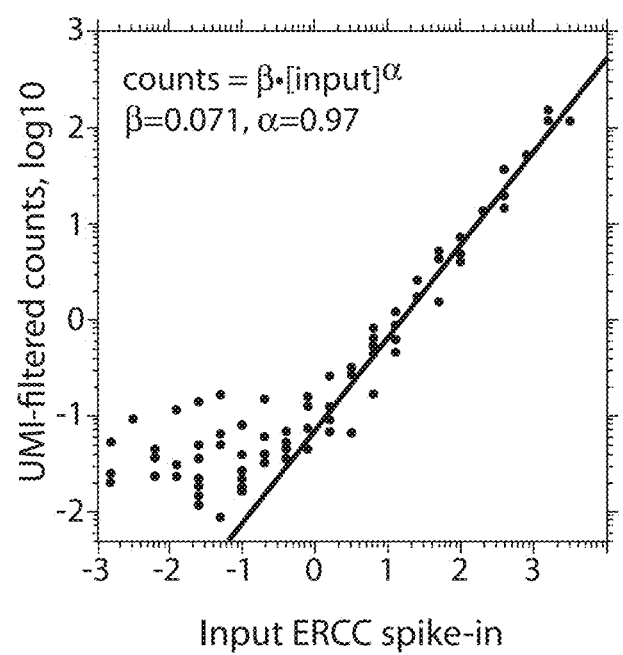
Figure 14E:
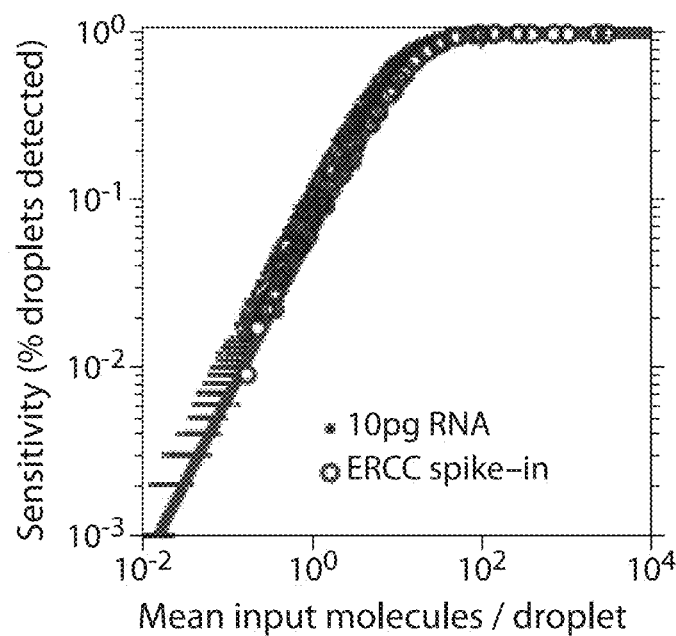

Another important measure of method performance is its sensitivity, i.e. the likelihood of detecting an expressed gene. The sensitivity was almost entirely a function of the transcript abundance (FIG. 14E), and was predicted extremely well for all genes based on the global capture efficiency of mRNA molecules (see below), measured from the ERCC spike-ins to be 7.1% (FIG. 14D). With this capture efficiency, genes were detected in 50% of droplets when 10 transcripts were present, and in >95% of droplets when >45 transcripts were present (FIG. 14E). This sensitivity and capture efficiency were higher than previously measured for CEL-Seq (3.4%).

Figure 14F:
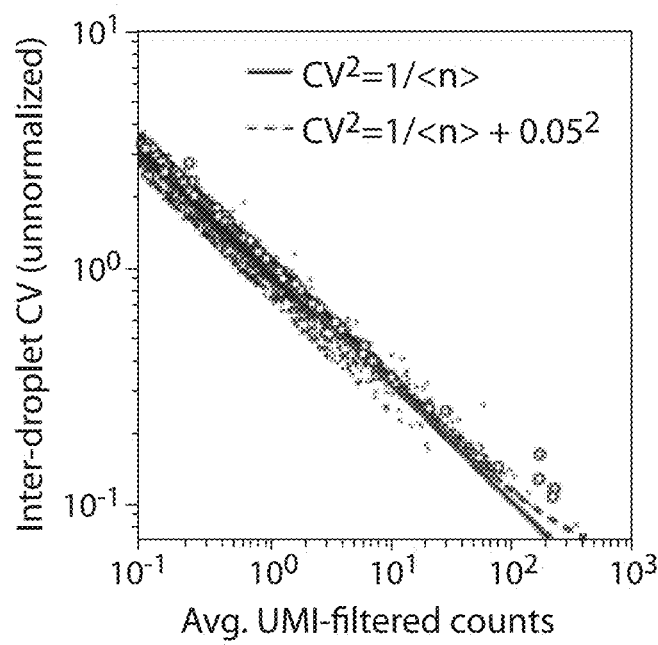

In accuracy, this showed very low levels of technical noise, which can be assessed by comparing the coefficient of variation (CV=standard deviation/mean) of each gene across the cell population to its mean expression level (FIG. 14F). In a system limited only by sampling noise, all genes should be narrowly distributed about the power law curve CV= (mean)$^{-1/2}$ (FIG. 14F). This was indeed observed. More formally, after normalization, 99.5% of detected genes (N=25,209) had a distribution consistent with a Poisson distribution with a baseline technical noise 5-10% (FIG. 14F, dashed curve).

FIG. 14B shows an experimental schematic and histogram of UMI-filtered mapped (UMIFM) reads for RNA-Seq technical control experiment. FIG. 14C shows the number unique gene symbols detected as a function of UMIFM reads per droplet. FIG. 14D shows the mean UMIFM reads for spike-in molecules linearly related to their input concentration, with a capture efficiency β (beta)=7.1%. FIG. 14E shows method sensitivity as a function of input RNA abundance; curve shows theory prediction, $1 - e^{-x*(1-e^{-\beta})}$, derived assuming only intrinsic sampling noise. FIG. 14F shows the coefficient of variation (CV) of spike-in and pure RNA transcripts plotted against the mean UMIFM counts after normalization. Solid curve shows the sampling noise limit; dashed curve shows the sampling noise limit with residual droplet-to-droplet variability in capture efficiency of 5%.

Example 8

Noise modeling of single cell data. In anticipation of the single ES cell data, this example shows a technical noise model to better understand the effects of the low sampling efficiency of transcripts when measured on a per cell basis as compared to bulk measurements. The low efficiency had effects both on the observed variability of gene expression between cells, and on the covariation of gene expression among the cells. Three characteristics contribute to the effects: the capture efficiency of transcripts averaged across all cells; the cell-to-cell variation in capture efficiency; and the choice of a normalization scheme. By refining previous noise models a relationship between biological and observed quantities was derived for the CVs of gene abundances across cells, the gene Fano Factors (variance/mean), and for pairwise correlations between genes (FIG. 14G; see below). The Fano Factor is a metric commonly used to measure noisy gene expression, and yet it is very sensitive to capture efficiency. This analysis revealed that technical noise introduces not just baseline noise as widely appreciated, but it also spuriously amplifies existing biological variation (FIG. 14G, Eq. 1). FIG. 14G shows a summary of relationships between observed and underlying biological quantities for the CV, Fano Factor and gene pairwise correlations.

Also showed is that low sampling efficiencies significantly dampen correlations between gene pairs in a predictable manner, setting an expectation to find relatively weak but significant correlations in the data (FIG. 14G, Eqs. 2-3). Knowing that relatively weak correlations are real and are an expected consequence of the statistics of single cell measurements helps derive useful information from the data including tests for highly variable genes (see below). These results also provide a basis for developing a process for formally de-convolving noise from biological measurements based on fundamental counting statistics.

In addition, unexpectedly encountered and eliminated was an important source of anomalous gene expression correlation arising from reads mapping to two or more gene transcripts. Sequence analysis pipelines intended for bulk (non-single cell) applications map ambiguous read probabilistically in a manner that can spuriously couple otherwise independently expressed genes. This problem may be particularly acute for 3'-sequencing of single cells since UTR regions can be similar across multiple genes; and in relatively uniform cell populations such as ES cells, which are characterized by a wide network of weak gene expression couplings that become comparable to those generated spuriously. The problem is, however, more general when sampling efficiencies are low, since these serve to weaken even strong biological correlations (FIG. 14G, Eq. 3). These examples show that the read-mapping problem was overcome using a novel bioinformatic pipeline (see below) that makes use of repeated UMI tags across different reads to minimize ambiguities in mapping.

Example 9

Single cell profiling of mouse ES cells. Single cell profiling is capable of identifying differentiated cell types from distinct lineages even with very low sequencing depths. What is less clear is the type of information that can be gained from studying a relatively uniform population that is subject to stochastic fluctuations or to a dynamic environment. To explore the kind of information obtainable from our new method, this example studies mouse ES cells maintained in serum, as these cells are well studied and exhibit well-characterized fluctuations, but they are still uniform compared to differentiated cell types and could pose a challenge for high throughput single cell sequencing.

To explore the behavior of drop-SEQ, different numbers of cells were harvested at different sequencing depths for each of the ES cell runs by collecting different emulsion volumes. 935 ES cells were collected for deep sequencing; 145, 302 and 2,160 cells after 2 days after LIF withdrawal; 683 cells after 4 days; and 169 and 799 cells after 7 days. The average number of reads obtained per cell in these runs ranged up to $208 \times 10^3$, and the average UMIFM counts ranged up to $29 \times 10^3$. Run statistics are detailed in Table 1.

Figure 15A:
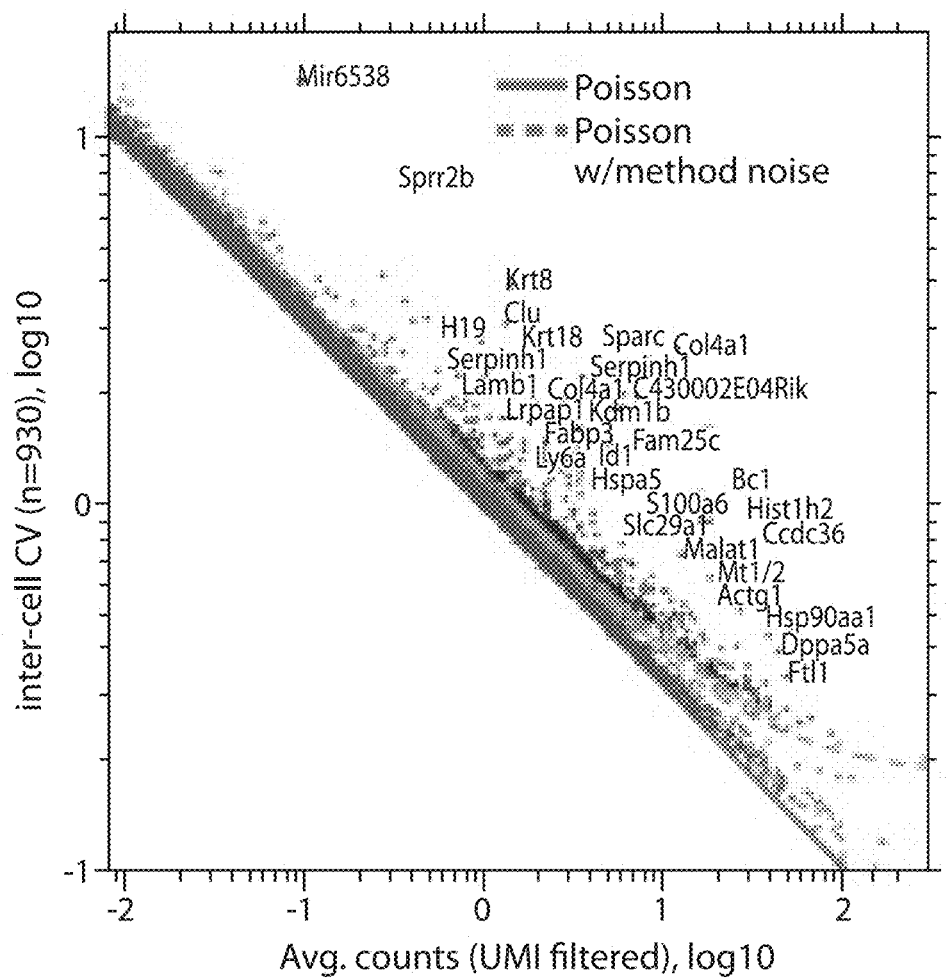
FIGS. 15A-15G illustrate the heterogeneous structure of certain ES cell populations, in yet another embodiment of the invention.
Figure 15B:
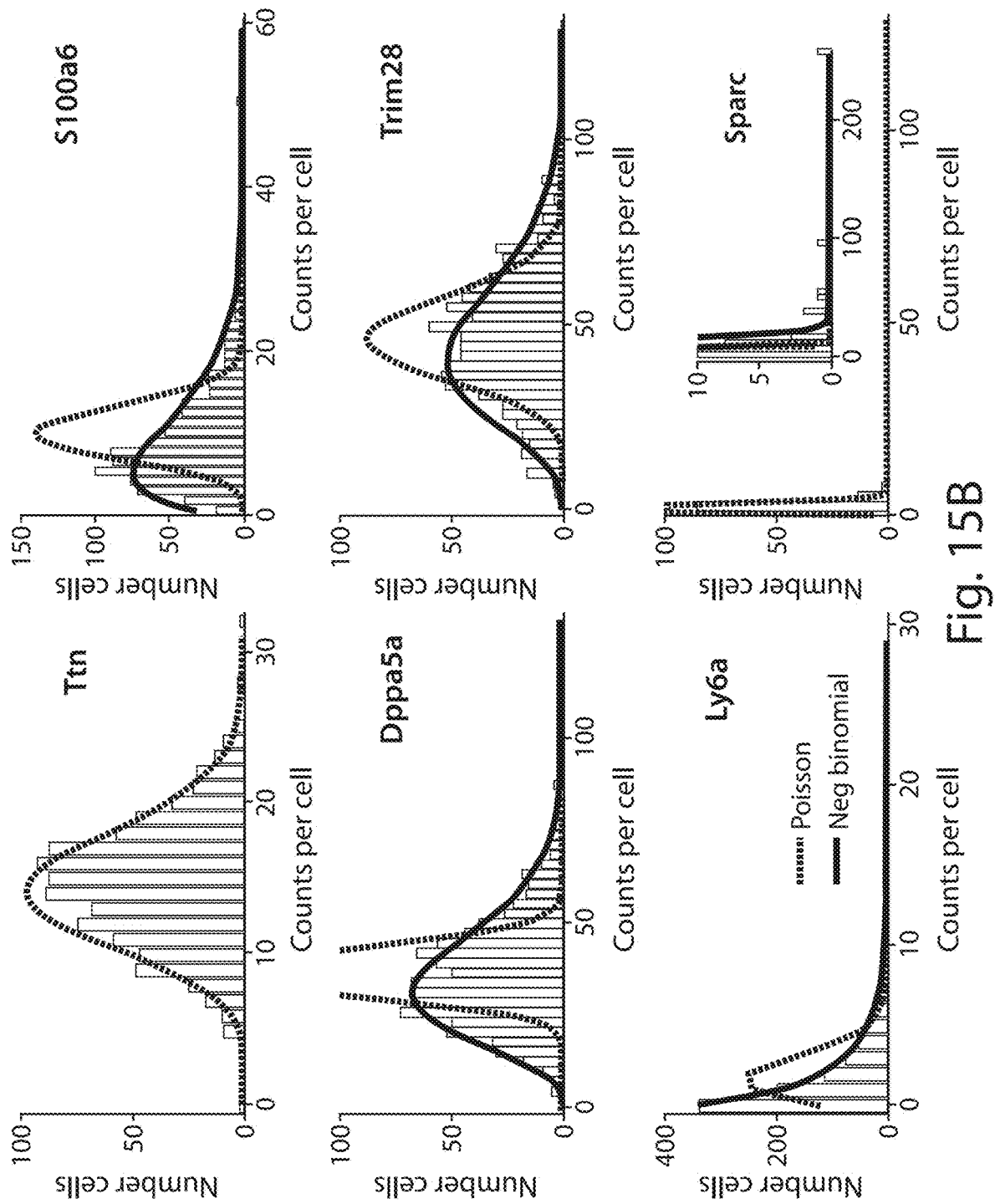
Figure 15C:
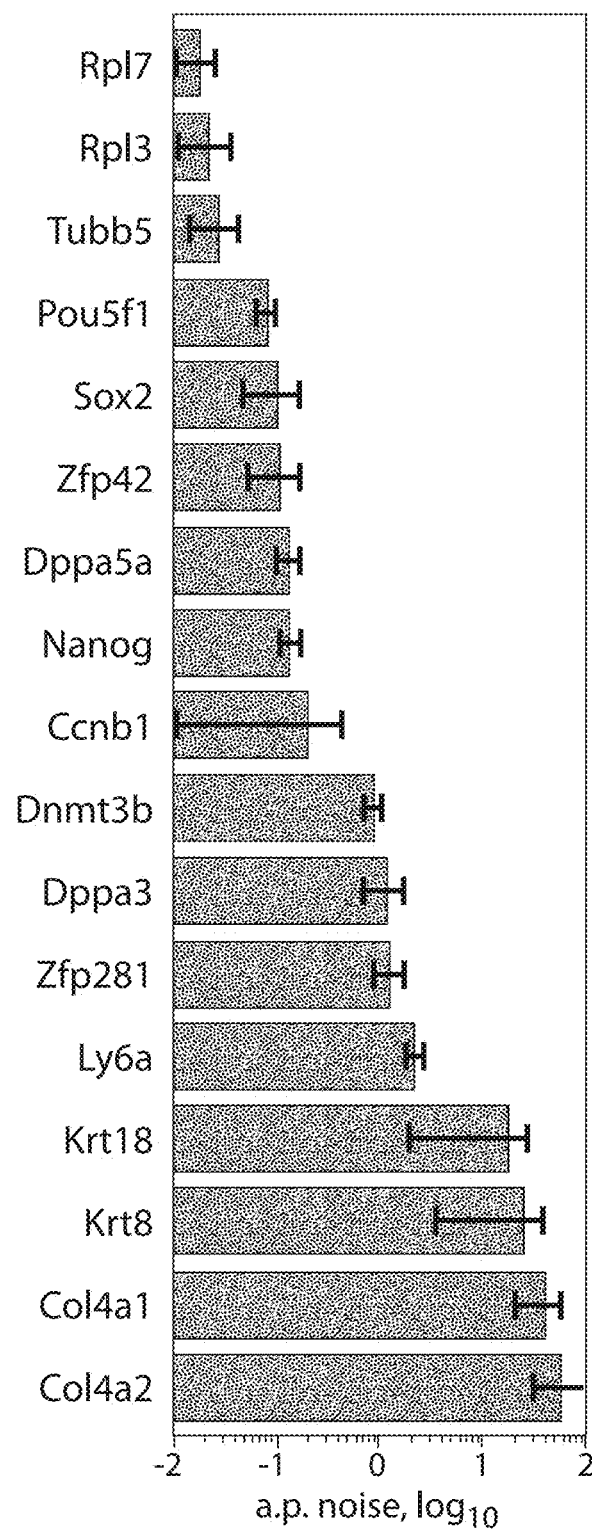

The structure of the ES cell population. For the 935 ES cells, 1,507 genes were identified that were significantly more variable than expected from Poisson statistics (10% FDR, see below and Table 2), and that were also expressed at a level of at least 10 UMIFM counts in at least one cell (FIGS. 15A, 15B). Of the 1,507 abundant and variable genes, pluripotency factors previously reported to fluctuate in ES cells were found (Nanog, Rex1/Zfp42, Dppa5a, Sox2, Esrrb). Notably, the most highly variable genes included known markers of Primitive Endoderm fate (Col4a1, Col4a2, Lamb1, Lama1, Sox17, Sparc), markers of Epiblast fate (Krt8, Krt18, S100a6), and epigenetic regulators of the ES cell state (Dnmt3b), but also genes with unknown association to ES cell regulation such as the stem cell antigen Sca-1/Ly6a, which may plays a role in regulating adult stem cell fate. Other genes showed very low noise profiles, consistent with Poisson statistics (e.g. Ttn, FIG. 15B). The above-Poisson noise, defined as $\eta$ (eta)$=CV^2-1/\mu$ ($\mu$ or mu being the mean UMIFM count), was evaluated for a select panel of genes (FIG. 15C) and found to be in qualitative agreement with previous reports. Unlike the CV or the Fano Factor, $\eta$ (eta) scales linearly with its true biological value even for low sampling efficiencies (FIG. 14G, Eq. (1)).

FIG. 15 shows that drop-SEQ profiling reveals the heterogeneous structure of ES cell populations. FIG. 15A shows CV plotted against mean UMIFM counts for the mES cell transcriptome (middle and upper points) and the pure RNA technical controls (lower points). Genes marked in black are identified as significantly more variable than the technical control. Solid and dashed curves are as in FIG. 14F, but with residual method noise of 20% in the cell experiment. A subset of variable genes are annotated. FIG. 15B shows illustrative gene expression distributions showing low (Ttn), moderate (Trim28, Ly6a, Dppa5a) and high (Sparc, S100a6) expression variability, with fits to Poisson and Negative Binomial distributions. FIG. 15C shows the above-Poisson (a.p.) noise, $CV^2-1$/mean, plotted for pluripotency factors and compared with other factors.

Example 10

Figure 15D:
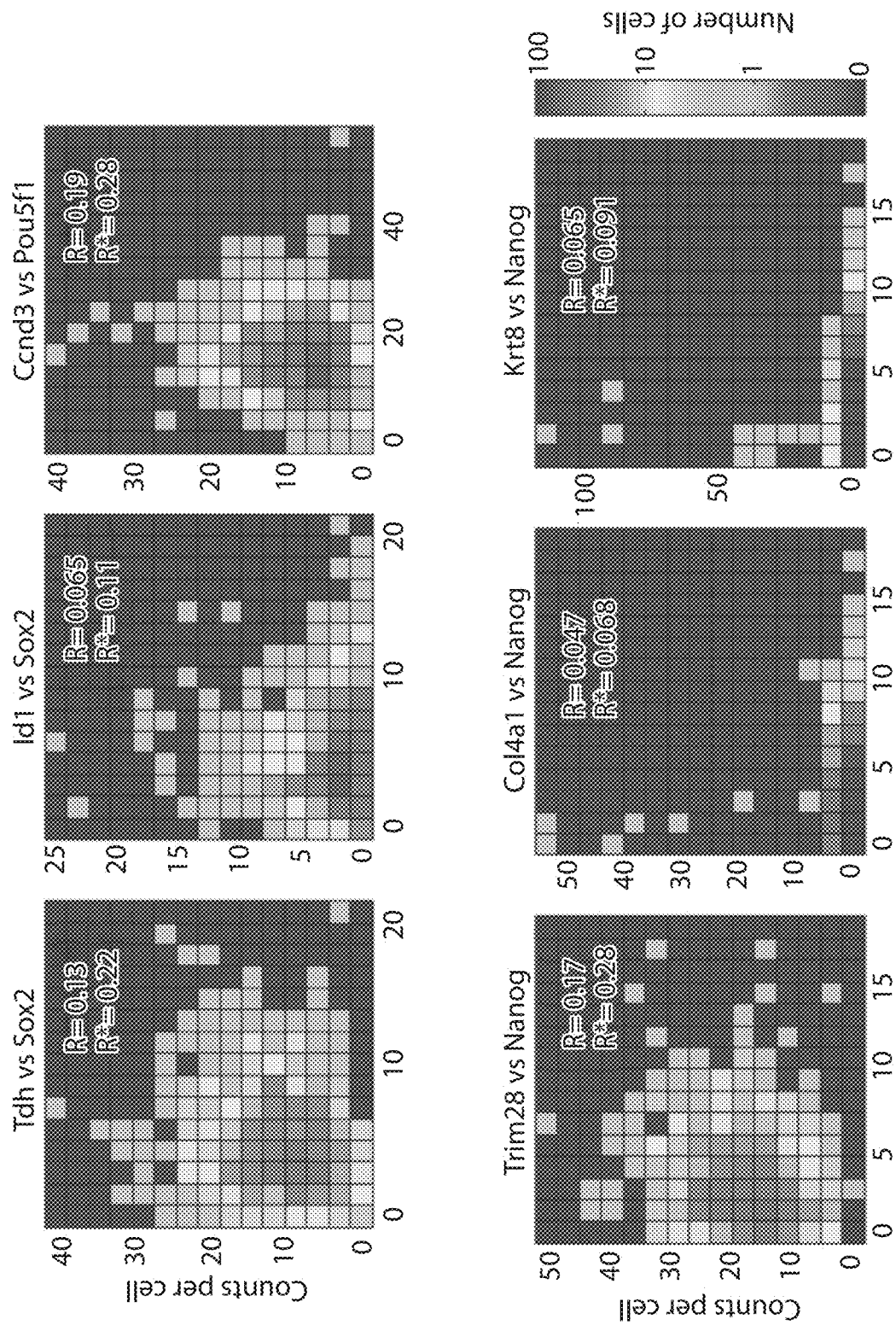

To test the idea that ES cells exhibit heterogeneity between a pluripotent ICM-like state and a more differentiated epiblast-like state, this example studied contrasting the expression of candidate pluripotency and differentiation markers in single ES cells. Gene pair correlations (FIG. 15D) at first appear consistent with a discrete two-state view, since both the epiblast marker Krt8 and the primitive Endoderm marker Col4a1 were expressed only in cells low for Pou5f1 (shown) and the other pluripotency markers (not shown). The differentiation-prone state was rare compared to the pluripotent state. The correlations also showed other known regulatory interactions in ES cells, for example Sox2, a known negative target of BMP signaling, was anti-correlated with the BMP target Id1. What was more surprising, however, was the finding that multiple pluripotency factors (Nanog, Trim28, Esrrb, Sox2, Klf4, Zfp42) fluctuated in tandem across the bulk of the cell population (FIG. 15D, 23, 24). These observations together were not explained by a simple two-state model, since they indicate that pluripotency factors remain correlated independently of epiblast gene expression; instead they suggest a continuum of states characterized by varying pluripotency. Not all pluripotency factors showed significant correlations, however: Oct4/ Pou5f1 was much more weakly correlated to other core pluripotency factors and other factors and instead correlated strongly with cyclin D3 (FIGS. 15D and 24), but not other cyclins, suggesting fluctuations that belie a specific regulatory origin.

Figure 15E:
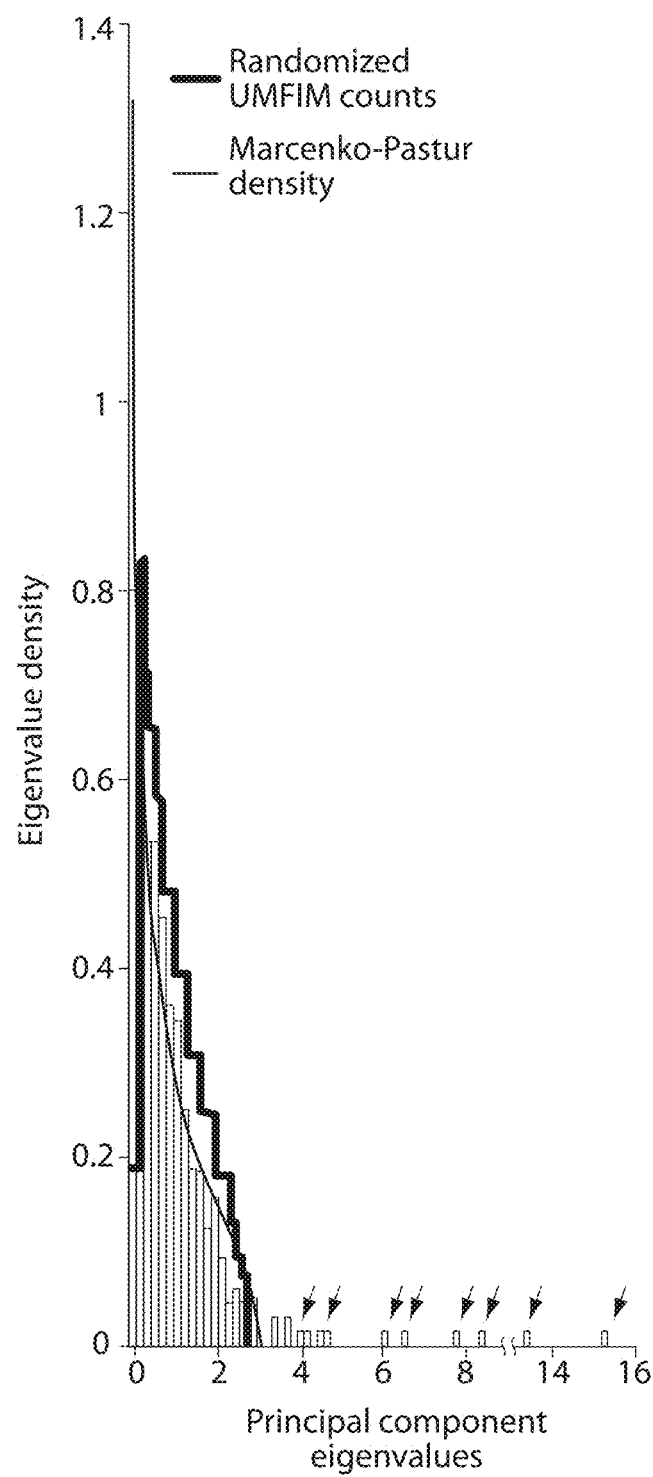

What then is the structure of the ES cell population inferred from the data? A principal component analysis (PCA) was conducted of the ES cell population for the highly variable genes, and it was found that multiple non-trivial dimensions of heterogeneity (12 dimensions with 95% confidence), corresponding to the number of principal components (PCs) in the data that cannot be explained by intrinsic noise in expression (see FIG. 15E). This observation confirmed the presence of additional sources of heterogeneity beyond the ICM-epiblast axis. Inspection of the first four principal components, and their loadings (FIG. 15F), revealed the presence of at least three small but distinct cell sub-populations: one rare population (6/935 cells) expressed very low levels of pluripotency markers and high levels of Col4a1/2, Lama1/b1/c1, Sparc, and Cd63, which unambiguously identify primitive endoderm (PrEn)-like cells; a second cell population (15/935 cells) expressed high levels of Krt8, Krt18, S100a6, Sfn and other markers of the epiblast lineage. The third population presented a seemingly uncharacterized state, marked by expression of heat shock proteins Hsp90, Hspa5 and other ER components such as the disulphide isomerase Pdia6. This population may represent ES cells under stress from dissociation.

Figure 15F:
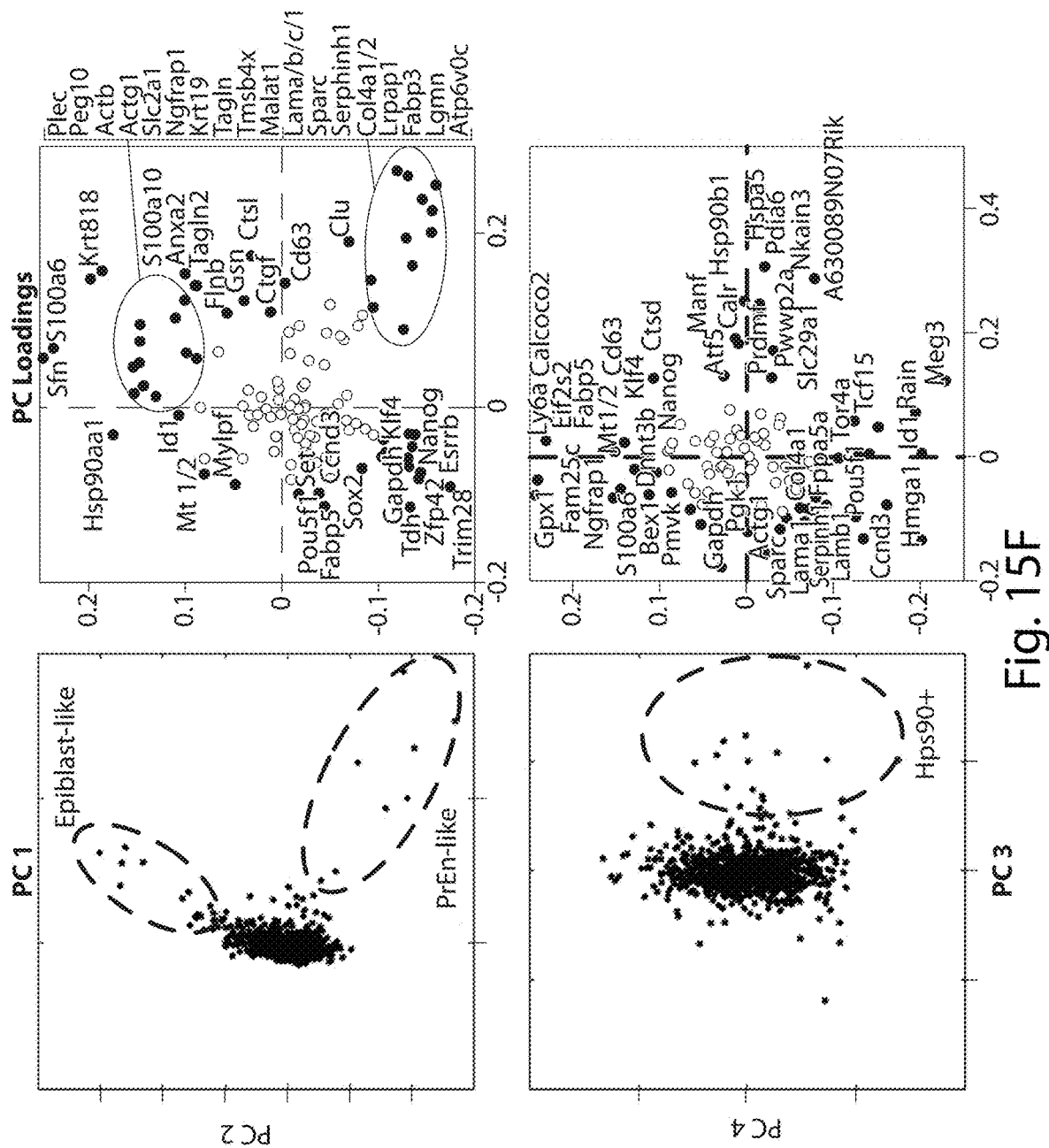
Figure 15G:
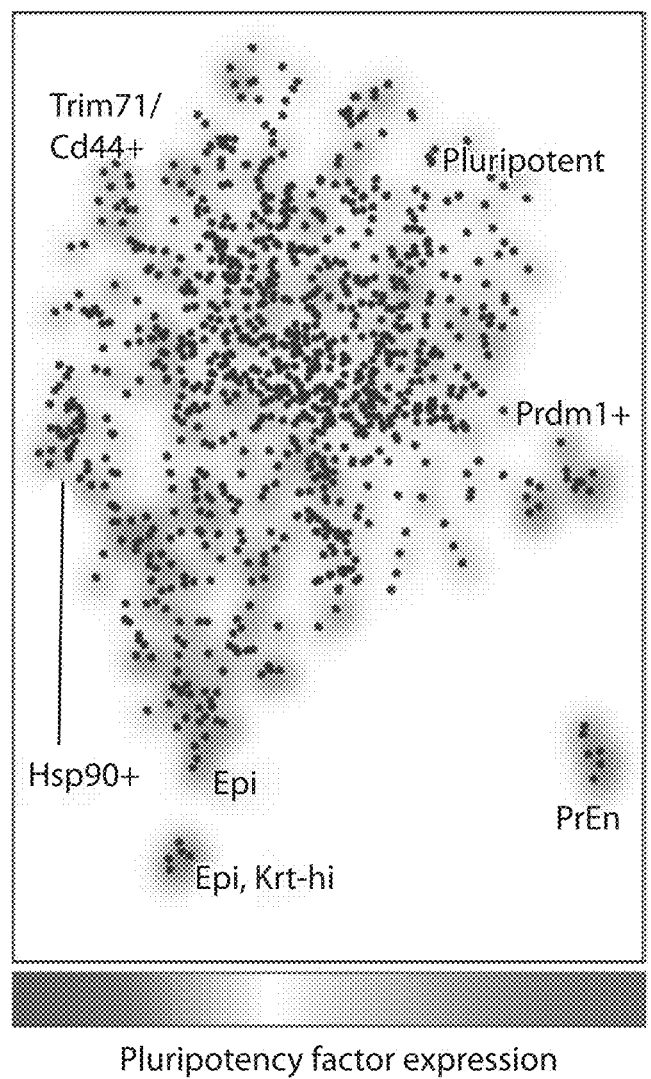

PCA analysis is a powerful tool for visualizing cell populations that can be fractionated with just two or three principal axes of gene expression. However, when more than three non-trivial principal components exist there are more appropriate techniques for dimensionality reduction that represent the local structure of high-dimensional data. This example applied a method for dimensionality reduction known as t-distributed Stochastic Neighbor Embedding (t-SNE) (FIG. 15G). The map revealed no large sub-populations of ES cells, as expected, but revealed a continuum from high pluripotency to low pluripotency, with outlier populations identified by PCA lying at the population fringes. The map also revealed three additional fringe sub-populations characterized respectively by high expression of Prdm1/Blimp1, Lin41/Trim71 and SSEA-1/Fut4. As with the Hsp90-hi population, it remains to be seen whether these populations represent distinct cell states endowed with distinct functional behaviors, or whether these are merely cells accessing outlier, but normal, states of ES cell gene expression. Thus, while the well-studied epiblast-like state in the ES cell population was identified, and evidence for collective fluctuations between ICM to epiblast-like state was found, these fluctuations are not the only axes of transcriptional heterogeneity in the ES cell population.

FIG. 15D shows heatmaps illustrating pairwise gene correlations. FIG. 15E shows an eigenvalue distribution obtained from principal component analysis of the mES cell population, revealing non-trivial modes of cellular heterogeneity detectable in the data (arrows). The smooth curve shows a typical eigenvalue distribution of a random permutation of the gene expression profile; the jagged curve shows the predicted Marcenko-Pastur eigenvalue distribution for a random matrix. Only eigenvalues lying beyond the curves were significant. FIG. 15F shows mES cell principal components and their loadings, showing the dominant uncorrelated modes of heterogeneity and revealing three rare ES cell sub-populations. FIG. 15G is a tSNE map of the mES cell population revealing additional fringe sub-populations and a pluripotency-to-epiblast axis.

FIG. 23 shows single cell gene expression of mES cells. Gene expression for principally variable genes at 0, 2, 4 and 7 days (FIGS. 23A-23D, respectively). Expression of each gene is z-score standardized.

FIG. 24 shows the structure of the mES cell population. FIG. 24A shows pairwise correlations of selected genes across 935 mES cells. As discussed herein, Oct4/Pou5f1 correlated more strongly with Cyclin D3 and more weakly with Sox2, Klf4 and other pluripotency factors. The correlations reported here are as observed with no correction for subsampling (cf. FIG. 14G, Eq. (3)). FIGS. 24B-24G show different projections of 3-dimensional tSNE map of the mES cell population reveal distinct cell sub-populations; the cells in each panel are colored according to the aggregate expression of the specified markers.

Example 11

Putative pluripotency factors from gene expression covariation. The observation that genes co-vary in a population raises the question of whether correlations might disclose commonalties in gene regulation or function. In complex mixtures of cells, attempts at such inference may be confounded because gene-gene correlations could primarily arise from trivial differences between cell types, which reflect large-scale epigenetic changes rather than a particular regulatory program. The situation is different in a population consisting of just a single cell type: here, one might be more optimistic that fluctuations in cell state could reveal functional dependencies. The mES cell population satisfies this requirement as it shows relatively little discrete structure, beyond the presence of the small sub-populations described above.

To test whether gene expression covariation might contain regulatory information, this example explored the covariation partners of known pluripotency factors using a custom network neighborhood analysis (NNA) scheme (FIG. 16, see below). This scheme defines the set of genes most closely correlated with a given gene (or genes) of interest, and which also most closely correlate with each other. Given the sensitivity of correlations to sampling efficiency (FIG. 14G, Eq. (3)), the NNA analysis—which is only sensitive to correlation network topology—be more robust than simply associating highly correlated genes. Remarkably, applied to the pluripotency factors Nanog and Sox2, the NNA scheme strongly enriched for other pluripotency factors: of the 20 nearest neighbors of Nanog, eleven are documented as pluripotency factors, three more are associated with pluripotency, and one (Slc2a3) is syntenic with Nanog. Only one gene (Rbpj) has been shown to be dispensable for pluripotency, leaving four genes with no previous documented connection to ES cells. It is tempting to predict that these genes also play a functional role in maintaining the pluripotent state. Similarly, the entire neighborhood of Sox2 included factors directly or indirectly associated with pluripotency—including core pluripotency factors (6/9 genes); the threonine catabolic enzyme Tdh, which was recently shown to be expressed at high levels in the ICM and is required for maintaining the pluripotent state; Pcbp1 shown to be a binding partner of the pluripotency factor Ronin/Thap11, and the translation initiation factor subunit Eif2s2 shown to be upregulated in response to Stat3 overexpression. Interestingly the same analysis may provide insight into other biological pathways. The neighborhood of Cyclin B (Ccnb1), for example, was small but contained other core cell cycle genes Cdk1, Ube2c and Plk1.

The scheme is not generally applicable however to all regulatory functions: it was found that many other pathways seemingly independent of mES cell biology appear to have no meaningful NNA associations. This suggests that single cell covariation may capture fluctuations most specific to the biology of the cells being studied, and could be harnessed more generally to identify other biological pathway components by artificially generating fluctuations through weak pathway-specific perturbations.

Example 12

Figure 17A:
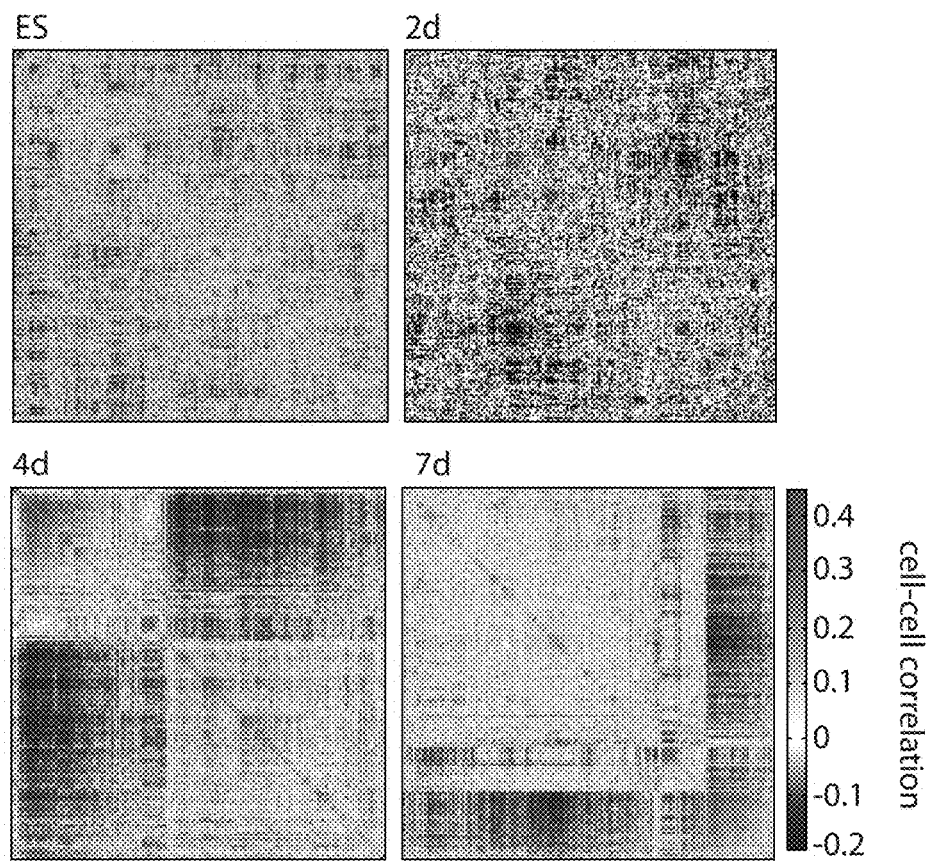
FIGS. 17A-17J illustrate temporal heterogeneity and population structure in differentiating ES cells, in yet another embodiment of the invention.

Population dynamics of differentiating ES cells. Upon LIF withdrawal, mES cells differentiate by a heterogeneous but poorly characterized process, leading eventually to the formation of predominantly somatic (epiblast) lineages. The fate of pre-existing PrEn cells is unclear, as is the question of whether other cell lineages might transiently emerge and then vanish. In the single cell analysis, following LIF withdrawal the differentiating ES cell population underwent significant changes in population structure, which can be qualitatively appreciated from hierarchically clustering cells according to the expression of highly variable genes (FIG. 17A). These changes and the following analysis reflect an unguided differentiation protocol; it would be instructive to apply the same methods to guided differentiation protocols in the future to identify how the inherent heterogeneity and variation in intermediate cell types depends on signaling.

To dissect the changes occurring in the cell population and to validate the quality of the data, this example first inspected the gene expression dynamics of pluripotency factors and differentiation markers (FIG. 17B-17E). The average expression of pluripotency factors Rex1/Zfp42 and Esrrb levels dropped rapidly; Pou5f1 and Sox2 dropped more gradually; the epiblast marker Krt8 increased steadily; and Otx2, a transcription factor required for transiting from the ICM to the epiblast state, transiently increased by day 2 and then decreased. It was however evident that the average expression was not representative of the dynamics in each cell: some cells failed to express epiblast markers and a fraction of cells continued to express pluripotency factors even seven days after LIF withdrawal, (FIG. 17C-17E), indicating that the timing of ES cell differentiation is itself heterogeneous.

A PCA analysis was performed of cells aggregated from all time points to identify whether this heterogeneity reflects global trends (FIG. 17F), and it was found that even after 7 days post-LIF withdrawal a fraction (5%, N=799) of cells overlapped with the mES cell population. The greatest temporal heterogeneity was evident at four days post-LIF, with cells spread broadly along the first principal component between the mES cell and differentiating state. The PCA analysis also revealed enrichment at days 2 and 4 for a strong metabolic signature (top GO annotation: Cellular Metobolic Process, $p=1.4\times10^{-8}$) consistent with the metabolic changes occurring upon emergence from the pluripotent state.

In addition to heterogeneity arising from asynchrony in differentiation, after four and seven days there was evidence of emerging sub-populations with distinct patterns of gene expression, not all of which could be immediately attributed to known cell types. The population structure was visualized at these time points by t-SNE (FIG. 17I and FIG. 25), and tabulated the distinct sub-population markers in Table 3. At two days and four days post-LIF withdrawal, a rare population of Zscan4+ cells was identified, previously identified as rare Trophectoderm-forming cells (REF); this population was no longer detected by day 7. At four and seven days, another, less rare population emerged expressing normally maternally imprinted genes H19, Rhox6/9, Peg10, Cdkn1 and others, suggesting widespread demethylation possibly associated with early primordial germ cell differentiation.

In addition to these populations, the resident PrEn cells could be detected at all time points (FIGS. 17H, 17I), with PrEn population appearing to expand at two and four days after LIF withdrawal, but then stagnating by seven days post-LIF. Overall, the analysis exposes the temporal heterogeneity of ES cell differentiation and the dynamics of distinct and novel ES cell sub-populations.

Figure 17B:
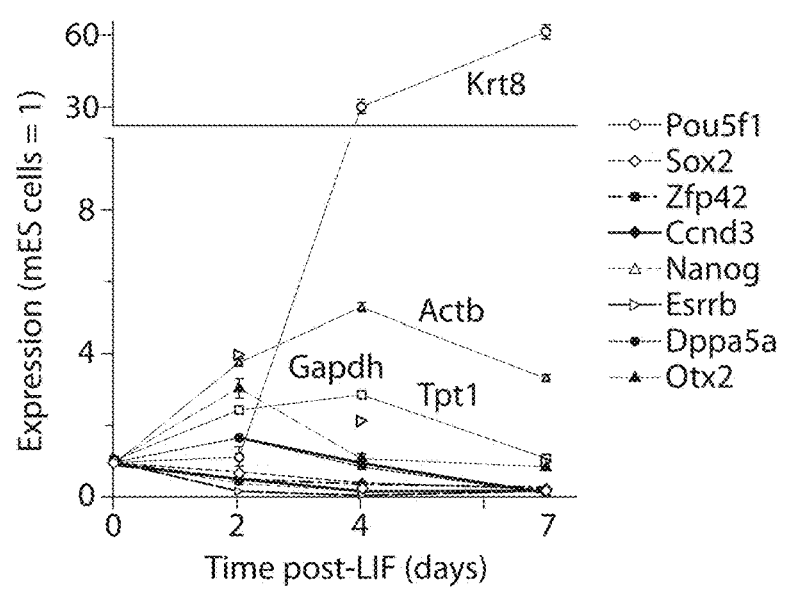
Figure 17C:
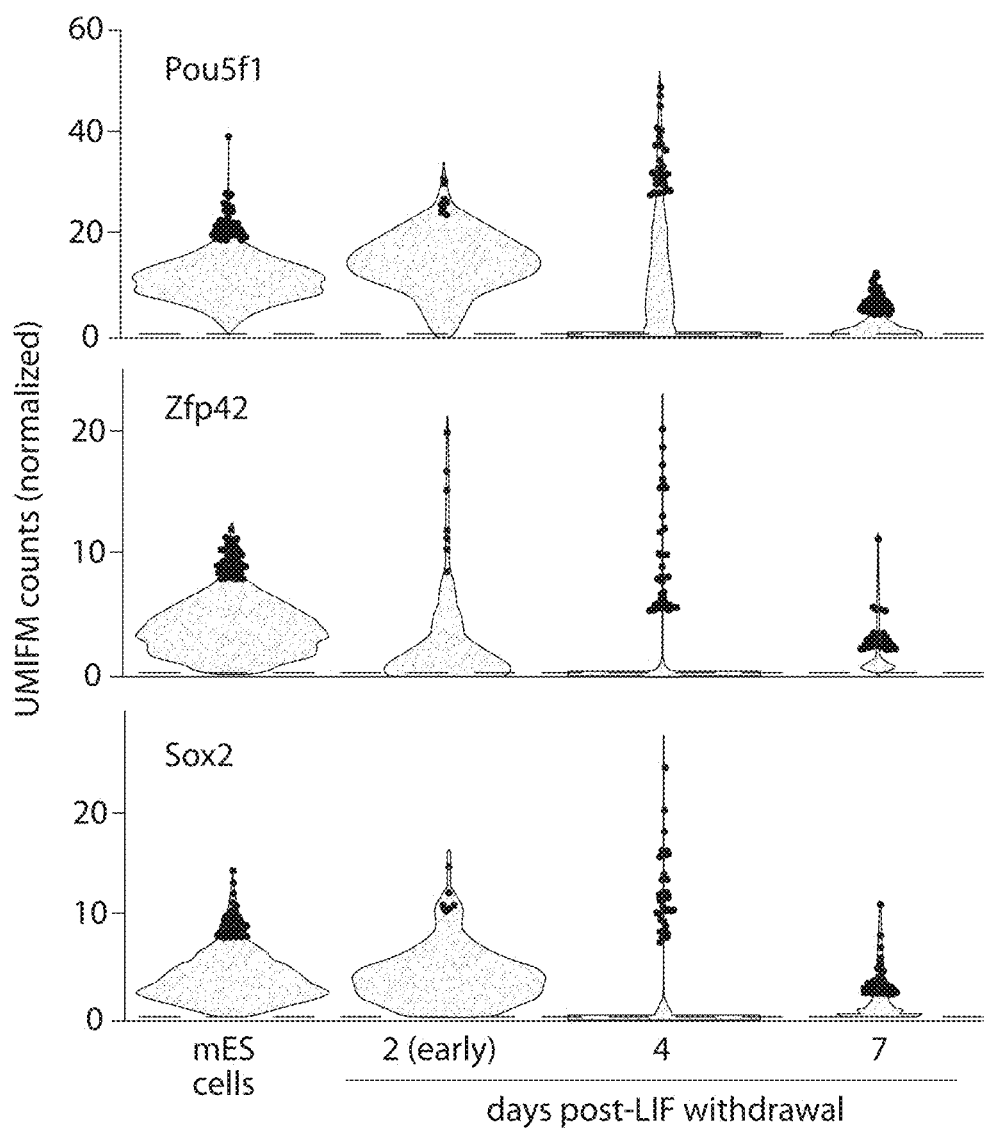
Figure 17D:
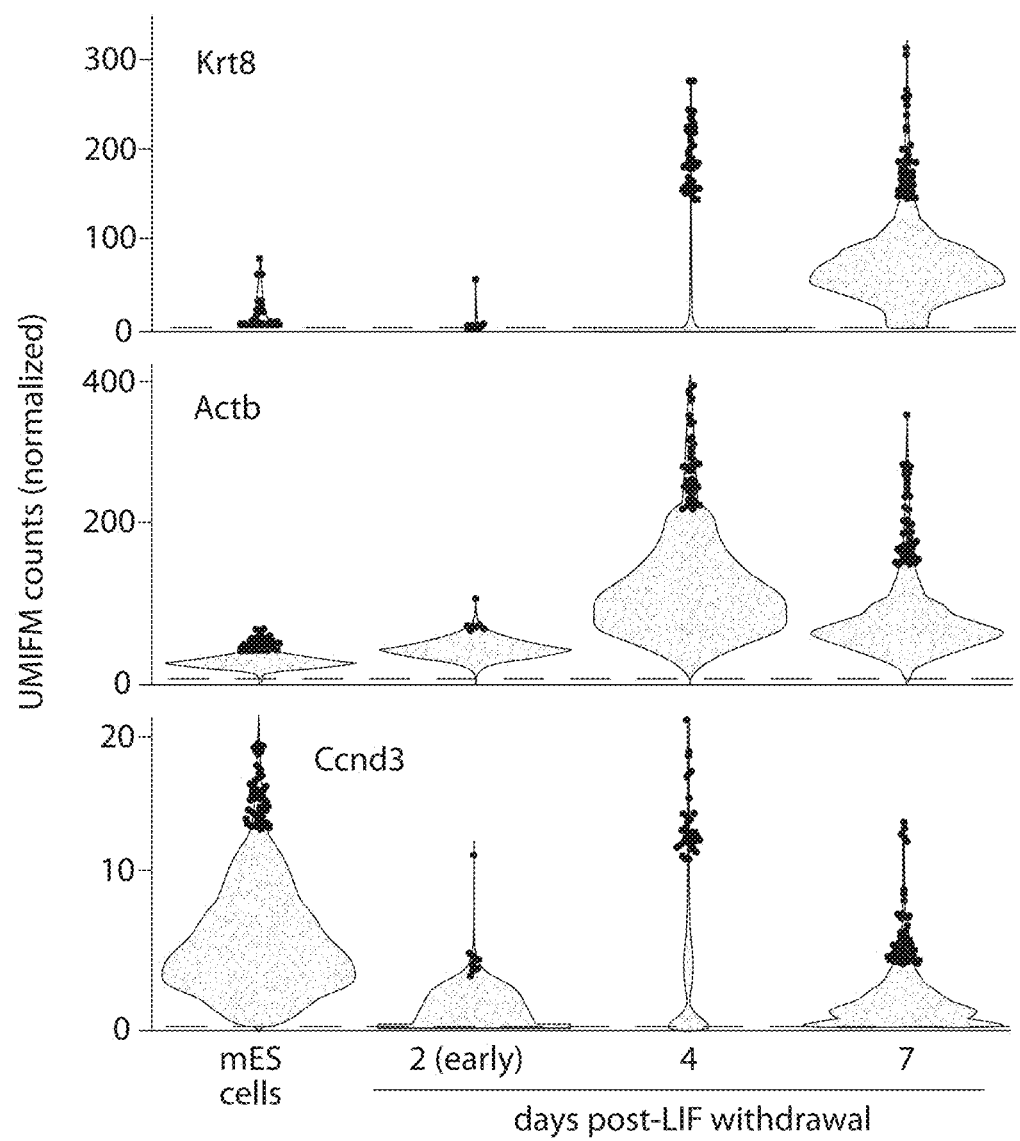
Figure 17E:
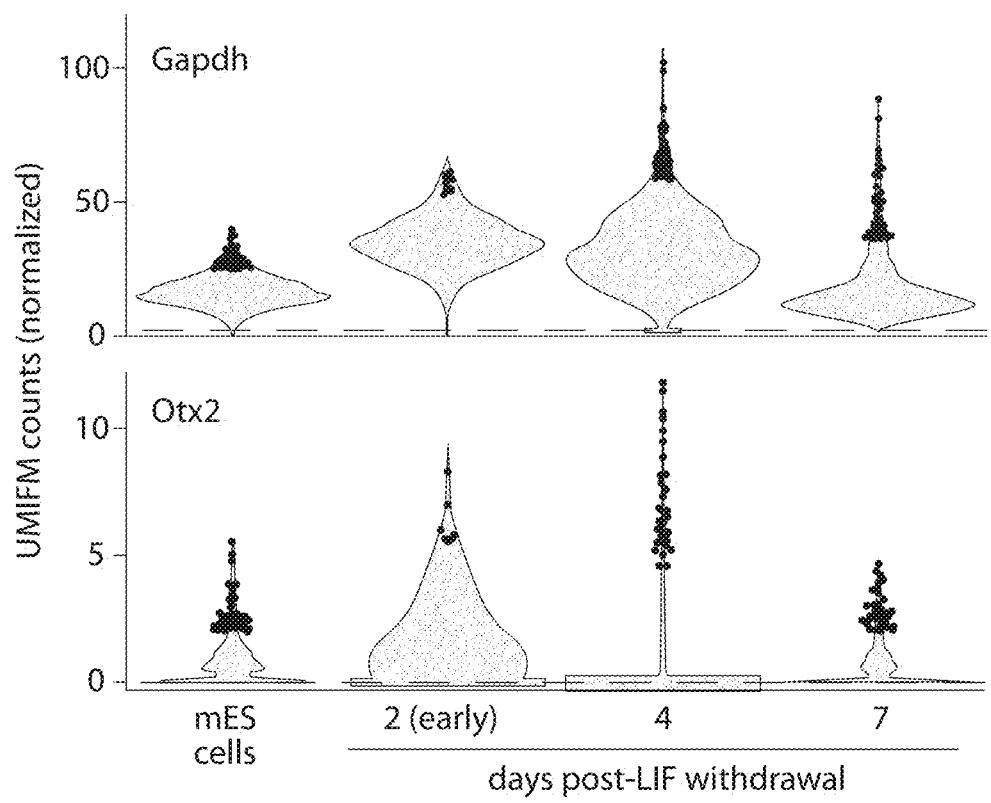
Figure 17F:
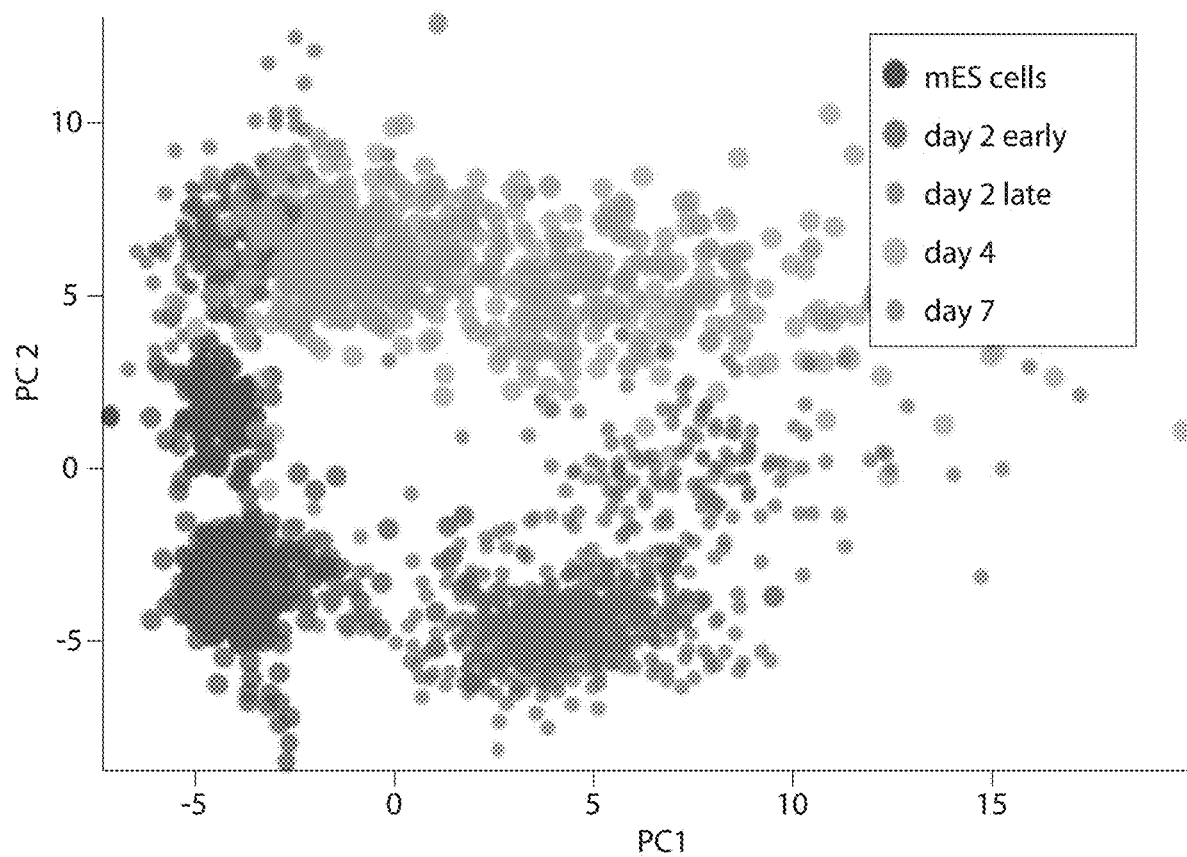
Figure 17G:
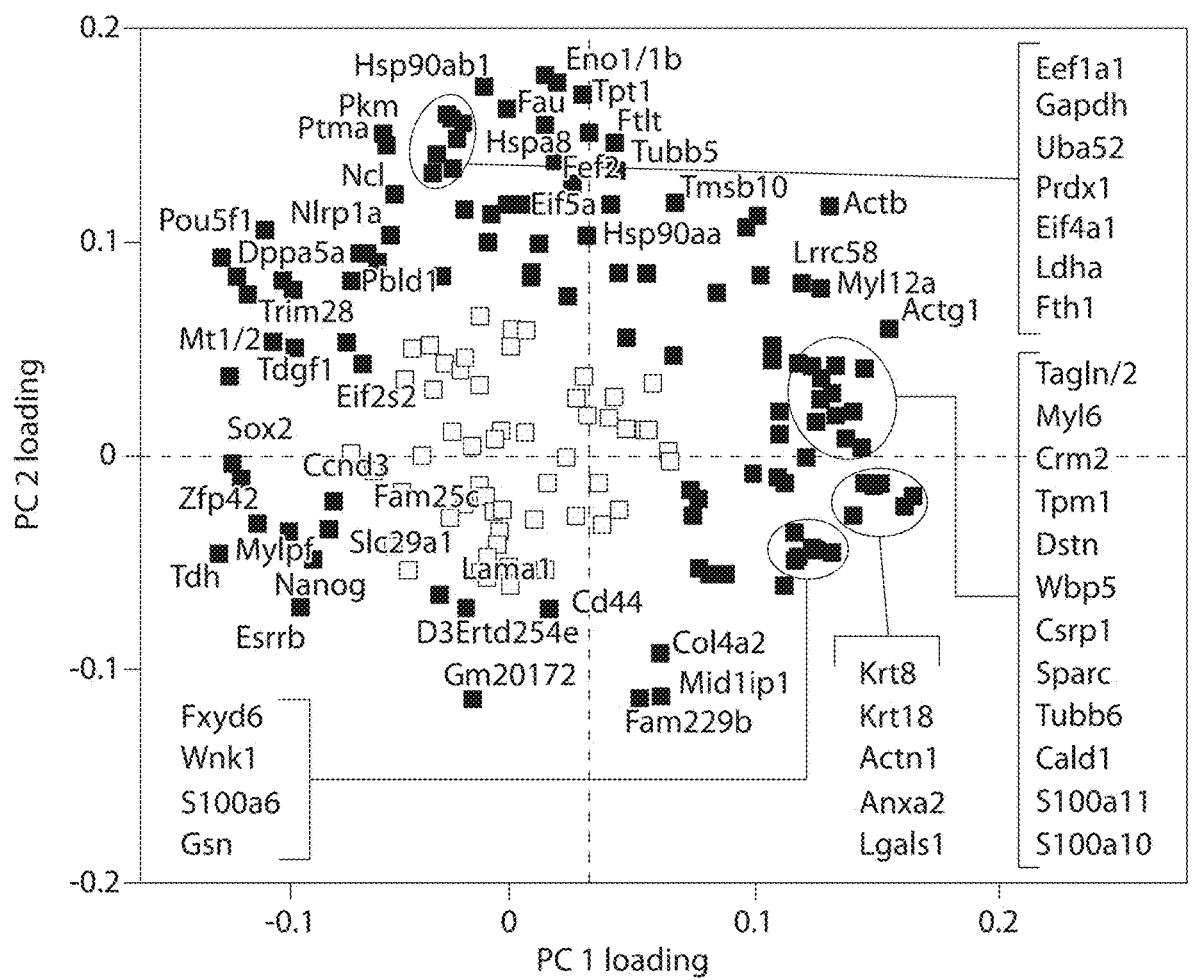
Figure 17H:
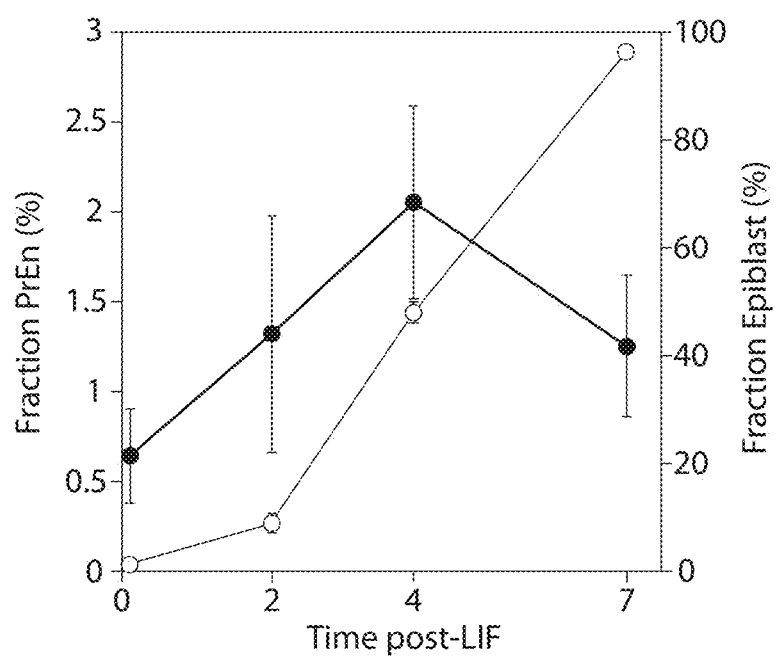
Figure 17I:
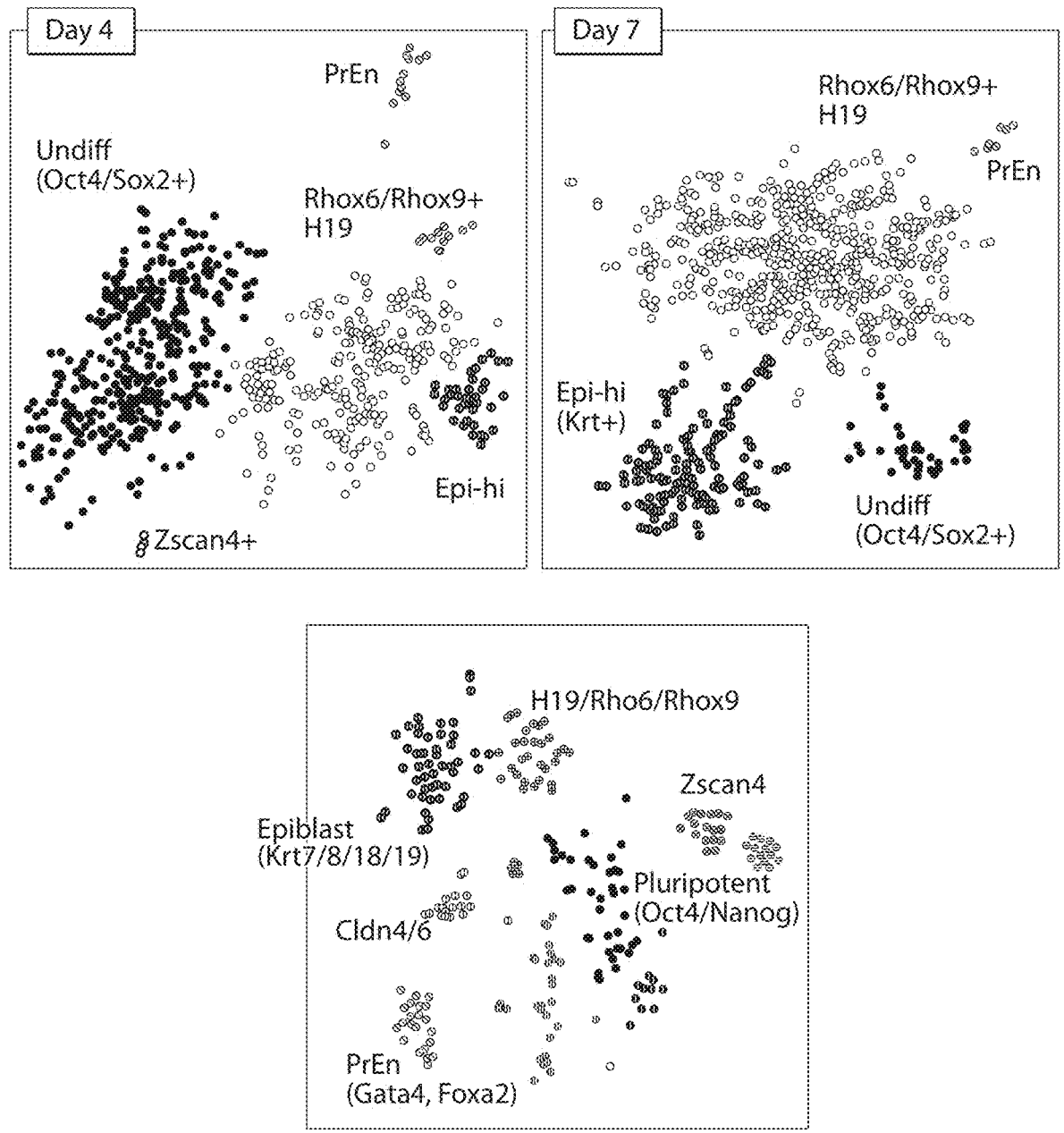

FIGS. 17A-17J show temporal heterogeneity and population structure in differentiating ES cells. FIG. 17A shows changes in global population structure after LIF withdrawal are seen qualitatively by hierarchically clustering heatmaps of cell-cell correlations over the highly variable genes at each time point. FIG. 17B shows average dynamics of gene expression after LIF withdrawal are consistent with known patterns of differentiation. FIGS. 17C-17E show the dynamics for the genes in FIG. 17B shown through probability density (violin) plots for the fraction of cells expressing a given number of counts. Data points show the top 5% of cells. FIGS. 17F and 17G show the first two principal components (PCs) (FIG. 17F), and PC loadings (FIG. 17G), of 3,034 cells from multiple time points showing rapid transient changes (PC 2) and asynchrony in differentiation (PC 1). FIG. 17H shows the dynamics of the fraction of epiblast and PrEn cells as a function of time post-LIF. FIG. 17I shows tSNE maps of the differentiating ES cells after 4.7 days post-LIF reveal transient and emerging population sub-structure, and a tSNE map of genes after 4 days post-LIF (right panel) reveal putative population markers.

Figure 25:
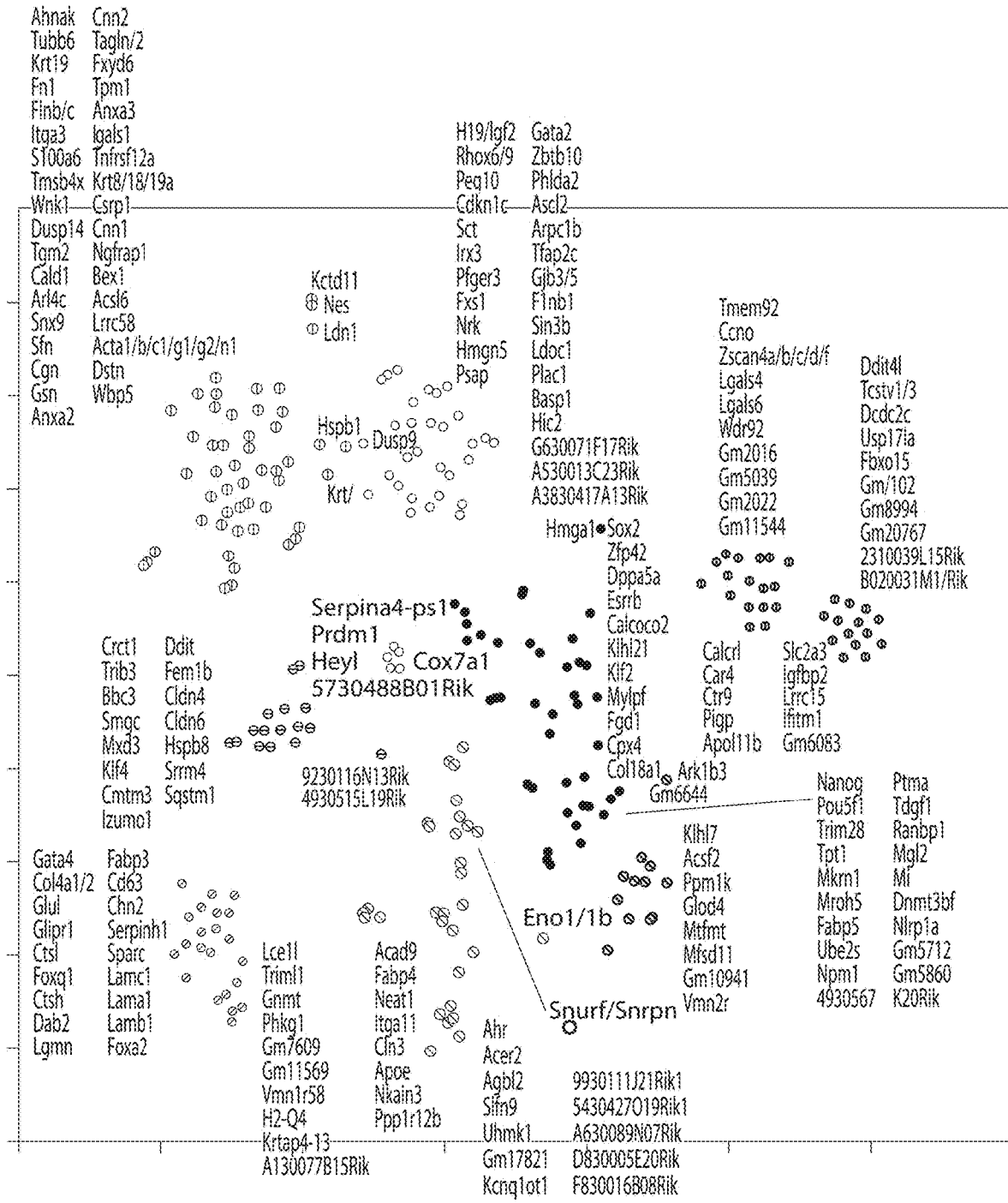
FIG. 25 illustrates, in still another embodiment of the invention, a tSNE map of principal genes.

FIG. 25 shows a tSNE map of principal genes at 4 days post-LIF withdrawal. This figure reproduces FIG. 17I with full gene annotation.

Example 13

A reduction in promiscuous gene expression fluctuations during mES cell differentiation. This example addresses the hypothesis that mES cells are characterized by promiscuous gene expression, involving weakly-coupled expression of a wide number of genes, which becomes refined during the process of differentiation. In a case where gene expression is more promiscuous, one might expect cells to occupy a larger sub-space of gene expression, as measured by the number of independent dimensions in which cells are distributed. By contrast, a more controlled pattern gene expression—even of a mixture of multiple cell types—would confine cells to a lower-dimensional manifold reflecting one or more coherent states of gene expression. This example evaluated the intrinsic dimensionality of the ES cells and differentiating cells. It was found that the intrinsic dimensionality of gene expression decreased after differentiation (FIG. 17J), while the dimensionality for pure RNA and randomized data was significantly higher than that of ES cells. This analysis supports the hypothesis that ES cell heterogeneity is associated with promiscuous weakly-coupled gene expression, which contrasts with heterogeneity after Lif withdrawal that arises from asynchrony in differentiation and a divergence of cell types.

Figure 17J:
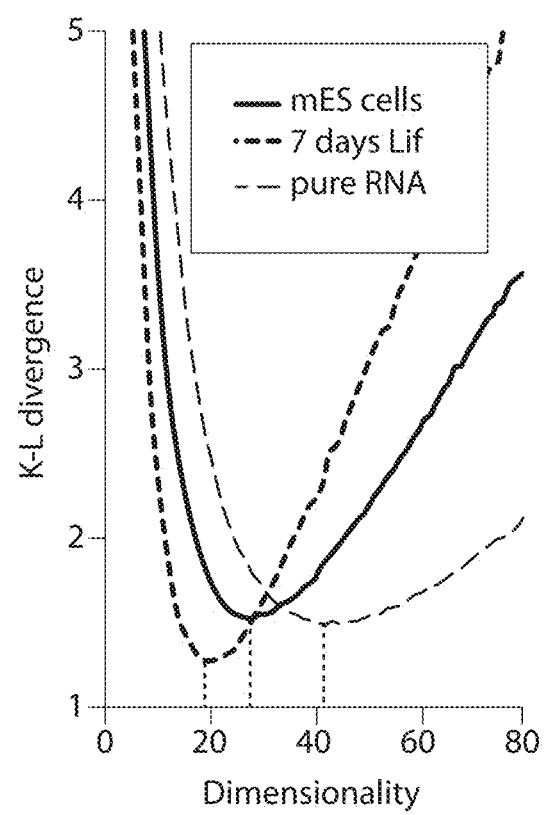

FIG. 17J shows an estimation of the intrinsic dimensionality of gene expression variability of mES cells and following 7 days post-LIF, showing a shrinking sub-space of fluctuations during differentiation. Results are contrasted with pure RNA, which should lack correlations and thus display a maximal fluctuation sub-space.

Example 14

These examples show the establishment of a platform for single cell capture, barcoding and transcriptome profiling, without physical limitations on the number of cells that can be processed. These examples showed high capture efficiencies, rapid collection times, very low inter-droplet CVs and a technical noise approaching the limits imposed by sampling statistics. These were reproducible across different experiments, devices, BHM batches and emulsion volumes (Table 1). These can be readily applied to single cell transcriptomics of small clinical samples including tumor samples and tissue micro-biopsies, giving a quantitative picture of tissue heterogeneity. Depending on the desired application, this allows trading off sequencing depth with the size of the cell population, by collecting different emulsion volumes. These examples allow for routinely identifying cell types, even rare sub-populations, based on gene expression. Owing to the low measurement noise, these allow one to distinguish discrete cell types from continuous fluctuations in gene expression, as was the case in ES cells. In addition to categorizing the cells, this type of data is valuable for identifying putative regulatory links between genes based on covariance, e.g., by exploiting natural and possibly subtle variation between individual cells in a population. These examples only highlighted a few simple examples of such inference (FIG. 16), but this type single cell data lends itself to more formal approaches of reverse engineering.

These examples can provide accurate information for many biological problems. This is illustrated by the complex and challenging problem of ES cell heterogeneity and its dynamics during early differentiation. The ES cells do not host large sub-populations of distinct cell types, and therefore, analysis of their heterogeneity requires a sensitive method. To interpret the data from these cells, a statistical model was developed of single cell noise that addresses the question of how biological gene-gene correlations are affected by low capture efficiencies and by technical variability between droplets, and we drew upon tools from machine learning to visualize the higher-dimensional organization of cells in gene expression 'space', and the dynamics of this organization. This analysis provided evidence in support of the hypothesis that ES cells fluctuate between a more pluripotent state and a more differentiated state when maintained in serum and LIF. However, in addition to an ICM-like population expressing the differentiation markers such as Krt8/18, S100a6 and Fgf5, other ES cell sub-populations were also identified associated with Primitive Endoderm fate, another sub-population expressing the primordial germ cell marker Blimp1/Prdm1, and sub-populations with less obvious fate associations marked by high levels of ER-related proteins or the E3 ligase Lin-41Trim71. The unbiased identification of these small cell sub-populations requires the scale enabled by drop-Seq. This is illustrated by the Primitive Endoderm-like cells, which represented less than ~1% of the cell population at all time points, and were too rare to be confidently detected by us in smaller samples of just 100-200 cells.

On the technical front, the drop-SEQ platform was developed for whole-transcriptome RNA sequencing, but the technology is highly flexible and should be readily adaptable to other applications requiring barcoding of RNA/DNA molecules, such as other RNA-Seq protocols, targeted sequencing approaches focusing on small panels of genes, ChIP-Seq, genomic sequencing, or chromatin proximity analysis (Hi-C). One implementation made use of a very simple droplet microfluidic chip, having just a single flow-focusing junction (FIG. 13C) to combine cells, barcodes and RT reagents. Other versions of the platform might take further advantage of droplet microfluidic functionalities to allow multi-step enzymatic reactions through reagent pico-injection into existing droplets, or to perform target cell enrichment prior to sequencing by sorting droplets on-chip. Moreover, drop-SEQ should be able to readily incorporate biochemical innovations targeting the relatively low capture efficiencies.

Figure 16A:
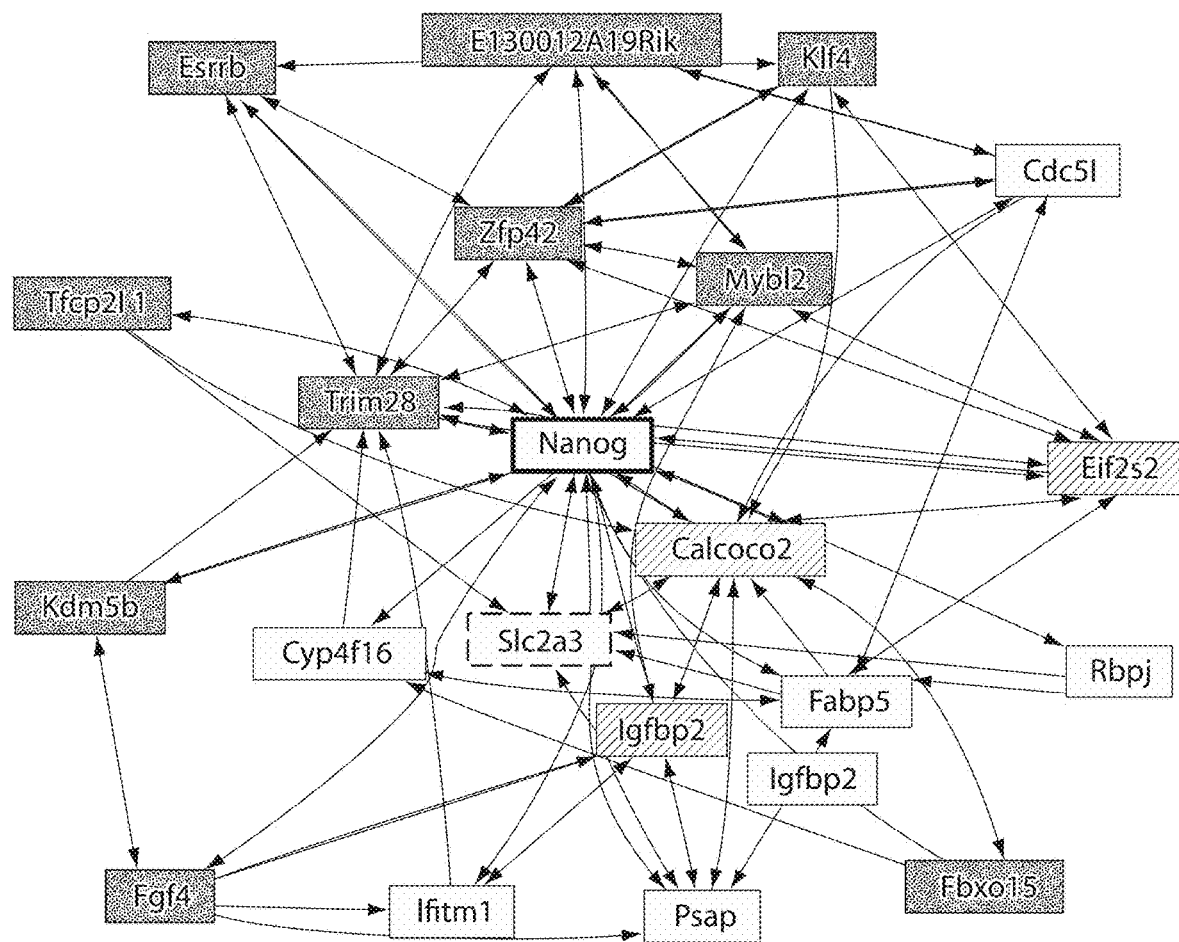
FIGS. 16A-16C illustrate a gene correlation network, produced in accordance with still another embodiment of the invention.
Figure 16B:
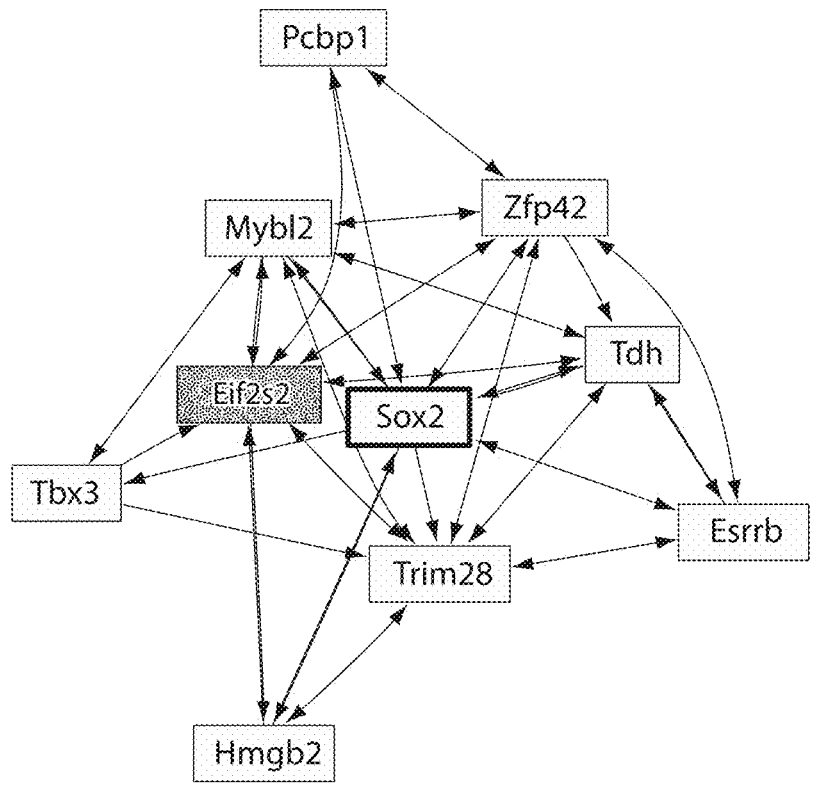
Figure 16C:
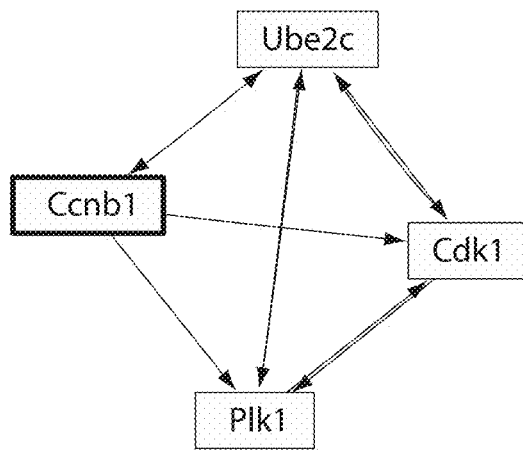

FIG. 16 shows a gene correlation network neighborhoods reveal pluripotency-associated factors. Connected correlation network neighborhoods of Nanog (FIG. 16A), Sox2 (FIG. 16B), and Cyclin B (FIG. 16C), generated by selecting network neighbors that have at least three mutual neighbors (see below). In FIGS. 16A and 16B, grey boxes indicate previously validated pluripotency factors; boxes Calcoco2, Eif2s2, and Igfbp2 indicate factors previously reported to be associated with a pluripotent state.

Example 15

This example illustrates various methods and systems used in the above examples.

Microfluidic device design and operation. The design of the microfluidics device used in some of these examples is indicated in FIG. 18 and integrates several features. As described above, it contains four inlets for, i) barcoded hydrogel microspheres (BHMs), ii) cell suspension, iii) reverse transcription (RT) and lysis reagent mix and iv) carrier oil, and one outlet port for droplet collection. To reduce flow fluctuations potentially arising due to mechanics of syringe pumps, fluid resistors were incorporated in the form of serpentine channels, while passive filters at each inlet prevent channels from clogging. The device included two junctions, one for bringing the three aqueous inputs together, and a second junction for sample encapsulation, where aqueous and oil phases meet and droplet generation occurs. To stabilize drops against coalescence, 0.75% (w/w) EA-surfactant (RAN Biotechnologies Inc.,) dissolved in HFE-7500 (3M) fluorinated fluid, was used. The dimensions of the microfluidic channels were carefully chosen to maximize the number of BHM and cell co-encapsulation events. The width (60 micrometers) of the BHM reinjection channel was designed such as that the BHMs (63 micrometers in diameter) passing through this channel become slightly squeezed thus facilitating their close packing and arrangement into a single-file. The BHMs entering into the main channel (70 micrometers wide) could then move freely downstream the flow before being encapsulated into individual droplets. Because of their close packing, the arrival of BHMs became highly regular, allowing nearly 100% loading of single-bead per droplet. This ensured that i) almost each cell encapsulated into a droplet was exposed to one barcoded primer, and ii) there was a minimal loss of non-barcoded-cells.

Soft lithography. The microfluidic device with rectangular microfluidic channels 80 micrometers deep was manufactured following established protocols. Briefly, a 3 inch size silicon wafer was coated with SU-8 3050 photoresist (MicroChem) at uniform 80 micrometer film thickness, baked at 65° C. for 20 min, and exposed to 365 nm UV light for 40 s (at ~8 mW cm$^2$) through the mask having a corresponding design indicated in FIG. 18 and baked for 5 min at 95° C.

The un-polymerized photoresist was dissolved with propylene glycol monomethyl ether acetate, silicon wafer rinsed with isopropanol and dried on a 95° C. hot plate for 1 min. The PDMS base and cross-linker (Dow Corning) was mixed at a 10:1 ratio and ~30 mL poured into the Petri dish containing a developed silicon wafer, degassed and incubated overnight at 65° C. The PDMS layer was then peeled-off and inlet-outlet ports were punched with a 1.2 mm biopsy punch (Harris Uni Core). The patterned side of PDMS was then treated with oxygen plasma and bounded to the clean glass slide. The micro-channels were treated with water repellent Aquapel (PPG Industries) and the device was then used in the above-described experiments.

Microfluidic device operation. During device operation, cell suspension and RT/lysis mix were cooled with ice-cold jackets, and droplets were collected into a single 1.5 mL tube (DNA LoBind, Eppendorf) placed on an ice-cold rack (Iso-Therm System, Eppendorf). To prevent water loss from the droplets due to evaporation during RT incubation, 200 microliters of mineral oil layer (Sigma) was placed on top of the emulsion. Throughout the experiments, flow rates at 100 microliters/hr for cell suspension, 100 microliters/hr for RT/lysis mix, 10-20 microliters/hr for BHMs and 80 microliters/hr for carrier oil were used to produce 4 nL drops at a frequency of 15 droplets per second. Each aqueous phase was injected into the microfluidic device via polyethylene tubing (ID 0.38×OD 1.09 mm, BB31695-PE/2) connected to a needle of a sterile 1 mL syringe (Braun) placed on a syringe pump (Harvard Apparatus, PC2 70-2226).

Loading barcoded hydrogel microspheres (BHMs) into the microfluidic device. After synthesis, BHMs were stored in $T_{10}E_{10}T_{0.1}$ buffer containing 10 mM Tris-HCl (pH 8.0), 10 mM EDTA, 0.1% (v/v) Tween-20. Before loading onto the microfluidic chip, BHMs were washed in $T_{10}E_{0.1}T_{0.1}$ buffer containing 10 mM Tris-HCl (pH 8.0), 0.1 mM EDTA and 0.1% (v/v) Tween-20, and then resuspended in 1×RT buffer (Invitrogen Superscript III buffer) supplemented with 0.5% (v/v) IGEPAL CA-630 and concentrated by centrifugation at 5000 rpm for 2 min. After removal of the supernatant BHMs were concentrated for a second time to achieve a close packing and eventually loaded directly into tubing connected to an oil-filled syringe for injection into the microfluidic device. The composition of BHMs sample was 100 microliters concentrated BHMs, 20 microliters 10% (v/v) IGEPAL CA-630, 40 microliters 5× First-Strand buffer and 40 microliters nuclease-free water (total aliquot volume 200 microliters).

Cell preparation and injection. The cell encapsulation process relies on random arrival of cells into the device. To minimize two or more cells from entering the same drop, diluted cell suspensions were used (~50-100,000 cells/mL) to obtain an average occupancy of 1 cell in 5-10 droplets. To prevent cell sedimentation in the syringe or other parts of the system, the cells were suspended in 1×PBS buffer with 16% (v/v) density gradient solution Optiprep (Sigma). 20,000 cells were typically used, suspended in 160 microliters 5×PBS (Lonza 17-516F), 32 microliters Optiprep (Axis-Shield 1114542) and 8 microliters 1% (v/v) BSA (Thermo Scientific B14), in a total volume 200 microliters.

Reverse transcription/lysis mix. The RT/lysis mix included 25 microliters 5× First-Strand buffer (18080-044 Life Technologies), 9 microliters 10% (v/v) IGEPAL CA-630 (#18896 Sigma), 6 microliters 25 mM dNTPs (Enzymatics N2050L), 6 microliters 0.1 M DTT (#18080-044, Life Technologies), 15 microliters 1 M Tris-HCl (pH 8.0) (51238 Lonza), 10 microliters Murine RNase inhibitor (M0314, NEB), 15 microliters SuperScript III RT enzyme (200 U/microliters, #18080-044, Life Technologies) and 60 microliters nuclease-free water (AM9937 Ambion), having a total volume 150 microliters.

Surfactant and carrier oil used for production of droplets. The carrier oil was HFE-7500 fluorinated fluid (3M) with 1% (w/w) EA surfactant (RAN Biotechnologies). EA-surfactant is a tri-block copolymer having an average molecular weight of ~13.000 g mol$^{-1}$. It has two perfluoropolyether tails ($M_W$~6.000 g mol$^{-1}$) connected via poly(ethylene) glycol ($M_W$~600 g mol$^{-1}$) head group. The surfactant was highly soluble in fluorinated fluids and nearly insoluble in the aqueous phase providing equilibrium interfacial tension of ~2 mN/m.

Barcoding inside droplets. After cell encapsulation primers were released from the BHMs by exposing the tube containing the emulsion droplets to UV light (365 nm at ~10 mW/cm$^2$, BlackRay Xenon Lamp) while on ice. Next, the tube was heated to 50° C. and incubated for 2 hours to allow cDNA synthesis to occur and then terminated by heating for 15 min at 70° C. The emulsion was then cooled on ice for 1 min and demulsified by adding 1 volume of PFO solution (20% (v/v) perfluorooctanol and 80% (v/v) HFE-7500). The aqueous phase from the broken droplets was transferred into a separate DNA Lo-Bind tube (Eppendorf) and processed as per the CEL-SEQ protocol with modifications described in the library preparation section.

Synthesis and quality control of Barcoded Hydrogel Microspheres. BHM synthesis relies on microfluidic emulsification of acrylamide:bis-acrylamide solution supplemented with acrydate-modified DNA primer, which is incorporated into the hydrogel mesh upon acrylamide polymerization. After polymerization, the BHMs are released from droplets, washed several times and processed by split-pool synthesis for combinatorial barcoding. Below is outlined a detailed protocol of performing such hydrogel bead synthesis followed by combinatorial barcoding.

BHM synthesis begins by emulsifying gel precursor solution into 62 micrometer size droplets using the microfludic chip indicated in FIG. 19. The composition of the dispersed phase was 10 mM Tris-HCl (pH 7.6), 1 mM EDTA, 15 mM NaCl containing 6.2% (v/v) acrylamide, 0.18% (v/v) bis-acrylamide, 0.3% (w/v) ammonium persulfate and 50 micromolar acrydate-modified DNA primer (IDT, see FIG. 20A for sequence). As a continuous phase, fluorinated fluid HFE-7500 was used, carrying 0.4% (v/v) TEMED and 1.5% (w/w) EA-surfactant. The flow rates were 400 microliters/hr for the aqueous phase and 900 microliters/hr for the oil phase. Droplets were collected into a 1.5 mL tube under 200 microliters mineral oil and incubated at 65° C. for 12 hours to allow polymerization of beads to occur. The resulting solidified beads were washed twice with 1 mL of 20% (v/v) 1H,1H,2H,2H-perfluorooctanol (B20156, Alfa Aesar) in HFE-7500 oil and twice with 1 mL of 1% (v/v) Span 80 (S6760, Sigma) in hexane (BDH1129-4LP, VWR) with 0.5-1 min incubation between each step and finally centrifuged at 5000 rcf for 30 s. After final centrifugation, the hexane phase was aspirated and the resulting BHM pellet was dissolved in 1 mL of TEBST buffer (10 mM Tris-HCl (pH 8.0), 137 mM NaCl, 2.7 mM KCl, 10 mM EDTA and 0.1% (v/v) Triton X-100). To remove traces of hexane, the beads were washed three times with 1 mL TEBST buffer at 5000 rcf for 30 s and finally resuspended in 1 mL TEBST buffer and stored at 4° C. These BHMs contained pores ~100 nm in size. In addition, the beads having elastic modulus of ~1 kPa were "squishy," which allows them to be packed into a concentrated gel mass without losing their integrity.

BHM split-pool combinatorial barcoding. To prepare barcoded primers on the hydrogel microspheres, the two-step enzymatic extension reaction summarized in FIG. 20B was used. To begin, a pre-loaded 384-well plate was used with 9 microliters of 15 micromolar primer 5'-W1*-bc1-PE1* encoding the first-half of a barcode (where 'bc1' indicates a unique sequence for each well, see also Table 1 for nucleotide sequence information). 6 microliters of reaction mix was added, containing ~40,000 hydrogel beads (carrying 5'-Ac-PC-T7p-PE1 primer), 2.5× isothermal amplification buffer (NEB) and 0.85 mM dNTP (Enzymatics) into each well (accounting ~$10^7$ beads in total). After denaturation at 85° C. for 2 min and hybridization at 60° C. for 20 min, 5 microliters of Bst enzyme mix was added (1.8 U of Bst 2.0 and 0.3 mM dNTP in 1× isothermal amplification buffer) giving a final volume in each well of 20 microliters. After incubation at 60° C. for 60 min, the reaction was stopped by adding 20 microliters of stop buffer into each well (100 mM KCl, 10 mM Tris-HCl (pH 8.0), 50 mM EDTA, 0.1% (v/v) Tween-20) and incubated on ice for 30 min to ensure that EDTA chelates magnesium ions and inactivates Bst enzyme. Next, the beads were collected into a 50 mL Falcon tube, centrifuged at 1000 rcf for 2 min and washed three times with 50 mL of STOP buffer containing 10 mM EDTA. To remove the second strand the gels were suspended in 20 mL of 150 mM NaOH, 0.5% (v/v) Brij 35P and washed twice with 10 mL of 100 mM NaOH, 0.5% (v/v) Brij 35P. The alkaline solution was then neutralized with buffer 100 mM NaCl, 100 mM Tris-HCl (pH 8.0), 10 mM EDTA, 0.1% (v/v) Tween-20 and washed once in 10 mL $T_{10}E_{10}T_{0.1}$ buffer (10 mM Tris-HCl (pH 8.0), 10 mM EDTA, 0.1% (v/v) Tween-20) and twice in 10 mL $T_{10}E_{0.1}T_{0.1}$ buffer (10 mM Tris-HCl (pH 8.0), 0.1 mM EDTA, 0.1% (v/v) Tween-20) and finally beads were suspended in 1.3 mL of DST buffer.

For the second barcoding step, a second 384-microtiter plate was prepared, pre-loaded with 9 microliters of 15 micromolar primer 5'-T19V*-UMI-bc2-W1* (where 'bc2' indicates a unique sequence for each well and UMI is a random hexanucleotide, see also Table 1 for sequence information), and repeated the procedure as for the first 384-well plate.

Quantification of ssDNA primers on the beads. To quantify the amount of the ssDNA primers per BHM, fluorescence in situ hybridization (FISH) was performed with complimentary DNA probes targeting the un-extended DNA "stub" (PE1), the barcoded primer after one extension step (W1) and the primer after two extension steps ($T_{19}V$) (see Table 1 for sequence information). Hybridization was performed in a 40 microliters volume at room temperature for 20 min by suspending ~4000 DNA-barcoding beads in hybridization buffer (1 M KCl, 5 mM Tris-HCl (pH 8.0), 5 mM EDTA, 0.05% (v/v) Tween-20) together with 10 micromolar FAM-labeled probe. The high salt concentration was used to avoid melting of the probe targeting $T_{19}V$ ($dA_{20}$-FAM), which has weak binding even at room temperature. The absence of background fluorescence was validated in microspheres lacking DNA primers. After incubation, beads were washed three times with 1.4 mL hybridization buffer, re-suspended in 40 microliters and fluorescence intensity recorded under confocal microscope (Leica). The average fluorescence intensity of beads with PE1*-FAM, W1*-FAM and dA20-FAM was 2286+/−271, 1165+/−160 and 718+/−145, respectively (FIGS. 21A-21D). This corresponds to incorporation efficiencies of ~50% for W1/PE1 and 60% for polyT/W1, which gives the final efficiency of 31% or ~15 micromolar of fully barcoded ssDNA primers per bead. Accounting of the BHM volume, this equals ~$10^9$ copies of fully extended ssDNA primers per single bead. To validate the release of primers from the hydrogel mesh, ~4000 beads was suspended in 20 microliters DST buffer and exposed to UV light (365 nm at ~10 mW/cm$^2$) for 8 min. A gel electropherogram of 1 microliters of supernatant using a BioAnalyzer High Sensitivity DNA Analysis Kit (Agilent Technologies) confirmed the presence of three DNA bands (FIG. 21E), which is in agreement with FISH results from above.

Single-molecule sequencing of primers from single BHMs. To test the composition of BHMs after synthesis, 10 BHMs were randomly picked and sequenced using the Illumina MiSeq sequencing platform. For this purpose, the BHMs were first hybridized to a fluorescent FISH probe (PE1-FAM) as described above, and were manually picked using a dissection microscope (Nikon) under fluorescent illumination and transferred into 0.2 mL PCR tubes pre-filled with 5 microliters DNA Suspension (DS) buffer (10 mM Tris-HCl pH 8.0, 0.1 mM EDTA). The tubes were then exposed to UV light (~10 mW/cm$^2$) for 15 min while keeping them on ice. After UV exposure, 0.5 microliters of 5 micromolar PE2-(barcode)$_n$-A19 primer (herein, n represents 10 different barcodes) was added to the tube and mixed with 4.5 microliters of Bst 2.0 ready-to-use reaction solution. The samples having 10 microliters final volume were then incubated at room temperature for 10 min, inactivated for 3 min at 95° C. and cooled down on ice. Next, 20 microliters of master mix containing 50% (v/v) Kapa HiFi HotStart ready mix (2×, KK2601), 15% (v/v) PE1/PE2 primers, and 35% (v/v) nuclease-free water were added into each tube, and DNA was amplified with PCR (95° C. for 5 min, 30 cycles at 98° C. for 20 s, 60° C. for 15 s, 72° C. for 30 s and final step at 72° C. for 5 min). The size of the PCR products was assessed by gel-electrophoresis, purified with GenElute PCR CleanUp Kit (Na1020-1KT, Sigma) and all samples diluted down to 10 ng/microliters. In the final step all samples were pooled together and sequenced using MiSeq Illumina platform by following manufacturer recommendations. Sequencing results of primers from 10 individual beads is presented in FIG. 21F-21H.

Limits on the number of cells per single sequencing run. For a large pool of barcoded hydrogel microspheres (BHMs), each carrying one of N barcodes, what is the maximum number of cells that can be captured before two or cells will carry the same barcode? This question is akin to the so-called birthday problem, with barcodes analogous to days of the year, and BHMs analogous to the people in a room. The expected number of observed barcodes from sampling n BHMs is $n_{obs}=N(1-e^{-n/N})$. Thus, the expected multi-barcoding error, defined as the fraction of cells carrying the same barcode, is approximately $f_{err}=1-n_{obs}/n$. The error becomes large when n·N, so in practice the number of sampled cells must be much smaller than the number of barcodes, i.e. n<<N, and therefore the limit of obtaining barcoded single-cells is $f_{err}\approx n/2N$. The number of barcoded single-cells n depends on the tolerated error, for example, allowing for an error of less than $f_{err}=1\%$ requires an upper limit n=N/50. Thus, for the value of N=384$^2$ which corresponds to two 384-well plates in our experiment, a 1% multiple-barcoding error arises at the limit n=2,949 cells. In practice, fewer cells can be used to produce negligible multi-barcoding errors.

Cell culture preparation. The mouse embryonic stem (mES) cells were maintained in ESC base media inside culture flasks pre-coated with gelatin at 37° C. in 5% $CO_2$ and 60-80% humidity at density ~3×10$^5$ cells ml$^{-1}$. The ESC media contained phenol red free DMEM (Gibco), supplemented with 15% (v/v) fetal bovine serum (Gibco), 2 mM L-glutamine, 1×MEM non-essential amino acids (Gibco), 1% (v/v) penicillin-streptomycin antibiotics, 110 micromolar beta-mercaptoethanol, 100 micromolar sodium pyruvate. For guided differentiation ESC base media was supplemented with Leukemia Inhibitory Factor (LIF) at final concentration 1000 U/mL and for unguided mES differentiation the media was without LIF. Within 2 days of LIF withdrawal the culture experienced significant morphological changes indicating the differentiation of mES cells.

Prior encapsulation the flask was washed with 1×PBS (without $Mg^{2+}$ and $Ca^{2+}$ ions) and treated with 1× trypsin/EDTA solution for 3 min at 37° C. The trypsin was quenched by adding equal volume of ESC base media. Detached cells were centrifuged at 260 g for 3 min and re-suspended in ~3 mL fresh ESC base media. After passing through the 40 micrometer size strainer, cells were counted with hemocytometer and diluted in 0.5×PBS supplemented with 0.04% (v/v) BSA and 16% (v/v) OptiPrep solution to obtain desirable amount of cells (typically 20,000 cells in 200 microliters). The suspension was transferred into 1 mL syringe connected to microfluidics device and injected at 100 microliter/hr flow rate. Following this procedure mES cells were prepared with LIF at Day 1 and without LIF at early Day 2, late Day 2, Day 4 and Day 7.

The K-562 cell line (ATCC, CCL-243) was maintained in DMEM supplemented with 10% (v/v) fetal bovine serum and 1% (v/v) penicillin-streptomycin at 37° C. in 5% $CO_2$ and 60-80% humidity atmosphere, at density ~$3 \times 10^5$ cells $ml^{-1}$. For encapsulation experiments K-562 cells were prepared as outlined above but using DMEM media and mixed with mES cells at ratio 1:1.

DNA-library preparation. Library preparation was based on a modified CEL-Seq protocol. The workflow of DNA library preparation can summarized as follows: RT--> ExoI-->SPRI purification (SPRIP)-->SSS-->SPRIP-->T7 in vitro transcription linear amplification-->SPRIP-->RNA Fragmentation-->SPRIP-->primer ligation-->RT-->library enrichment PCR.

Referring to the detailed protocol in Jaitin D A, et al. (2014) Massively parallel single-cell RNA-seq for marker-free decomposition of tissues into cell types. Science 343 (6172):776-779, the following modifications were made to the protocol: the RT primer included the P5/PE1 adaptor while the ligation primer includes the P7/PE2 adaptor, a flipped orientation to that in the protocol; prior to ExoI treatment, the aqueous phase from broken droplets was centrifuged at 4° C. for 15 minutes at 14krcf to pellet cell debris and gels; during ExoI treatment, 10 U HinFI were added to digest primer dimers that may have formed during the RT reaction; the original DNAse digestion step was omitted after linear amplification; after linear amplification the resulting amplified RNA libraries were analyzed on an Agilent BioAnalyzer before proceeding; before primer ligation, the samples were treated with Shrimp Alkaline Phosphatase for 30 minutes. The number of final PCR cycles required for final library enrichment PCR ranged from 10-13 cycles. The remaining steps are otherwise unchanged.

Bioinformatic analysis. Paired-end sequencing was performed on Illumina MiSeq, HiSeq 2500 and NextSeq machines as detailed in Table 1. Read 1 was used to obtain the sample barcode and UMI sequences; read 2 was then mapped to a reference transcriptome as described below. The reads were first filtered based on presence in read 1 of two sample barcode components separated by the W1 adaptor sequence (see FIG. 20 and Table 4). Read 2 was then trimmed using Trimomatic (5) (version 0.30; parameters: LEADING:28 SLIDINGWINDOW:4:20 MINLEN19). Barcodes for each read were matched against a list of the $384^2$ pre-determined barcodes, and errors of up to two nucleotides mismatch were corrected. Reads with a barcode separated by more than two nucleotides from the reference list were discarded. The reads were then split into barcode-specific files for mapping and UMI filtering.

The trimmed reads were aligned using Bowtie (version 0.12.0, parameters: -n 1-115-e 300-m 200-best-strata-a) to the mouse transcriptome. The data sets were also reprocessed with different bowtie parameter sets without changing the qualitative results of the analysis. The reference transcriptome was built using all annotated transcripts (extended with a 125 bp poly-A tail) from the UCSC mm10 genome assembly. A custom Python and PySAM script was used to process mapped reads into counts of UMI-filtered transcripts per gene. Alignments from bowtie were filtered in the following way: (1) for each read, we retained at most one alignment per gene, across all isoforms, by choosing the alignment closest to the end of the transcript. (2) If a read aligned to multiple genes, we excluded any alignments more than 400 bp away from the end of the transcript; this is motivated by the strong 3' bias of the CEL-SEQ method. (3) Reads mapping to more than 10 genes were excluded, and (4) a UMI filtering step described in the following paragraph was performed. Finally, (5) if a read still aligned to more than 2 genes after UMI filtering, the read was excluded altogether. In reporting the counts, for each gene, any other genes from which it could not be distinguished in at least one read was also reported; this allowed the exclusion of spurious correlations in our downstream analysis resulting from mapping ambiguities. The robustness of the pipeline to this final step was confirmed by re-processing the data with a maximum of 1-4 alignments per read. After steps (1-5) were carried out separately for each sample, the resulting gene expression tables were concatenated and loaded into MATLAB for analysis.

UMI filtering (step 4 above) was carried out as follows. Each distinct UMI was associated with a set of genes through the set of reads carrying the UMI. For each UMI, the minimal set of genes that can account for the full set of reads with this UMI was identified. This problem is known as the 'Hitting Set Problem' (or 'Set Cover Problem'). A greedy algorithm was applied to obtain the most parsimonious gene set for each UMI. Only one read per gene per UMI was kept. With this approach, some subsets of genes may still be undistinguishable from each other because they are supported by the same set of ambiguously aligned reads. Step (5) in the previous paragraph was thus used to eliminate ambiguous reads beyond a predetermined threshold. To illustrate the UMI filtering step, consider a UMI with two reads, the first aligning to genes A and B and the second aligning to genes B and C. Although neither read is aligns unambiguously, gene B can explain the presence of both reads and thus the alignments to genes A and C are discarded, and just one of the two reads is kept for gene B.

UMI-filtered count normalization. Prior to normalization, the variation in the total UMI-filtered mapped (UMIFM) counts per sample barcode was 21% to 55% (coefficient of variation), see Table 1. The CV appeared to grow during differentiation, suggesting that some of the variation in total UMIFM counts arose from differences in cell size rather than in variation in RT efficiency. All counts were normalized by total-count normalization, i.e. the normalized counts for gene j in cell i is given in terms of the un-normalized counts, $m_{i,j}$, as $\hat{m}_{i,j} = m_{i,j}\overline{M}/M_i$, where $M_i = \Sigma_j m_{i,j}$ and $\overline{M}$ is the average of $M_t$ over all cells. Similar results are also obtained using sub-sample normalization.

Predicting method sensitivity. This section derives the form of the sensitivity curve (solid curve) in FIG. 14E, predicted for a case where the only limitation to detection is the capture efficiency, β or beta, which is assumed to be unbiased and uniform across all gene transcripts. All other biases, such as sequence-specific or length-specific bias, are assumed negligible. The excellent fit reinforces these assumptions. Let n be the number of transcripts for a given gene in a given droplet. The probability of detecting zero transcripts for the gene in this droplet is $p_0(n)=e^{-\beta n}$. The sensitivity S is then obtained by marginalizing $p_0(n)$ over the distribution of n, which, in the case of the pure RNA sample, is Poisson-distributed about a mean value $\bar{n}$. One obtains $S(\bar{n})=\Sigma_{n=0}^{\infty}p_0(n)\text{Poiss}[n,\bar{n}]$, giving $S(\bar{n})=e^{-\bar{n}(1-e^{-\beta})}$, which is the curve plotted in FIG. 14E, with the value of β (beta) measured from FIG. 14D. This curve can also be identified as the moment generating function (MGF) of the Poisson distribution evaluated at β (beta). The quality of the fit demands that variations in β (beta) between droplets be small, which is consistent with the low CV in the total counts between control droplets. For non-control samples, the input distribution for each gene is no longer a Poisson distribution, and the detection frequency $S(\bar{n})$ is instead different for each gene and, under the assumptions given here, is equal to the MGF of the underlying gene expression distribution evaluated at β (beta).

Selection and filtering of principal gene sets for PCA and tSNE analysis. Since each gene carries intrinsic sampling noise that is uncorrelated to other genes, it is expected that for whole-transcriptome data, a large fraction of the variability observed across all genes will not be explained by the top principal components. For the same reasons, differences between cell sub-populations may appear weak if a large number of "bystander" genes (which vary little between populations) are included in evaluating cell-cell correlations. To overcome these sampling limitations, the ES cell population structure was analyzed using only a sub-set of genes chosen to reflect known ES cell biology while also reporting on the most variable genes at each time point. The general strategy for selecting an appropriate gene set was as follows: (1) for each time point, the top 200 most variable genes were included, as determined by the v-score (Table 2), which is closely related to the gene Fano Factors; these genes were complemented with a curated list of genes implicated in ES cell biology. (2) To reduce the gene set, a preliminary principal component analysis (PCA) was performed on the cell population, using the initial gene set, and used the results to select only "principal genes", i.e. genes contributing to non-random principal components (PCs) as determined by matrix randomization in FIG. 150E. The principal genes are those with the highest loading coefficients for each non-random PC, with the selection threshold set dynamically for each PC to reflect the structure of the loading coefficient distribution. (3) For each gene g in the set, the set was then re-expanded to include up to two additional genes that correlated most strongly with g. This final step allows inclusion of genes not present in the initial set, but which correlated strongly with the highly variable gene set. The final gene set derived at the end of step (3) was used for subsequent PCA and tSNE analysis at each time point.

Network neighborhood analysis. The distance metric d=(1-(Pearson correlation)) was used to define the distance between two genes, where the correlation is taken over all cells. An unweighted, directed network was constructed as follows: for a given gene $G_0$ of interest, a directed edge to its N nearest neighbor genes $G_1$ was defined (i.e. genes with the highest correlation to $G_0$). N additional directed edges were added from each member of the set $G_1$ to its N nearest neighbors, together forming a set $G_2$. The resulting preliminary network has (N+1)*N directed edges in total, and up to 1+(N+1)*N vertices representing $G_0$, $G_1$ and $G_2$. The network was then trimmed iteratively by removing any vertex that has fewer than X incoming edges. The final network is the "X-connected neighborhood of gene $G_0$." If it is not an empty set, it has: the gene $G_0$; some members of $G_1$ that are also nearest neighbors of at least X−1 other members of $G_1$; and some members of $G_2$ that are the nearest neighbors of at least X members of $G_1$. For the networks plotted in FIG. 16, the parameters N=50, X=3 were used.

TABLE 1

Sequencing run statistics

| Sample (days post-LIF) | Emulsion volume (uL) | Platform | Total library reads (unfiltered) | Number cells/ barcodes | Average filtered reads/cell | UMI Filtered Mapped (UMIFM) counts/cell | |
|---|---|---|---|---|---|---|---|
| | | | | | | Average | Coeff. of variation (CV) |
| Pure RNA control | 16 | HiSeq 2500 | 166,031,332 | 953 | 89,116 | 24,191 | 21% |
| mES LIF+ | 40 | NextSeq | 413,138,104 | 935 | 199,193 | 29,239 | 36% |
| mES day 2, (early) | 6 | HiSeq 2500 | 119,859,024 | 145 | 119,386 | 20,524 | 35% |
| mES day 2, (late) | 26 | MiSeq | 17,660,550 | 303 | 38,788 | 8,441 | 36% |
| mES day 4 | 40 | MiSeq | 11,557,428 | 683 | 10,237 | 4,661 | 43% |
| mES day 7 | 8 | HiSeq 2500 | 92,805,168 | 169 | 153,035 | 27,065 | 38% |
| mES day 7 | 40 | NextSeq | 250,187,951 | 799 | 208,231 | 26,216 | 55% |
| mES day 2, early | 95 | HiSeq 2500 | 33,751,186 | 2,168 | 4,987 | 2,608 | 42% |

TABLE 3 mES cell sub-population markers across time points

| Data set | Cell group description | Cell group size (number/ total) | Clustering index (−1 < x < 1) | High-expressed genes |
|---|---|---|---|---|
| mES day 0 | Primitive endoderm-like | 6/935 | 0.76 | Gsn, Col4a1/2, Serpinh1, Lama1/b1/c1, Sparc, Srgn, P4ha2, Lrpap1, Podxl, Ctsl, S100a10, Pgk1, Slc2a3, Tfpi, Amn, Fbp2, Gpx3, Man2c1os, Lpar3, Cd63 |
| | Epiblast-like | 40/935 (all) 6/935 (Krt8-high) | 0.20 (all) 0.55 (Krt8-high) | Actg1, Anxa2, Krt8/18/19, Plaur, Cnn1, Tagln, Plin2, Flnc, Tinagl1, Slc2a1, Fam160b2, Mmab, Sfn, Plec, S100a6, Flnb, Ngfrap1 |
| | Hsp90-high | 10/935 | 0.47 | Atf5, Calr, Hsp90b1, Hspa5, Manf, Pdia6, Creld2, Hyou1, Derl3, Prph, Chchd10 |
| | Prdm1-high | 13/935 | 0.47 | Prdm1, Baat, Nsun6, Parp4, Srgn, Ssh1 |
| | Trim71-high | 12/935 | 0.31 | Trim71, Cd44, Med10, Myo15, Bcl2/Cep83, Kdm1b, Sbk1, Csf1r Psg18/20, Prss44 |
| 4, 7 days post-LIF withdrawal | H19/Rhox6/9+ | 14/683, 10/899 | 0.36, 0.20 | H19, Igf2, Rhox6/9, Fabp3, Igfbp2, Sct, Vgf, Pmp22, Rhox5, Itm2a, Rhox5, 1700001F09Rik, Peg10 |
| | Pluripotency-high | 21/683, 31/899 | 0.16, 0.15 | Trim28, Tex19.1, Tdh, Tdgfl, Spry4, Sox2, Psorslc2, Pou5f1, Phc1, Ogfod3, Mylpf, Mt1/2, Mkrn1, Mkrn1, L1td1, Kcnj14, Gad1, G3bp2, Dnmt3l, Cdh16, Nlrp1a, 4930526L06Rik, 3110021A11Rik |
| | Zscan4-hi | 4/683, 0/899 | 0.45, N/A | Zscan4a/c/d/f, Fbxo15, Tcstv1/3, Dazl, Calcoco2, Mylpf, Dcdc2c, Lmx1a, Ddit4l, Aqr, Clp1, Tmem92, Usp17la, 2310039L15Rik, B020031M17Rik, Gm4027, Gm20767, Gm7102, Gm8994 |
| | Primitive endoderm-like | 7/683, 4/899 | 0.55, 0.65 | Gata6, Amn, Ctsl, Cd63, Col4a1/2, Lama1/b1/c1, Upp1, Sparc, P4ha2, Serpinh1, Fst, Lrpap1, P4hb, Ctsh, Clu, Epas1, Pga5 |

TABLE 4

List of DNA oligonucleotides

1. BHM synthesis:

| | |
|---|---|
| Hydrogel-incorporated DNA primer | 5'-/5Acryd/iSpPC/CGATGACG TAATACGACTCACTATAGGG ATACCACCATGG CTCTTTCCCTACACGACGCTCTTC-3' |
| barcode 1 (W1*-bc1-PE1*) | 5'-AAGGCGTCACAAGCAATCACTC 10987654321 AGATCGGAAGAGCGTCGTGTAGGGAAAGAG-3' |
| Barcode 2/UMI (Ti9V*-UMI-bc2-W1*): | 5'-BAAAAAAAAAAAAAAAAAAA NNNNNN 87654321 AAGGCGTCACAAGCAATCACTC-3' |
| FAM-PE1* | /56-FAM/ AGATCGGAAGAGCGTCGTGTAGGGAAAGAG |
| FAM-W1* | /56-FAM/AAGGCGTCACAAGCAATCACTC |
| FAM-A20 | /56-FAM/AAAAAAAAAAAAAAAAAAAA |
| Fully assembled DNA primers: | CGATGACG TAATACGACTCACTATAGGG ATACCACCATGG CTCTTTCCCTACACGACGCTCTTCCGATCT 1234567890 GAGTGATTGCTTGTGACGCCTT 12345678 NNNNNN TTTTTTTTTTTTTTTTTTTTV |

2. Library preparation:

| | |
|---|---|
| RNA ligation: | /5Phos/ AGATCGGAAGAGCGGTTCAGCAGGAATGCC/ 3SpC3/ |
| 2nd RT primer: | GTCTCGGCATTCCTGCTGAAC |
| PCR enrichment primers: | AATGATACGGCGACCACCGAGATCTACACTC TTTCCCTACACGA CAAGCAGAAGACGGCATACGAGATCGGTCTC GGCATTCCTGCTGAAC |

Example 16

This example illustrates a method of encapsulating cells into droplets. In this example, a droplet-barcoding-sequencing platform was used to encapsulate cells into droplets with lysis buffer, reverse transcription (RT) reagents, and barcoded oligonucleotide primers. mRNA released from each lysed cell remains trapped in the same droplet and was barcoded during synthesis of complementary DNA (cDNA). After barcoding, the material from all cells is combined by breaking the droplets, and the cDNA library was processed for sequencing (FIG. 27).

Figure 27:
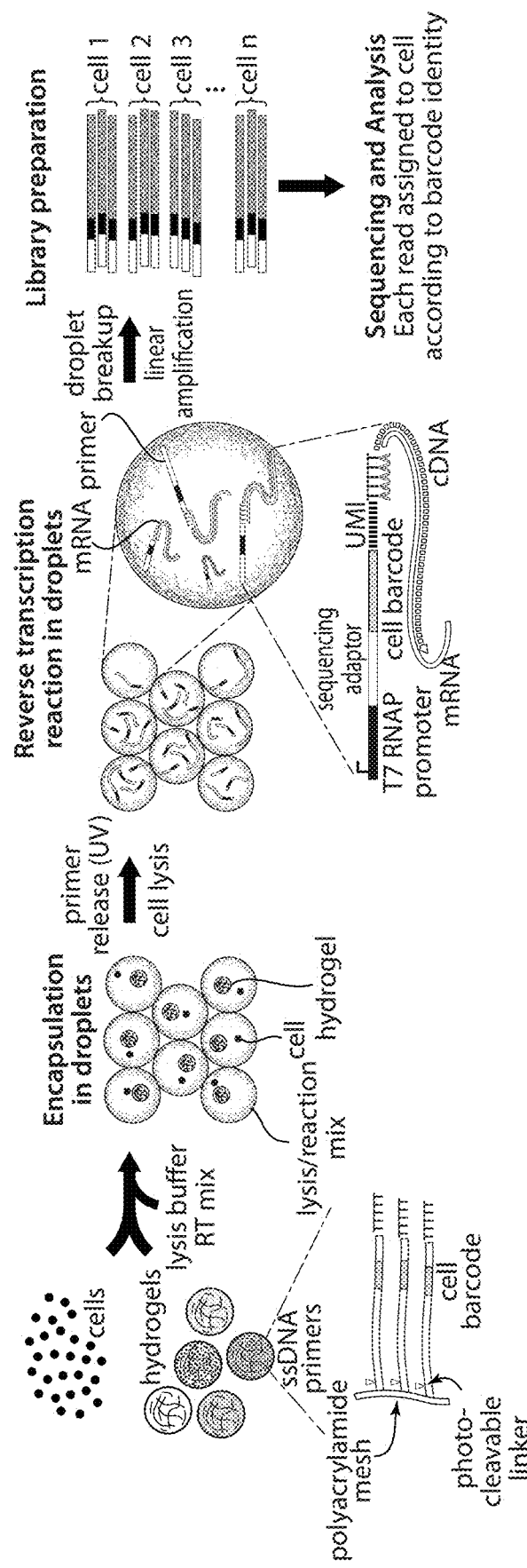
FIG. 27 illustrates a microfluidic device in another embodiment of the invention.

In this example, a library of barcoded hydrogel microspheres (BHMs) were synthesized that were coencapsulated with cells (FIG. 27). The BHMs carried covalently coupled, photoreleasable primers encoding one of $384^2$ (i.e. 147,456)

pre-defined barcodes. This pool size allowed randomly labeling 3,000 cells with 99% unique labeling, and the number of cells that can be barcoded is far larger through the use of library barcodes to mark collection tubes of ~3 k cells each. The method can be extended in a straightforward manner if larger-scale cell capture in a single library is desired.

FIG. 27 shows a droplet microfluidic platform for DNA barcoding thousands of cells. Schematic of single cell droplet barcoding. Cells are co-encapsulated with lysis buffer, reverse-transcription (RT) mix, and hydrogel microspheres carrying barcoded RT primers; after encapsulation primers are released from the hydrogels, and cDNA product in the droplets is tagged with a DNA barcode during reverse transcription. Droplets are then broken and material from all cells is linearly amplified before sequencing. UMI=a random hexamer unique molecular identifier.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An article, comprising:
a plurality of particles, at least about 90% of the particles each comprising an oligonucleotide tag attached thereto, the oligonucleotide tag comprising at least 2 primer sites and at least 2 barcode regions unique to the oligonucleotide tag attached to each particle,
wherein at least about 90% of the particles are distinguishable from the other particles of the plurality of particles on the basis of the barcode regions of the oligonucleotide tag,
wherein the oligonucleotide tag further comprises a random nucleotide sequence flanked by one of the at least 2 barcode regions.

2. The article of claim 1, wherein the plurality of particles is contained within a plurality of microfluidic droplets.

3. The article of claim 2, wherein the plurality of particles is contained within a plurality of at least 100 microfluidic droplets.

4. The article of claim 1, wherein at least some of the particles are hydrogel particles.

5. The article of claim 1, wherein at least some of the particles are polymeric particles.

6. The article of claim 1, wherein at least some of the oligonucleotide tags comprise at least two barcode sequences and wherein the at least two barcode sequences are selected from a different pool of barcode sequences.

7. The article of claim 1, wherein at least some of the oligonucleotide tags comprise a primer sequence.

8. The article of claim 1, wherein at least some of the oligonucleotide tags comprise a cleavable linker.

9. The article of claim 8, wherein the cleavable linker is a photocleavable linker.

10. The article of claim 1, wherein at least some of the oligonucleotide tags comprise a poly-T sequence.

11. The article of claim 1, wherein at least some of the oligonucleotide tags comprise a random DNA sequence.

12. The article of claim 1, wherein at least some of the oligonucleotide tags comprise a sequence able to specifically bind a gene.

13. A method, comprising:
providing a plurality of particles;
providing first oligonucleotides comprising a photocleavable linker, wherein the first oligonucleotides are taken from a pool of at least 10 unique first oligonucleotides;
attaching first oligonucleotides to the plurality of particles via the photocleavable linker such that at least about 90% of the particles have bonded thereto only one first oligonucleotide; and
attaching second oligonucleotides to the first oligonucleotides such that at least about 90% of the first oligonucleotides has bonded thereto only one second oligonucleotide, thereby forming an oligonucleotide tag, wherein the second oligonucleotides are taken from a pool of at least 10 unique second oligonucleotides, wherein the second oligonucleotides further comprise a random nucleotide sequence; and
generating a plurality of sequencing reads of the oligonucleotide tags, wherein generating the plurality of sequencing reads comprises filtering the sequencing reads based on the presence of the random nucleotide sequence.

14. The method of claim 13, wherein at least some of the oligonucleotide tags comprise at least two barcode sequences and wherein the at least two barcode sequences is selected from a different pool of barcode sequences.

15. The method of claim 13, further comprising releasing at least some of the oligonucleotide tags from the particles.

16. The method of claim 13, comprising releasing at least some of the oligonucleotide tags from the particles by applying light.

17. A method, comprising:
encapsulating a cell and a hydrogel particle within a droplet, the hydrogel particle having attached thereto a barcoded nucleic acid;
lysing the cell within the droplet to render accessible nucleic acid from the cell;
enzymatically reacting the accessible nucleic acid with the barcoded nucleic acid, thereby obtaining a oligonucleotide tag, wherein the barcoded nucleic acid comprises a random nucleotide sequence; and
generating a plurality of sequencing reads of the oligonucleotide tag, wherein generating the plurality of sequencing reads comprises filtering the sequencing reads based on the presence of the random nucleotide sequence.

18. The method of claim 17, wherein the cell is one of a plurality of cells and the droplet is one of a plurality of microfluidic droplets, the method comprising encapsulating the plurality of cells in the plurality of microfluidic droplets such that at least about 90% of the microfluidic droplets contain one cell or no cell.

19. The method of claim 18, comprising releasing at least some of the oligonucleotide tags from the particles followed by breaking the droplets.

20. The method of claim 18, comprising breaking the droplets and releasing at least some of the oligonucleotide tags from the particles after breaking the droplets.

* * * * *

UNITED STATES PATENT AND TRADEMARK OFFICE
CERTIFICATE OF CORRECTION

| | |
|---|---|
| PATENT NO. | : 11,052,368 B2 |
| APPLICATION NO. | : 15/991600 |
| DATED | : July 6, 2021 |
| INVENTOR(S) | : David A. Weitz et al. |

It is certified that error appears in the above-identified patent and that said Letters Patent is hereby corrected as shown below:

In the Specification

At Column 1, Lines 22-25, please change the paragraph:
"This invention was made with government support under Grant No. R21DK098818 awarded by the National Institutes of Health. The government has certain rights in the invention."
To:
-- This invention was made with government support under HD073104, and DK098818 awarded by the National Institutes of Health. The government has certain rights in the invention. --

Signed and Sealed this
Sixth Day of August, 2024

Katherine Kelly Vidal
*Director of the United States Patent and Trademark Office*